(12) United States Patent
Graziani et al.

(10) Patent No.: US 11,999,732 B2
(45) Date of Patent: Jun. 4, 2024

(54) P2X₃ RECEPTOR ANTAGONISTS

(71) Applicant: RECORDATI INDUSTRIA CHIMICA E FARMACEUTICA SPA, Milan (IT)

(72) Inventors: Davide Graziani, Milan (IT); Sergio Menegon, Milan (IT); Patrizia Angelico, Milan (IT); Carlo Riva, Milan (IT)

(73) Assignee: RECORDATI INDUSTRIA CHIMICA E FARMACEUTICA SPA, Milan (IT)

( * ) Notice: Subject to any disclaimer, the term of this patent is extended or adjusted under 35 U.S.C. 154(b) by 0 days.

(21) Appl. No.: 17/259,511

(22) PCT Filed: Jul. 11, 2019

(86) PCT No.: PCT/EP2019/068681
§ 371 (c)(1),
(2) Date: Jan. 11, 2021

(87) PCT Pub. No.: WO2020/011921
PCT Pub. Date: Jan. 16, 2020

(65) Prior Publication Data
US 2021/0246139 A1 Aug. 12, 2021

(30) Foreign Application Priority Data
Jul. 12, 2018 (GB) ...................................... 1811452

(51) Int. Cl.
*C07D 471/14* (2006.01)
*A61K 31/519* (2006.01)
*C07D 487/14* (2006.01)
*C07D 491/22* (2006.01)
*C07D 519/00* (2006.01)

(52) U.S. Cl.
CPC ......... *C07D 471/14* (2013.01); *C07D 487/14* (2013.01); *C07D 491/22* (2013.01); *C07D 519/00* (2013.01)

(58) Field of Classification Search
CPC .. C07D 471/14; C07D 487/14; A61K 31/519; A61P 29/00
USPC ........................ 544/251, 115; 514/257, 233.2
See application file for complete search history.

(56) References Cited

U.S. PATENT DOCUMENTS

| | | | |
|---|---|---|---|
| 4,585,772 A * | 4/1986 | Junge ........................ | A61P 9/10 514/91 |
| 4,713,383 A | 12/1987 | Francis et al. | |
| 6,013,650 A | 1/2000 | Thurkauf et al. | |
| 9,284,335 B2 * | 3/2016 | Allan ........................ | A61P 9/00 |
| 2016/0083400 A1 | 3/2016 | Burdi et al. | |

FOREIGN PATENT DOCUMENTS

| | | |
|---|---|---|
| EP | 053 767 | 6/1982 |
| EP | 0 263 071 | 4/1988 |
| EP | 1 719 756 | 11/2006 |
| JP | 2001/160488 | 6/2001 |
| JP | 2011 119576 A | 6/2011 |
| WO | WO 94/26742 | 11/1994 |
| WO | WO 00/29412 A1 | 5/2000 |
| WO | WO 2004/094425 | 11/2004 |
| WO | WO 2011/017142 | 2/2011 |
| WO | WO 2013/192229 | 12/2013 |

OTHER PUBLICATIONS

Crean, C.W. et al.: Synthesis of N3- and 2-NH2-substituted 6,7-diphenylpteridines and their use as intermediate conjugates for the preparation of oligonucleotide conjugates designed to target photooxidative damage on single-stranded DNA. Organic and Biomolec. Chem., vol. 2, pp. 3588-3601, 2004.*
Giudice, M.R.D. et al.: New fused triazolo pyrimidines; synthesis of pyrido triazolo pyrimidine, pyrimidotriazolopyrimidine and triazolopteridine derivatives. J. heterocyc. Chem., vol. 31, pp. 1503-1507, 1994.*
Sugimito, T. et al.: Imidazopteridines, synthesis of imidazopteridines with a functional group at the 6-position. Bull. Chem. Soc. Jpn., vol. 52, pp. 867-870, 1979.*
Compounds with RN 70750-94-6 and 70750-95-7 (entered STN on Nov. 16, 1984).*

(Continued)

*Primary Examiner* — Charanjit Aulakh
(74) *Attorney, Agent, or Firm* — Knobbe, Martens, Olson & Bear, LLP

(57) ABSTRACT

This invention relates to compounds of formula I;

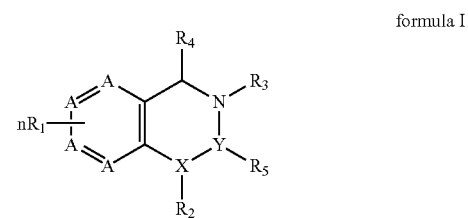

formula I and their use as antagonists of P2X₃ and P2X₂/₃ receptor activity, pharmaceutical compositions comprising such compounds, and methods of treatment therewith. Compounds of the invention can be used for the treatment and/or prevention of pain and chronic pain and tolerance to analgesic, respiratory disorders and dysfunctions, and treatment of overactive bladder, bladder pain syndrome, dysuria and in general in genitourinary diseases, cardiovascular disorders and more in general for the potential treatment of visceral organ diseases and disorders characterized by the involvement of P2X₃ and P2X₂/₃ receptors.

16 Claims, No Drawings

(56) References Cited

OTHER PUBLICATIONS

B. Stanovnik et al. "AZA-transfer reactions into a novel method for the conversion of monosubstituted hydrazine compounds into hydrocarbons", Tetrahedron Lettters, vol. 19, No. 33, Jan. 1, 1978, pp. 3059-3062.
Satoko Ohkubo et al. "Effects of P 1 and P2 receptor antagonists on [beta],[gamma]-methyleneATP- and CGS21680-induced cyclic AMP formation in NG108-15 cells", British Journal of Pharmacology, vo. 129, No. 2, Jan. 1, 2000, pp. 291-298.
Patent Cooperation Treaty, International Search Report, Application No. PCT/EP2019/068681, dated Sep. 20, 2019, in 4 pages.
Schrag, et al., "Neoadjuvant Chemotherapy Without Routine Use Of Radiation Therapy For Patients With Locally Advanced Rectal Cancer: A Pilot Trial" in Journal of Clinical Oncology (2014), vol. 32, No. 6, pp. 513-518.
Beneng, Kiran, et al. "Sensory purinergic receptor P2X3 is elevated in burning mouth syndrome." *International journal of oral and maxillofacial surgery* 39.8 (2010): 815-819.
Burnstock, G. "Discovery of purinergic signalling, the initial resistance and current explosion of interest." *British Journal of Pharmacology* 167.2 (2012): 238-255.
Ding, Shaojie, et al. "P2X3 receptor involvement in endometriosis pain via ERK signaling pathway." *PLoS One* 12.9 (2017): e0184647.
Feller, L., et al. "Burning mouth syndrome: aetiopathogenesis and principles of management." *Pain Res. Manag.* (2017): 1926269.
Gever, Joel R., et al. "AF-353, a novel, potent and orally bioavailable P2X3/P2X2/3 receptor antagonist." *British journal of pharmacology* 160.6 (2010): 1387-1398.
Giniatullin, Rashid and A. Nistri. "Desensitization properties of P2X3 receptors shaping pain signaling." *Frontiers in Cellular Neuroscience* 7 (2013): 245.
Ito, Katsuaki, et al. "Therapeutic effects of the putative P2X 3/P2X 2/3 antagonist A-317491 on cyclophosphamide-induced cystitis in rats." *Naunyn-Schmiedeberg's archives of pharmacology* 377 (2008): 483-490.
Jung, Young-Hwan, et al. "Discovery of potent antiallodynic agents for neuropathic pain targeting P2X3 receptors." *ACS Chemical Neuroscience* 8.7 (2017): 1465-1478.
Kuan, Yung-Hui and B. Shyu. "Noiceptive transmission and modulation via P2X receptors in central pain syndrome." *Molecular Brain* 9.58 (2016): s13041-016-0240-4.
Ma, Xiaqing, et al. "Blockade and reversal of spinal morphine tolerance by P2X3 receptor antagonist." *Behavioural Pharmacology* 26.3 (2015): 260-267.
Moss, G. P. "Extension and revision of the nomenclature for spiro compounds." *Pure Appl. Chem.* 71.3 (1999): 531-558.
Moss, G. P. "Nomenclature of fused and bridged fused ring systems." *Pure & Appl. Chem.* 70.1 (1998): 143-216.
North, R. Alan. "P2X3 receptors and peripheral pain mechanisms." *The Journal of physiology* 554.2 (2004): 301-308.
North, R. Alan. "Molecular physiology of P2X receptors." *Physiol. Rev.* 82 (2002): 1013-1067.
Shinoda, Masamichi, Bin Feng, and G. F. Gebhart. "Peripheral and central P2X3 receptor contributions to colon mechanosensitivity and hypersensitivity in the mouse." *Gastroenterology* 137.6 (2009): 2096-2104.
Spinaci, Andrea, et al. "P2X3 receptor ligands: structural features and potential therapeutic applications." *Frontiers in Pharmacology* 12 (2021): 653561.
Strathy, Janette H., et al. "Endometriosis and infertility: a laparoscopic study of endometriosis among fertile and infertile women." *Fertility and Sterility* 38.6 (1982): 668-672. Strathy, Janette H., et al. "Endometriosis and infertility: a laparoscopic study of endometriosis among fertile and infertile women." *Fertility and sterility* 44.2 (1985): 83-88.
Tai, Yueh-Hua, et al. "Purinergic P2X receptor regulates N-methyl-D-aspartate receptor expression and synaptic excitatory amino acid concentration in morphine tolerant rats." *Anesthesiology* 113 (2010): 1163-1175.
Volonte, Cinzia and G. Burnstock. "P2X3 receptor: a novel 'CASKade' of signaling?" *J. Neurochem.* 126 (2013): 1-3.

\* cited by examiner

P2X₃ RECEPTOR ANTAGONISTS

CROSS REFERENCE TO RELATED APPLICATIONS

This application is the U.S. National Stage Application under 35 U.S.C. § 371 of International Application No. PCT/EP2019/068681, filed Jul. 11, 2019, designating the U.S. and published in English as WO 2020/011921 on Jan. 16, 2020, which claims the benefit of Great Britain Patent Application No. GB 1811452.0, filed Jul. 12, 2018. Any and all applications for which a foreign or a domestic priority is claimed is/are identified in the Application Data Sheet filed herewith and is/are hereby incorporated by reference in their entirety under 37 C.F.R. § 1.57.

FIELD OF THE INVENTION

This invention relates to fused heterocyclic derivatives, including 4-imino-1H-pyrido[3,2-d]pyrimidin-2-one and 7H-pyrido[2,3-d]pyridazin-8-imine derivatives, and their use as antagonists of $P2X_3$ and $P2X_{2/3}$ receptor activity, pharmaceutical compositions comprising such compounds, and methods of treatment therewith.

BACKGROUND TO THE INVENTION

Adenosine-5'-triphosphate (ATP) acts as an extracellular signalling molecule after release from healthy or damaged cells (G. Burnstock, "Discovery of purinergic signalling, the initial resistance and current explosion of interest", *Br. J. Pharmacol*. (2012), No. 167, pp. 238-55) on two different classes of purinergic receptors: the ionotropic P2X receptors and the G-protein-coupled P2Y receptors.

P2X receptors are ion channels resulting by seven $P2X_{1-7}$ subunits association as homo- or hetero-trimers (R. A. North, "Molecular physiology of P2X receptors". *Physiol. Rev*. (2002), No. 82, pp. 1013-67).

The homo trimer $P2X_3$ receptor and the hetero-trimer $P2X_{2/3}$ receptor are predominantly localized on small- to medium-diameter C- and Aδ-fiber sensory neurons within the dorsal root ganglion and cranial sensory ganglia, and on their peripheral nerve terminals in tissues comprising skin, joints, and viscera. The $P2X_3$ receptor is also present on central projections of sensory neurons within the dorsal horn of the spinal cord and in the brainstem, where it plays a role in augmenting the release of glutamate and substance P. Because of its specific and limited location, the $P2X_3$ receptor subtype thus offers unique opportunity to investigate sensory and nociceptive mechanisms (C. Volonté, G. Burnstock, "P2X₃ receptor—a novel 'CASKade' of signalling", *J. Neurochem*. (2013), No. 126, pp. 1-3).

The $P2X_3$ receptors is also involved in many conditions where pain symptoms originate from chronic sensitization of peripheral afferent pathways (e.g., overactive bladder, irritable bowel syndrome, chronic itch and cough, airways hyperreactivity).

The afferent fibres that evoke cough are almost completely confined to the vagus nerve and preclinical studies suggest key roles for both C fibres (chemoreceptors) and Aδ fibres (mechanoreceptors). $P2X_3$ receptors are ATP-gated ion channels selectively localized on populations of primary afferent nerves arising from both cranial and dorsal root ganglia.

In guinea pigs, vagal C fibres innervating the airways express $P2X_3$ receptors, and can be activated by ATP released into the airways. Moreover, when guinea pigs are exposed to ATP and histamine aerosols, cough responses to tussive stimuli are increased via P2X receptors. The $P2X_3R$ is also involved in many conditions where pain symptoms originate from chronic sensitization of peripheral afferent pathways (e.g., overactive bladder, irritable bowel syndrome, chronic itch and cough, airways hyperreactivity).

$P2X_3$ ion channel receptors are expressed by a subpopulation of small-diameter primary nociceptors in the trigeminal nervous system and when activated by adenosine triphosphate (ATP) they can evoke a sensation of burning pain. $P2X_3$ receptors, coupled with the transient receptor potential subfamily member V 1 (TRPV1) ion channel, and of nerve growth factor NGF are upregulated in Burning Mouth Syndrome. For this reason, compounds acting on the $P2X_3$ receptors may have a potential role in the treatment of Burning Mouth Syndrome ("Burning Mouth Syndrome: Aetiopathogenesis and Principles of Management", L. Feller, J. Fourie, M. Bouckaert, R. A. G. Khammissa, R. Ballyram, and J. Lemmer, *Pain Research and Management*, Vol. 2017, Article ID 1926269, 6 pages).

Daily systemic injection of an orthosteric $P2X_3$ receptor antagonist attenuated the morphine-induced antinociceptive tolerance to von Frey and thermal stimuli, in comparison with morphine alone, showing that a $P2X_3$ receptor antagonist is able to reverse morphine tolerance and it may be a new therapeutic target in the prevention of tolerance to morphine-induced antinociception ("Blockade and reversal of spinal morphine tolerance by $P2X_3$ receptor antagonist", Ma X and Xu T, Xu H, Jiang W, *Behavioural Pharmacology*, (2015), Vol. 26(3), pp. 260-267). $P2X_3$ receptor antagonist morphine tolerance attenuation may be attributed to downregulation of N-methyl-D-aspartate receptor subunits NR1 and NR2B expression in the synaptosomal membrane and inhibition of excitatory amino acids release in morphine-tolerant rats ("Purinergic P2X Receptor Regulates N-Methyl-D-aspartate Receptor Expression and Synaptic Excitatory Amino Acid Concentration in Morphine-tolerant Rats", Yueh-Hua Tai, Pao-Yun Cheng, Ru-Yin Tsai, Yuh-Fung Chen, Chih-Shung Wong, *Anesthesiology*, (2010), Vol. 113(5), pp. 1163-75).

Currently, the carotid body is under consideration as a therapeutic target for hypertension because sympathoexcitatory response is potentiated in hypertensive rats and human. Moreover, the aberrant signalling that contributes to high blood pressure may be normalized by carotid body denervation in rats. $P2X_3$ receptor mRNA expression is upregulated in chemoreceptive petrosal ganglion neurons in hypertensive rats. These neurons generate both tonic drive and hyperreflexia in hypertensive rats, and both phenomena are normalized by $P2X_3$ receptor antagonists. Antagonism of $P2X_3$ receptors also reduces arterial pressure and basal sympathetic activity and normalizes carotid body hyperreflexia in conscious rats with hypertension. The purinergic receptors present in the carotid body can be considered as a potential new target for the control of human hypertension (Wioletta Pijacka, Davi J A Moraes, Laura E K Ratcliffe, Angus K Nightingale, Emma C Hart, Melina P da Silva, Benedito H Machado, Fiona D McBryde, Ana P Abdala, Anthony P Ford & Julian F R Paton).

Endometriosis is a common gynecological disease characterized by the presence of functional endometrium outside the uterine cavity, resulting in dysmenorrhea, dyspareunia, pelvic pain, and infertility, with lack of effective clinical treatment (Strathy J H, Molgaard C A, Coulam C B, Melton L J 3rd. "Endometriosis and infertility: a laparoscopic study of endometriosis among fertile and infertile women", *Fertility and sterility*, (1982), Vol. 38(6), pp. 667-72). Endometriosis is considered as a kind of inflammatory and neuropathic pain with increasing evidences indicating the importance of adenosine triphosphate (ATP) and $P2X_3$ receptors in endometriosis pain sensitization and transduction. $P2X_3$ are expressed on endometrial epithelial cells and on endometrial stromal cells. $P2X_3$ are overexpressed in the endometriosis endometrium and endometriotic lesions and both significantly higher as compared with control endometrium, and both positively correlated with pain, and with the severity of pain in women affected with endometriosis. The expression levels of phosphorylated±ERK (p-ERK), phosphorylated-cAMP-response element binding protein (p-CREB), and $P2X_3$ in endometriotic stromal cells (ESCs) were all significantly increased in comparison to the initial levels after treated with interleukin (IL)-1β or adenosine triphosphate (ATP), respectively, and did not increase after the ESCs were pretreated with $ERK_{1/2}$ inhibitor. $P2X_3$ receptor may represent a highly innovative target for the non-hormonal treatment of endometriosis ("$P2X_3$ receptor involvement in endometriosis pain via ERK signaling pathway", Shaojie Ding, Libo Zhu, Yonghong Tian, Tianhong Zhu, Xiufeng Huang, Xinmei Zhang; *PLoS ONE*, (2017), Vol. 12(9): e0184647).

Several P2X receptor subtypes, including $P2X_2$, $P2X_3$, $P2X_4$, and $P2X_7$, have been shown to play diverse roles in the pathogenesis of central pain including the mediation of fast transmission in the peripheral nervous system and modulation of neuronal activity in the central nervous system. $P2X_3$ receptors play a significant role in neuropathic and inflammatory pain. Long-lasting allodynia that is produced by intrathecal administration of ATP likely occurs through $P2X_{2/3}$ receptors. Spinal $P2X_2$ and $P2X_3$ receptors have been reported to be involve in neuropathic pain in a mouse model of chronic constriction injury ("Nociceptive transmission and modulation via P2X receptors in central pain syndrome.", Kuan, Y. H., and Shyu, B. C. *Mol. Brain* (2016), Vol. 9, pp. 58). $P2X_3$ receptors show a combination of fast desensitization onset and slow recovery. $P2X_3$ receptors represent an attractive target for development of new analgesic drugs via promotion of desensitization aimed at suppressing chronic pain, such as: Inflammatory and Neuropathic Pain, Migraine and Trigeminal Pain, and Cancer Pain ("Desensitization properties of $P2X_3$ receptors shaping pain signalling, Rashid Giniatullin and Andrea Nistri", *Front. Cell. Neurosci.*, (2013), Vol. 7, pp. 245).

SUMMARY OF THE INVENTION

The invention provides a compound according to general formula I:

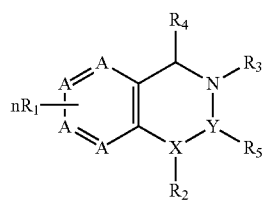

formula I or an enantiomer, diastereomer, N-oxide, or a pharmaceutically acceptable salt or combinations thereof, wherein:
each A independently represents an atom selected from C, N, S or O;
X and Y are selected from C and N atoms, wherein the unit X—Y represents either a N—C group, or a C═N group respectively;
each $R_1$ independently represents hydrogen, a halogen atom, or an, optionally substituted, hydroxy, carbonyl, carboxyl, amino, amido, $C_1$-$C_6$ alkyl or $C_1$-$C_6$ alkoxy group, an, optionally substituted, mono-, bi- or tricyclic $C_6$-$C_{14}$ aryl group or an, optionally substituted, mono-, bi- or tricyclic $C_1$-$C_{13}$ heterocyclic group containing from 1 to 5 heteroatoms selected from N, O or S;
$R_2$ represents hydrogen or an, optionally substituted, $C_1$-$C_6$ alkyl group, $C_1$-$C_6$ alkoxy group, $C_4$-$C_{14}$ arylalkyl group, $C_4$-$C_{14}$ heteroarylalkyl group, $C_3$-$C_7$ cycloalkyl group, a mono-, bi- or tricyclic $C_6$-$C_{14}$ aryl group or a mono-, bi- or tricyclic $C_1$-$C_{13}$ heterocyclic group containing from 1 to 5 heteroatoms selected from N, O or S;
groups $R_3$ and $R_4$, or alternatively groups $R_3$ and $R_5$, are linked to each other to form a five- or six-membered heterocyclic ring containing from 2 to 3 heteroatoms atoms selected from N, O and S, optionally substituted with one or more groups $nR_6$, with the proviso that the remainder of $R_4$ or $R_5$ not linked with group $R_3$ to form the heterocyclic ring is absent, or is an atom independently selected from N, O or S which is double-bonded directly to the X—Y containing ring;
each $R_6$ independently represents hydrogen, a halogen atom selected from F, Cl, Br or I; or an, optionally substituted, carbonyl, oxo, $C_1$-$C_6$ alkyl, $C_1$-$C_6$ alkoxy or $C_3$-$C_7$ cycloalkyl group, an, optionally substituted, mono-, bi- or tricyclic $C_6$-$C_{14}$ aryl group or an, optionally substituted, mono-, bi- or tricyclic $C_1$-$C_{13}$ heterocyclic group containing from 1 to 5 heteroatoms selected from N, O or S or alternatively, two $R_6$ groups are linked to each other to form a group of the formula -(Zp)- wherein p is an integer of from 3 to 5 and each Z independently represents an oxygen atom or an optionally substituted methylene group, provided that no two adjacent Y moieties represent oxygen atoms; and
n is an integer independently selected from 0 to 3.

Preferably, compounds of the invention can be used for the treatment and/or prevention of pain and chronic pain and tolerance to analgesic, respiratory disorders and dysfunctions, and treatment of overactive bladder, bladder pain syndrome, dysuria and in general in genitourinary diseases, cardiovascular disorders and more in general for the potential treatment of visceral organ diseases and disorders characterized by the involvement of $P2X_3$ and $P2X_{2/3}$ receptors.

Preferably, the optional substituents are independently selected from the group consisting of halogen atoms, $C_1$-$C_6$ alkyl, $C_1$-$C_6$ alkoxy, hydroxy, mercapto, nitro, cyano, oxo, halo($C_1$-$C_6$)alkyl, halo($C_1$-$C_6$)alkoxy, $C_1$-$C_6$ alkylthio, $C_1$-$C_6$ alkylsulphonyl, $C_1$-$C_6$ alkylcarbonyl, sulphamoyl, $C_1$-$C_6$ alkylsulphamoyl, di($C_1$-$C_6$)alkylsulphamoyl, ($C_1$-$C_6$) alkoxycarbonyl and ($C_1$-$C_6$)alkylcarbonyl($C_1$-$C_6$)alkyl groups, and from groups of the formulae —NR*R*, —C(═O)—NR*R*, -D, —O-D, —C(═O)-D, —(CH$_2$)q-D, —NR-D, —C(═O)—NR-D, —NR**C(═O)-D and —O—C(═O)-D wherein each R* independently represents a hydrogen atom or a $C_1$-$C_6$ alkyl, $C_1$-$C_6$ alkoxy, $C_1$-$C_6$ alkylcarbonyl, phenyl or benzyl group, R** represents a hydrogen atom or a $C_1$-$C_6$ alkyl group, q is an integer from 1 to 6 and D represents a phenyl group or a $C_1$-$C_8$ heterocyclic group containing from 1 to 3 heteroatoms selected from N, O and S; a $C_1$-$C_6$ cycloalkyl group; each group D being further optionally substituted with from 1 to 3 groups independently selected from halo, hydroxy, cyano, nitro and $C_1$-$C_6$, alkyl, preferably wherein the optional substituents are selected from the groups consisting of halogen atoms and $C_1$-$C_6$, alkyl groups.

Preferred compounds of the invention are those in which one of the A groups comprises a heteroatom and the remaining three A groups comprise carbons atoms. A non-limiting example includes the situation where one of the A groups comprises a nitrogen atom, and the remaining three A groups each comprise carbon atoms, such that the heterocyclic ring so-formed is a pyridine ring.

Preferred compounds of the invention are those in which two of the A groups comprise heteroatoms and the two remaining A groups comprise carbon atoms. Non-limiting examples include the situation where two of the A groups comprise nitrogen atoms, and the remaining two A groups each comprise carbon atoms, such that the heterocyclic ring so-formed is a pyridazine, pyrimidine or pyrazine ring.

Preferred compounds of the invention are those in which three of the A groups comprise heteroatoms and the remaining A group comprises a carbon atom. Non-limiting examples include the situation where three of the A groups comprise nitrogen atoms, and the remaining A group comprises a carbon atom, such that the heterocyclic ring so-formed is a 1,2,3-triazine or 1,2,4-triazine ring.

Preferred compounds of the invention are those in which all four of the A groups comprise heteroatoms. A non-limiting example includes the situation where all four of the A groups comprises nitrogen atoms, such that the heterocyclic ring so-formed is a 1,2,3,4-tetrazine ring.

The skilled person will appreciate that for each of the examples described above, each A group comprising a carbon or other heterocyclic atom, or the heterocyclic ring so-formed, may further comprise one or more hydrogen atoms directly attached to one or more of the ring atoms, and/or n groups of $R_1$ (as defined above) to satisfy the usual rules relating to atomic bonding and valences.

The invention also provides for other such combinations of heteroatoms including, but not limited to, heterocyclic rings formed from each A group being independently represented by an atom selected from C, N, S or O, such that the resulting heterocyclic ring so-formed is a piperidine, pyridine, tetrahydropyran, pyran, thiane, thiopyran, morpholine, oxazine, thiomorpholine, thiazine, dioxane, dioxine, dithiane, dithiin, trioxane or trithiane derivative.

Preferred non-limiting examples include the resulting heterocyclic ring so-formed being a 2H-1,2-oxazine, 4H-1,2-oxazine, 6H-1,2-oxazine, 2H-1,3-oxazine, 4H-1,3-oxazine, 6H-1,3-oxazine, 2H-1,4-oxazine, 4H-1,4-oxazine, thiomorpholine, 1,2-thiazine, 1,3-thiazine, 1,4-thiazine, 1,4-dioxane, 1,2-dioxin, 1,4-dioxin, 1,2-dithiane, 1,3-dithiane, 1,4-dithiane, 1,2-dithiin and 1,4-dithiin, 1,2,3-trioxane or 1,2,4-trioxane derivative.

Preferred compounds of the invention are those in which group X—Y represents a N—C group, such that the six-membered central heterocyclic ring so-formed is a pyrimidine ring.

Preferred compounds of the invention are those in which group X—Y represents a C═N group, such that the six-membered central heterocyclic ring so-formed is a pyradizine ring.

Preferred compounds of the invention are those in which group X—Y represents a N—C group, groups $R_3$ and $R_4$ are linked to each other to form a five- or six-membered heterocyclic ring containing from 2 to 3 nitrogen heteroatoms atoms, optionally substituted with one or more groups $nR_6$, as defined above, and $R_5$ is a carbonyl group.

Preferred compounds of the invention are those in which group X—Y represents a N—C group, and groups $R_3$ and $R_4$ are linked to each other to form a five- or six-membered heterocyclic ring containing from 2 to 3 nitrogen heteroatoms atoms (e.g. 2-imidazoline, imidazole, 1,2,4-triazole or pyrimidine), selected from but not limited to a pyrido[2,3-e]imidazolo[1,2-d]pyrimidine, pyrido[2,3-e]imidazo[1,2-d]pyrimidine, pyrido[2,3-e]1,2,4-triazolo[1,2-d]pyrimidine or 1,4,5,6-tetrahydropyrimido[2,1-f]pyrido[3,2-d]pyrimidine derivative, and $R_5$ is a carbonyl group.

Preferred compounds of the invention are those in which group X—Y represents a N—C group, groups $R_3$ and $R_5$ are linked to each other to form a five-membered heterocyclic ring containing from 2 to 3 nitrogen heteroatoms atoms, optionally substituted with one or more groups $nR_6$, as defined above, and $R_4$ is a carbonyl group.

Preferred compounds of the invention are those in which group X—Y represents a N—C group, and groups $R_3$ and $R_5$ are linked to each other to form a five-membered heterocyclic ring containing from 2 to 3 nitrogen heteroatoms atoms (e.g. 1,2,4-triazole), selected from but not limited to a pyrido[2,3-e]1,2,4-triazolo[2,1-b]pyrimidine derivative, and $R_4$ is a carbonyl group.

Preferred compounds of the invention are those in which group X—Y represents a C═N group, groups $R_3$ and $R_4$ are linked to each other to form a five- or six-membered heterocyclic ring containing from 2 to 3 nitrogen heteroatoms atoms, optionally substituted with one or more groups $nR_6$, as defined above, and $R_5$ is absent.

Preferred compounds of the invention are those in which group X—Y represents a C═N group, and groups $R_3$ and $R_4$ are linked to each other to form a five- or six-membered heterocyclic ring containing from 2 to 3 nitrogen heteroatoms atoms (e.g. 1,2,4-triazole), selected from but not limited to a pyrido[3,2-d]1,2,4-triazolo[1,2-d]1,4,5,6-tetrahydropyridazine derivative, and $R_5$ is a carbonyl group.

Preferred compounds of the invention are those in which $R_1$ is selected from the group comprising H, Br, hydroxy, carboxyl, methoxy, methoxyethylamino, 2-hydroxyethylamino, tertiarybutoxycarbonylamino, 2-hydroxyethylaminocarbonyl, an optionally substituted azetidinyl, morpholinyl, oxetanyl, piperazinyl, piperidinyl, pyranyl or pyrrolidinyl moiety or derivative thereof, or an optionally substituted, spiro-fused bi- or tricyclic $C_1$-$C_{13}$ heterocyclic group containing from 1 to 5 heteroatoms selected from N, O or S.

Highly preferred compounds of the invention are those in which $R_1$ is selected from the group comprising 2-oxa-6-azaspiro[3.3]heptan-6-yl, 3-methoxymethylazetidin-1-yl, 3-methoxypyrrolidin-1-yl, 4-acetylpiperazin-1-yl, 4-aminopiperidin-1-yl, 4-hydroxypiperidin-1-yl, 4-hydroxypiperidin-1-yl-carbonyl, 4-methoxypiperidin-1-yl, 4-morpholinyl, dimethylaminopiperidin-1-yl, hydroxymethylpiperidin-1-yl, morpholin-4-ylcarbonyl, tetrahydro-2H-pyran-4-ylamino or tetrahydro-2H-pyran-4-ylaminocarbonyl.

Preferred compounds of the invention are those in which $R_2$ is a hydrogen atom or an optionally substituted benzyl group or derivative thereof.

Highly preferred compounds of the invention are those in which $R_2$ is a hydrogen atom, or is selected from the group comprising 3,5-dimethoxybenzyl, 4-methoxybenzyl, 4-methylbenzyl, 4-chlorobenzyl or 4-chloro-2,6-difluorobenzyl.

Preferred compounds of the invention are those in which $R_6$ is selected from the group comprising phenyl, (1-phenyl)ethyl, 1-ethyl-1H-pyrazol-3-yl, 1-ethyl-H-pyrazol-5-yl, (tetrahydro-2H-pyran-4-yl)methyl, (tetrahydro-2H-pyran-4-yloxy)methyl, (tetrahydro-2H-pyran-4-yl)ethyl, 3,5-dimethyl-1,2oxazol-4-yl, 2-hydroxypyridin-3-yl, 2-methylpyridin-3- yl, morpholin-4-yl-carbonyl, pyridin-3-yl-methyl, oxo, methyl, ethyl, iso-propyl, tertiary-butyl, methylpropyl, 2,2-dimethylpropyl, 3-methylbutyl, 2,2,2-trifluoroethyl, methoxymethyl, methoxyethyl, (propan-2-yloxy)methyl, tertiary-butoxymethyl, prop-1-en-2-yl, propan-2-yl-acetamide, cyclopropyl, cyclobutyl, cyclohexyl, 1-methylcyclopropyl.

Preferred compounds of the invention are those in which -(Zp)- represents a group selected from —O—$(CH_2)_2$—O—, —O—$(CH_2)_3$—O—, —O—$(CH_2)_2$—, —O—$(CH_2)_3$—, —$CH_2$—O—$CH_2$— or —$(CH_2)_2$—O—$(CH_2)_2$.

Preferred compounds of the invention are those in which one of the A groups is a nitrogen atom and the three remaining A groups are carbon atoms, the X—Y unit is a N—C group, groups $R_3$ and $R_4$ are linked to each other to form a five-membered heterocyclic ring containing 2 nitrogen heteroatoms atoms and $R_5$ is an oxygen atom double-bonded directly to the X—Y containing ring (carbonyl group), such that the compound so formed is a pyrido[2,3-e]imidazolo[1,2-d]pyrimidine derivative and has a structure in accordance with formula 1a below:

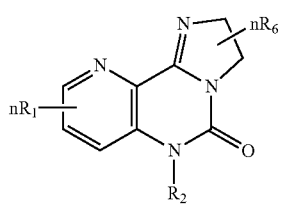

formula 1a wherein groups $R_1$, $R_2$, $R_6$ and n are as defined for formula I above.

Preferred compounds of the invention are those in which one of the A groups is a nitrogen atom and the three remaining A groups are carbon atoms, the X—Y unit is a N—C group, groups $R_3$ and $R_4$ are linked to each other to form a five-membered heterocyclic ring containing 2 nitrogen heteroatoms atoms and $R_5$ is an oxygen atom double-bonded directly to the X—Y containing ring (carbonyl group), such that the compound so formed is a pyrido[2,3-e]imidazo[1,2-d]pyrimidine derivative and has a structure in accordance with formula 1b below:

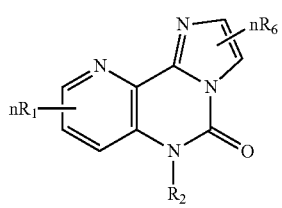

formula 1b wherein groups $R_1$, $R_2$, $R_6$ and n are as defined for formula I above.

Preferred compounds of the invention are those in which one of the A groups is a nitrogen atom and the three remaining A groups are carbon atoms, the X—Y unit is a N—C group, groups $R_3$ and $R_4$ are linked to each other to form a five-membered heterocyclic ring containing 3 nitrogen heteroatoms atoms and $R_5$ is an oxygen atom double-bonded directly to the X—Y containing ring (carbonyl group), such that the compound so formed is a pyrido[2,3-e]1,2,4-triazolo[1,2-d]pyrimidine derivative and has a structure in accordance with formula 1c below:

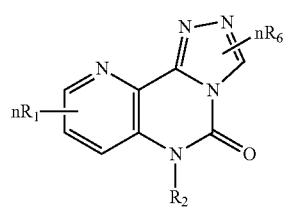

formula 1c wherein groups $R_1$, $R_2$, $R_6$ and n are as defined for formula I above.

Preferred compounds of the invention are those in which one of the A groups is a nitrogen atom and the three remaining A groups are carbon atoms, the X—Y unit is a N═C group, groups $R_3$ and $R_4$ are linked to each other to form a five-membered heterocyclic ring containing 3 nitrogen heteroatoms atoms and $R_5$ is an oxygen atom double-bonded directly to the X—Y containing ring (carbonyl group), such that the compound so formed is a pyrido[3,2-d]1,2,4-triazolo[1,2-d]1,4,5,6-tetrahydropyridazine derivative and has a structure in accordance with formula 1d below:

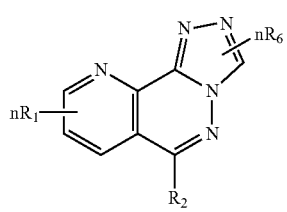

formula 1d wherein groups $R_1$, $R_2$, $R_6$ and n are as defined for formula I above.

Preferred compounds of the invention are those in which one of the A groups is a nitrogen atom and the three remaining A groups are carbon atoms, the X—Y unit is a N—C group, groups $R_3$ and $R_4$ are linked to each other to form a six-membered heterocyclic ring containing 2 nitrogen heteroatoms atoms and $R_5$ is an oxygen atom double-bonded directly to the X—Y containing ring (carbonyl group), such that the compound so formed is a 1,4,5,6-tetrahydropyrimido[2,1-f]pyrido[3,2-d]pyrimidine derivative and has a structure in accordance with formula 1e below:

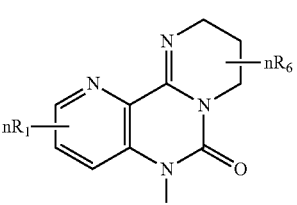

formula 1e wherein groups $R_1$, $R_2$, $R_6$ and n are as defined for formula I above.

Preferred compounds of the invention are those in which one of the A groups is a nitrogen atom and the three remaining A groups are carbon atoms, the X—Y unit is a N—C group, groups R₃ and R₅ are linked to each other to form a five-membered heterocyclic ring containing 3 nitrogen heteroatoms atoms and R₄ is an oxygen atom double-bonded directly to the X—Y containing ring (carbonyl group), such that the compound so formed is a pyrido[2,3-e]1,2,4-triazolo[2,1-b]pyrimidine derivative and has a structure in accordance with formula 1f below:

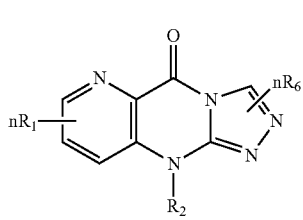

formula 1f wherein groups R₁, R₂, R₆ and n are as defined for formula I above.

Preferred compounds of the invention are those in which one of the A groups is a nitrogen atom and the three remaining A groups are carbon atoms, the X—Y unit is a N—C group, groups R₃ and R₄ are linked to each other to form a five-membered heterocyclic ring containing 2 nitrogen heteroatoms atoms, R₅ is an oxygen atom double-bonded directly to the X—Y containing ring (carbonyl group) and at least one group nR₆ is an oxygen atom double-bonded directly to the R₃/R₄ linked five-membered heterocyclic (imidazoline) ring, such that the compound so formed is a pyrido[2,3-e]imidazo[1,2-d]pyrimidine dione derivative and has a structure in accordance with formula 1g below:

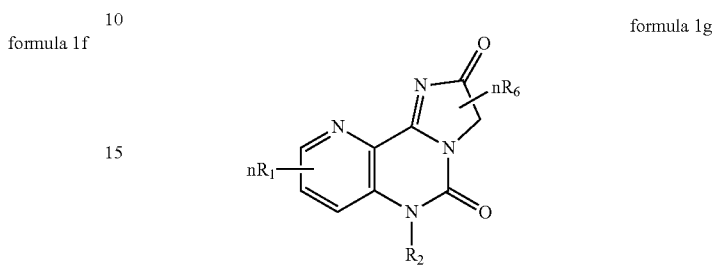

formula 1g wherein groups R₁, R₂, R₆ and n are as defined for formula I above.

Preferred compounds according to the invention are compounds or an enantiomer, diastereomer, N-oxide, or a pharmaceutically acceptable salt or combinations thereof, which are provided according to general formula 1a or 1g selected from the compounds in Table 1 below:

TABLE 1

Selected compounds of the invention according to formula 1a and 1g.

| Example | Structure | Name |
|---|---|---|
| 1 | 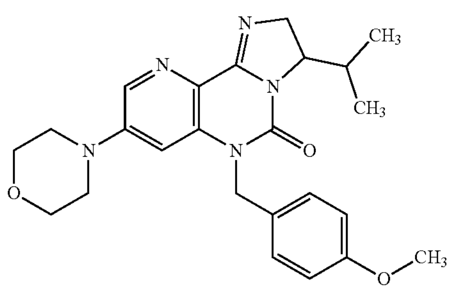 [SMILES: COc1ccc(CN2C(=O)N3C(=NCC3C(C)C)c3ncc(N4CCOCC4)cc32)cc1] | 6-(4-methoxybenzyl)-8-(morpholin-4-yl)-3-(propan-2-yl)-2,6-dihydroimidazo[1,2-c]pyrido[2,3-e]pyrimidin-5(3H)-one |
| 2 | 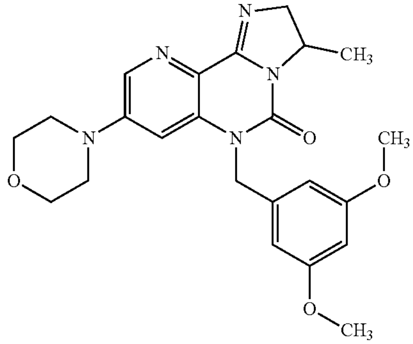 [SMILES: COc1cc(CN2C(=O)N3C(=NCC3C)c3ncc(N4CCOCC4)cc32)cc(OC)c1] | 6-(3,5-dimethoxybenzyl)-3-methyl-8-(morpholin-4-yl)-2,6-dihydroimidazo[1,2-c]pyrido[2,3-e]pyrimidin-5(3H)-one |

TABLE 1-continued

Selected compounds of the invention according to formula 1a and 1g.

| Example | Structure | Name |
|---|---|---|
| 3 | 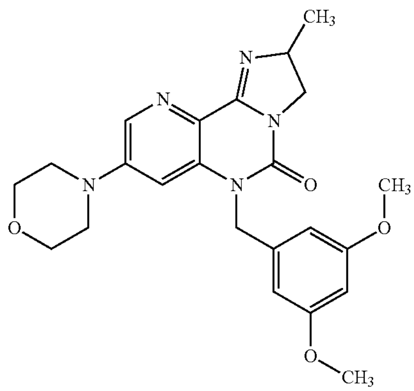 [SMILES: COc1cc(CN2C(=O)N3CC(C)N=C3c3ncc(N4CCOCC4)cc32)cc(OC)c1] | 6-(3,5-dimethoxybenzyl)-2-methyl-8-(morpholin-4-yl)-2,6-dihydroimidazo[1,2-c]pyrido[2,3-e]pyrimidin-5(3H)-one |
| 4 | 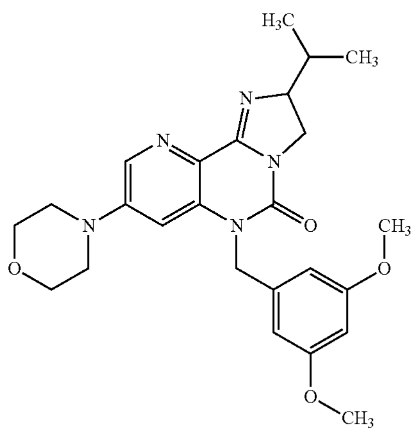 [SMILES: COc1cc(CN2C(=O)N3CC(C(C)C)N=C3c3ncc(N4CCOCC4)cc32)cc(OC)c1] | 6-(3,5-dimethoxybenzyl)-8-(morpholin-4-yl)-2-(propan-2-yl)-2,6-dihydroimidazo[1,2-c]pyrido[2,3-e]pyrimidin-5(3H)-one |
| 5 | 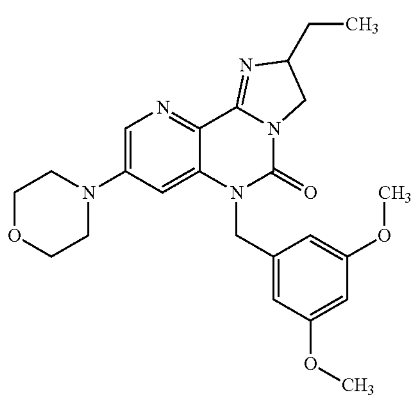 [SMILES: CCC1CN2C(=O)N(Cc3cc(OC)cc(OC)c3)c3cc(N4CCOCC4)cnc3C2=N1] | 6-(3,5-dimethoxybenzyl)-2-ethyl-8-(morpholin-4-yl)-2,6-dihydroimidazo[1,2-c]pyrido[2,3-e]pyrimidin-5(3H)-one |
| 6 | 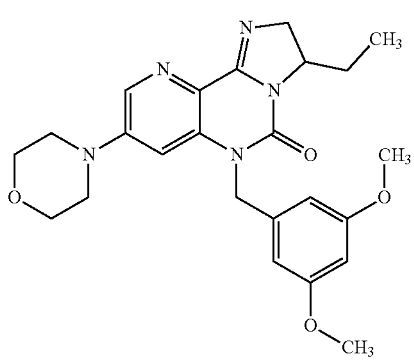 [SMILES: CCC1CN=C2c3ncc(N4CCOCC4)cc3N(Cc3cc(OC)cc(OC)c3)C(=O)N21] | 6-(3,5-dimethoxybenzyl)-3-ethyl-8-(morpholin-4-yl)-2,6-dihydroimidazo[1,2-c]pyrido[2,3-e]pyrimidin-5(3H)-one |

TABLE 1-continued

Selected compounds of the invention according to formula 1a and 1g.

| Example | Structure | Name |
|---|---|---|
| 7 | 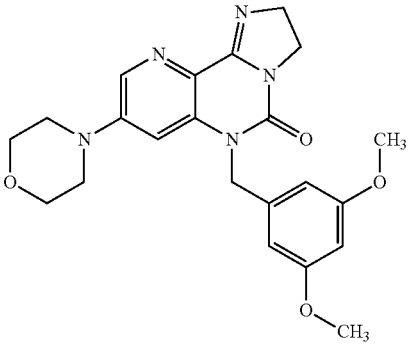 [SMILES: COc1cc(CN2C(=O)N3CCN=C3c3ncc(N4CCOCC4)cc32)cc(OC)c1] | 6-(3,5-dimethoxybenzyl)-8-(morpholin-4-yl)-2,6-dihydroimidazo[1,2-c]pyrido[2,3-e]pyrimidin-5(3H)-one |
| 8 | 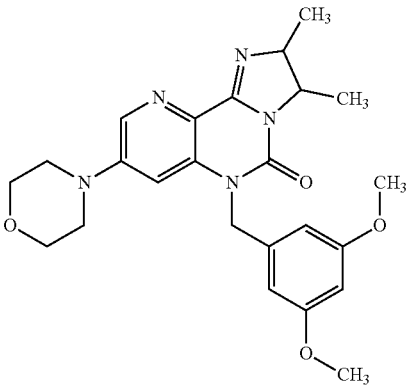 | 6-(3,5-dimethoxybenzyl)-2,3-dimethyl-8-(morpholin-4-yl)-2,6-dihydroimidazo[1,2-c]pyrido[2,3-e]pyrimidin-5(3H)-one |
| 9 | 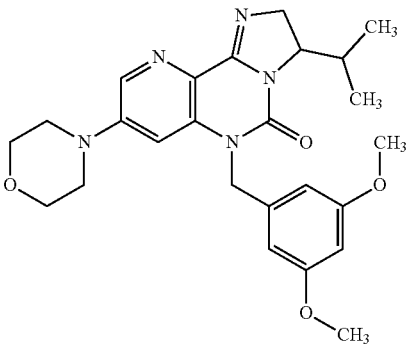 [SMILES: COc1cc(CN2C(=O)N3C(=NCC3C(C)C)c3ncc(N4CCOCC4)cc32)cc(OC)c1] | 6-(3,5-dimethoxybenzyl)-8-(morpholin-4-yl)-3-(propan-2-yl)-2,6-dihydroimidazo[1,2-c]pyrido[2,3-e]pyrimidin-5(3H)-one |
| 10 | 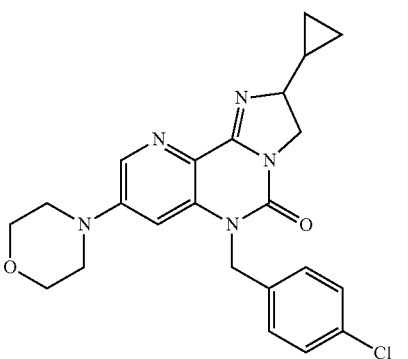 [SMILES: O=C1N2CC(C3CC3)N=C2c2ncc(N3CCOCC3)cc2N1Cc1ccc(Cl)cc1] | 6-(4-chlorobenzyl)-2-cyclopropyl-8-(morpholin-4-yl)-2,6-dihydroimidazo[1,2-c]pyrido[2,3-e]pyrimidin-5(3H)-one |

TABLE 1-continued

Selected compounds of the invention according to formula 1a and 1g.

| Example | Structure | Name |
|---|---|---|
| 11 | 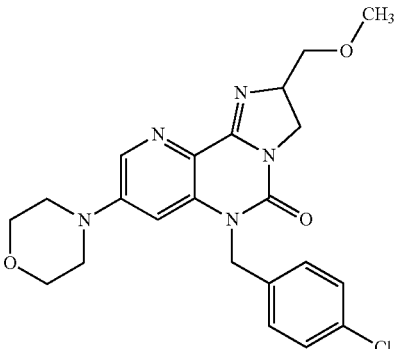 | 6-(4-chlorobenzyl)-2-(methoxymethyl)-8-(morpholin-4-yl)-2,6-dihydroimidazo[1,2-c]pyrido[2,3-e]pyrimidin-5(3H)-one |
| 12 | 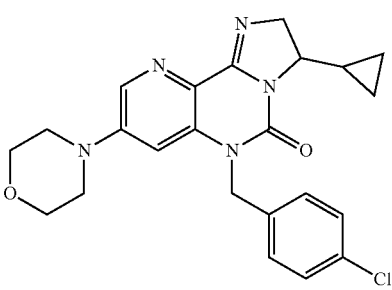 [SMILES: O=C1N(Cc2ccc(Cl)cc2)c2cc(N3CCOCC3)cnc2C2=NCC(C3CC3)N12] | 6-(4-chlorobenzyl)-3-cyclopropyl-8-(morpholin-4-yl)-2,6-dihydroimidazo[1,2-c]pyrido[2,3-e]pyrimidin-5(3H)-one |
| 13 | 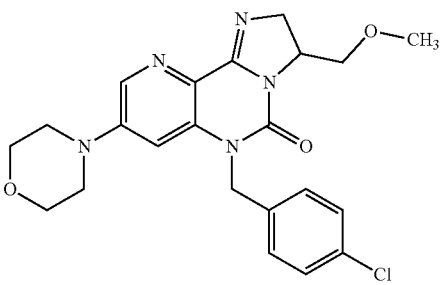 [SMILES: COCC1CN=C2c3ncc(N4CCOCC4)cc3N(Cc3ccc(Cl)cc3)C(=O)N21] | 6-(4-chlorobenzyl)-3-(methoxymethyl)-8-(morpholin-4-yl)-2,6-dihydroimidazo[1,2-c]pyrido[2,3-e]pyrimidin-5(3H)-one |
| 14 | 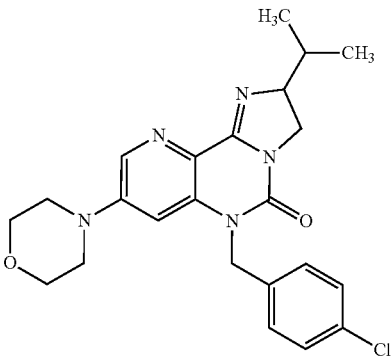 [SMILES: CC(C)C1CN2C(=O)N(Cc3ccc(Cl)cc3)c3cc(N4CCOCC4)cnc3C2=N1] | 6-(4-chlorobenzyl)-8-(morpholin-4-yl)-2-(propan-2-yl)-2,6-dihydroimidazo[1,2-c]pyrido[2,3-e]pyrimidin-5(3H)-one |

TABLE 1-continued

Selected compounds of the invention according to formula 1a and 1g.

| Example | Structure | Name |
|---|---|---|
| 15 | 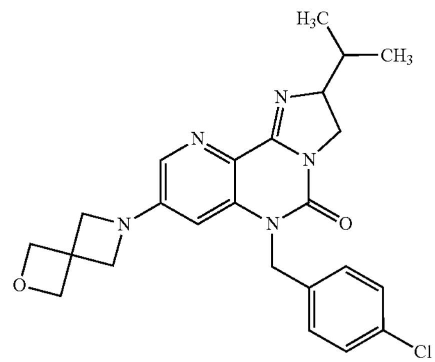 [SMILES: CC(C)C1CN2C(=O)N(Cc3ccc(Cl)cc3)c3cc(N4CC5(COC5)C4)cnc3C2=N1] | 6-(4-chlorobenzyl)-8-(2-oxa-6-azaspiro[3.3]heptan-6-yl)-2-(propan-2-yl)-2,6-dihydroimidazo[1,2-c]pyrido[2,3-e]pyrimidin-5(3H)-one |
| 16 | 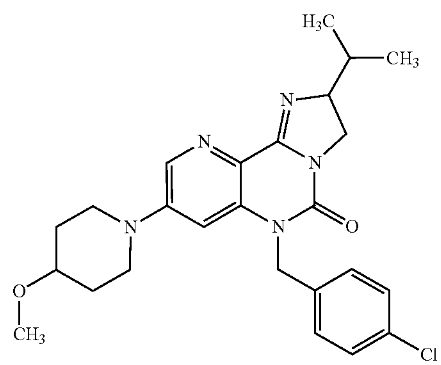 [SMILES: COC1CCN(c2cnc3c(c2)N(Cc2ccc(Cl)cc2)C(=O)N2CC(C(C)C)N=C32)CC1] | 6-(4-chlorobenzyl)-8-(4-methoxypiperidin-1-yl)-2-(propan-2-yl)-2,6-dihydroimidazo[1,2-c]pyrido[2,3-e]pyrimidin-5(3H)-one |
| 17 | 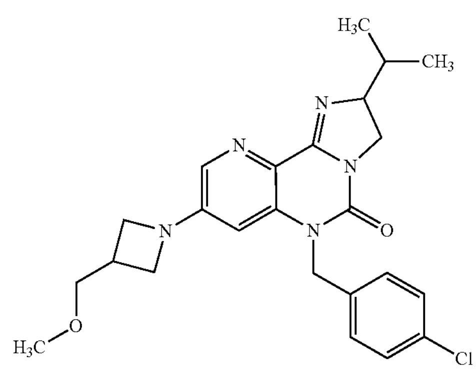 [SMILES: COCC1CN(c2cnc3c(c2)N(Cc2ccc(Cl)cc2)C(=O)N2CC(C(C)C)N=C32)C1] | 6-(4-chlorobenzyl)-8-[3-(methoxymethyl)azetidin-1-yl]-2-(propan-2-yl)-2,6-dihydroimidazo[1,2-c]pyrido[2,3-e]pyrimidin-5(3H)-one |
| 18 | 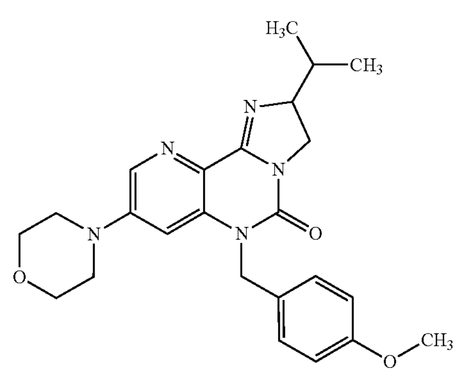 [SMILES: COc1ccc(CN2C(=O)N3CC(C(C)C)N=C3c3ncc(N4CCOCC4)cc32)cc1] | 6-(4-methoxybenzyl)-8-(morpholin-4-yl)-2-(propan-2-yl)-2,6-dihydroimidazo[1,2-c]pyrido[2,3-e]pyrimidin-5(3H)-one |

TABLE 1-continued

Selected compounds of the invention according to formula 1a and 1g.

| Example | Structure | Name |
|---|---|---|
| 19 | 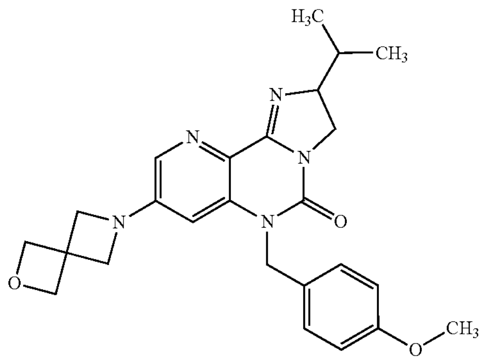 [SMILES: COc1ccc(CN2C(=O)N3CC(C(C)C)N=C3c3ncc(N4CC5(COC5)C4)cc32)cc1] | 6-(4-methoxybenzyl)-8-(2-oxa-6-azaspiro[3.3]heptan-6-yl)-2-(propan-2-yl)-2,6-dihydroimidazo[1,2-c]pyrido[2,3-e]pyrimidin-5(3H)-one |
| 20 | 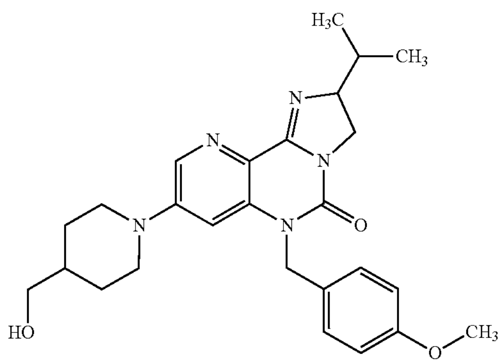 [SMILES: COc1ccc(CN2C(=O)N3CC(C(C)C)N=C3c3ncc(N4CCC(CO)CC4)cc32)cc1] | 8-[4-(hydroxymethyl)piperidin-1-yl]-6-(4-methoxybenzyl)-2-(propan-2-yl)-2,6-dihydroimidazo[1,2-c]pyrido[2,3-e]pyrimidin-5(3H)-one |
| 21 | 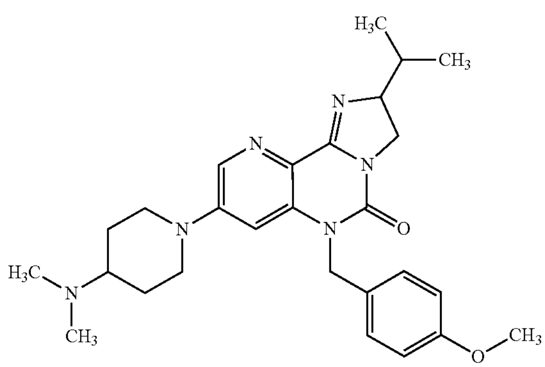 | 8-[4-(dimethylamino)piperidin-1-yl]-6-(4-methoxybenzyl)-2-(propan-2-yl)-2,6-dihydroimidazo[1,2-c]pyrido[2,3-e]pyrimidin-5(3H)-one |
| 22 | 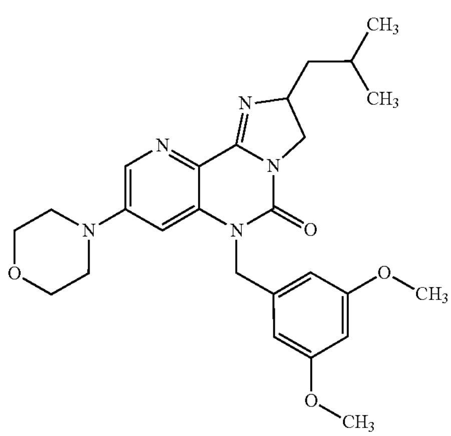 [SMILES: COc1cc(CN2C(=O)N3CC(CC(C)C)N=C3c3ncc(N4CCOCC4)cc32)cc(OC)c1] | 6-(3,5-dimethoxybenzyl)-2-(2-methylpropyl)-8-(morpholin-4-yl)-2,6-dihydroimidazo[1,2-c]pyrido[2,3-e]pyrimidin-5(3H)-one |

TABLE 1-continued

Selected compounds of the invention according to formula 1a and 1g.

| Example | Structure | Name |
|---|---|---|
| 23 | 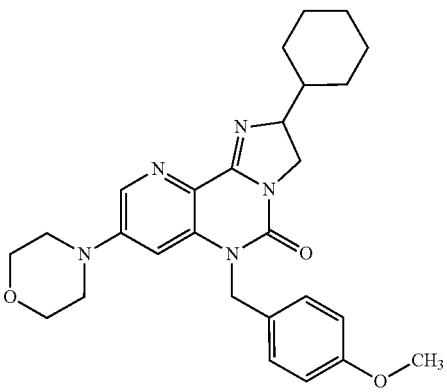 [SMILES: COc1ccc(CN2C(=O)N3CC(C4CCCCC4)N=C3c3ncc(N4CCOCC4)cc32)cc1] | 2-cyclohexyl-6-(4-methoxybenzyl)-8-(morpholin-4-yl)-2,6-dihydroimidazo[1,2-c]pyrido[2,3-e]pyrimidin-5(3H)-one |
| 24 | 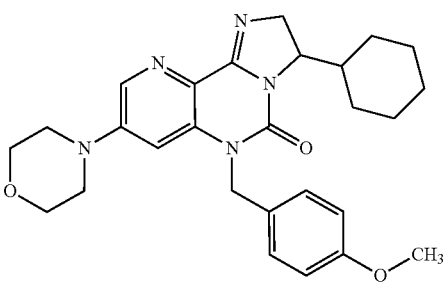 [SMILES: COc1ccc(CN2C(=O)N3C(=NCC3C3CCCCC3)c3ncc(N4CCOCC4)cc32)cc1] | 3-cyclohexyl-6-(4-methoxybenzyl)-8-(morpholin-4-yl)-2,6-dihydroimidazo[1,2-c]pyrido[2,3-e]pyrimidin-5(3H)-one |
| 25 | 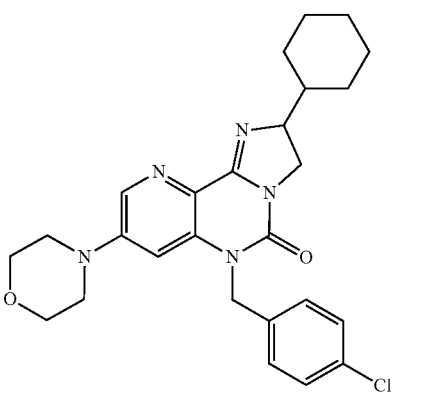 [SMILES: O=C1N2CC(C3CCCCC3)N=C2c2ncc(N3CCOCC3)cc2N1Cc1ccc(Cl)cc1] | 6-(4-chlorobenzyl)-2-cyclohexyl-8-(morpholin-4-yl)-2,6-dihydroimidazo[1,2-c]pyrido[2,3-e]pyrimidin-5(3H)-one |
| 26 | 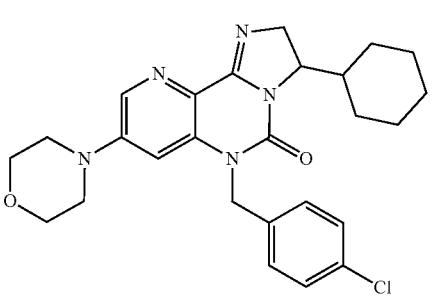 [SMILES: O=C1N(Cc2ccc(Cl)cc2)c2cc(N3CCOCC3)cnc2C2=NCC(C3CCCCC3)N12] | 6-(4-chlorobenzyl)-3-cyclohexyl-8-(morpholin-4-yl)-2,6-dihydroimidazo[1,2-c]pyrido[2,3-e]pyrimidin-5(3H)-one |

TABLE 1-continued

Selected compounds of the invention according to formula 1a and 1g.

| Example | Structure | Name |
|---|---|---|
| 27 | 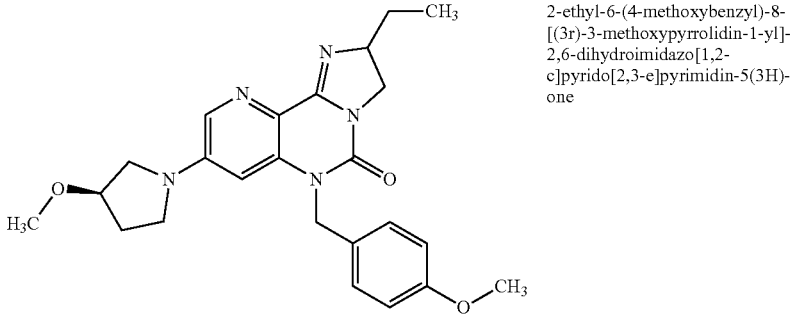 | 2-ethyl-6-(4-methoxybenzyl)-8-[(3r)-3-methoxypyrrolidin-1-yl]-2,6-dihydroimidazo[1,2-c]pyrido[2,3-e]pyrimidin-5(3H)-one |
| 28 | 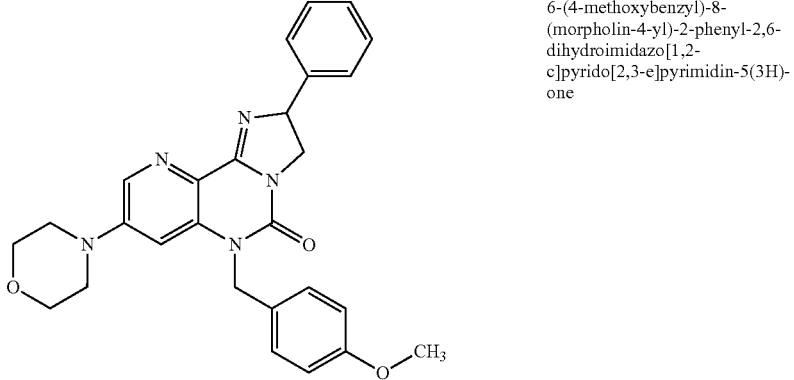 | 6-(4-methoxybenzyl)-8-(morpholin-4-yl)-2-phenyl-2,6-dihydroimidazo[1,2-c]pyrido[2,3-e]pyrimidin-5(3H)-one |
| 29 | 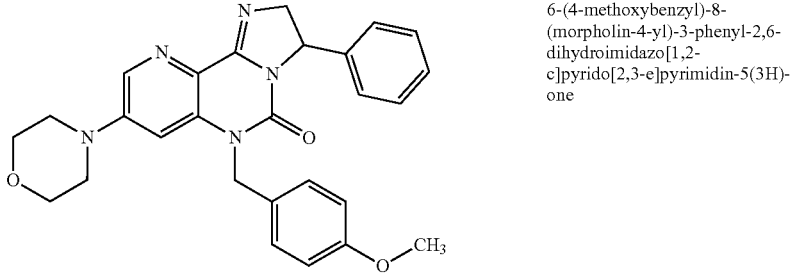 | 6-(4-methoxybenzyl)-8-(morpholin-4-yl)-3-phenyl-2,6-dihydroimidazo[1,2-c]pyrido[2,3-e]pyrimidin-5(3H)-one |
| 30 | 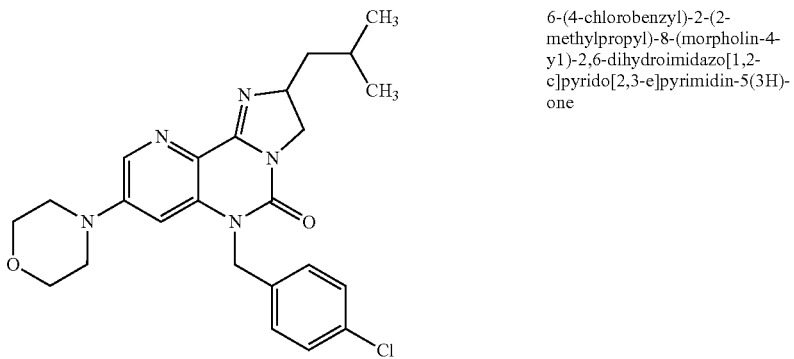 | 6-(4-chlorobenzyl)-2-(2-methylpropyl)-8-(morpholin-4-yl)-2,6-dihydroimidazo[1,2-c]pyrido[2,3-e]pyrimidin-5(3H)-one |

TABLE 1-continued

Selected compounds of the invention according to formula 1a and 1g.

| Example | Structure | Name |
|---|---|---|
| 31 | 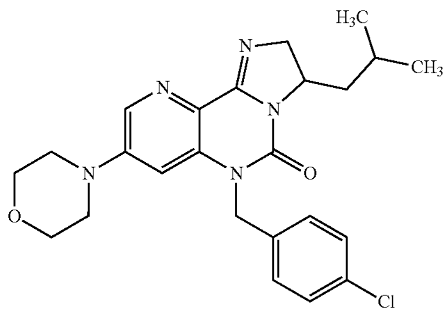 [SMILES: CC(C)CC1CN=C2c3ncc(N4CCOCC4)cc3N(Cc3ccc(Cl)cc3)C(=O)N21] | 6-(4-chlorobenzyl)-3-(2-methylpropyl)-8-(morpholin-4-yl)-2,6-dihydroimidazo[1,2-c]pyrido[2,3-e]pyrimidin-5(3H)-one |
| 32 | 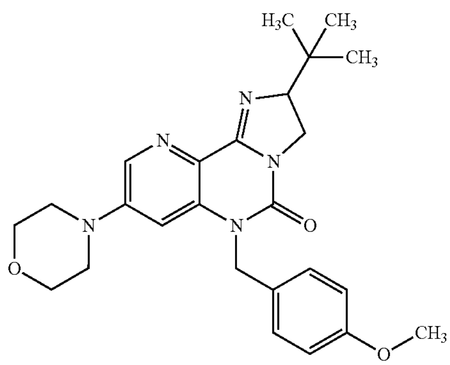 [SMILES: COc1ccc(CN2C(=O)N3CC(C(C)(C)C)N=C3c3ncc(N4CCOCC4)cc32)cc1] | 2-tert-butyl-6-(4-methoxybenzyl)-8-(morpholin-4-yl)-2,6-dihydroimidazo[1,2-c]pyrido[2,3-e]pyrimidin-5(3H)-one |
| 33 | 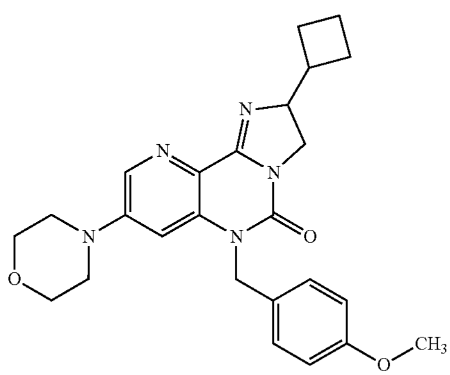 [SMILES: COc1ccc(CN2C(=O)N3CC(C4CCC4)N=C3c3ncc(N4CCOCC4)cc32)cc1] | 2-cyclobutyl-6-(4-methoxybenzyl)-8-(morpholin-4-yl)-2,6-dihydroimidazo[1,2-c]pyrido[2,3-e]pyrimidin-5(3H)-one |
| 34 | 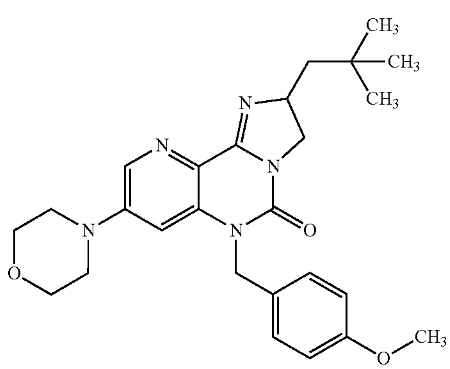 [SMILES: COc1ccc(CN2C(=O)N3CC(CC(C)(C)C)N=C3c3ncc(N4CCOCC4)cc32)cc1] | 2-(2,2-dimethylpropyl)-6-(4-methoxybenzyl)-8-(morpholin-4-yl)-2,6-dihydroimidazo[1,2-c]pyrido[2,3-e]pyrimidin-5(3H)-one |

TABLE 1-continued

Selected compounds of the invention according to formula 1a and 1g.

| Example | Structure | Name |
|---|---|---|
| 35 | 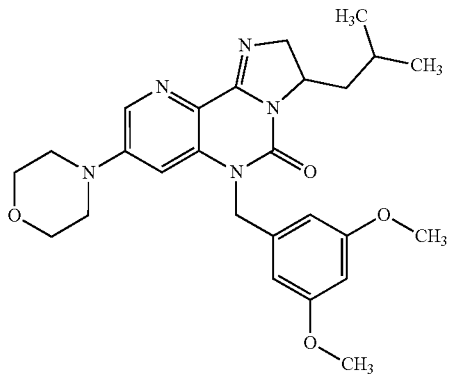 [SMILES: COc1cc(CN2C(=O)N3C(=NCC3CC(C)C)c3ncc(N4CCOCC4)cc32)cc(OC)c1] | 6-(3,5-dimethoxybenzyl)-3-(2-methylpropyl)-8-(morpholin-4-yl)-2,6-dihydroimidazo[1,2-c]pyrido[2,3-e]pyrimidin-5(3H)-one |
| 36 | 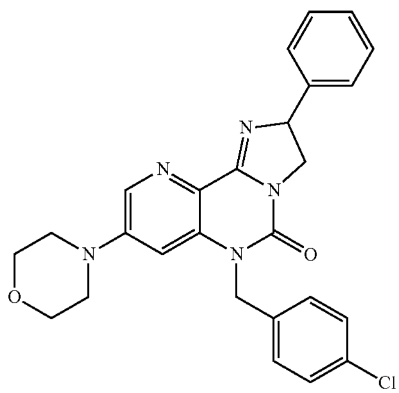 [SMILES: O=C1N2CC(c3ccccc3)N=C2c2ncc(N3CCOCC3)cc2N1Cc1ccc(Cl)cc1] | 6-(4-chlorobenzyl)-8-(morpholin-4-yl)-2-phenyl-2,6-dihydroimidazo[1,2-c]pyrido[2,3-e]pyrimidin-5(3H)-one |
| 37 | 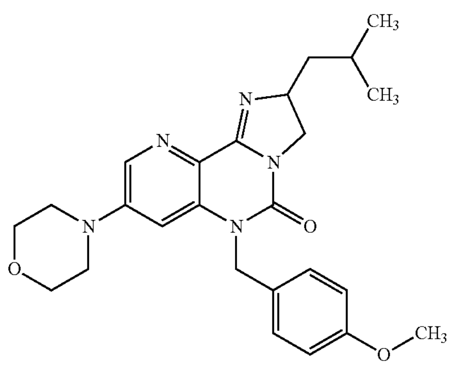 [SMILES: COc1ccc(CN2C(=O)N3CC(CC(C)C)N=C3c3ncc(N4CCOCC4)cc32)cc1] | 6-(4-methoxybenzyl)-2-(2-methylpropyl)-8-(morpholin-4-yl)-2,6-dihydroimidazo[1,2-c]pyrido[2,3-e]pyrimidin-5(3H)-one |
| 38 | 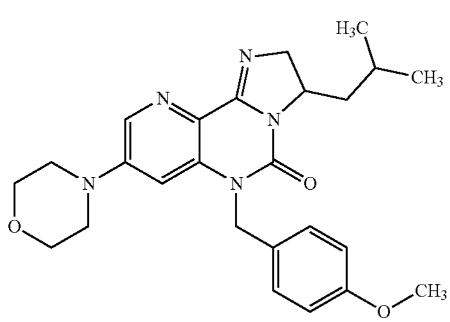 [SMILES: COc1ccc(CN2C(=O)N3C(=NCC3CC(C)C)c3ncc(N4CCOCC4)cc32)cc1] | 6-(4-methoxybenzyl)-3-(2-methylpropyl)-8-(morpholin-4-yl)-2,6-dihydroimidazo[1,2-c]pyrido[2,3-e]pyrimidin-5(3H)-one |

TABLE 1-continued

Selected compounds of the invention according to formula 1a and 1g.

| Example | Structure | Name |
|---|---|---|
| 39 | 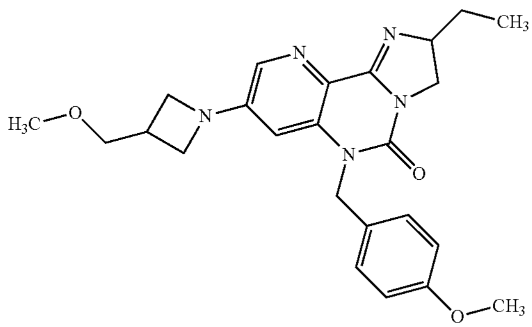 [SMILES: CCC1CN2C(=O)N(Cc3ccc(OC)cc3)c3cc(N4CC(COC)C4)cnc3C2=N1] | 2-ethyl-6-(4-methoxybenzyl)-8-[3-(methoxymethyl)azetidin-1-yl]-2,6-dihydroimidazo[1,2-c]pyrido[2,3-e]pyrimidin-5(3H)-one |
| 40 | 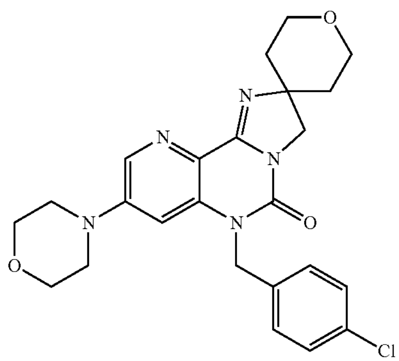 [SMILES: O=C1N2CC3(CCOCC3)N=C2c2ncc(N3CCOCC3)cc2N1Cc1ccc(Cl)cc1] | 6-(4-chlorobenzyl)-8-(morpholin-4-yl)-2',3',5',6'-tetrahydrospiro[imidazo[1,2-c]pyrido[2,3-e]pyrimidine-2,4'-pyran]-5(6H)-one |
| 41 | 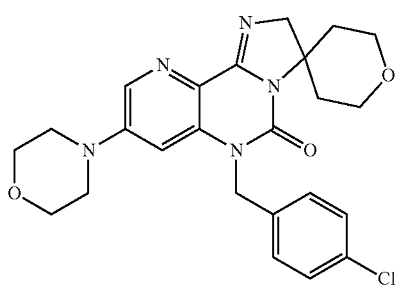 [SMILES: O=C1N(Cc2ccc(Cl)cc2)c2cc(N3CCOCC3)cnc2C2=NCC3(CCOCC3)N12] | 6-(4-chlorobenzyl)-8-(morpholin-4-yl)-2,2',3',5',6,6'-hexahydro-5h-spiro[imidazo[1,2-c]pyrido[2,3-e]pyrimidine-3,4'-pyran]-5-one |
| 42 | 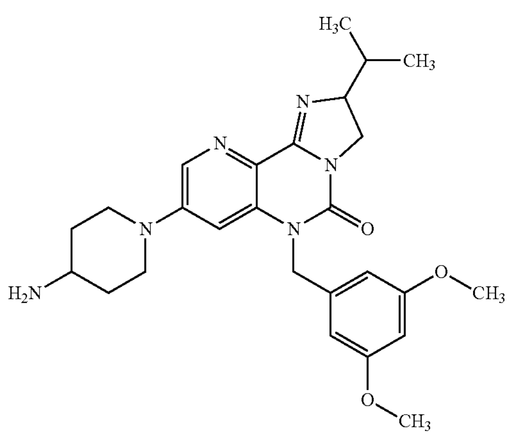 [SMILES: COc1cc(CN2C(=O)N3CC(C(C)C)N=C3c3ncc(N4CCC(N)CC4)cc32)cc(OC)c1] | 8-(4-aminopiperidin-1-yl)-6-(3,5-dimethoxybenzyl)-2-(propan-2-yl)-2,6-dihydroimidazo[1,2-c]pyrido[2,3-e]pyrimidin-5(3H)-one |

TABLE 1-continued

Selected compounds of the invention according to formula 1a and 1g.

| Example | Structure | Name |
|---|---|---|
| 43 | 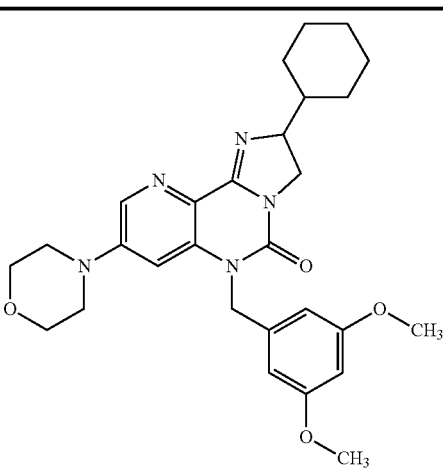 | 2-cyclohexyl-6-(3,5-dimethoxybenzyl)-8-(morpholin-4-yl)-2,6-dihydroimidazo[1,2-c]pyrido[2,3-e]pyrimidin-5(3H)-one |
| 44 | 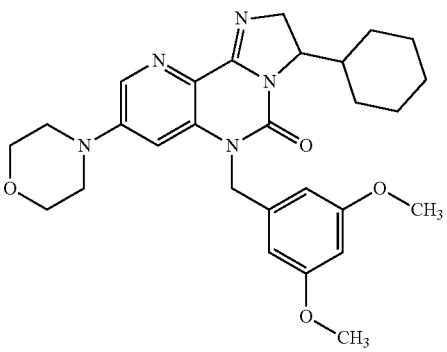 [SMILES: COc1cc(CN2C(=O)N3C(=NCC3C3CCCCC3)c3ncc(N4CCOCC4)cc32)cc(OC)c1] | 3-cyclohexyl-6-(3,5-dimethoxybenzyl)-8-(morpholin-4-yl)-2,6-dihydroimidazo[1,2-c]pyrido[2,3-e]pyrimidin-5(3H)-one |
| 45 | 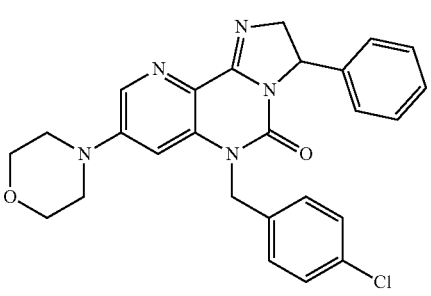 [SMILES: O=C1N(Cc2ccc(Cl)cc2)c2cc(N3CCOCC3)cnc2C2=NCC(c3ccccc3)N12] | 6-(4-chlorobenzyl)-8-(morpholin-4-yl)-3-phenyl-2,6-dihydroimidazo[1,2-c]pyrido[2,3-e]pyrimidin-5(3H)-one |
| 46 | 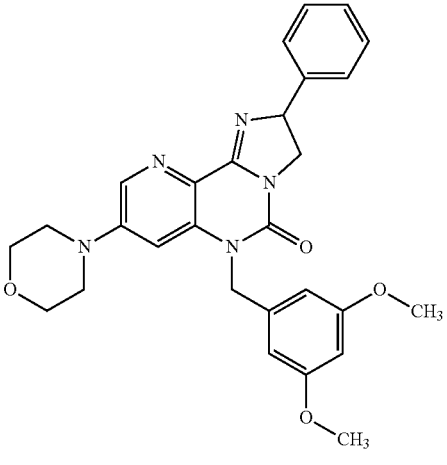 [SMILES: COc1cc(CN2C(=O)N3CC(c4ccccc4)N=C3c3ncc(N4CCOCC4)cc32)cc(OC)c1] | 6-(3,5-dimethoxybenzyl)-8-(morpholin-4-yl)-2-phenyl-2,6-dihydroimidazo[1,2-c]pyrido[2,3-e]pyrimidin-5(3H)-one |

TABLE 1-continued

Selected compounds of the invention according to formula 1a and 1g.

| Example | Structure | Name |
|---|---|---|
| 47 | 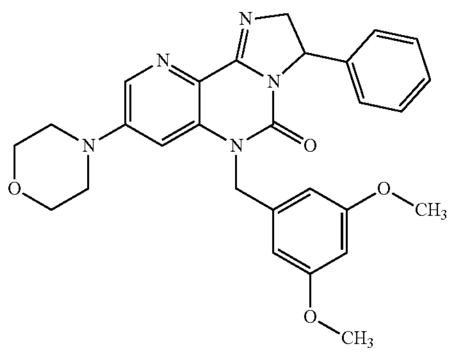 [SMILES: COc1cc(CN2C(=O)N3C(=NCC3c3ccccc3)c3ncc(N4CCOCC4)cc32)cc(OC)c1] | 6-(3,5-dimethoxybenzyl)-8-(morpholin-4-yl)-3-phenyl-2,6-dihydroimidazo[1,2-c]pyrido[2,3-e]pyrimidin-5(3H)-one |
| 48 | 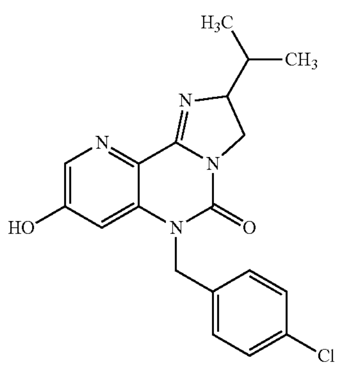 [SMILES: CC(C)C1CN2C(=O)N(Cc3ccc(Cl)cc3)c3cc(O)cnc3C2=N1] | 6-(4-chlorobenzyl)-8-hydroxy-2-(propan-2-yl)-2,6-dihydroimidazo[1,2-c]pyrido[2,3-e]pyrimidin-5(3H)-one |
| 49 | 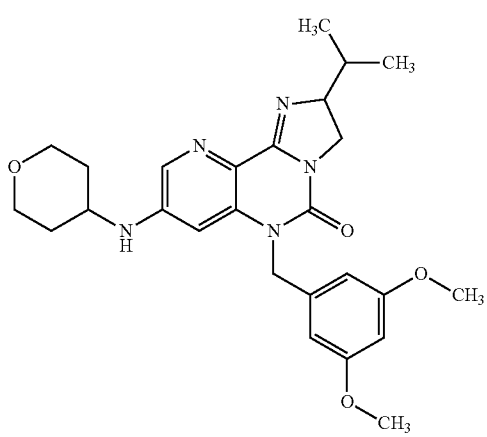 [SMILES: COc1cc(CN2C(=O)N3CC(C(C)C)N=C3c3ncc(NC4CCOCC4)cc32)cc(OC)c1] | 6-(3,5-dimethoxybenzyl)-2-(propan-2-yl)-8-(tetrahydro-2H-pyran-4-ylamino)-2,6-dihydroimidazo[1,2-c]pyrido[2,3-e]pyrimidin-5(3H)-one |
| 50 | 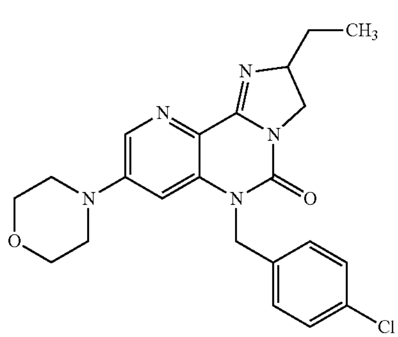 [SMILES: CCC1CN2C(=O)N(Cc3ccc(Cl)cc3)c3cc(N4CCOCC4)cnc3C2=N1] | 6-(4-chlorobenzyl)-2-ethyl-8-(morpholin-4-yl)-2,6-dihydroimidazo[1,2-c]pyrido[2,3-e]pyrimidin-5(3H)-one |

TABLE 1-continued

Selected compounds of the invention according to formula 1a and 1g.

| Example | Structure | Name |
|---|---|---|
| 51 | 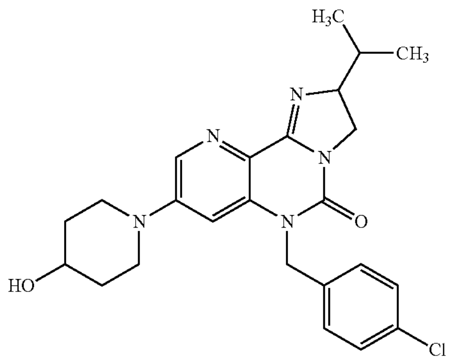 [SMILES: CC(C)C1CN2C(=O)N(Cc3ccc(Cl)cc3)c3cc(N4CCC(O)CC4)cnc3C2=N1] | 6-(4-chlorobenzyl)-8-(4-hydroxypiperidin-1-yl)-2-(propan-2-yl)-2,6-dihydroimidazo[1,2-c]pyrido[2,3-e]pyrimidin-5(3H)-one |
| 52 | 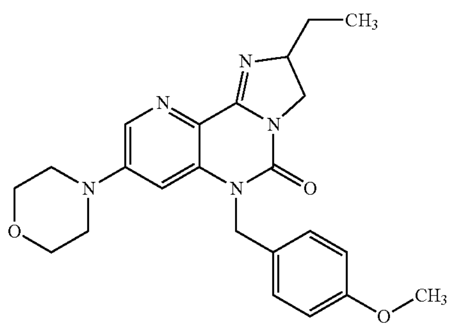 [SMILES: CCC1CN2C(=O)N(Cc3ccc(OC)cc3)c3cc(N4CCOCC4)cnc3C2=N1] | 2-ethyl-6-(4-methoxybenzyl)-8-(morpholin-4-yl)-2,6-dihydroimidazo[1,2-c]pyrido[2,3-e]pyrimidin-5(3H)-one |
| 53 | 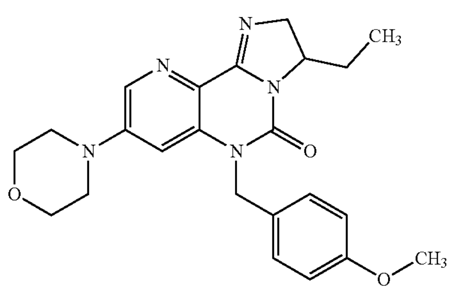 [SMILES: CCC1CN=C2c3ncc(N4CCOCC4)cc3N(Cc3ccc(OC)cc3)C(=O)N21] | 3-ethyl-6-(4-methoxybenzyl)-8-(morpholin-4-yl)-2,6-dihydroimidazo[1,2-c]pyrido[2,3-e]pyrimidin-5(3H)-one |
| 54 | 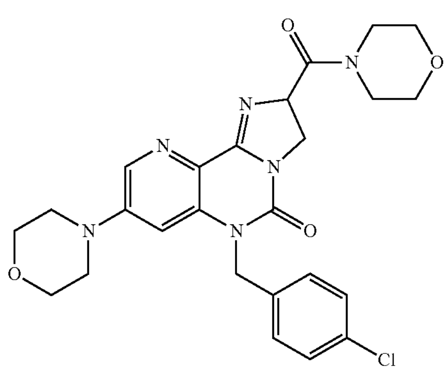 [SMILES: O=C(C1CN2C(=O)N(Cc3ccc(Cl)cc3)c3cc(N4CCOCC4)cnc3C2=N1)N1CCOCC1] | 6-(4-chlorobenzyl)-8-(morpholin-4-yl)-2-(morpholin-4-ylcarbonyl)-2,6-dihydroimidazo[1,2-c]pyrido[2,3-e]pyrimidin-5(3H)-one |

TABLE 1-continued

Selected compounds of the invention according to formula 1a and 1g.

| Example | Structure | Name |
|---|---|---|
| 55 | 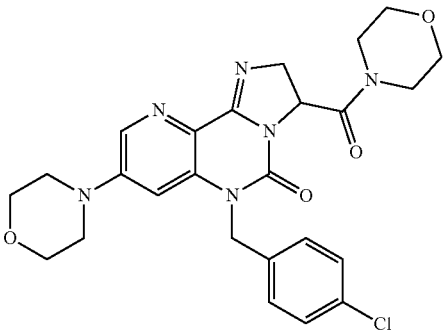 [SMILES: O=C(C1CN=C2c3ncc(N4CCOCC4)cc3N(Cc3ccc(Cl)cc3)C(=O)N21)N1CCOCC1] | 6-(4-chlorobenzyl)-8-(morpholin-4-yl)-3-(morpholin-4-ylcarbonyl)-2,6-dihydroimidazo[1,2-c]pyrido[2,3-e]pyrimidin-5(3H)-one |
| 56 | 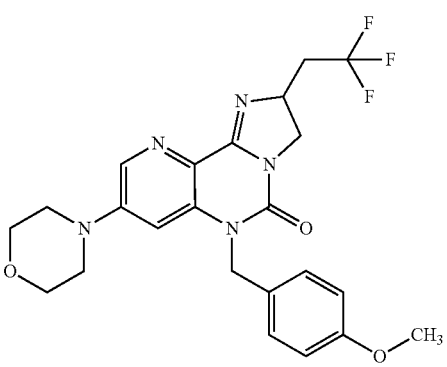 [SMILES: COc1ccc(CN2C(=O)N3CC(CC(F)(F)F)N=C3c3ncc(N4CCOCC4)cc32)cc1] | 6-(4-methoxybenzyl)-8-(morpholin-4-yl)-2-(2,2,2-trifluoroethyl)-2,6-dihydroimidazo[1,2-c]pyrido[2,3-e]pyrimidin-5(3H)-one |
| 57 | 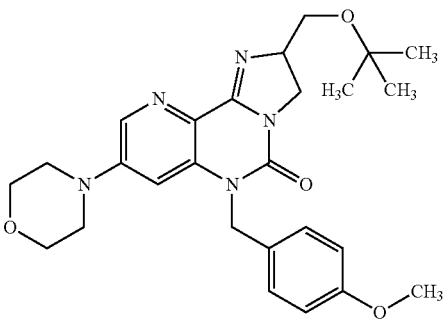 [SMILES: COc1ccc(CN2C(=O)N3CC(COC(C)(C)C)N=C3c3ncc(N4CCOCC4)cc32)cc1] | 2-(tert-butoxymethyl)-6-(4-methoxybenzyl)-8-(morpholin-4-yl)-2,6-dihydroimidazo[1,2-c]pyrido[2,3-e]pyrimidin-5(3H)-one |
| 58 | 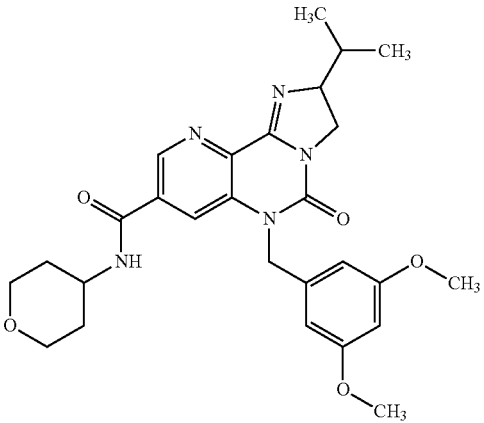 [SMILES: COc1cc(CN2C(=O)N3CC(C(C)C)N=C3c3ncc(C(=O)NC4CCOCC4)cc32)cc(OC)c1] | 6-(3,5-dimethoxybenzyl)-5-oxo-2-(propan-2-yl)-n-(tetrahydro-2H-pyran-4-yl)-2,3,5,6-tetrahydroimidazo[1,2-c]pyrido[2,3-e]pyrimidine-8-carboxamide |

TABLE 1-continued

Selected compounds of the invention according to formula 1a and 1g.

| Example | Structure | Name |
|---|---|---|
| 59 | 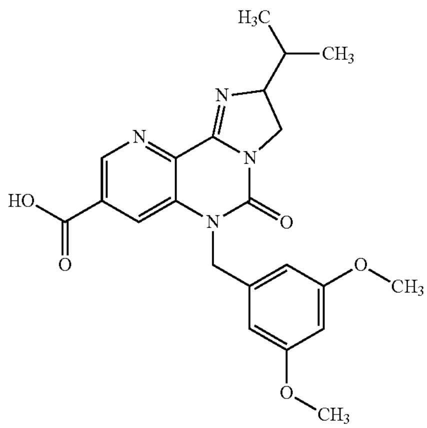 [SMILES: COc1cc(CN2C(=O)N3CC(C(C)C)N=C3c3ncc(C(=O)O)cc32)cc(OC)c1] | 6-(3,5-dimethoxybenzyl)-5-oxo-2-(propan-2-yl)-2,3,5,6-tetrahydroimidazo[1,2-c]pyrido[2,3-e]pyrimidine-8-carboxylic acid |
| 60 | 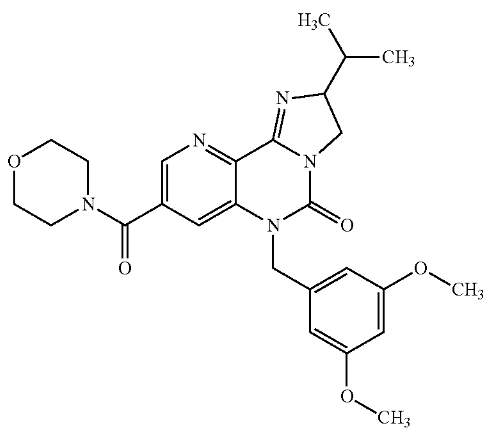 [SMILES: COc1cc(CN2C(=O)N3CC(C(C)C)N=C3c3ncc(C(=O)N4CCOCC4)cc32)cc(OC)c1] | 6-(3,5-dimethoxybenzyl)-8-(morpholin-4-ylcarbonyl)-2-(propan-2-yl)-2,6-dihydroimidazo[1,2-c]pyrido[2,3-e]pyrimidin-5(3H)-one |
| 61 | 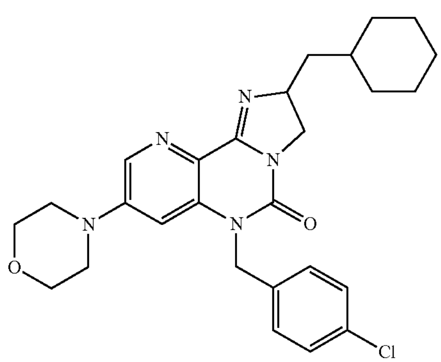 [SMILES: O=C1N2CC(CC3CCCCC3)N=C2c2ncc(N3CCOCC3)cc2N1Cc1ccc(Cl)cc1] | 6-(4-chlorobenzyl)-2-(cyclohexylmethyl)-8-(morpholin-4-yl)-2,6-dihydroimidazo[1,2-c]pyrido[2,3-e]pyrimidin-5(3H)-one |
| 62 | 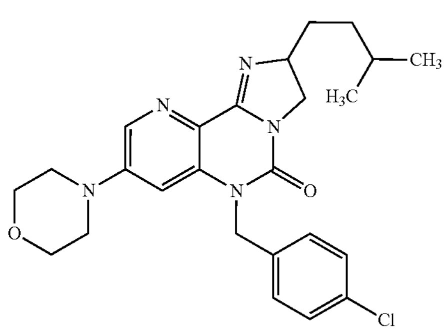 [SMILES: CC(C)CCC1CN2C(=O)N(Cc3ccc(Cl)cc3)c3cc(N4CCOCC4)cnc3C2=N1] | 6-(4-chlorobenzyl)-2-(3-methylbutyl)-8-(morpholin-4-yl)-2,6-dihydroimidazo[1,2-c]pyrido[2,3-e]pyrimidin-5(3H)-one |

TABLE 1-continued

Selected compounds of the invention according to formula 1a and 1g.

| Example | Structure | Name |
|---|---|---|
| 63 | 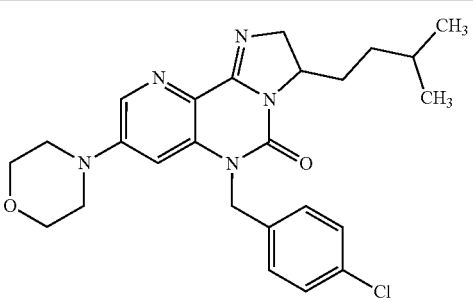 [SMILES: CC(C)CCC1CN=C2c3ncc(N4CCOCC4)cc3N(Cc3ccc(Cl)cc3)C(=O)N21] | 6-(4-chlorobenzyl)-3-(3-methylbutyl)-8-(morpholin-4-yl)-2,6-dihydroimidazo[1,2-c]pyrido[2,3-e]pyrimidin-5(3H)-one |
| 64 | 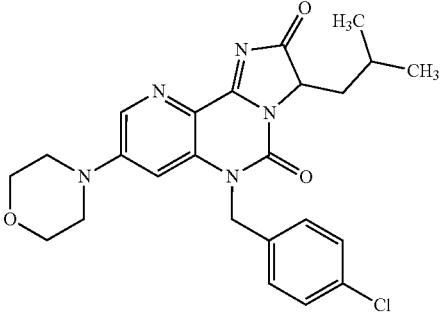 [SMILES: CC(C)CC1C(=O)N=C2c3ncc(N4CCOCC4)cc3N(Cc3ccc(Cl)cc3)C(=O)N21] | 6-(4-chlorobenzyl)-3-(2-methylpropyl)-8-(morpholin-4-yl)imidazo[1,2-c]pyrido[2,3-e]pyrimidine-2,5(3H,6H)-dione |
| 65 | 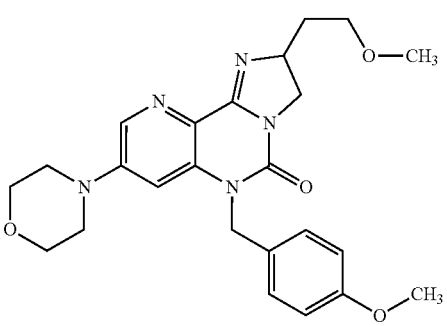 [SMILES: COCCC1CN2C(=O)N(Cc3ccc(OC)cc3)c3cc(N4CCOCC4)cnc3C2=N1] | 6-(4-methoxybenzyl)-2-(2-methoxyethyl)-8-(morpholin-4-yl)-2,6-dihydroimidazo[1,2-c]pyrido[2,3-e]pyrimidin-5(3H)-one |
| 66 | 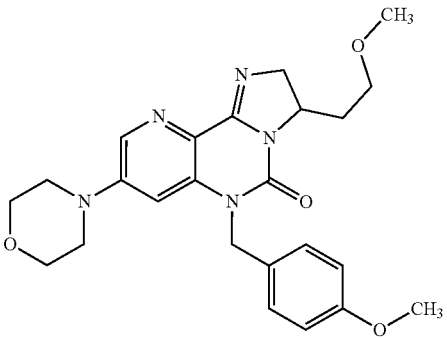 [SMILES: COCCC1CN=C2c3ncc(N4CCOCC4)cc3N(Cc3ccc(OC)cc3)C(=O)N21] | 6-(4-methoxybenzyl)-3-(2-methoxyethyl)-8-(morpholin-4-yl)-2,6-dihydroimidazo[1,2-c]pyrido[2,3-e]pyrimidin-5(3H)-one |

TABLE 1-continued

Selected compounds of the invention according to formula 1a and 1g.

| Example | Structure | Name |
|---|---|---|
| 67 | 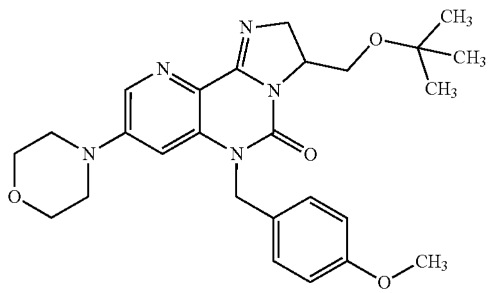 [SMILES: COc1ccc(CN2C(=O)N3C(=NCC3COC(C)(C)C)c3ncc(N4CCOCC4)cc32)cc1] | 3-(tert-butoxymethyl)-6-(4-methoxybenzyl)-8-(morpholin-4-yl)-2,6-dihydroimidazo[1,2-c]pyrido[2,3-e]pyrimidin-5(3H)-one |
| 68 | 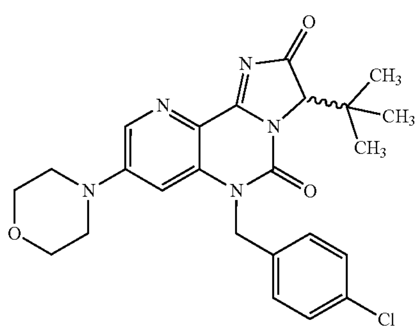 [SMILES: CC(C)(C)C1C(=O)N=C2c3ncc(N4CCOCC4)cc3N(Cc3ccc(Cl)cc3)C(=O)N21] | 3-tert-butyl-6-(4-chlorobenzyl)-8-(morpholin-4-yl)imidazo[1,2-c]pyrido[2,3-e]pyrimidine-2,5(3H,6H)-dione |
| 69 | 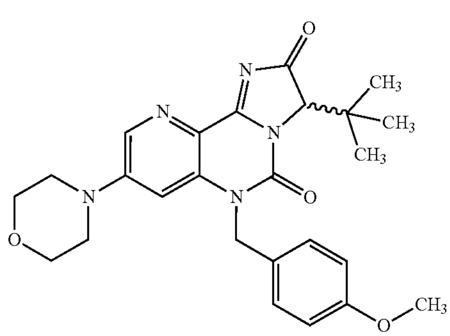 [SMILES: COc1ccc(CN2C(=O)N3C(=NC(=O)C3C(C)(C)C)c3ncc(N4CCOCC4)cc32)cc1] | 3-tert-butyl-6-(4-methoxybenzyl)-8-(morpholin-4-yl)imidazo[1,2-c]pyrido[2,3-e]pyrimidine-2,5(3H,6H)-dione |

Preferred compounds according to the invention are compounds or an enantiomer, diastereomer, N-oxide, or a pharmaceutically acceptable salt or combinations thereof, which are provided according to general formula 1b or 1c selected from the compounds in Table 2 below:

TABLE 2

Selected compounds of the invention according to formula 1b and 1c.

| Example | Structure | Name |
| --- | --- | --- |
| 70 | 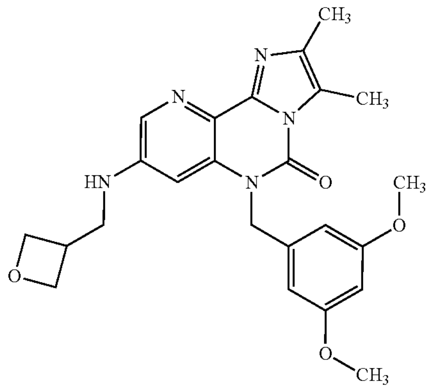 [SMILES: COc1cc(Cn2c(=O)n3c(C)c(C)nc3c3ncc(NCC4COC4)cc32)cc(OC)c1] | 6-(3,5-dimethoxybenzyl)-2,3-dimethyl-8-{[(oxetan-3-yl)methyl]amino}imidazo[1,2-c]pyrido[2,3-e]pyrimidin-5(6H)-one |
| 71 | 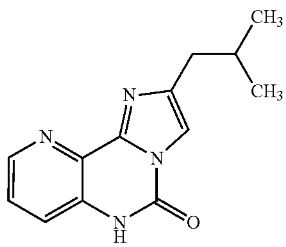 [SMILES: CC(C)Cc1cn2c(=O)[nH]c3cccnc3c2n1] | 2-(2-methylpropyl)imidazo[1,2-c]pyrido[2,3-e]pyrimidin-5(6H)-one |
| 72 | 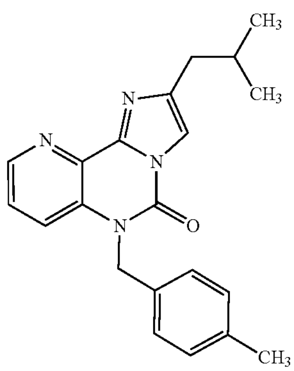 [SMILES: Cc1ccc(Cn2c(=O)n3cc(CC(C)C)nc3c3ncccc32)cc1] | 6-(4-methylbenzyl)-2-(2-methylpropyl)imidazo[1,2-c]pyrido[2,3-e]pyrimidin-5(6H)-one |
| 73 | 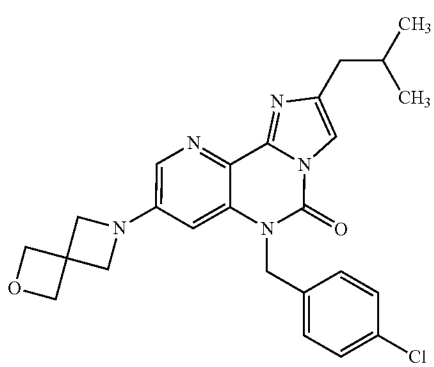 [SMILES: CC(C)Cc1cn2c(=O)n(Cc3ccc(Cl)cc3)c3cc(N4CC5(COC5)C4)cnc3c2n1] | 6-(4-chlorobenzyl)-2-(2-methylpropyl)-8-(2-oxa-6-azaspiro[3.3]heptan-6-yl)imidazo[1,2-c]pyrido[2,3-e]pyrimidin-5(6H)-one |

TABLE 2-continued

Selected compounds of the invention according to formula 1b and 1c.

| Example | Structure | Name |
|---|---|---|
| 74 | 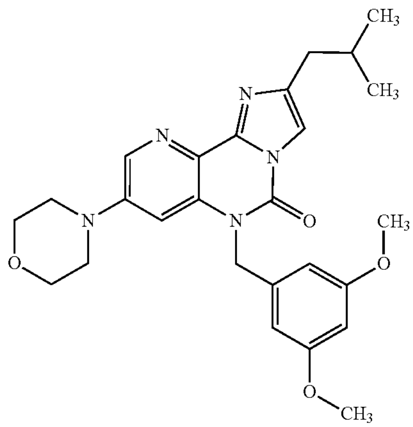 [SMILES: COc1cc(Cn2c(=O)n3cc(CC(C)C)nc3c3ncc(N4CCOCC4)cc32)cc(OC)c1] | 6-(3,5-dimethoxybenzyl)-2-(2-methylpropyl)-8-(morpholin-4-yl)imidazo[1,2-c]pyrido[2,3-e]pyrimidin-5(6H)-one |
| 75 | 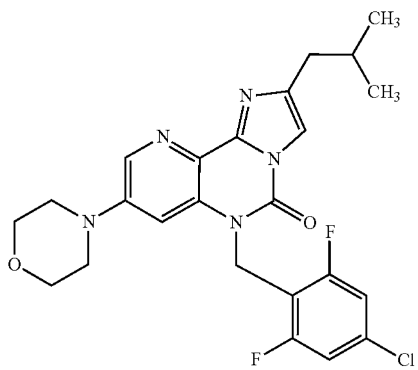 [SMILES: CC(C)Cc1cn2c(=O)n(Cc3c(F)cc(Cl)cc3F)c3cc(N4CCOCC4)cnc3c2n1] | 6-(4-chloro-2,6-difluorobenzyl)-2-(2-methylpropyl)-8-(morpholin-4-yl)imidazo[1,2-c]pyrido[2,3-e]pyrimidin-5(6H)-one |
| 76 | 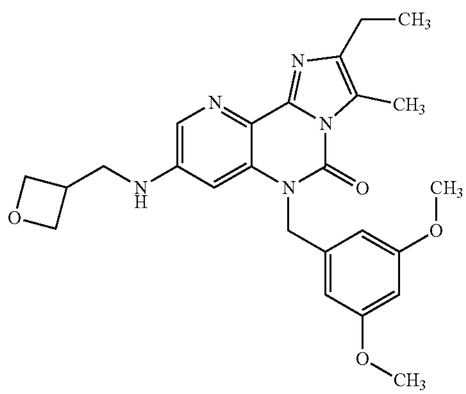 [SMILES: CCc1nc2c3ncc(NCC4COC4)cc3n(Cc3cc(OC)cc(OC)c3)c(=O)n2c1C] | 6-(3,5-dimethoxybenzyl)-2-ethyl-3-methyl-8-{[(oxetan-3-yl)methyl]amino}imidazo[1,2-c]pyrido[2,3-e]pyrimidin-5(6H)-one |
| 77 | 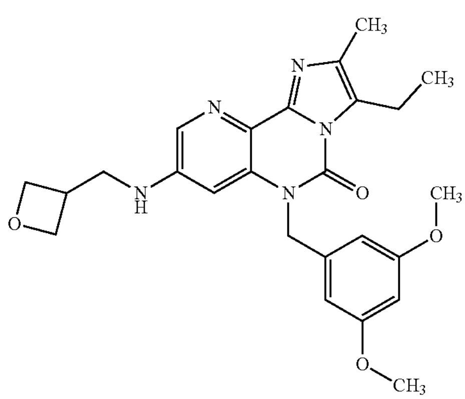 [SMILES: CCc1c(C)nc2c3ncc(NCC4COC4)cc3n(Cc3cc(OC)cc(OC)c3)c(=O)n12] | 6-(3,5-dimethoxybenzyl)-3-ethyl-2-methyl-8-{[(oxetan-3-yl)methyl]amino}imidazo[1,2-c]pyrido[2,3-e]pyrimidin-5(6H)-one |

TABLE 2-continued

Selected compounds of the invention according to formula 1b and 1c.

| Example | Structure | Name |
|---|---|---|
| 78 | 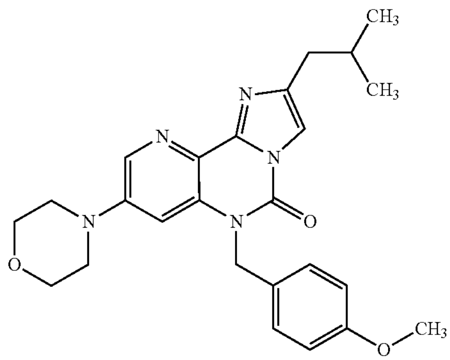 [SMILES: COc1ccc(Cn2c(=O)n3cc(CC(C)C)nc3c3ncc(N4CCOCC4)cc32)cc1] | 6-(4-methoxybenzyl)-2-(2-methylpropyl)-8-(morpholin-4-yl)imidazo[1,2-c]pyrido[2,3-e]pyrimidin-5(6H)-one |
| 79 | 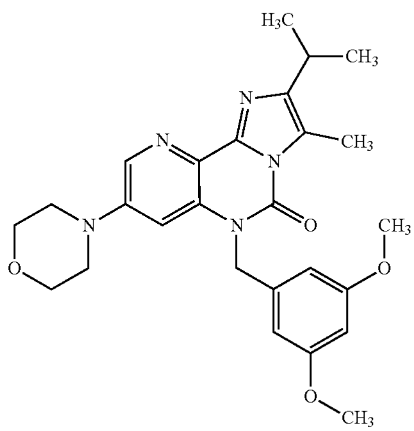 [SMILES: COc1cc(Cn2c(=O)n3c(C)c(C(C)C)nc3c3ncc(N4CCOCC4)cc32)cc(OC)c1] | 6-(3,5-dimethoxybenzyl)-3-methyl-8-(morpholin-4-yl)-2-(propan-2-yl)imidazo[1,2-c]pyrido[2,3-e]pyrimidin-5(6H)-one |
| 80 | 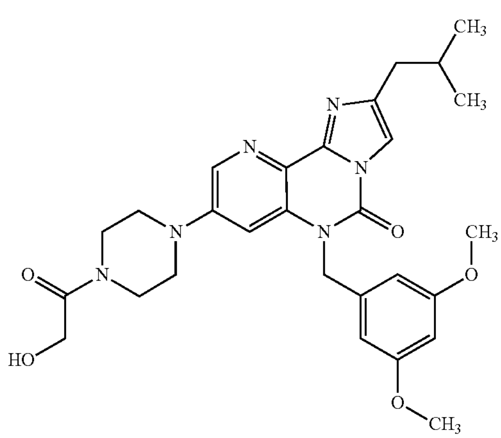 [SMILES: COc1cc(Cn2c(=O)n3cc(CC(C)C)nc3c3ncc(N4CCN(C(=O)CO)CC4)cc32)cc(OC)c1] | 6-(3,5-dimethoxybenzyl)-8-[4-(hydroxyacetyl)piperazin-1-yl]-2-(2-methylpropyl)imidazo[1,2-c]pyrido[2,3-e]pyrimidin-5(6H)-one |

TABLE 2-continued

Selected compounds of the invention according to formula 1b and 1c.

| Example | Structure | Name |
|---|---|---|
| 81 | 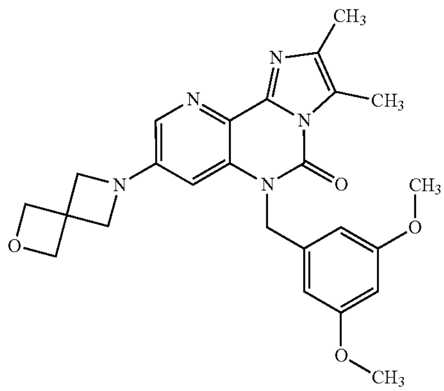 [SMILES: COc1cc(Cn2c(=O)n3c(C)c(C)nc3c3ncc(N4CC5(COC5)C4)cc32)cc(OC)c1] | 6-(3,5-dimethoxybenzyl)-2,3-dimethyl-8-(2-oxa-6-azaspiro[3.3]heptan-6-yl)imidazo[1,2-c]pyrido[2,3-e]pyrimidin-5(6H)-one |
| 82 | 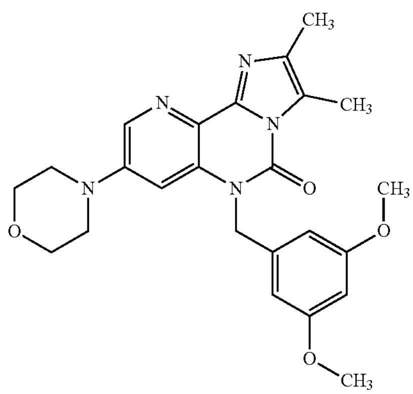 [SMILES: COc1cc(Cn2c(=O)n3c(C)c(C)nc3c3ncc(N4CCOCC4)cc32)cc(OC)c1] | 6-(3,5-dimethoxybenzyl)-2,3-dimethyl-8-(morpholin-4-yl)imidazo[1,2-c]pyrido[2,3-e]pyrimidin-5(6H)-one |
| 83 | 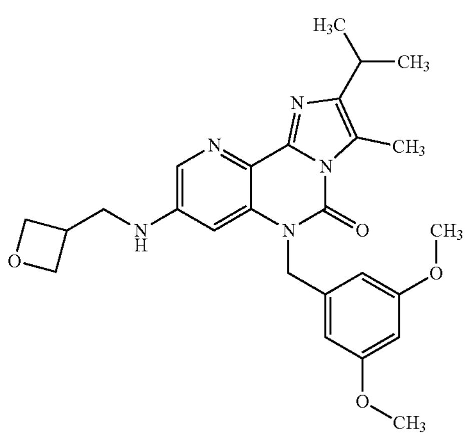 [SMILES: COc1cc(Cn2c(=O)n3c(C)c(C(C)C)nc3c3ncc(NCC4COC4)cc32)cc(OC)c1] | 6-(3,5-dimethoxybenzyl)-3-methyl-8-[(oxetan-3-ylmethyl)amino]-2-(propan-2-yl)imidazo[1,2-c]pyrido[2,3-e]pyrimidin-5(6H)-one |

TABLE 2-continued

Selected compounds of the invention according to formula 1b and 1c.

| Example | Structure | Name |
|---|---|---|
| 84 | 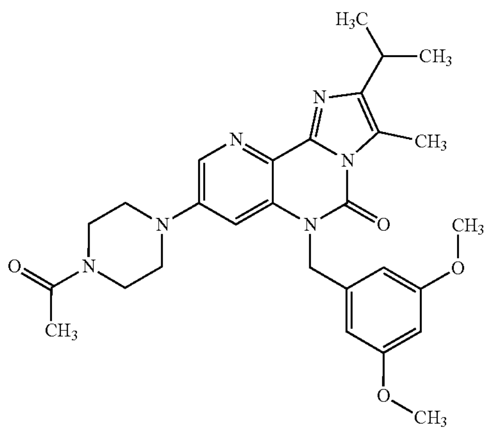 [SMILES: COc1cc(Cn2c(=O)n3c(C)c(C(C)C)nc3c3ncc(N4CCN(C(C)=O)CC4)cc32)cc(OC)c1] | 8-(4-acetylpiperazin-1-yl)-6-(3,5-dimethoxybenzyl)-3-methyl-2-(propan-2-yl)imidazo[1,2-c]pyrido[2,3-e]pyrimidin-5(6H)-one |
| 85 | 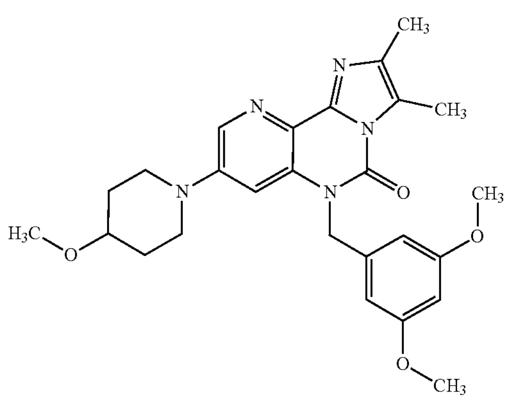 | 6-(3,5-dimethoxybenzyl)-8-(4-methoxypiperidin-1-yl)-2,3-dimethylimidazo[1,2-c]pyrido[2,3-e]pyrimidin-5(6H)-one |
| 86 | 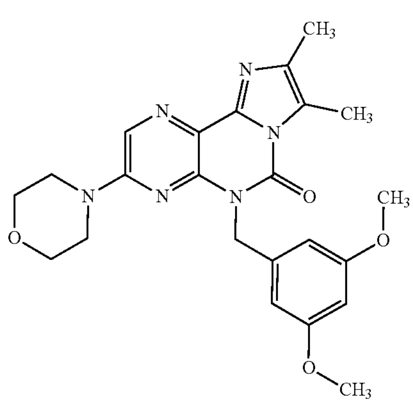 [SMILES: COc1cc(Cn2c(=O)n3c(C)c(C)nc3c3ncc(N4CCOCC4)nc32)cc(OC)c1] | 5-(3,5-dimethoxybenzyl)-8,9-dimethyl-3-(morpholin-4-yl)imidazo[1,2-c]pteridin-6(5h)-one |

TABLE 2-continued

Selected compounds of the invention according to formula 1b and 1c.

| Example | Structure | Name |
|---|---|---|
| 87 | 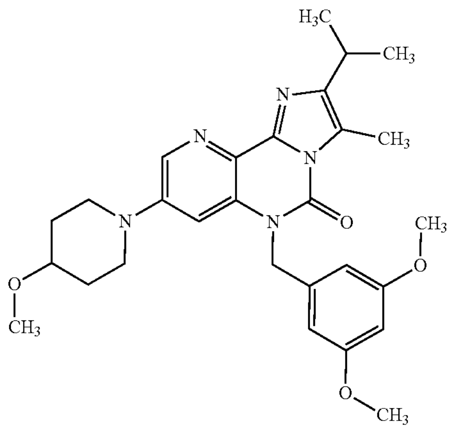 [SMILES: COc1cc(Cn2c(=O)n3c(C)c(C(C)C)nc3c3ncc(N4CCC(OC)CC4)cc32)cc(OC)c1] | 6-(3,5-dimethoxybenzyl)-8-(4-methoxypiperidin-1-yl)-3-methyl-2-(propan-2-yl)imidazo[1,2-c]pyrido[2,3-e]pyrimidin-5(6H)-one |
| 88 | 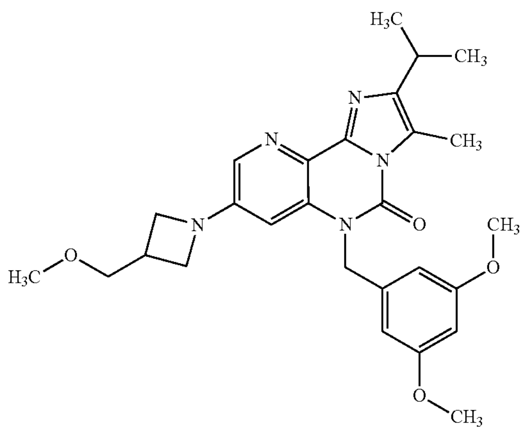 | 6-(3,5-dimethoxybenzyl)-8-[3-(methoxymethyl)azetidin-1-yl]-3-methyl-2-(propan-2-yl)imidazo[1,2-c]pyrido[2,3-e]pyrimidin-5(6H)-one |
| 89 | 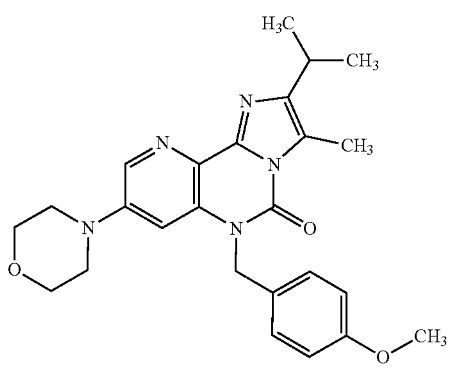 [SMILES: COc1ccc(Cn2c(=O)n3c(C)c(C(C)C)nc3c3ncc(N4CCOCC4)cc32)cc1] | 6-(4-methoxybenzyl)-3-methyl-8-(morpholin-4-yl)-2-(propan-2-yl)imidazo[1,2-c]pyrido[2,3-e]pyrimidin-5(6H)-one |
| 90 | 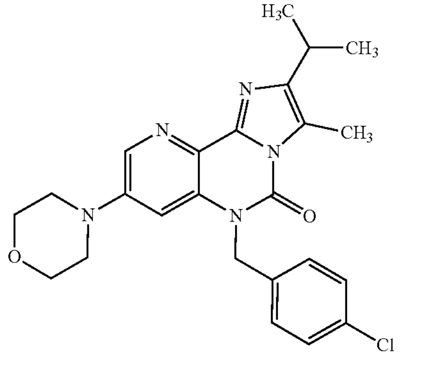 [SMILES: Cc1c(C(C)C)nc2c3ncc(N4CCOCC4)cc3n(Cc3ccc(Cl)cc3)c(=O)n12] | 6-(4-chlorobenzyl)-3-methyl-8-(morpholin-4-yl)-2-(propan-2-yl)imidazo[1,2-c]pyrido[2,3-e]pyrimidin-5(6H)-one |

TABLE 2-continued

Selected compounds of the invention according to formula 1b and 1c.

| Example | Structure | Name |
|---|---|---|
| 91 | 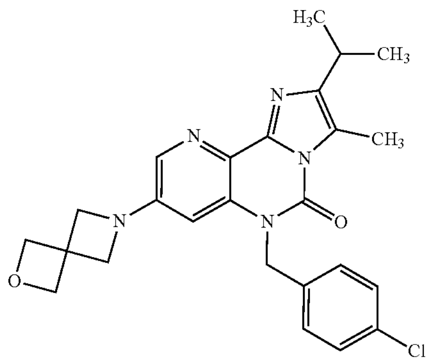 [SMILES: Cc1c(C(C)C)nc2c3ncc(N4CC5(COC5)C4)cc3n(Cc3ccc(Cl)cc3)c(=O)n12] | 6-(4-chlorobenzyl)-3-methyl-8-(2-oxa-6-azaspiro[3.3]heptan-6-yl)-2-(propan-2-yl)imidazo[1,2-c]pyrido[2,3-e]pyrimidin-5(6H)-one |
| 92 | 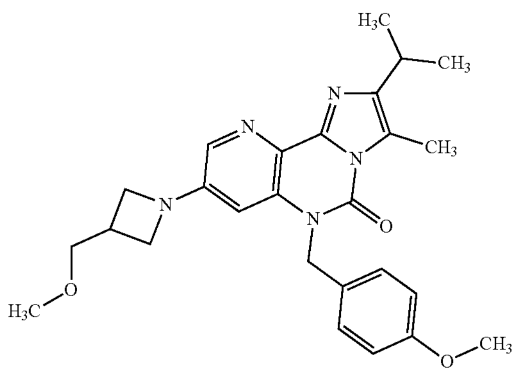 | 6-(4-methoxybenzyl)-8-[3-(methoxymethyl)azetidin-1-yl]-3-methyl-2-(propan-2-yl)imidazo[1,2-c]pyrido[2,3-e]pyrimidin-5(6H)-one |
| 93 | 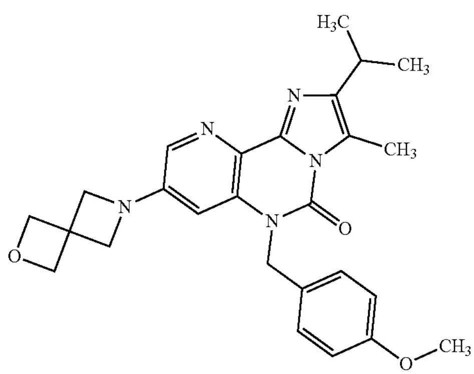 [SMILES: COc1ccc(Cn2c(=O)n3c(C)c(C(C)C)nc3c3ncc(N4CC5(COC5)C4)cc32)cc1] | 6-(4-methoxybenzyl)-3-methyl-8-(2-oxa-6-azaspiro[3.3]heptan-6-yl)-2-(propan-2-yl)imidazo[1,2-c]pyrido[2,3-e]pyrimidin-5(6H)-one |
| 94 | 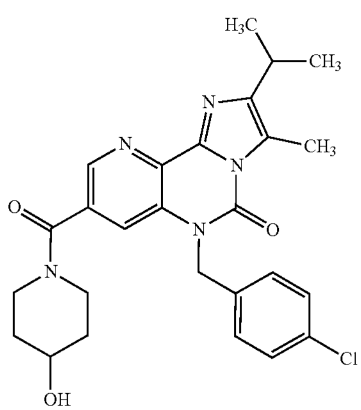 [SMILES: Cc1c(C(C)C)nc2c3ncc(C(=O)N4CCC(O)CC4)cc3n(Cc3ccc(Cl)cc3)c(=O)n12] | 6-(4-chlorobenzyl)-8-[(4-hydroxypiperidin-1-yl)carbonyl]-3-methyl-2-(propan-2-yl)imidazo[1,2-c]pyrido[2,3-e]pyrimidin-5(6H)-one |

TABLE 2-continued

Selected compounds of the invention according to formula 1b and 1c.

| Example | Structure | Name |
|---|---|---|
| 95 | 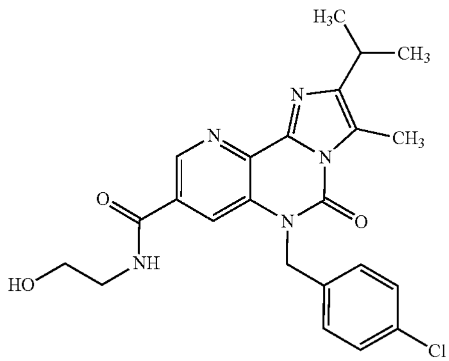 [SMILES: Cc1c(C(C)C)nc2c3ncc(C(=O)NCCO)cc3n(Cc3ccc(Cl)cc3)c(=O)n12] | 6-(4-chlorobenzyl)-n-(2-hydroxyethyl)-3-methyl-5-oxo-2-(propan-2-y1)-5,6-dihydroimidazo[1,2-c]pyrido[2,3-e]pyrimidine-8-carboxamide |
| 96 | 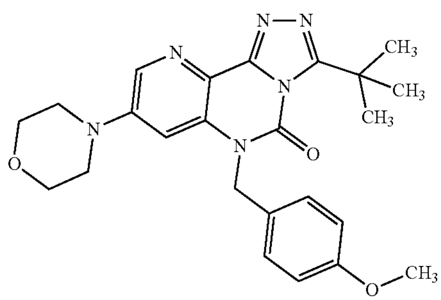 [SMILES: COc1ccc(Cn2c(=O)n3c(C(C)(C)C)nnc3c3ncc(N4CCOCC4)cc32)cc1] | 3-tert-butyl-6-(4-methoxybenzyl)-8-(morpholin-4-yl)pyrido[2,3-e][1,2,4]triazolo[4,3-c]pyrimidin-5(6H)-one |
| 97 | 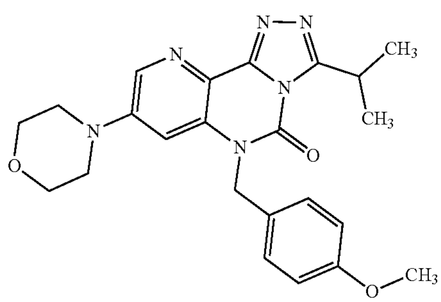 [SMILES: COc1ccc(Cn2c(=O)n3c(C(C)C)nnc3c3ncc(N4CCOCC4)cc32)cc1] | 6-(4-methoxybenzyl)-8-(morpholin-4-yl)-3-(propan-2-yl)pyrido[2,3-e][1,2,4]triazolo[4,3-c]pyrimidin-5(6H)-one |
| 98 | 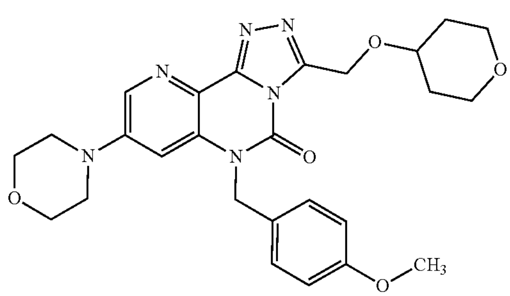 [SMILES: COc1ccc(Cn2c(=O)n3c(COC4CCOCC4)nnc3c3ncc(N4CCOCC4)cc32)cc1] | 6-(4-methoxybenzyl)-8-(morpholin-4-yl)-3-[(tetrahydro-2H-pyran-4-yloxy)methyl]pyrido[2,3-e][1,2,4]triazolo[4,3-c]pyrimidin-5(6H)-one |
| 99 | 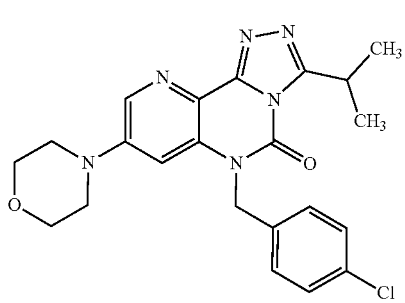 [SMILES: CC(C)c1nnc2c3ncc(N4CCOCC4)cc3n(Cc3ccc(Cl)cc3)c(=O)n12] | 6-(4-chlorobenzyl)-8-(morpholin-4-yl)-3-(propan-2-yl)pyrido[2,3-e][1,2,4]triazolo[4,3-c]pyrimidin-5(6H)-one |

TABLE 2-continued

Selected compounds of the invention according to formula 1b and 1c.

| Example | Structure | Name |
| --- | --- | --- |
| 100 | 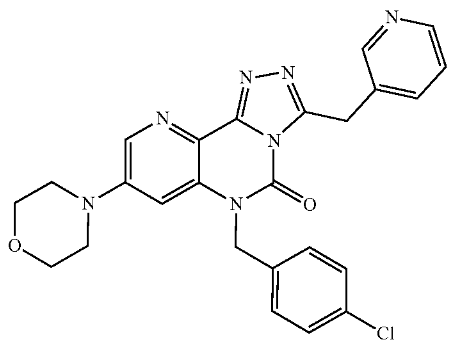 [SMILES: O=c1n(Cc2ccc(Cl)cc2)c2cc(N3CCOCC3)cnc2c2nnc(Cc3cccnc3)n12] | 6-(4-chlorobenzyl)-8-(morpholin-4-yl)-3-(pyridin-3-ylmethyl)pyrido[2,3-e][1,2,4]triazolo[4,3-c]pyrimidin-5(6H)-one |
| 101 | 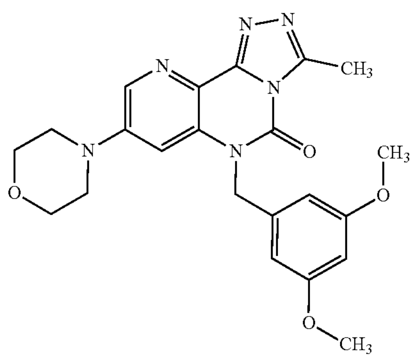 [SMILES: COc1cc(Cn2c(=O)n3c(C)nnc3c3ncc(N4CCOCC4)cc32)cc(OC)c1] | 6-(3,5-dimethoxybenzyl)-3-methyl-8-(morpholin-4-yl)pyrido[2,3-e][1,2,4]triazolo[4,3-c]pyrimidin-5(6H)-one |
| 102 | 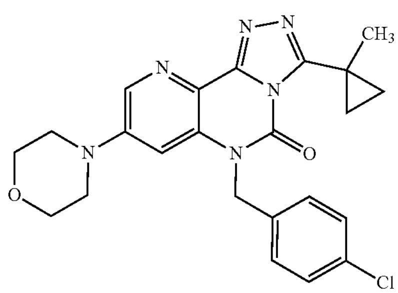 [SMILES: CC1(c2nnc3c4ncc(N5CCOCC5)cc4n(Cc4ccc(Cl)cc4)c(=O)n23)CC1] | 6-(4-chlorobenzyl)-3-(1-methylcyclopropyl)-8-(morpholin-4-yl)pyrido[2,3-e][1,2,4]triazolo[4,3-c]pyrimidin-5(6H)-one |
| 103 | 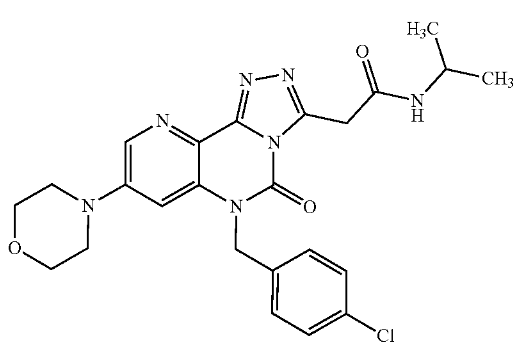 [SMILES: CC(C)NC(=O)Cc1nnc2c3ncc(N4CCOCC4)cc3n(Cc3ccc(Cl)cc3)c(=O)n12] | 2-[6-(4-chlorobenzyl)-8-(morpholin-4-yl)-5-oxo-5,6-dihydropyrido[2,3-e][1,2,4]triazolo[4,3-c]pyrimidin-3-yl]-n-(propan-2-yl)acetamide |

TABLE 2-continued

Selected compounds of the invention according to formula 1b and 1c.

| Example | Structure | Name |
|---|---|---|
| 104 | 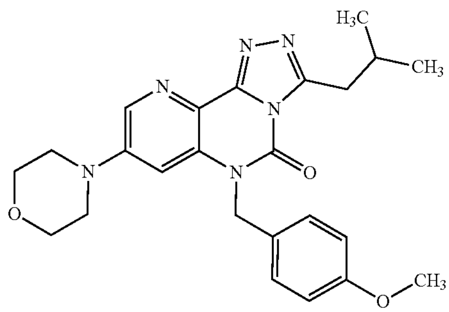 [SMILES: COc1ccc(Cn2c(=O)n3c(CC(C)C)nnc3c3ncc(N4CCOCC4)cc32)cc1] | 6-(4-methoxybenzyl)-3-(2-methylpropyl)-8-(morpholin-4-yl)pyrido[2,3-e][1,2,4]triazolo[4,3-c]pyrimidin-5(6H)-one |
| 105 | 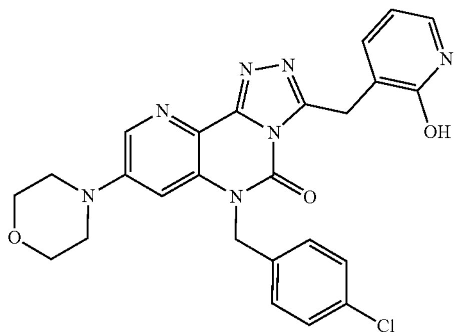 [SMILES: O=c1n(Cc2ccc(Cl)cc2)c2cc(N3CCOCC3)cnc2c2nnc(Cc3cccnc3O)n12] | 6-(4-chlorobenzyl)-3-[(2-hydroxypyridin-3-yl)methyl]-8-(morpholin-4-yl)pyrido[2,3-e][1,2,4]triazolo[4,3-c]pyrimidin-5(6H)-one |
| 106 | 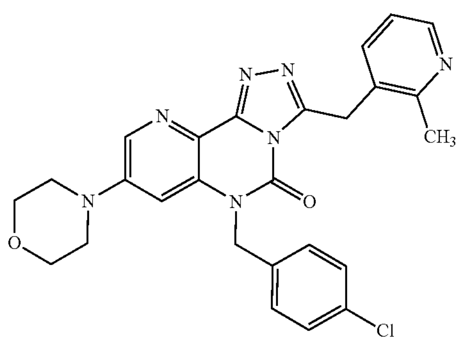 [SMILES: Cc1ncccc1Cc1nnc2c3ncc(N4CCOCC4)cc3n(Cc3ccc(Cl)cc3)c(=O)n12] | 6-(4-chlorobenzyl)-3-[(2-methylpyridin-3-yl)methyl]-8-(morpholin-4-yl)pyrido[2,3-e][1,2,4]triazolo[4,3-c]pyrimidin-5(6H)-one |
| 107 | 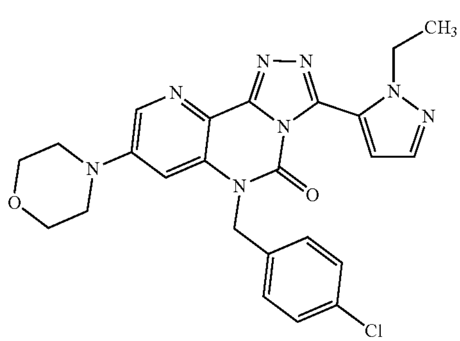 [SMILES: CCn1nccc1-c1nnc2c3ncc(N4CCOCC4)cc3n(Cc3ccc(Cl)cc3)c(=O)n12] | 6-(4-chlorobenzyl)-3-(1-ethyl-1h-pyrazol-5-yl)-8-(morpholin-4-yl)pyrido[2,3-e][1,2,4]triazolo[4,3-c]pyrimidin-5(6H)-one |

TABLE 2-continued

Selected compounds of the invention according to formula 1b and 1c.

| Example | Structure | Name |
| --- | --- | --- |
| 108 | 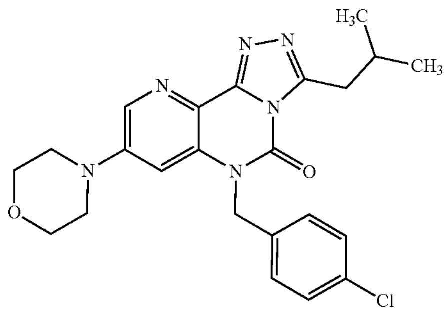 [SMILES: CC(C)Cc1nnc2c3ncc(N4CCOCC4)cc3n(Cc3ccc(Cl)cc3)c(=O)n12] | 6-(4-chlorobenzyl)-3-(2-methylpropyl)-8-(morpholin-4-yl)pyrido[2,3-e][1,2,4]triazolo[4,3-c]pyrimidin-5(6H)-one |
| 109 | 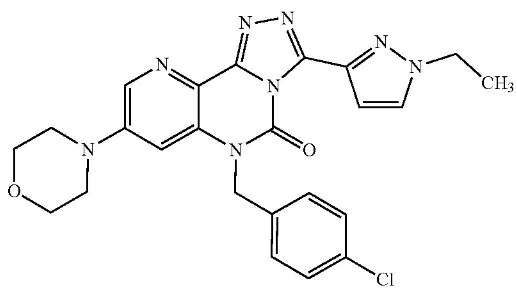 [SMILES: CCn1ccc(-c2nnc3c4ncc(N5CCOCC5)cc4n(Cc4ccc(Cl)cc4)c(=O)n23)n1] | 6-(4-chlorobenzyl)-3-(1-ethyl-1h-pyrazol-3-yl)-8-(morpholin-4-yl)pyrido[2,3-e][1,2,4]triazolo[4,3-c]pyrimidin-5(6H)-one |
| 110 | 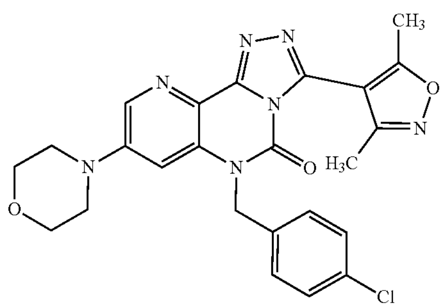 [SMILES: Cc1noc(C)c1-c1nnc2c3ncc(N4CCOCC4)cc3n(Cc3ccc(Cl)cc3)c(=O)n12] | 6-(4-chlorobenzyl)-3-(3,5-dimethyl-1,2-oxazol-4-yl)-8-(morpholin-4-yl)pyrido[2,3-e][1,2,4]triazolo[4,3-c]pyrimidin-5(6H)-one |

Preferred compounds according to the invention are compounds or an enantiomer, diastereomer, N-oxide, or a pharmaceutically acceptable salt or combinations thereof, is provided according to general formula Id selected from the compounds in Table 3 below:

TABLE 3

Selected compounds of the invention according to formula 1d.

| Example | Structure | Name |
| --- | --- | --- |
| 111 | 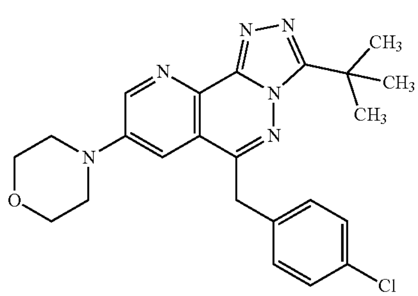 [SMILES: CC(C)(C)c1nnc2c3ncc(N4CCOCC4)cc3c(Cc3ccc(Cl)cc3)nn12] | 3-tert-butyl-6-(4-chlorobenzyl)-8-(morpholin-4-yl)pyrido[2,3-d][1,2,4]triazolo[4,3-b]pyridazine |

TABLE 3-continued

Selected compounds of the invention according to formula 1d.

| Example | Structure | Name |
|---|---|---|
| 112 | 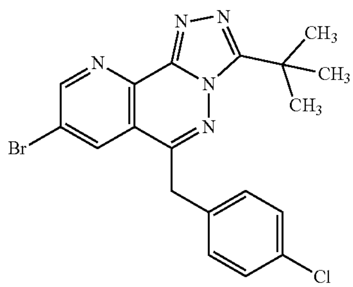 [SMILES: CC(C)(C)c1nnc2c3ncc(Br)cc3c(Cc3ccc(Cl)cc3)nn12] | 8-bromo-3-tert-butyl-6-(4-chlorobenzyl)pyrido[2,3-d][1,2,4]triazolo[4,3-b]pyridazine |
| 113 | 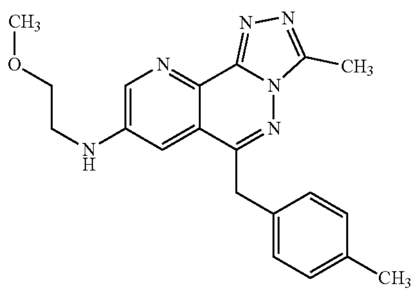 [SMILES: COCCNc1cnc2c(c1)c(Cc1ccc(C)cc1)nn1c(C)nnc21] | n-(2-methoxyethyl)-3-methyl-6-(4-methylbenzyl)pyrido[2,3-d][1,2,4]triazolo[4,3-b]pyridazin-8-amine |
| 114 | 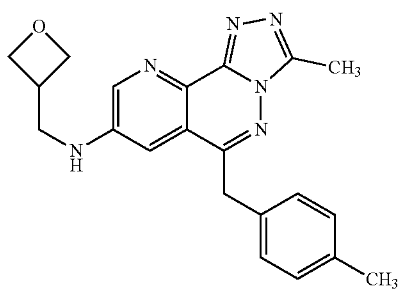 [SMILES: Cc1ccc(Cc2nn3c(C)nnc3c3ncc(NCC4COC4)cc23)cc1] | 3-methyl-6-(4-methylbenzyl)-n-(oxetan-3-ylmethyl)pyrido[2,3-d][1,2,4]triazolo[4,3-b]pyridazin-8-amine |
| 115 | 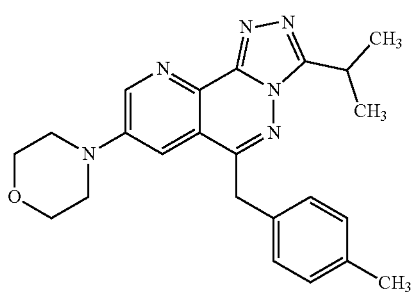 [SMILES: Cc1ccc(Cc2nn3c(C(C)C)nnc3c3ncc(N4CCOCC4)cc23)cc1] | 6-(4-methylbenzyl)-8-(morpholin-4-yl)-3-(propan-2-yl)pyrido[2,3-d][1,2,4]triazolo[4,3-b]pyridazine |
| 116 | 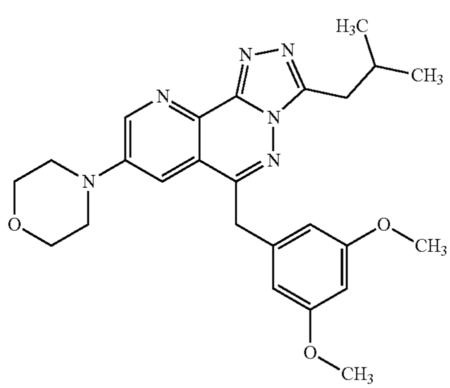 [SMILES: COc1cc(Cc2nn3c(CC(C)C)nnc3c3ncc(N4CCOCC4)cc23)cc(OC)c1] | 6-(3,5-dimethoxybenzyl)-3-(2-methylpropyl)-8-(morpholin-4-yl)pyrido[2,3-d][1,2,4]triazolo[4,3-b]pyridazine |

TABLE 3-continued

Selected compounds of the invention according to formula 1d.

| Example | Structure | Name |
| --- | --- | --- |
| 117 | 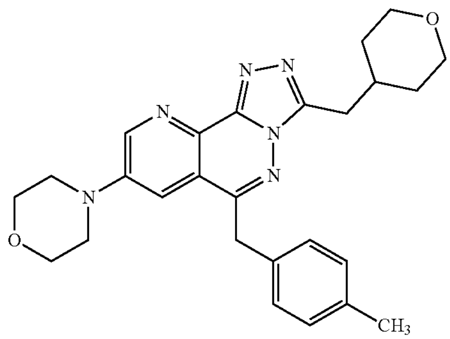 [SMILES: Cc1ccc(Cc2nn3c(CC4CCOCC4)nnc3c3ncc(N4CCOCC4)cc23)cc1] | 6-(4-methylbenzyl)-8-(morpholin-4-yl)-3-(tetrahydro-2H-pyran-4-ylmethyl)pyrido[2,3-d][1,2,4]triazolo[4,3-b]pyridazine |
| 118 | 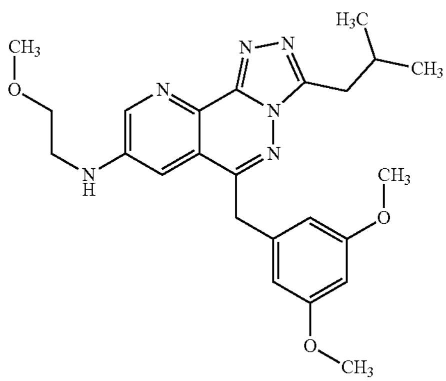 [SMILES: COCCNc1cnc2c(c1)c(Cc1cc(OC)cc(OC)c1)nn1c(CC(C)C)nnc21] | 6-(3,5-dimethoxybenzyl)-n-(2-methoxyethyl)-3-(2-methylpropyl)pyrido[2,3-d][1,2,4]triazolo[4,3-b]pyridazin-8-amine |
| 119 | 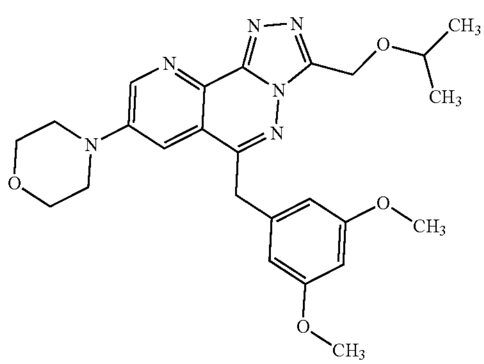 [SMILES: COc1cc(Cc2nn3c(COC(C)C)nnc3c3ncc(N4CCOCC4)cc23)cc(OC)c1] | 6-(3,5-dimethoxybenzyl)-8-(morpholin-4-yl)-3-[(propan-2-yloxy)methyl]pyrido[2,3-d][1,2,4]triazolo[4,3-b]pyridazine |
| 120 | 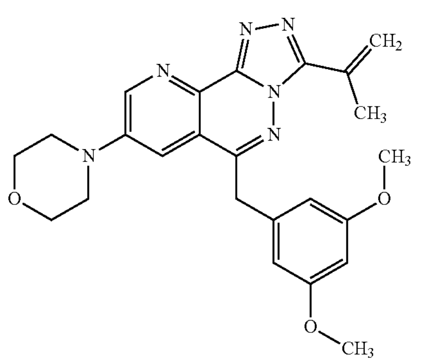 [SMILES: C=C(C)c1nnc2c3ncc(N4CCOCC4)cc3c(Cc3cc(OC)cc(OC)c3)nn12] | 6-(3,5-dimethoxybenzyl)-8-(morpholin-4-yl)-3-(prop-1-en-2-yl)pyrido[2,3-d][1,2,4]triazolo[4,3-b]pyridazine |

TABLE 3-continued

Selected compounds of the invention according to formula 1d.

| Example | Structure | Name |
|---|---|---|
| 121 | 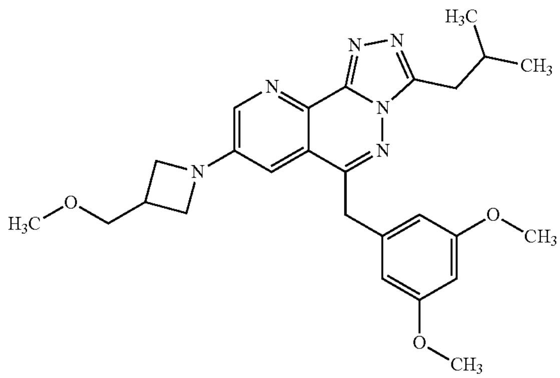 | 6-(3,5-dimethoxybenzyl)-8-[3-(methoxymethyl)azetidin-1-yl]-3-(2-methylpropyl)pyrido[2,3-d][1,2,4]triazolo[4,3-b]pyridazine |
| 122 | 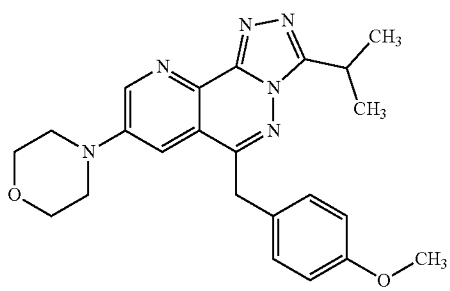 [SMILES: COc1ccc(Cc2nn3c(C(C)C)nnc3c3ncc(N4CCOCC4)cc23)cc1] | 6-(4-methoxybenzyl)-8-(morpholin-4-yl)-3-(propan-2-yl)pyrido[2,3-d][1,2,4]triazolo[4,3-b]pyridazine |
| 123 | 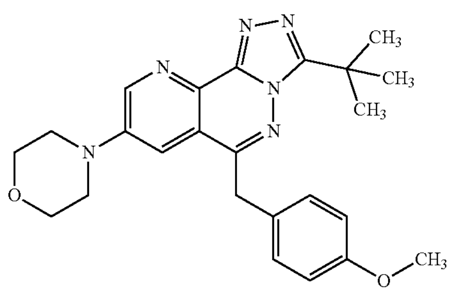 [SMILES: COc1ccc(Cc2nn3c(C(C)(C)C)nnc3c3ncc(N4CCOCC4)cc23)cc1] | 3-tert-butyl-6-(4-methoxybenzyl)-8-(morpholin-4-yl)pyrido[2,3-d][1,2,4]triazolo[4,3-b]pyridazine |
| 124 | 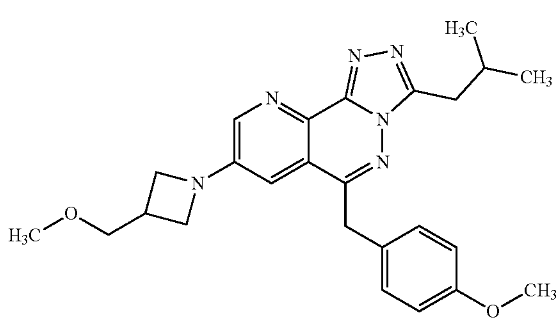 | 6-(4-methoxybenzyl)-8-[3-(methoxymethyl)azetidin-1-yl]-3-(2-methylpropyl)pyrido[2,3-d][1,2,4]triazolo[4,3-b]pyridazine |

TABLE 3-continued

Selected compounds of the invention according to formula 1d.

| Example | Structure | Name |
|---|---|---|
| 125 | 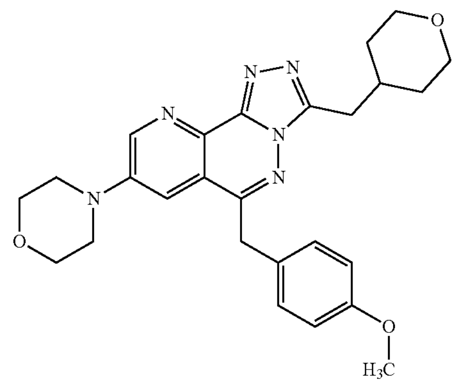 [SMILES: COc1ccc(Cc2nn3c(CC4CCOCC4)nnc3c3ncc(N4CCOCC4)cc23)cc1] | 6-(4-methoxybenzyl)-8-(morpholin-4-yl)-3-(tetrahydro-2H-pyran-4-ylmethyl)pyrido[2,3-d][1,2,4]triazolo[4,3-b]pyridazine |
| 126 | 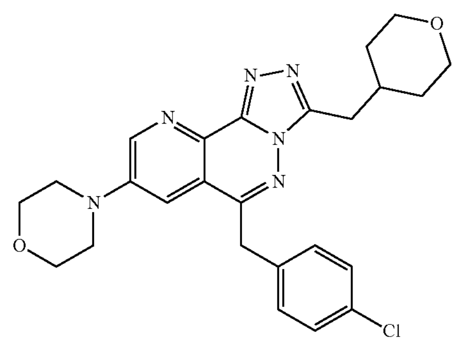 [SMILES: Clc1ccc(Cc2nn3c(CC4CCOCC4)nnc3c3ncc(N4CCOCC4)cc23)cc1] | 6-(4-chlorobenzyl)-8-(morpholin-4-yl)-3-(tetrahydro-2H-pyran-4-ylmethyl)pyrido[2,3-d][1,2,4]triazolo[4,3-b]pyridazine |
| 127 | 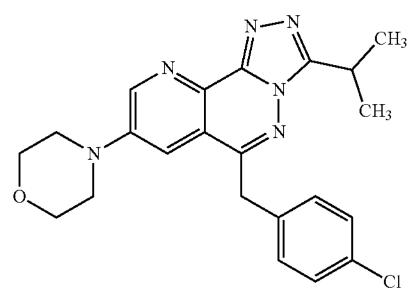 [SMILES: CC(C)c1nnc2c3ncc(N4CCOCC4)cc3c(Cc3ccc(Cl)cc3)nn12] | 6-(4-chlorobenzyl)-8-(morpholin-4-yl)-3-(propan-2-yl)pyrido[2,3-d][1,2,4]triazolo[4,3-b]pyridazine |
| 128 | 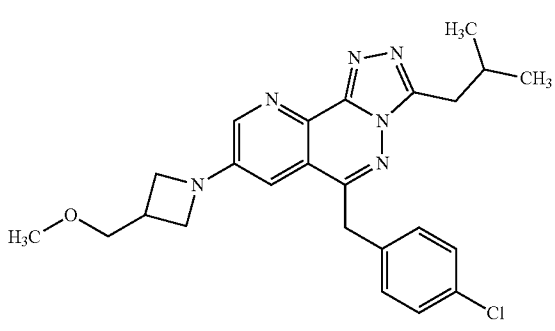 [SMILES: COCC1CN(c2cnc3c(c2)c(Cc2ccc(Cl)cc2)nn2c(CC(C)C)nnc32)C1] | 6-(4-chlorobenzyl)-8-[3-(methoxymethyl)azetidin-1-yl]-3-(2-methylpropyl)pyrido[2,3-d][1,2,4]triazolo[4,3-b]pyridazine |

TABLE 3-continued

Selected compounds of the invention according to formula 1d.

| Example | Structure | Name |
|---|---|---|
| 129 | 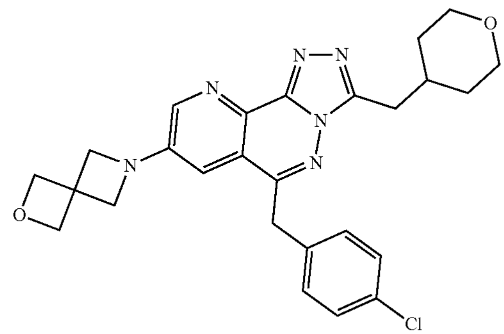 [SMILES: Clc1ccc(Cc2nn3c(CC4CCOCC4)nnc3c3ncc(N4CC5(COC5)C4)cc23)cc1] | 6-(4-chlorobenzyl)-8-(2-oxa-6-azaspiro[3.3]heptan-6-yl)-3-(tetrahydro-2H-pyran-4-ylmethyl)pyrido[2,3-d][1,2,4]triazolo[4,3-b]pyridazine |
| 130 | 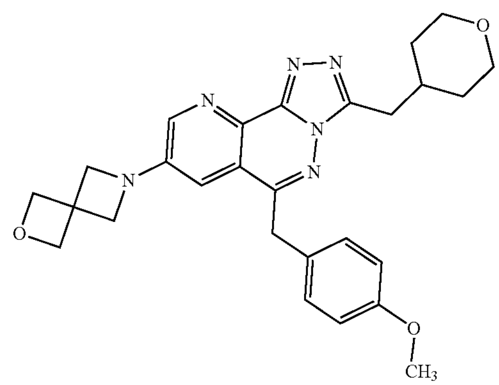 [SMILES: COc1ccc(Cc2nn3c(CC4CCOCC4)nnc3c3ncc(N4CC5(COC5)C4)cc23)cc1] | 6-(4-methoxybenzyl)-8-(2-oxa-6-azaspiro[3.3]heptan-6-yl)-3-(tetrahydro-2H-pyran-4-ylmethyl)pyrido[2,3-d][1,2,4]triazolo[4,3-b]pyridazine |
| 131 | 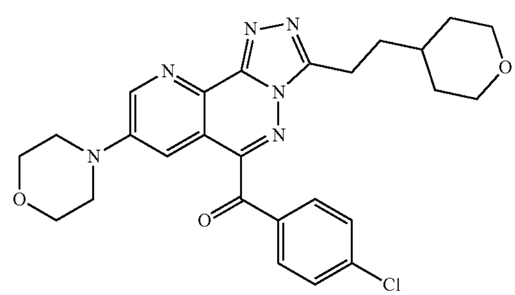 [SMILES: O=C(c1ccc(Cl)cc1)c1nn2c(CCC3CCOCC3)nnc2c2ncc(N3CCOCC3)cc12] | (4-chlorophenyl){8-(morpholin-4-yl)-3-[2-(tetrahydro-2H-pyran-4-yl)ethyl]pyrido[2,3-d][1,2,4]triazolo[4,3-b]pyridazin-6-yl}methanone |
| 132 | 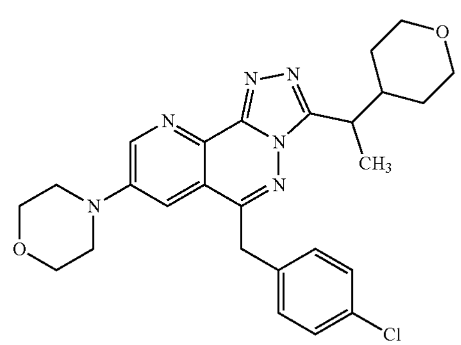 [SMILES: CC(c1nnc2c3ncc(N4CCOCC4)cc3c(Cc3ccc(Cl)cc3)nn12)C1CCOCC1] | 6-(4-chlorobenzyl)-8-(morpholin-4-yl)-3-[1-(tetrahydro-2H-pyran-4-yl)ethyl]pyrido[2,3-d][1,2,4]triazolo[4,3-b]pyridazine |

TABLE 3-continued

Selected compounds of the invention according to formula 1d.

| Example | Structure | Name |
|---|---|---|
| 133 | 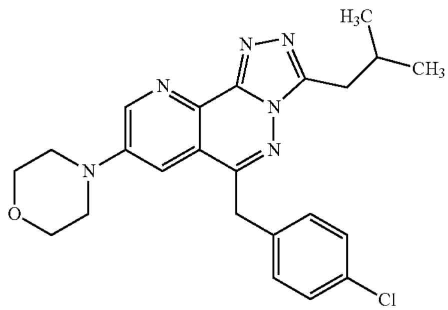 [SMILES: CC(C)Cc1nnc2c3ncc(N4CCOCC4)cc3c(Cc3ccc(Cl)cc3)nn12] | 6-(4-chlorobenzyl)-3-(2-methylpropyl)-8-(morpholin-4-yl)pyrido[2,3-d][1,2,4]triazolo[4,3-b]pyridazine |
| 134 | 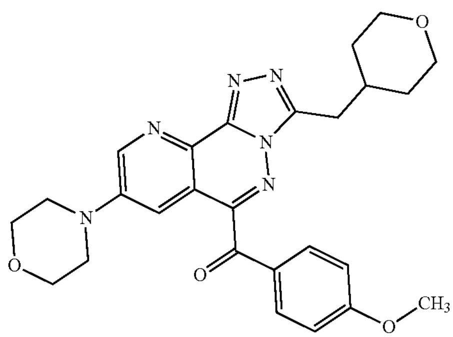 [SMILES: COc1ccc(C(=O)c2nn3c(CC4CCOCC4)nnc3c3ncc(N4CCOCC4)cc23)cc1] | (4-methoxyphenyl)[8-(morpholin-4-yl)-3-(tetrahydro-2H-pyran-4-ylmethyl)pyrido[2,3-d][1,2,4]triazolo[4,3-b]pyridazin-6-yl]methanone |
| 135 | 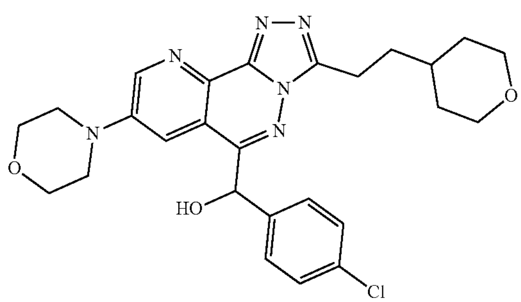 [SMILES: OC(c1ccc(Cl)cc1)c1nn2c(CCC3CCOCC3)nnc2c2ncc(N3CCOCC3)cc12] | (4-chlorophenyl){8-(morpholin-4-yl)-3-[2-(tetrahydro-2H-pyran-4-yl)ethyl]pyrido[2,3-d][1,2,4]triazolo[4,3-b]pyridazin-6-yl}methanol |
| 136 | 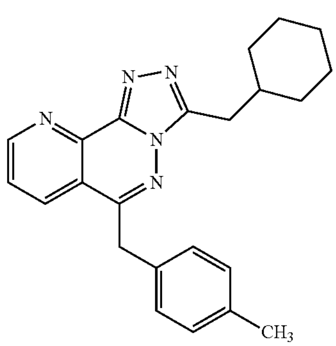 [SMILES: Cc1ccc(Cc2nn3c(CC4CCCCC4)nnc3c3ncccc23)cc1] | 3-(cyclohexylmethyl)-6-(4-methylbenzyl)pyrido[2,3-d][1,2,4]triazolo[4,3-b]pyridazine |

TABLE 3-continued

Selected compounds of the invention according to formula 1d.

| Example | Structure | Name |
|---|---|---|
| 137 | 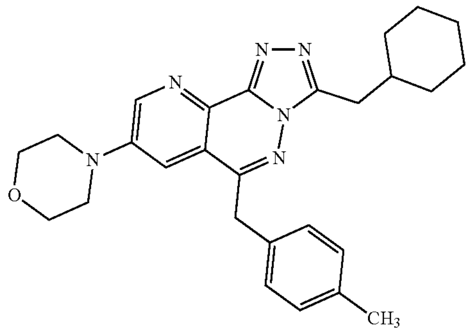 [SMILES: Cc1ccc(Cc2nn3c(CC4CCCCC4)nnc3c3ncc(N4CCOCC4)cc23)cc1] | 3-(cyclohexylmethyl)-6-(4-methylbenzyl)-8-(morpholin-4-yl)pyrido[2,3-d][1,2,4]triazolo[4,3-b]pyridazine |
| 138 | 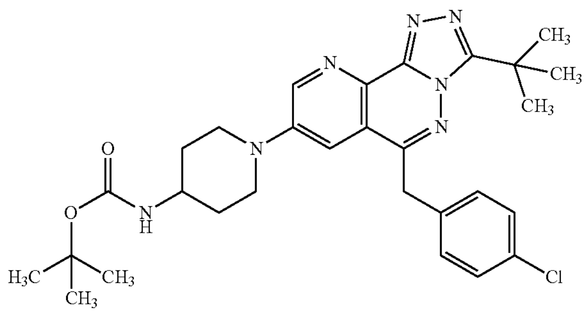 [SMILES: CC(C)(C)OC(=O)NC1CCN(c2cnc3c(c2)c(Cc2ccc(Cl)cc2)nn2c(C(C)(C)C)nnc32)CC1] | tert-butyl n-[1-[5-tert-butyl-8-(4-chlorobenzyl)-3,4,6,7,13-pentazatricyclo[7.4.0.02,6]trideca-1(9),2,4,7,10,12-hexaen-11-yl]-4-piperidyl]carbamate |
| 139 | 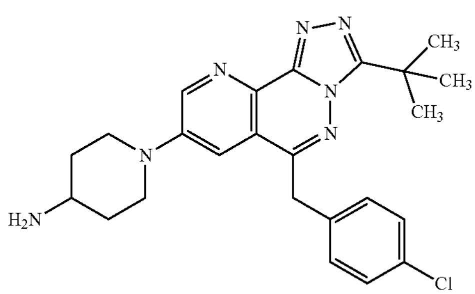 [SMILES: CC(C)(C)c1nnc2c3ncc(N4CCC(N)CC4)cc3c(Cc3ccc(Cl)cc3)nn12] | 1-[5-tert-butyl-8-(4-chlorobenzyl)-3,4,6,7,13-pentazatricyclo[7.4.0.02,6]trideca-1(9),2,4,7,10,12-hexaen-11-yl]piperidin-4-amine |
| 140 | 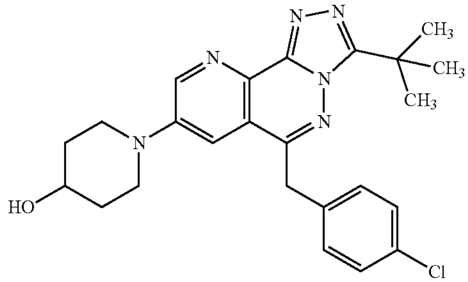 [SMILES: CC(C)(C)c1nnc2c3ncc(N4CCC(O)CC4)cc3c(Cc3ccc(Cl)cc3)nn12] | 1-[5-tert-butyl-8-(4-chlorobenzyl)-3,4,6,7,13-pentazatricyclo[7.4.0.02,6]trideca-1(9),2,4,7,10,12-hexaen-11-yl]piperidin-4-ol |

Preferred compounds according to the invention are compounds or an enantiomer, diastereomer, N-oxide, or a pharmaceutically acceptable salt or combinations thereof, is provided according to general formula 1e selected from the compounds in Table 4 below:

TABLE 4

Selected compounds of the invention according to formula 1e.

| Example | Structure | Name |
|---|---|---|
| 141 | 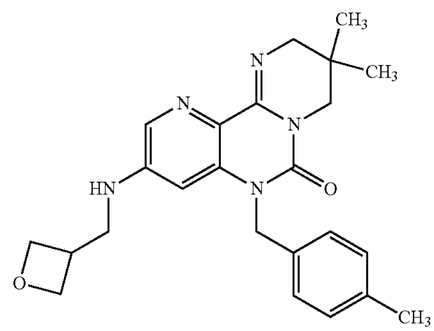 [SMILES: Cc1ccc(CN2C(=O)N3CC(C)(C)CN=C3c3ncc(NCC4COC4)cc32)cc1] | 9,9-dimethyl-5-(4-methylbenzyl)-3-{[(oxetan-3-yl)methyl]amino}-5,8,9,10-tetrahydro-6H-pyrido[2,3-e]pyrimido[1,2-c]pyrimidin-6-one |
| 142 | 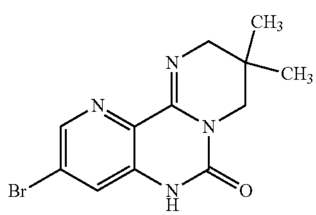 [SMILES: CC1(C)CN=C2c3ncc(Br)cc3NC(=O)N2C1] | 3-bromo-9,9-dimethyl-5,8,9,10-tetrahydro-6H-pyrido[2,3-e]pyrimido[1,2-c]pyrimidin-6-one |
| 143 | 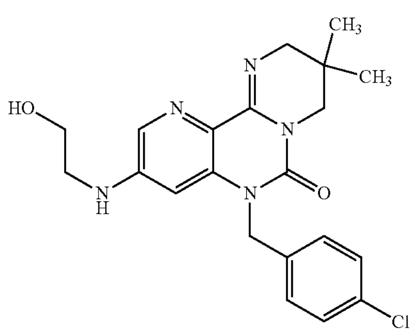 [SMILES: CC1(C)CN=C2c3ncc(NCCO)cc3N(Cc3ccc(Cl)cc3)C(=O)N2C1] | 5-(4-chlorobenzyl)-3-[(2-hydroxyethyl)amino]-9,9-dimethyl-5,8,9,10-tetrahydro-6H-pyrido[2,3-e]pyrimido[1,2-c]pyrimidin-6-one |
| 144 | 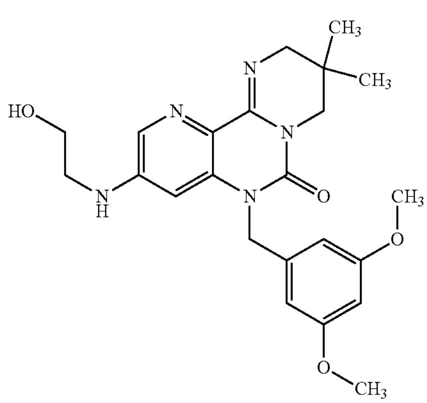 [SMILES: COc1cc(CN2C(=O)N3CC(C)(C)CN=C3c3ncc(NCCO)cc32)cc(OC)c1] | 5-(3,5-dimethoxybenzyl)-3-[(2-hydroxyethyl)amino]-9,9-dimethyl-5,8,9,10-tetrahydro-6H-pyrido[2,3-e]pyrimido[1,2-c]pyrimidin-6-one |

TABLE 4-continued

Selected compounds of the invention according to formula 1e.

| Example | Structure | Name |
|---|---|---|
| 145 | 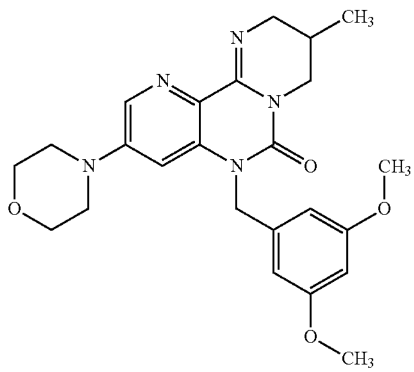 [SMILES: COc1cc(CN2C(=O)N3CC(C)CN=C3c3ncc(N4CCOCC4)cc32)cc(OC)c1] | 5-(3,5-dimethoxybenzyl)-9-methyl-3-(morpholin-4-yl)-5,8,9,10-tetrahydro-6H-pyrido[2,3-e]pyrimido[1,2-c]pyrimidin-6-one |
| 146 | 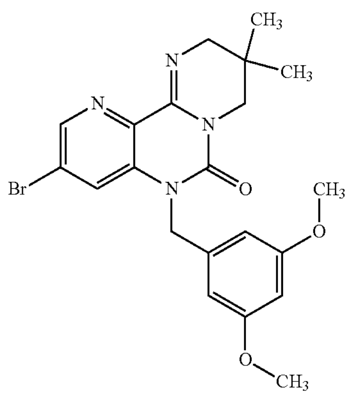 [SMILES: COc1cc(CN2C(=O)N3CC(C)(C)CN=C3c3ncc(Br)cc32)cc(OC)c1] | 3-bromo-5-(3,5-dimethoxybenzyl)-9,9-dimethyl-5,8,9,10-tetrahydro-6H-pyrido[2,3-e]pyrimido[1,2-c]pyrimidin-6-one |
| 147 | 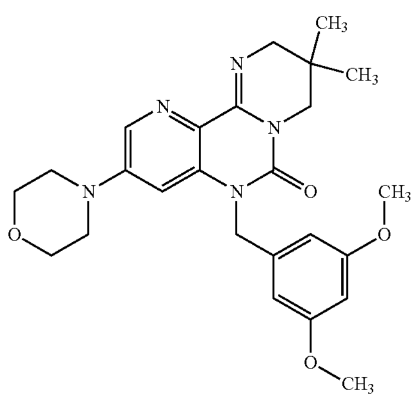 [SMILES: COc1cc(CN2C(=O)N3CC(C)(C)CN=C3c3ncc(N4CCOCC4)cc32)cc(OC)c1] | 5-(3,5-dimethoxybenzyl)-9,9-dimethyl-3-(morpholin-4-yl)-5,8,9,10-tetrahydro-6H-pyrido[2,3-e]pyrimido[1,2-c]pyrimidin-6-one |
| 148 | 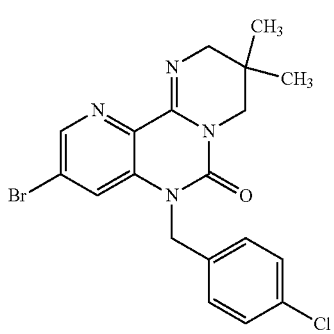 [SMILES: CC1(C)CN=C2c3ncc(Br)cc3N(Cc3ccc(Cl)cc3)C(=O)N2C1] | 3-bromo-5-(4-chlorobenzyl)-9,9-dimethyl-5,8,9,10-tetrahydro-6H-pyrido[2,3-e]pyrimido[1,2-c]pyrimidin-6-one |

TABLE 4-continued

Selected compounds of the invention according to formula 1e.

| Example | Structure | Name |
|---|---|---|
| 149 | 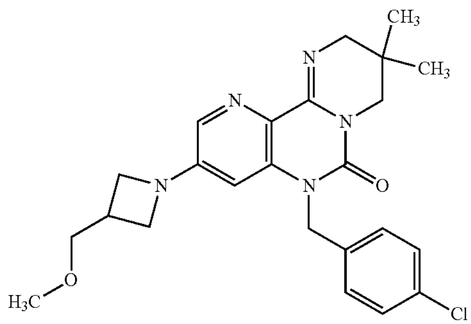 [SMILES: COCC1CN(c2cnc3c(c2)N(Cc2ccc(Cl)cc2)C(=O)N2CC(C)(C)CN=C32)C1] | 5-(4-chlorobenzyl)-3-[3-(methoxymethyl)azetidin-1-yl]-9,9-dimethyl-5,8,9,10-tetrahydro-6H-pyrido[2,3-e]pyrimido[1,2-c]pyrimidin-6-one |
| 150 | 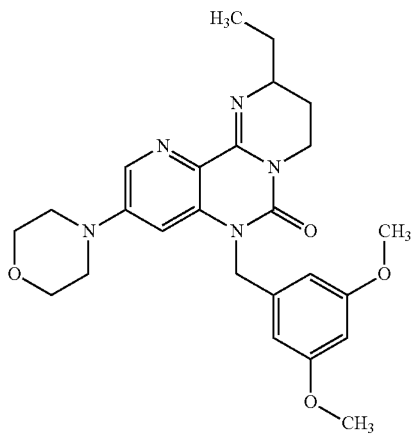 [SMILES: CCC1CCN2C(=O)N(Cc3cc(OC)cc(OC)c3)c3cc(N4CCOCC4)cnc3C2=N1] | 5-(3,5-dimethoxybenzyl)-10-ethyl-3-(morpholin-4-yl)-5,8,9,10-tetrahydro-6H-pyrido[2,3-e]pyrimido[1,2-c]pyrimidin-6-one |
| 151 | 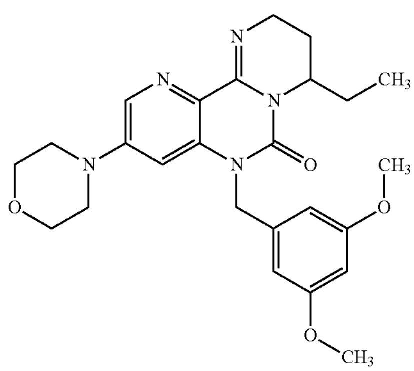 [SMILES: CCC1CCN=C2c3ncc(N4CCOCC4)cc3N(Cc3cc(OC)cc(OC)c3)C(=O)N21] | 5-(3,5-dimethoxybenzyl)-8-ethyl-3-(morpholin-4-yl)-5,8,9,10-tetrahydro-6H-pyrido[2,3-e]pyrimido[1,2-c]pyrimidin-6-one |
| 152 | 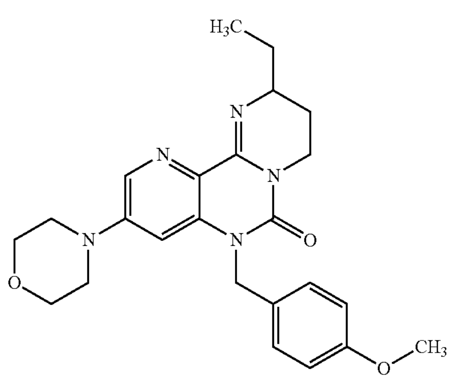 [SMILES: CCC1CCN2C(=O)N(Cc3ccc(OC)cc3)c3cc(N4CCOCC4)cnc3C2=N1] | 10-ethyl-5-(4-methoxybenzyl)-3-(morpholin-4-yl)-5,8,9,10-tetrahydro-6H-pyrido[2,3-e]pyrimido[1,2-c]pyrimidin-6-one |

TABLE 4-continued

Selected compounds of the invention according to formula 1e.

| Example | Structure | Name |
|---|---|---|
| 153 | 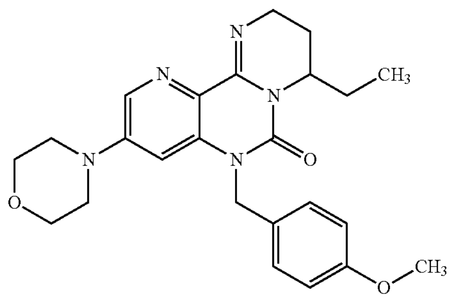 [SMILES: CCC1CCN=C2c3ncc(N4CCOCC4)cc3N(Cc3ccc(OC)cc3)C(=O)N21] | 8-ethyl-5-(4-methoxybenzyl)-3-(morpholin-4-yl)-5,8,9,10-tetrahydro-6H-pyrido[2,3-e]pyrimido[1,2-c]pyrimidin-6-one |
| 154 | 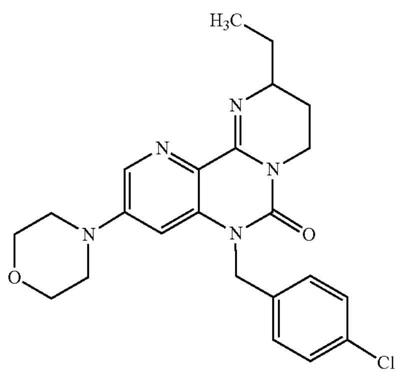 [SMILES: CCC1CCN2C(=O)N(Cc3ccc(Cl)cc3)c3cc(N4CCOCC4)cnc3C2=N1] | 5-(4-chlorobenzyl)-10-ethyl-3-(morpholin-4-yl)-5,8,9,10-tetrahydro-6H-pyrido[2,3-e]pyrimido[1,2-c]pyrimidin-6-one |
| 155 | 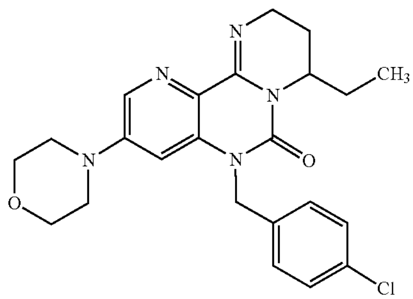 [SMILES: CCC1CCN=C2c3ncc(N4CCOCC4)cc3N(Cc3ccc(Cl)cc3)C(=O)N21] | 5-(4-chlorobenzyl)-8-ethyl-3-(morpholin-4-yl)-5,8,9,10-tetrahydro-6H-pyrido[2,3-e]pyrimido[1,2-c]pyrimidin-6-one |

Preferred compounds according to the invention are compounds or an enantiomer, diastereomer, N-oxide, or a pharmaceutically acceptable salt or combinations thereof, which are provided according to general formula 1a-1f selected from the compounds in Table 5 below:

TABLE 5

Selected compounds of the invention according to formula 1a-1f.

| Example | Structure | Name |
|---|---|---|
| 156 | 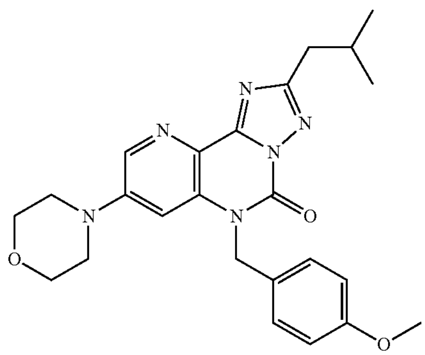 [SMILES: COc1ccc(Cn2c(=O)n3nc(CC(C)C)nc3c3ncc(N4CCOCC4)cc32)cc1] | 6-(4-methoxybenzyl)-2-(2-methylpropyl)-8-(morpholin-4-yl)pyrido[2,3-e][1,2,4]triazolo[1,5-c]pyrimidin-5(6H)-one |
| 157 | 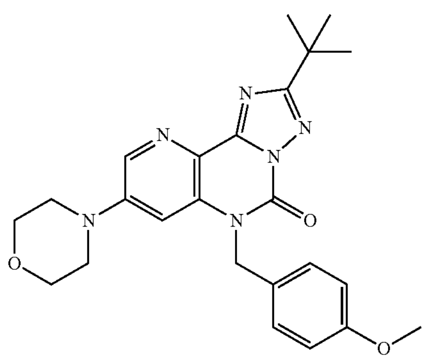 [SMILES: COc1ccc(Cn2c(=O)n3nc(C(C)(C)C)nc3c3ncc(N4CCOCC4)cc32)cc1] | 2-tert-butyl-6-(4-methoxybenzyl)-8-(morpholin-4-yl)pyrido[2,3-e][1,2,4]triazolo[1,5-c]pyrimidin-5(6H)-one |
| 158 | 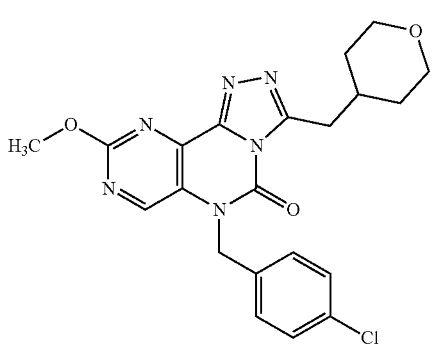 [SMILES: COc1ncc2c(n1)c1nnc(CC3CCOCC3)n1c(=O)n2Cc1ccc(Cl)cc1] | 6-(4-chlorobenzyl)-9-methoxy-3-(tetrahydro-2H-pyran-4-ylmethyl)pyrimido[4,5-e][1,2,4]triazolo[4,3-c]pyrimidin-5(6H)-one |

TABLE 5-continued

Selected compounds of the invention according to formula 1a-1f.

| Example | Structure | Name |
|---|---|---|
| 159 | 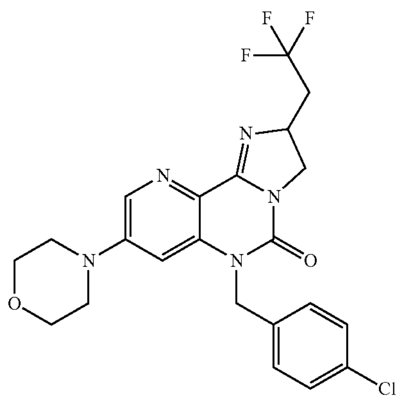 [SMILES: O=C1N2CC(CC(F)(F)F)N=C2c2ncc(N3CCOCC3)cc2N1Cc1ccc(Cl)cc1] | 6-(4-chlorobenzyl)-8-morpholino-2-(2,2,2-trifluoroethyl)-2,6-dihydroimidazo[1,2-c]pyrido[2,3-e]pyrimidin-5(3H)-one |
| 160 | 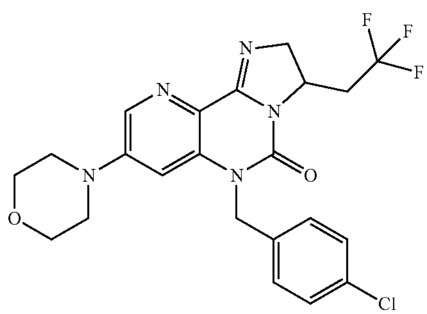 [SMILES: O=C1N(Cc2ccc(Cl)cc2)c2cc(N3CCOCC3)cnc2C2=NCC(CC(F)(F)F)N12] | 6-(4-chlorobenzyl)-8-morpholino-3-(2,2,2-trifluoroethyl)-2,6-dihydroimidazo[1,2-c]pyrido[2,3-e]pyrimidin-5(3H)-one |
| 161 | 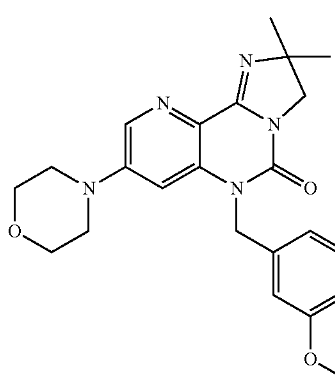 | 6-(3,5-dimethoxybenzyl)-2,2-dimethyl-8-(morpholin-4-yl)-2,6-dihydroimidazo[1,2-c]pyrido[2,3-e]pyrimidin-5(3H)-one |
| 162 | 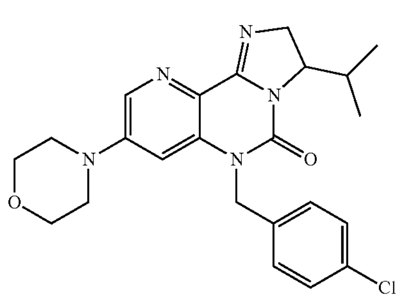 [SMILES: CC(C)C1CN=C2c3ncc(N4CCOCC4)cc3N(Cc3ccc(Cl)cc3)C(=O)N21] | 6-(4-chlorobenzyl)-8-(morpholin-4-yl)-3-(propan-2-yl)-2,6-dihydroimidazo[1,2-c]pyrido[2,3-e]pyrimidin-5(3H)-one |

TABLE 5-continued

Selected compounds of the invention according to formula 1a-1f.

| Example | Structure | Name |
|---|---|---|
| 163 | 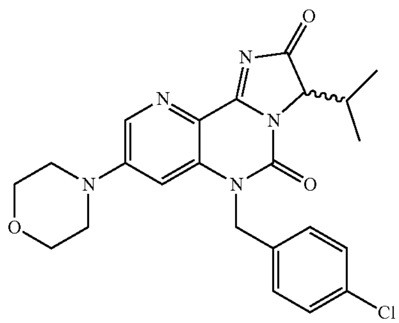 [SMILES: CC(C)C1C(=O)N=C2c3ncc(N4CCOCC4)cc3N(Cc3ccc(Cl)cc3)C(=O)N21] | 6-(4-chlorobenzyl)-8-(morpholin-4-yl)-3-(propan-2-yl)imidazo[1,2-c]pyrido[2,3-e]pyrimidine-2,5(3H,6H)-dione |
| 164 | 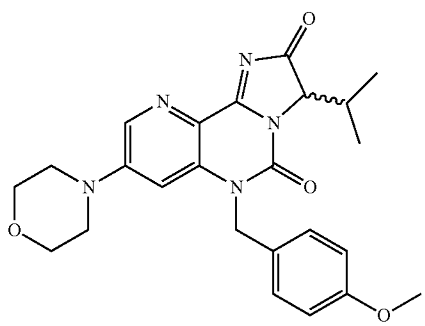 [SMILES: COc1ccc(CN2C(=O)N3C(=NC(=O)C3C(C)C)c3ncc(N4CCOCC4)cc32)cc1] | 6-(4-methoxybenzyl)-8-(morpholin-4-yl)-3-(propan-2-yl)imidazo[1,2-c]pyrido[2,3-e]pyrimidine-2,5(3H,6H)-dione |
| 165 | 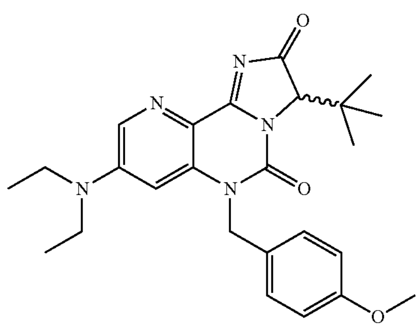 [SMILES: CCN(CC)c1cnc2c(c1)N(Cc1ccc(OC)cc1)C(=O)N1C2=NC(=O)C1C(C)(C)C] | 3-tert-butyl-8-(diethylamino)-6-(4-methoxybenzyl)imidazo[1,2-c]pyrido[2,3-e]pyrimidine-2,5(3H,6H)-dione |
| 166 | 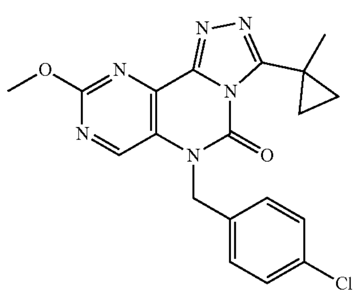 [SMILES: COc1ncc2c(n1)c1nnc(C3(C)CC3)n1c(=O)n2Cc1ccc(Cl)cc1] | 6-(4-chlorobenzyl)-9-methoxy-3-(1-methylcyclopropyl)pyrimido[4,5-e][1,2,4]triazolo[4,3-c]pyrimidin-5(6H)-one |
| 167 | 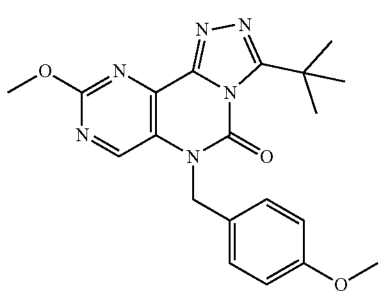 | 3-tert-butyl-9-methoxy-6-(4-methoxybenzyl)pyrimido[4,5-e][1,2,4]triazolo[4,3-c]pyrimidin-5(6H)-one |

TABLE 5-continued

Selected compounds of the invention according to formula 1a-1f.

| Example | Structure | Name |
|---|---|---|
| 168 | 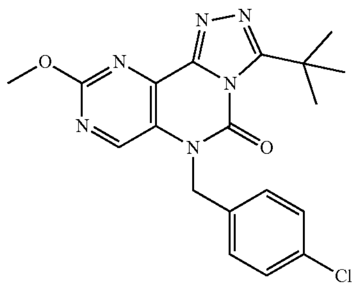 [SMILES: COc1ncc2c(n1)c1nnc(C(C)(C)C)n1c(=O)n2Cc1ccc(Cl)cc1] | 3-tert-butyl-6-(4-chlorobenzyl)-9-methoxypyrimido[4,5-e][1,2,4]triazolo[4,3-c]pyrimidin-5(6H)-one |
| 169 | 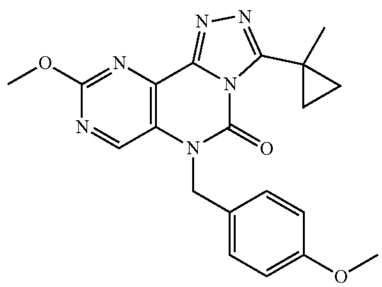 | 9-methoxy-6-(4-methoxybenzyl)-3-(1-methylcyclopropyl)pyrimido[4,5-e][1,2,4]triazolo[4,3-c]pyrimidin-5(6H)-one |
| 170 | 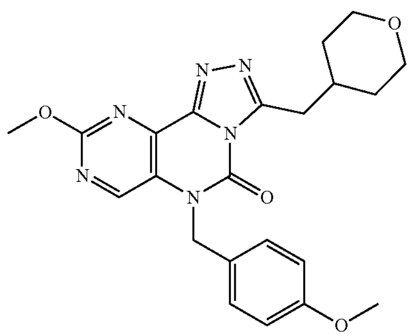 [SMILES: COc1ccc(Cn2c(=O)n3c(CC4CCOCC4)nnc3c3nc(OC)ncc32)cc1] | 9-methoxy-6-(4-methoxybenzyl)-3-(tetrahydro-2H-pyran-4-ylmethyl)pyrimido[4,5-e][1,2,4]triazolo[4,3-c]pyrimidin-5(6H)-one |
| 171 | 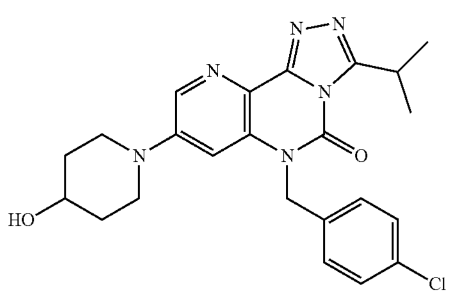 [SMILES: CC(C)c1nnc2c3ncc(N4CCC(O)CC4)cc3n(Cc3ccc(Cl)cc3)c(=O)n12] | 6-(4-chlorobenzyl)-8-(4-hydroxypiperidin-1-yl)-3-(propan-2-yl)pyrido[2,3-e][1,2,4]triazolo[4,3-c]pyrimidin-5(6H)-one |
| 172 | 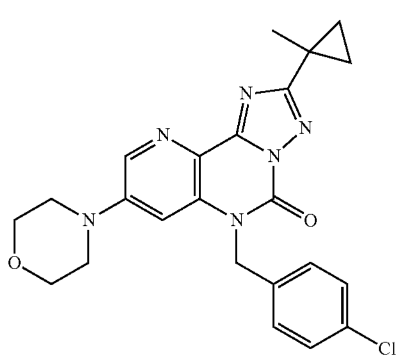 [SMILES: CC1(c2nc3c4ncc(N5CCOCC5)cc4n(Cc4ccc(Cl)cc4)c(=O)n3n2)CC1] | 6-(4-chlorobenzyl)-2-(1-methylcyclopropyl)-8-(morpholin-4-yl)pyrido[2,3-e][1,2,4]triazolo[1,5-c]pyrimidin-5(6H)-one |

TABLE 5-continued

Selected compounds of the invention according to formula 1a-1f.

| Example | Structure | Name |
|---|---|---|
| 173 | 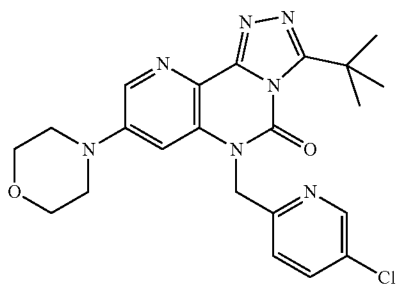 [SMILES: CC(C)(C)c1nnc2c3ncc(N4CCOCC4)cc3n(Cc3ccc(Cl)cn3)c(=O)n12] | 3-tert-butyl-6-[(5-chloropyridin-2-yl)methyl]-8-(morpholin-4-yl)pyrido[2,3-e][1,2,4]triazolo[4,3-c]pyrimidin-5(6H)-one |
| 174 | 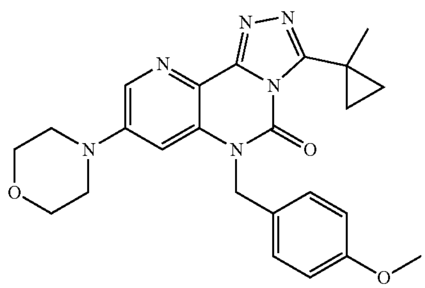 [SMILES: COc1ccc(Cn2c(=O)n3c(C4(C)CC4)nnc3c3ncc(N4CCOCC4)cc32)cc1] | 6-(4-methoxybenzyl)-3-(1-methylcyclopropyl)-8-(morpholin-4-yl)pyrido[2,3-e][1,2,4]triazolo[4,3-c]pyrimidin-5(6H)-one |
| 175 | 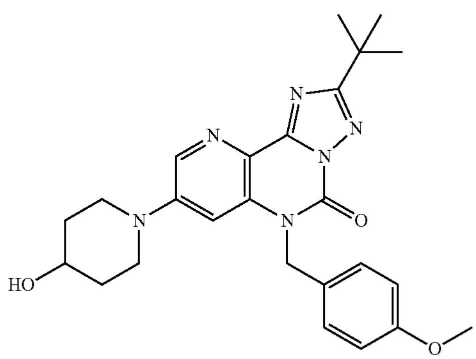 [SMILES: COc1ccc(Cn2c(=O)n3nc(C(C)(C)C)nc3c3ncc(N4CCC(O)CC4)cc32)cc1] | 2-tert-butyl-8-(4-hydroxypiperidin-1-yl)-6-(4-methoxybenzyl)pyrido[2,3-e][1,2,4]triazolo[1,5-c]pyrimidin-5(6H)-one |
| 176 | 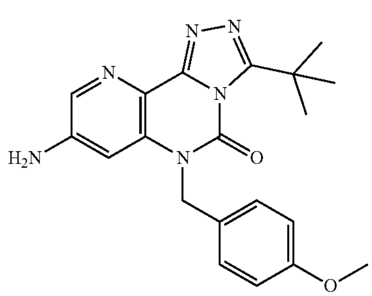 [SMILES: COc1ccc(Cn2c(=O)n3c(C(C)(C)C)nnc3c3ncc(N)cc32)cc1] | 8-amino-3-tert-butyl-6-(4-methoxybenzyl)pyrido[2,3-e][1,2,4]triazolo[4,3-c]pyrimidin-5(6H)-one |
| 177 | 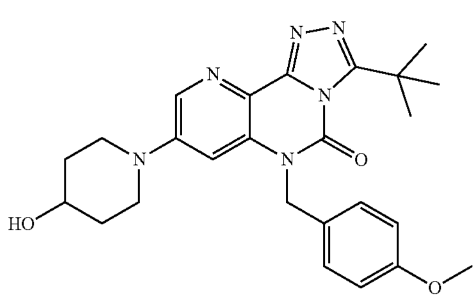 [SMILES: COc1ccc(Cn2c(=O)n3c(C(C)(C)C)nnc3c3ncc(N4CCC(O)CC4)cc32)cc1] | 3-tert-butyl-8-(4-hydroxypiperidin-1-yl)-6-(4-methoxybenzyl)pyrido[2,3-e][1,2,4]triazolo[4,3-c]pyrimidin-5(6H)-one |

TABLE 5-continued

Selected compounds of the invention according to formula 1a-1f.

| Example | Structure | Name |
|---|---|---|
| 178 | 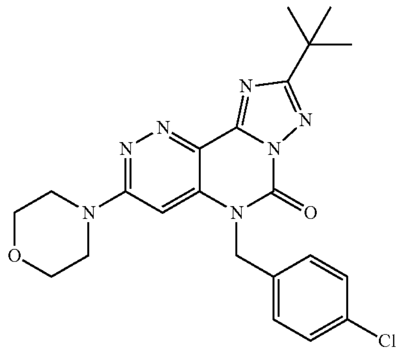 [SMILES: CC(C)(C)c1nc2c3nnc(N4CCOCC4)cc3n(Cc3ccc(Cl)cc3)c(=O)n2n1] | 9-tert-butyl-5-(4-chlorobenzyl)-3-(morpholin-4-yl)[1,2,4]triazolo[1',5':1,6]pyrimido[5,4-c]pyridazin-6(5h)-one |
| 179 | 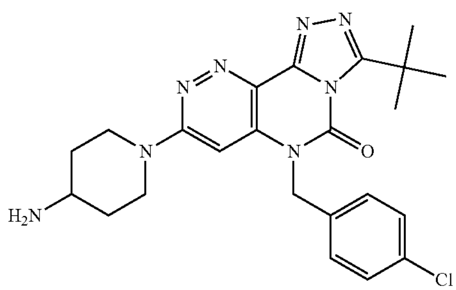 [SMILES: CC(C)(C)c1nnc2c3nnc(N4CCC(N)CC4)cc3n(Cc3ccc(Cl)cc3)c(=O)n12] | 8-(4-aminopiperidin-1-yl)-3-tert-butyl-6-(4-chlorobenzyl)[1,2,4]triazolo[4',3':1,6]pyrimido[5,4-c]pyridazin-5(6H)-one |
| 180 | 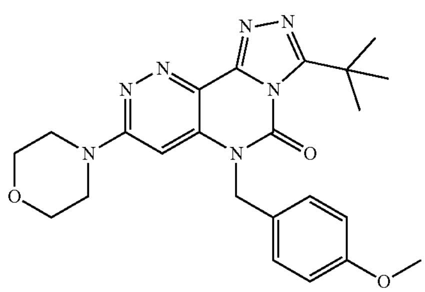 [SMILES: COc1ccc(Cn2c(=O)n3c(C(C)(C)C)nnc3c3nnc(N4CCOCC4)cc32)cc1] | 3-tert-butyl-6-(4-methoxybenzyl)-8-(morpholin-4-yl)[1,2,4]triazolo[4',3':1,6]pyrimido[5,4-c]pyridazin-5(6H)-one |
| 181 | 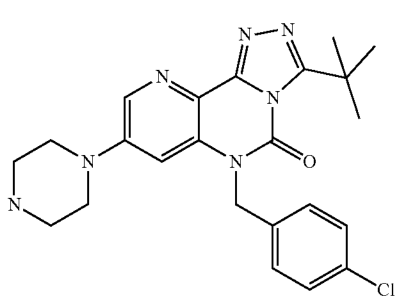 [SMILES: CC(C)(C)c1nnc2c3ncc(N4CCNCC4)cc3n(Cc3ccc(Cl)cc3)c(=O)n12] | 3-tert-butyl-6-(4-chlorobenzyl)-8-(piperazin-1-yl)pyrido[2,3-e][1,2,4]triazolo[4,3-c]pyrimidin-5(6H)-one |

TABLE 5-continued

Selected compounds of the invention according to formula 1a-1f.

| Example | Structure | Name |
|---|---|---|
| 182 | 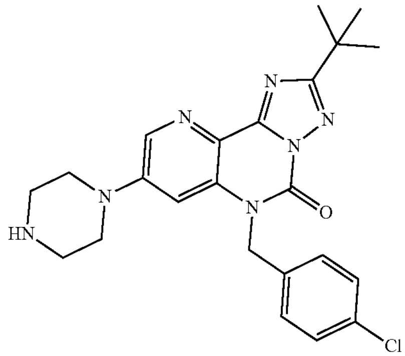 [SMILES: CC(C)(C)c1nc2c3ncc(N4CCNCC4)cc3n(Cc3ccc(Cl)cc3)c(=O)n2n1] | 2-tert-butyl-6-(4-chlorobenzyl)-8-(piperazin-1-yl)pyrido[2,3-e][1,2,4]triazolo[1,5-c]pyrimidin-5(6H)-one |
| 183 | 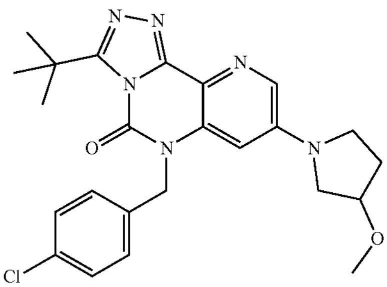 [SMILES: COC1CCN(c2cnc3c(c2)n(Cc2ccc(Cl)cc2)c(=O)n2c(C(C)(C)C)nnc32)C1] | 3-(tert-butyl)-6-(4-chlorobenzyl)-8-(3-methoxypyrrolidin-1-yl)pyrido[2,3-e][1,2,4]triazolo[4,3-c]pyrimidin-5(6H)-one |
| 184 | 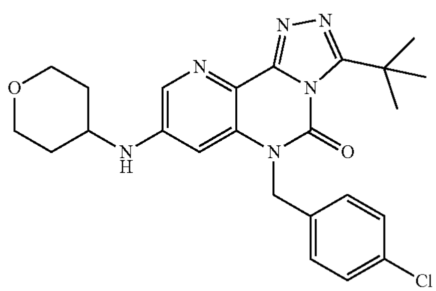 [SMILES: CC(C)(C)c1nnc2c3ncc(NC4CCOCC4)cc3n(Cc3ccc(Cl)cc3)c(=O)n12] | 3-tert-butyl-6-(4-chlorobenzyl)-8-(tetrahydro-2H-pyran-4-ylamino)pyrido[2,3-e][1,2,4]triazolo[4,3-c]pyrimidin-5(6H)-one |
| 185 | 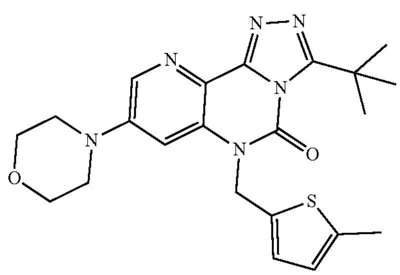 [SMILES: Cc1ccc(Cn2c(=O)n3c(C(C)(C)C)nnc3c3ncc(N4CCOCC4)cc32)s1] | 3-tert-butyl-6-[(5-methylthiophen-2-yl)methyl]-8-(morpholin-4-yl)pyrido[2,3-e][1,2,4]triazolo[4,3-c]pyrimidin-5(6H)-one |
| 186 | 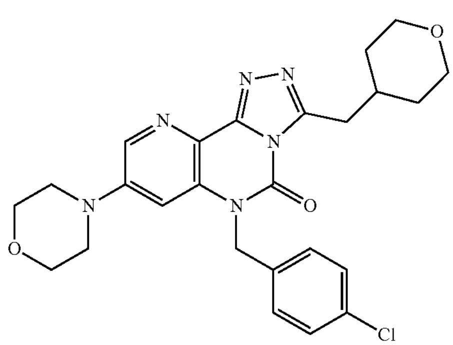 [SMILES: O=c1n(Cc2ccc(Cl)cc2)c2cc(N3CCOCC3)cnc2c2nnc(CC3CCOCC3)n12] | 6-(4-chlorobenzyl)-8-(morpholin-4-yl)-3-(tetrahydro-2H-pyran-4-ylmethyl)pyrido[2,3-e][1,2,4]triazolo[4,3-c]pyrimidin-5(6H)-one |

TABLE 5-continued

Selected compounds of the invention according to formula 1a-1f.

| Example | Structure | Name |
|---|---|---|
| 187 | 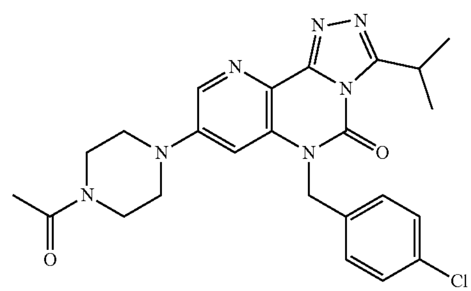 [SMILES: CC(=O)N1CCN(c2cnc3c(c2)n(Cc2ccc(Cl)cc2)c(=O)n2c(C(C)C)nnc32)CC1] | 8-(4-acetylpiperazin-1-yl)-6-(4-chlorobenzyl)-3-(propan-2-yl)pyrido[2,3-e][1,2,4]triazolo[4,3-c]pyrimidin-5(6H)-one |
| 188 | 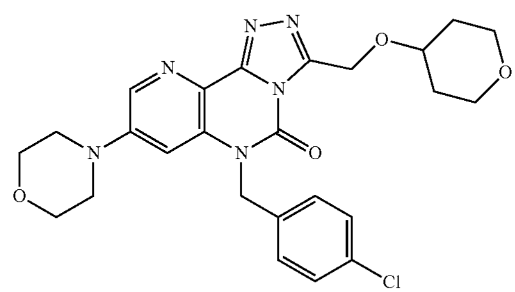 [SMILES: O=c1n(Cc2ccc(Cl)cc2)c2cc(N3CCOCC3)cnc2c2nnc(COC3CCOCC3)n12] | 6-(4-chlorobenzyl)-8-(morpholin-4-yl)-3-[(tetrahydro-2H-pyran-4-yloxy)methyl]pyrido[2,3-e][1,2,4]triazolo[4,3-c]pyrimidin-5(6H)-one |
| 189 | 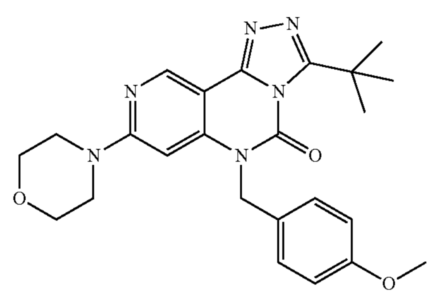 [SMILES: COc1ccc(Cn2c(=O)n3c(C(C)(C)C)nnc3c3cnc(N4CCOCC4)cc32)cc1] | 3-tert-butyl-6-(4-methoxybenzyl)-8-(morpholin-4-yl)pyrido[3,4-e][1,2,4]triazolo[4,3-c]pyrimidin-5(6H)-one |
| 190 | 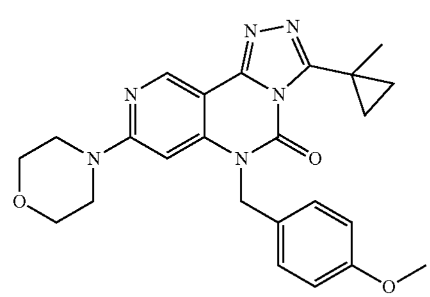 [SMILES: COc1ccc(Cn2c(=O)n3c(C4(C)CC4)nnc3c3cnc(N4CCOCC4)cc32)cc1] | 6-(4-methoxybenzyl)-3-(1-methylcyclopropyl)-8-(morpholin-4-yl)pyrido[3,4-e][1,2,4]triazolo[4,3-c]pyrimidin-5(6H)-one |
| 191 | 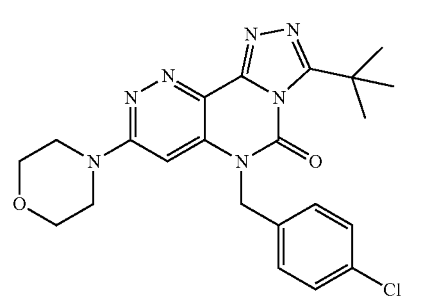 [SMILES: CC(C)(C)c1nnc2c3nnc(N4CCOCC4)cc3n(Cc3ccc(Cl)cc3)c(=O)n12] | 3-tert-butyl-6-(4-chlorobenzyl)-8-(morpholin-4-yl)[1,2,4]triazolo[4',3':1,6]pyrimido[5,4-c]pyridazin-5(6H)-one |

TABLE 5-continued

Selected compounds of the invention according to formula 1a-1f.

| Example | Structure | Name |
|---|---|---|
| 192 | 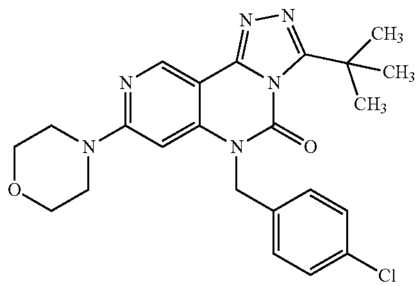 [SMILES: CC(C)(C)c1nnc2c3cnc(N4CCOCC4)cc3n(Cc3ccc(Cl)cc3)c(=O)n12] | 3-tert-butyl-6-(4-chlorobenzyl)-8-(morpholin-4-yl)pyrido[3,4-e][1,2,4]triazolo[4,3-c]pyrimidin-5(6H)-one |
| 193 | 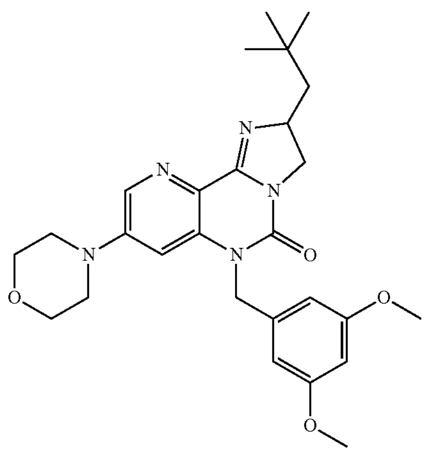 [SMILES: COc1cc(CN2C(=O)N3CC(CC(C)(C)C)N=C3c3ncc(N4CCOCC4)cc32)cc(OC)c1] | 6-(3,5-dimethoxybenzyl)-2-(2,2-dimethylpropyl)-8-(morpholin-4-yl)-2,6-dihydroimidazo[1,2-c]pyrido[2,3-e]pyrimidin-5(3H)-one |
| 194 | 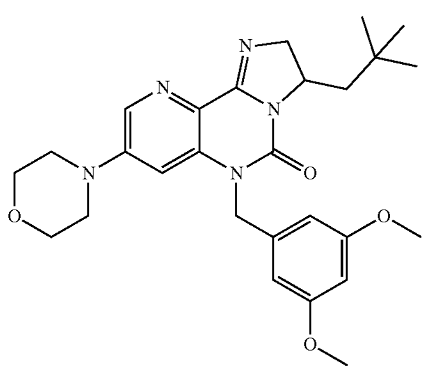 [SMILES: COc1cc(CN2C(=O)N3C(=NCC3CC(C)(C)C)c3ncc(N4CCOCC4)cc32)cc(OC)c1] | 6-(3,5-dimethoxybenzyl)-3-(2,2-dimethylpropyl)-8-(morpholin-4-yl)-2,6-dihydroimidazo[1,2-c]pyrido[2,3-e]pyrimidin-5(3H)-one |

The invention also provides for a pharmaceutical composition comprising a compound of formula I:

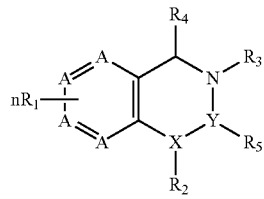

formula I or an enantiomer, diastereomer, N-oxide, or a pharmaceutically acceptable salt or combinations thereof, and a pharmaceutically acceptable carrier, wherein A, X, Y, $R_1$ through $R_6$ and n have the meanings ascribed to them above, for use in the treatment and/or prevention of pain, chronic pain and tolerance to analgesic, respiratory disorders and dysfunctions, overactive bladder, bladder pain syndrome, dysuria and in general in genitourinary diseases, cardiovascular disorders and more in general for the potential treatment of visceral organ diseases and disorders characterized by the involvement of $P_2X_3$ and $P_2X_{2/3}$.

The invention also provides for a pharmaceutical composition comprising a compound of any of formulae 1a to 1g:

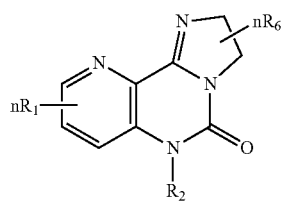

formula 1a

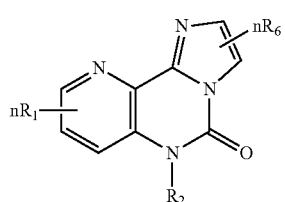

formula 1b

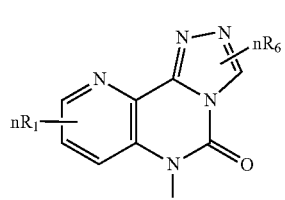

formula 1c

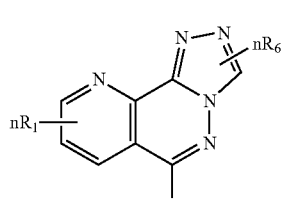

formula 1d

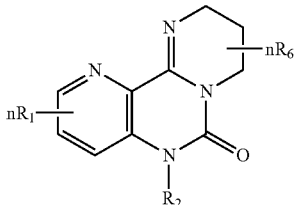

formula 1e

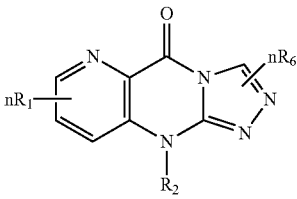

formula 1f

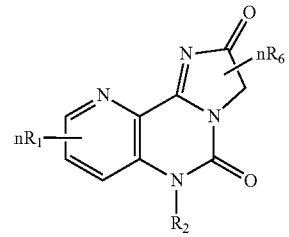

formula 1g or an enantiomer, diastereomer, N-oxide, or a pharmaceutically acceptable salt or combinations thereof, and a pharmaceutically acceptable carrier, wherein A, X, Y, $R_1$ through $R_6$ and n have the meanings ascribed to them above, for use in the treatment and/or prevention of pain, chronic pain and tolerance to analgesic, respiratory disorders and dysfunctions, genitourinary diseases and cardiovascular disorders, in general, for the potential treatment of visceral organ diseases and disorders characterized by the involvement of $P_2X_3$ and $P_2X_{2/3}$.

The invention also provides for compounds according to any of formula I or formulae 1a to 1g shown above, which is used in the treatment and/or prevention of, dysfunction including without any limitation involving ATP release, and in general, for the potential treatment of sensory and visceral organ diseases and disorders characterized by the involvement of $P2X_3$ and $P2X_23$ receptors; for the treatment and/or prevention of pain, chronic pain and cancer pain, addiction and tolerance to analgesic; for the treatment of asthma, cough, COPD and refractory chronic cough and in general of respiratory disorders and dysfunctions; for the treatment of overactive bladder, urinary incontinence, bladder pain syndrome, dysuria and endometriosis and in general in genitourinary diseases; for treatment of cardiovascular disorders, irritable bowel syndrome (IBS), Burning Mouth Syndrome (BMS) migraine and itch.

Terms and Definitions Used

Except where stated otherwise, the following definitions apply throughout the present specification and claims. These definitions apply regardless of whether a term is used by itself or in combination with other terms. For example, the definition of "alkyl" applies not only to alkyl groups per se, but also to the alkyl portions of alkoxy, alkylamino, alkylthio or alkylcarbonyl groups etc. Furthermore, all ranges described for a chemical group, for example "from 1 to 13 carbon atoms" or "$C_1$-$C_6$ alkyl" include all combinations and sub-combinations of ranges and specific numbers of carbon atoms therein.

The skilled person will be aware that groups A, X, Y, $R_1$ to $R_6$ and n all have the meanings given to them as described herein. For example, "groups X and Y are selected from C and N atoms, wherein the unit X—Y represents either a N—C group, or a C=N group respectively".

"Alkyl" means a straight chain or branched chain aliphatic hydrocarbon group having from 1 to 20 carbon atoms in the chain. Preferred alkyl groups have from 1 to 12 carbon atoms in the chain. More preferred alkyl groups have from 1 to 6 carbon atoms in the chain. "Lower alkyl" means an alkyl group having about 1 to about 6 carbon atoms in the chain which may be straight or branched. Examples of suitable alkyl groups include methyl, ethyl, n-propyl, isopropyl, sec-butyl, n-butyl, and t-butyl.

"Alkenyl" means a straight chain or branched chain aliphatic hydrocarbon group having at least one carbon-carbon double bond and having from 2 to 15 carbon atoms in the chain. Preferred alkenyl groups have from 2 to 12 carbon atoms in the chain. More preferred alkenyl groups have from 2 to 6 carbon atoms in the chain. "Lower alkenyl" means an alkenyl group having 2 to about 6 carbon atoms in the chain, which may be straight or branched. Examples of suitable alkenyl groups include ethenyl, propenyl, isopropenyl, n-butenyl, 1-hexenyl and 3-methylbut-2-enyl.

"Alkynyl" means a straight chain or branched chain aliphatic hydrocarbon group having at least one carbon-carbon triple bond and having from 2 to 15 carbon atoms in the chain. Preferred alkynyl groups have from 2 to 12 carbon atoms in the chain. More preferred alkynyl groups have from 2 to 6 carbon atoms in the chain. "Lower alkynyl" means an alkynyl group having 2 to about 6 carbon atoms in the chain, which may be straight or branched. Examples of suitable alkynyl groups include ethynyl, propynyl and 2-butynyl.

"Mono-, bi-, or tricyclic heterocyclic" means an aromatic or non-aromatic saturated mono- bi- or tricyclic ring system having from 2 to 14 ring carbon atoms, and containing from 1 to 5 ring atoms selected from N, O and S, alone or in combination. Bi- and tricyclic heterocyclic groups are fused at 2 or 4 points or joined at one point via a bond or a heteroatom linker (O, S, NH, or N($C_1$-$C_6$ alkyl). The "mono- bi- or tricyclic heterocyclic" can be optionally substituted on the ring by replacing an available hydrogen on the ring by one or more substituents which may be the same or different. The nitrogen or sulphur atom of the heterocyclic can be optionally oxidized to the corresponding N-oxide, S-oxide or S-dioxide. Examples of suitable heterocyclics include furanyl, imidazolyl, isoxazolyl, oxadiazolyl, oxazolyl, pyrrolyl, pyridyl, pyrimidyl, pyridazinyl, thiazolyl, triazolyl, tetrazolyl, thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, isoindolyl, acridinyl and benzoisoxazolyl, aziridinyl, piperidinyl, pyrrolidinyl, piperazinyl, tetrahydropyranyl, tetrahydrofuranyl, tetrahydrothiophenyl, morpholinyl and thiomorpholinyl.

Heterocyclics with aromatic characteristics may be referred to as heteroaryls or heteroaromatics. Examples of suitable heteroaromatics include furanyl, imidazolyl, isoxazolyl, oxadiazolyl, oxazolyl, pyrrolyl, pyridyl, pyrimidyl, pyridazinyl, thiazolyl, triazolyl, tetrazolyl, thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, isoindolyl, acridinyl, benzoisoxazolyl, tetrahydroquinolinyl, tetrahydroisoquinolinyl, 3-phenylpyridine, 3-cyclohexylpyridine, 3-(pyridin-3-yl)morpholine, 3-phenylisoxazole and 2-(piperidin-1-yl)pyrimidine.

"Mono-, bi- or tricyclic aryl" means an aromatic monocyclic, bicyclic or tricyclic ring system comprising 6 to 14 carbon atoms. Bi- and tricyclic aryl groups are fused at 2 or 4 points or joined at one point via a bond or a heteroatom linker (O, S, NH, or N($C_1$-$C_6$ alkyl) (e.g., biphenyl, 1-phenylnapthyl). The aryl group can be optionally substituted on the ring with one or more substituents, preferably 1 to 6 substituents, which may be the same or different. Examples of suitable aryl groups include phenyl and naphthyl.

"Cycloalkyl" means a monocyclic or bicyclic carbon ring system having from 3 to 14 carbon atoms, preferably from 3 to 6 carbon atoms. The cycloalkyl can be optionally substituted on the ring by replacing an available hydrogen on the ring by one or more substituents which may be the same or different. Examples of suitable monocyclic cycloalkyls include cyclopropyl, cyclopentyl, cyclohexyl and cycloheptyl. Examples of suitable multicyclic cycloalkyls include 1-decalinyl, norbornyl and adamantyl.

"Cycloalkenyl" has a meaning corresponding to that of cycloalkyl, but with one or two double bonds within the ring (e.g., cyclohexenyl, cyclohexadiene).

"Amines" are derivatives of ammonia, wherein one or more hydrogen atoms have been replaced by a substituent such as an alkyl or aryl group. These may respectively be called alkylamines and arylamines; amines in which both types of substituent are attached to one nitrogen atom may be called alkylarylamines.

Amines can be further organized into four sub-categories. Primary amines arise when one of the three hydrogen atoms in ammonia is replaced by an alkyl or aromatic group (an N-alkylamino or N-arylamino respectively). Examples of suitable primary alkyl amines include methylamine or ethanolamine, or aniline (phenylamine) as an example of an aromatic amine. Secondary amines have two organic substituents (independently alkyl or aryl groups) bound to the nitrogen atom together with one hydrogen (or no hydrogen if one of the substituent bonds is double). Examples of suitable secondary amines include dimethylamine and methylethanolamine, while an example of an aromatic amine would be diphenylamine. Such compounds may also be referred to as "N,N-dialkylamino", "N,N-diarylamino" or "N,N-alkylarylamino" groups depending on the nature of the substituents. A secondary amine substituted by an alkoxy group, as defined herein, would be termed an "N-alkyl-N-alkoxyamino" compound for example. In tertiary amines, all three hydrogen atoms are replaced by organic substituents, such as trimethylamine. The final sub-category is cyclic amines which are either secondary or tertiary amines. Examples of suitable cyclic amines include the 3-member ring aziridine and the six-membered ring piperidine. N-methylpiperidine and N-phenylpiperidine are suitable examples of cyclic tertiary amines.

"Amides" are compounds with a nitrogen atom attached to a carbonyl group, thus having the structure R—CO—NR'R", with groups R' and R" being independently selected from alkyl or aromatic groups as defined herein. For example, when R' is hydrogen and R" is a 3-pyridyl group, the resulting amide has a 3-pyridylamino substituent. Alternatively, when R' is hydrogen and R" is a cyclopentyl group, the resulting amide has a cyclopentylamino substituent.

"Halogen", "halide" or "halo" means fluorine, chlorine, bromine or iodine. Preferred halogens are fluorine, chlorine or bromine, and most preferred are fluorine and chlorine.

The term "acyl", whether used alone, or within a term such as "acylamino", denotes a radical provided by the residue after removal of hydroxyl from an organic acid. The term "acylamino" refers to an amino radical substituted with an acyl group. An example of an "acylamino" radical is $CH_3C(=O)—NH—$ where the amine may be further substituted with alkyl, aryl or aralkyl groups.

The term "condensed ring" refers to a polycyclic ring system in a molecule in which two rings share two or more common atoms. Two rings that have only two atoms and one bond in common are said to be ortho-fused, e.g. naphthalene. In a polycyclic compound, a ring ortho-fused to different sides of two other rings that are themselves ortho-fused together (i.e. there are three common atoms between the first ring and the other two) is said to be ortho- and peri-fused to the other two rings. Phenalene is considered as being composed of three benzene rings, each of which is ortho- and peri-fused to the other two. Fusion nomenclature is concerned with a two-dimensional representation of a polycyclic ring system with the maximum number of non-cumulative double bonds. In addition, this system may be bridged, or involved in assemblies or spiro-systems (see below). For ring systems any ring fused to other rings on all sides must be itself named (i.e. it is not treated as a hole). For nomenclature purposes two rings which have two atoms and one bond in common may be regarded as being derived from the two rings as separate entities. The process of joining rings in this way is termed fusion. Any fusion compound illustrated or described herein, is named in accordance and with reference to "*Nomenclature of fused and bridged fused ring systems*" (IUPAC Recommendations 1998)", IUPAC, *Pure Appl. Chem.*, (1999), Vol. 70, pp. 143-216.

A spiro compound has two (or three) rings which have only one atom in common and the two (or three) rings are not linked by a bridge. The rings may form part of other ring systems (fused ring, bridged fused ring, system named by von Baeyer nomenclature, etc.). The common atom is known as a spiro atom, and spiro-fusion has also been termed spiro union. Monospiro hydrocarbons with two monocyclic rings are named by the prefix spiro before a von Baeyer descriptor (indicating the numbers of carbon atoms linked to the spiro atom in each ring in ascending order and separated by a full stop) placed in square brackets and then the name of the parent hydrocarbon indicating the total number of skeletal atoms, e.g. spiro[4.4]nonane. Monospiro hydrocarbons with two monocyclic rings are numbered consecutively starting in the smaller ring at an atom next to the spiro atom, proceeding around the smaller ring back to the spiro atom and then round the second ring. Heteroatoms are indicated by replacement prefixes and unsaturation is indicated in the usual way by the endings ene, diene, etc. Low locants are allocated for radical positions, or, if the ring system is a substituent, its point of attachment. If there is a choice of numbers the name that gives the lower locants for spiro atoms is selected. Any spiro compound illustrated or described herein, is named in accordance and with reference to "*Extension and revision of the nomenclature for spiro compounds*" (IUPAC Recommendations 1999)", IUPAC, *Pure Appl. Chem.*, (1999), Vol. 71, pp. 531.538.

An asterisk may be used in subgeneric-formulas or groups to indicate the bond which is connected to a parent or core molecule as defined herein.

The term "treatment" and the like as used herein encompasses eliminating or alleviating symptoms of diseases or disorders and keeping them from worsening (stabilization) and more generally bringing about a desired physiological or pharmacological effect. The term "prevention" and the like as used herein encompasses inhibiting or retarding the manifestation of symptoms of such diseases or disorders or reducing (or increasing as the case may be) or eliminating abnormal values in markers thereof.

Stereochemistry

Unless specifically indicated, throughout the specification and claims, a given chemical formula or name shall encompass tautomers and all stereo, optical and geometrical isomers (e.g. enantiomers, diastereomers, +/−, R/S, E/Z isomers etc.) racemic mixtures and racemates thereof. This includes mixtures in different proportions of the separate enantiomers, mixtures of diastereomers, or mixtures of any of the foregoing forms where such isomers and enantiomers exist, as well as salts, including pharmaceutically acceptable salts and solvates thereof such as hydrates, solvates of the free compounds or solvates of a salt of the compound.

Derivatives of Compounds of the Invention

The invention further encompasses salts, solvates, hydrates, N-oxides, produgs and active metabolites of the compounds of formula I.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2"-nitrilotris(ethanol)), tromethamine, zinc hydroxide, acetic acid, 2,2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals such as aluminium, calcium, lithium, magnesium, potassium, sodium, zinc and the like (see Pharmaceutical salts, Berge, S. M. et al., *J. Pharm. Sci.*, (1977), Vol. 66, pp. 1-19).

Pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts), also comprise a part of the invention.

Typically, a pharmaceutically acceptable salt of a compound of formula I may be readily prepared by using a desired acid or base as appropriate. The salt may precipitate from solution and be collected by filtration or may be recovered by evaporation of the solvent. For example, an aqueous solution of an acid such as hydrochloric acid may be added to an aqueous suspension of a compound of formula I and the resulting mixture evaporated to dryness (lyophilized) to obtain the acid addition salt as a solid. Alternatively, a compound of formula I may be dissolved in a suitable solvent, for example an alcohol such as isopropanol, and the acid may be added in the same solvent or another suitable solvent. The resulting acid addition salt may then be precipitated directly, or by addition of a less polar solvent such as diisopropyl ether or hexane, and isolated by filtration.

The acid addition salts of the compounds of formula I may be prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the invention.

Also included are both total and partial salts, that is to say salts with 1, 2 or 3, preferably 2, equivalents of base per mole of acid of formula I or salts with 1, 2 or 3 equivalents, preferably 1 equivalent, of acid per mole of base of formula I.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine.

The base addition salts of said acidic compounds are prepared by contacting the free acid form with a sufficient amount of the desired base to produce the salt in the conventional manner. The free acid form may be regenerated by contacting the salt form with an acid and isolating the free acid.

Compounds of the invention may have both a basic and an acidic centre and may therefore be in the form of zwitterions or internal salts.

Typically, a pharmaceutically acceptable salt of a compound of formula I may be readily prepared by using a desired acid or base as appropriate. The salt may precipitate from solution and be collected by filtration or may be recovered by evaporation of the solvent. For example, an aqueous solution of an acid such as hydrochloric acid may be added to an aqueous suspension of a compound of formula I and the resulting mixture evaporated to dryness (lyophilized) to obtain the acid addition salt as a solid. Alternatively, a compound of formula I may be dissolved in a suitable solvent, for example an alcohol such as isopropanol, and the acid may be added in the same solvent or another suitable solvent. The resulting acid addition salt may then be precipitated directly, or by addition of a less polar solvent such as diisopropyl ether or hexane, and isolated by filtration.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of the invention are within the scope of the invention. The salts of the compound of formula I may form solvates (e.g., hydrates) and the invention also includes all such solvates. The meaning of the word "solvates" is well known to those skilled in the art as a compound formed by interaction of a solvent and a solute (i.e., solvation). Techniques for the preparation of solvates are well established in the art (see, for example, Brittain. *Polymorphism in Pharmaceutical solids.* Marcel Decker, New York, 1999).

The invention also encompasses N-oxides of the compounds of formula I. The term "N-oxide" means that for heterocycles containing an otherwise unsubstituted $sp^2$ N atom, the N atom may bear a covalently bound O atom, i.e., —N→O. Examples of such N-oxide substituted heterocycles include pyridyl N-oxides, pyrimidyl N-oxides, pyrazinyl N-oxides and pyrazolyl N-oxides.

The invention also encompasses prodrugs of the compounds of formula I, i.e., compounds which release an active parent drug according to formula I in vivo when administered to a mammalian subject. A prodrug is a pharmacologically active or more typically an inactive compound that is converted into a pharmacologically active agent by a metabolic transformation. Prodrugs of a compound of formula I are prepared by modifying functional groups present in the compound of formula I in such a way that the modifications may be cleaved in vivo to release the parent compound. In vivo, a prodrug readily undergoes chemical changes under physiological conditions (e.g., are acted on by naturally occurring enzyme(s)) resulting in liberation of the pharmacologically active agent. Prodrugs include compounds of formula I wherein a hydroxy, amino, or carboxy group of a formula I compound is bonded to any group that may be cleaved in vivo to regenerate the free hydroxyl, amino or carboxy group, respectively. Examples of prodrugs include esters (e.g., acetate, formate, and benzoate derivatives) of compounds of formula I or any other derivative which upon being brought to the physiological pH or through enzyme action is converted to the active parent drug. Conventional procedures for the selection and preparation of suitable prodrug derivatives are described in the art (see, for example, Bundgaard. *Design of Prodrugs.* Elsevier, 1985).

Prodrugs may be administered in the same manner as and in effective amounts analogous to the active ingredient to which they convertor they may be delivered in a reservoir form, e.g., a transdermal patch or other reservoir which is adapted to permit (by provision of an enzyme or other appropriate reagent) conversion of a prodrug to the active ingredient slowly over time, and delivery of the active ingredient to the patient.

The invention also encompasses metabolites. A "metabolite" of a compound disclosed herein is a derivative of a compound which is formed when the compound is metabolised. The term "active metabolite" refers to a biologically active derivative of a compound which is formed when the compound is metabolized. The term "metabolized" refers to the sum of the processes by which a particular substance is changed in the living body. In brief, all compounds present in the body are manipulated by enzymes within the body in order to derive energy and/or to remove them from the body. Specific enzymes produce specific structural alterations to the compound. For example, cytochrome P450 catalyses a variety of oxidative and reductive reactions while uridine diphosphate glucuronyltransferases catalyse the transfer of an activated glucuronic-acid molecule to aromatic alcohols, aliphatic alcohols, carboxylic acids, amines and free sulphydryl groups. Further information on metabolism may be obtained from *The Pharmacological Basis of Therapeutics*, 9th Edition, McGraw-Hill (1996), pages 11-17.

Metabolites of the compounds disclosed herein can be identified either by administration of compounds to a host and analysis of tissue samples from the host, or by incubation of compounds with hepatic cells in vitro and analysis of the resulting compounds. Both methods are well known in the art.

The term "carrier" refers to a diluent, excipient, and/or vehicle with which an active compound is administered. The pharmaceutical compositions of the invention may contain combinations of more than one carrier. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition.

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the present application includes both one and more than one such excipient.

The compounds of the invention may be formulated for administration in any convenient way for use in human or veterinary medicine and the invention therefore includes within its scope pharmaceutical compositions comprising a compound of the invention adapted for use in human or veterinary medicine. Such compositions may be presented for use in a conventional manner with the aid of one or more suitable carriers. Acceptable carriers for therapeutic use are well-known in the pharmaceutical art, and are described, for example, in Remington's Pharmaceutical Sciences, Mack Publishing Co. (A. R. Gennaro edit. 1985). The choice of pharmaceutical carrier can be selected with regard to the intended route of administration and standard pharmaceutical practice. The pharmaceutical compositions may comprise as, in addition to, the carrier any suitable binder(s), lubricant(s), suspending agent(s), coating agent(s), and/or solubilizing agent(s).

Pharmaceutical Compositions Comprising a Compound of Formula I

While it is possible that a compound I may be administered as the bulk substance, it is preferable to present the active ingredient in a pharmaceutical formulation, e.g., wherein the agent is in admixture with a pharmaceutically acceptable carrier selected with regard to the intended route of administration and standard pharmaceutical practice.

Accordingly, the invention further provides a pharmaceutical composition comprising a compound of formula I or a solvate, hydrate, isomer (e.g., enantiomer, diastereomer, etc.), N-oxide or pharmaceutically acceptable salt thereof in admixture with a pharmaceutically acceptable carrier. The term "carrier" refers to a diluent, excipient, and/or vehicle with which an active compound is administered.

A compound of formula I may be used in combination with other therapies and/or active agents. Accordingly, the invention provides, in a further aspect, a pharmaceutical composition comprising a compound of formula I or a solvate, hydrate, isomer (e.g., enantiomer, diastereomer, etc.), N-oxide or pharmaceutically acceptable salt thereof, a second active agent, and a pharmaceutically acceptable carrier.

The pharmaceutical compositions may comprise as, in addition to, the carrier any suitable binder, lubricant, suspending agent, coating agent and/or solubilizing agent.

Preservatives, stabilizers, dyes and flavouring agents also may be provided in the pharmaceutical composition. Antioxidants and suspending agents may be also used.

The compounds of the invention may be reduced to fine particulate form (e.g., milled using known milling procedures such as wet milling) to obtain a particle size appropriate for tablet formation and for other formulation types. Finely divided (nanoparticulate) preparations of the compounds of the invention may be prepared by processes known in the art, for example see WO2/00196.

Routes of Administration and Unit Dosage Forms

The routes for administration include oral (e.g., as a tablet, capsule, or as an ingestible solution), topical, mucosal (e.g., as a nasal spray or aerosol for inhalation), nasal, parenteral (e.g., by an injectable form), gastrointestinal, intraspinal, intraperitoneal, intramuscular, intravenous, intrauterine, intraocular, intradermal, intracranial, intrathecal, intratracheal, intravaginal, intracerebroventricular, intracerebral, subcutaneous, ophthalmic (including intravitreal or intracameral), transdermal, rectal, buccal, epidural and sublingual. The compositions of the invention may be especially formulated for any of those administration routes. In preferred embodiments, the pharmaceutical compositions of the invention are formulated in a form that is suitable for oral delivery.

There may be different composition/formulation requirements depending on the different delivery systems. It is to be understood that not all of the compounds need to be administered by the same route. Likewise, if the composition comprises more than one active component, then those components may be administered by different routes. By way of example, the pharmaceutical composition of the invention may be formulated to be delivered using a minipump or by a mucosal route, for example, as a nasal spray or aerosol for inhalation or ingestible solution, or parenterally in which the composition is formulated by an injectable form, for delivery, by, for example, an intravenous, intramuscular or subcutaneous route. Alternatively, the formulation may be designed to be delivered by multiple routes.

Where the agent is to be delivered mucosally through the gastiointestinal mucosa, it should be able to remain stable during transit though the gastrointestinal tract; for example, it should be resistant to proteolytic degradation, stable at acid pH and resistant to the detergent effects of bile. For example, the compound of Formula I may be coated with an enteric coating layer. The enteric coating layer material may be dispersed or dissolved in either water or in a suitable organic solvent. As enteric coating layer polymers, one or more, separately or in combination, of the following can be used; e.g., solutions or dispersions of methacrylic acid copolymers, cellulose acetate phthalate, cellulose acetate butyrate, hydroxypropyl methylcellulose phthalate, hydroxypropyl methylcellulose acetate succinate, polyvinyl acetate phthalate, cellulose acetate trimellitate, carboxymethylethylcellulose, shellac or other suitable enteric coating layer polymer(s). For environmental reasons, an aqueous coating process may be preferred. In such aqueous processes methacrylic acid copolymers are most preferred.

When appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously. For buccal or sublingual administration, the compositions may be administered in the form of tablets or lozenges, which can be formulated in a conventional manner.

When the composition of the invention is to be administered parenterally, such administration includes one or more of intravenously, intraarterially, intraperitoneally, intrathecally, intraventricularly, intraurethrally, intrasternally, intracranially, intramuscularly or subcutaneously administering the agent; and/or by using infusion techniques.

Pharmaceutical compositions of the invention can be administered parenterally, e.g., by infusion or injection. Pharmaceutical compositions suitable for injection or infusion may be in the form of a sterile aqueous solution, a dispersion or a sterile powder that contains the active ingredient, adjusted, if necessary, for preparation of such a sterile solution or dispersion suitable for infusion or injection. This preparation may optionally be encapsulated into liposomes. In all cases, the final preparation must be sterile, liquid, and stable under production and storage conditions. To improve storage stability, such preparations may also contain a preservative to prevent the growth of microorganisms. Prevention of the action of micro-organisms can be achieved by the addition of various antibacterial and antifungal agents, e.g., paraben, chlorobutanol, sodium acetate, sodium lactate, sodium citrate or ascorbic acid. In many cases isotonic substances are recommended, e.g., sugars, buffers and sodium chloride to assure osmotic pressure similar to those of body fluids, particularly blood. Prolonged absorption of such injectable mixtures can be achieved by introduction of absorption-delaying agents, such as aluminium monostearate or gelatin.

Dispersions can be prepared in a liquid carrier or intermediate, such as glycerin, liquid polyethylene glycols, triacetin oils, and mixtures thereof. The liquid carrier or intermediate can be a solvent or liquid dispersive medium that contains, for example, water, ethanol, a polyol (e.g., glycerol, propylene glycol or the like), vegetable oils, non-toxic glycerine esters and suitable mixtures thereof. Suitable flowability may be maintained, by generation of liposomes, administration of a suitable particle size in the case of dispersions, or by the addition of surfactants.

For parenteral administration, the compound is best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Sterile injectable solutions can be prepared by mixing a compound of formula I with an appropriate solvent and one or more of the aforementioned carriers, followed by sterile filtering. In the case of sterile powders suitable for use in the preparation of sterile injectable solutions, preferable preparation methods include drying in vacuum and lyophilization, which provide powdery mixtures of the aldosterone receptor antagonists and desired excipients for subsequent preparation of sterile solutions.

The compounds according to the invention may be formulated for use in human or veterinary medicine by injection (e.g., by intravenous bolus injection or infusion or via intramuscular, subcutaneous or intrathecal routes) and may be presented in unit dose form, in ampoules, or other unit-dose containers, or in multi-dose containers, if necessary with an added preservative. The compositions for injection may be in the form of suspensions, solutions, or emulsions, in oily or aqueous vehicles, and may contain formulatory agents such as suspending, stabilizing, solubilizing and/or dispersing agents. Alternatively, the active ingredient may be in sterile powder form for reconstitution with a suitable vehicle, e.g., sterile, pyrogen-free water, before use.

The compounds of the invention can be administered (e.g., orally or topically) in the form of tablets, capsules, ovules, elixirs, solutions or suspensions, which may contain flavouring or colouring agents, for immediate-, delayed-, modified-, sustained-, pulsed- or controlled-release applications.

The compounds of the invention may also be presented for human or veterinary use in a form suitable for oral or buccal administration, for example in the form of solutions, gels, syrups, mouth washes or suspensions, or a dry powder for constitution with water or other suitable vehicle before use, optionally with flavouring and colouring agents. Solid compositions such as tablets, capsules, lozenges, pastilles, pills, boluses, powder, pastes, granules, bullets or premix preparations may also be used. Solid and liquid compositions for oral use may be prepared according to methods well-known in the art. Such compositions may also contain one or more pharmaceutically acceptable carriers and excipients which may be in solid or liquid form.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia.

Additionally, lubricating agents such as magnesium stearate, stearic acid, glyceryl behenate and talc may be included.

The compositions may be administered orally, in the form of rapid or controlled release tablets, microparticles, mini tablets, capsules, sachets, and oral solutions or suspensions, or powders for the preparation thereof. In addition to the new solid-state forms of pantoprazole of the invention as the active substance, oral preparations may optionally include various standard pharmaceutical carriers and excipients, such as binders, fillers, buffers, lubricants, glidants, dyes, disintegrants, odourants, sweeteners, surfactants, mold release agents, antiadhesive agents and coatings. Some excipients may have multiple roles in the compositions, e.g., act as both binders and disintegrants.

Examples of pharmaceutically acceptable disintegrants for oral compositions include starch, pre-gelatinized starch, sodium starch glycolate, sodium carboxymethylcellulose, croscarmellose sodium, microcrystalline cellulose, alginates, resins, surfactants, effervescent compositions, aqueous aluminum silicates and cross-linked polyvinylpyrrolidone.

Examples of pharmaceutically acceptable binders for oral compositions include acacia; cellulose derivatives, such as methylcellulose, carboxymethylcellulose, hydroxypropylmethylcellulose, hydroxypropylcellulose or hydroxyethylcellulose; gelatin, glucose, dextrose, xylitol, polymethacrylates, polyvinylpyrrolidone, sorbitol, starch, pre-gelatinized starch, tragacanth, xanthane resin, alginates, magnesium-aluminum silicate, polyethylene glycol or bentonite.

Examples of pharmaceutically acceptable fillers for oral compositions include lactose, anhydrolactose, lactose monohydrate, sucrose, dextrose, mannitol, sorbitol, starch, cellulose (particularly microcrystalline cellulose), dihydro- or anhydro-calcium phosphate, calcium carbonate and calcium sulphate.

Examples of pharmaceutically acceptable lubricants useful in the compositions of the invention include magnesium stearate, talc, polyethylene glycol, polymers of ethylene oxide, sodium lauryl sulphate, magnesium lauryl sulphate, sodium oleate, sodium stearyl fumarate, and colloidal silicon dioxide.

Examples of suitable pharmaceutically acceptable odourants for the oral compositions include synthetic aromas and natural aromatic oils such as extracts of oils, flowers, fruits (e.g., banana, apple, sour cherry, peach) and combinations thereof, and similar aromas. Their use depends on many factors, the most important being the organoleptic acceptability for the population that will be taking the pharmaceutical compositions.

Examples of suitable pharmaceutically acceptable dyes for the oral compositions include synthetic and natural dyes such as titanium dioxide, beta-carotene and extracts of grapefruit peel.

Examples of useful pharmaceutically acceptable coatings for the oral compositions, typically used to facilitate swallowing, modify the release properties, improve the appearance, and/or mask the taste of the compositions include hydroxypropylmethylcellulose, hydroxypropylcellulose and acrylate-methacrylate copolymers.

Examples of pharmaceutically acceptable sweeteners for the oral compositions include aspartame, saccharin, saccharin sodium, sodium cyclamate, xylitol, mannitol, sorbitol, lactose and sucrose.

Examples of pharmaceutically acceptable buffers include citric acid, sodium citrate, sodium bicarbonate, dibasic sodium phosphate, magnesium oxide, calcium carbonate and magnesium hydroxide.

Examples of pharmaceutically acceptable surfactants include sodium lauryl sulphate and polysorbates.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavouring agents, colouring matter or dyes, with emulsifying and/or suspending agents and with diluents such as water, ethanol, propylene glycol and glycerin, and combinations thereof.

The compounds of the invention may also, for example, be formulated as suppositories e.g., containing conventional suppository bases for use in human or veterinary medicine or as pessaries e.g., containing conventional pessary bases.

The compounds according to the invention may be formulated for topical administration, for use in human and veterinary medicine, in the form of ointments, creams, gels, hydrogels, lotions, solutions, shampoos, powders (including spray or dusting powders), pessaries, tampons, sprays, dips, aerosols, drops (e.g., eye ear or nose drops) or pour-ons.

For application topically to the skin, the agent of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax, sorbitan monostearate, a polyethylene glycol, liquid paraffin, polysorbate 60, cetyl esters wax, cetearyl alcohol, 2-octyldodecanol, benzyl alcohol, and water. Such compositions may also contain other pharmaceutically acceptable excipients, such as polymers, oils, liquid carriers, surfactants, buffers, preservatives, stabilizers, antioxidants, moisturizers, emollients, colourants, and odourants.

Examples of pharmaceutically acceptable polymers suitable for such topical compositions include acrylic polymers; cellulose derivatives, such as carboxymethylcellulose sodium, methylcellulose or hydroxypropylcellulose; natural polymers, such as alginates, tragacanth, pectin, xanthan and cytosan.

Examples of suitable pharmaceutically acceptable oils which are so useful include mineral oils, silicone oils, fatty acids, alcohols, and glycols.

Examples of suitable pharmaceutically acceptable liquid carriers include water, alcohols or glycols such as ethanol, isopropanol, propylene glycol, hexylene glycol, glycerol and polyethylene glycol, or mixtures thereof in which the pseudopolymorph is dissolved or dispersed, optionally with the addition of non-toxic anionic, cationic or non-ionic surfactants, and inorganic or organic buffers.

Examples of pharmaceutically acceptable preservatives include sodium benzoate, ascorbic acid, esters of p-hydroxybenzoic acid and various antibacterial and antifungal agents such as solvents, for example ethanol, propylene glycol, benzyl alcohol, chlorobutanol, quaternary ammonium salts, and parabens (such as methyl paraben, ethyl paraben and propyl paraben).

Examples of pharmaceutically acceptable stabilizers and antioxidants include ethylenediaminetetraacetic acid (EDTA), thiourea, tocopherol and butyl hydroxyanisole.

Examples of pharmaceutically acceptable moisturizers include glycerine, sorbitol, urea and polyethylene glycol.

Examples of pharmaceutically acceptable emollients include mineral oils, isopropyl myristate, and isopropyl palmitate.

The compounds may also be dermally or transdermally administered, for example, by use of a skin patch.

For ophthalmic use, the compounds can be formulated as micronized suspensions in isotonic, pH adjusted, sterile saline, or, preferably, as solutions in isotonic, pH adjusted, sterile saline, optionally in combination with a preservative such as a benzylalkonium chloride.

As indicated, the compounds of the invention can be administered intranasally or by inhalation and is conveniently delivered in the form of a dry powder inhaler or an aerosol spray presentation from a pressurized container, pump, spray or nebulizer with the use of a suitable propellant, e.g., dichlorodifluoromethane, trichlorofluoromethane, dichlorotetrafluoroethane, a hydrofluoroalkane such as 1,1,1,2-tetrafluoroethane (HFA 134AT) or 1,1,1,2,3,3,3-heptafluoropropane (HFA 227EA), carbon dioxide or other suitable gas. In the case of a pressurized aerosol, the dosage unit may be determined by providing a valve to deliver a metered amount. The pressurized container, pump, spray or nebulizer may contain a solution or suspension of the active compound, e.g., using a mixture of ethanol and the propellant as the solvent, which may additionally contain a lubricant, e.g., sorbitan trioleate.

Capsules and cartridges (made, for example, from gelatin) for use in an inhaler or insufflator may be formulated to contain a powder mix of the compound and a suitable powder base such as lactose or starch.

For topical administration by inhalation the compounds according to the invention may be delivered for use in human or veterinary medicine via a nebulizer.

The pharmaceutical compositions of the invention may contain from 0.01 to 99% weight per volume of the active material. For topical administration, for example, the composition will generally contain from 0.01-10%, more preferably 0.01-1% of the active material.

The active agents can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The pharmaceutical composition or unit dosage form of the invention may be administered according to a dosage and administration regimen defined by routine testing in the light of the guidelines given above in order to obtain optimal activity while minimizing toxicity or side effects for a particular patient. However, such fine tuning of the therapeutic regimen is routine in the light of the guidelines given herein.

The dosage of the active agents of the invention may vary according to a variety of factors such as underlying disease conditions, the individual's condition, weight, gender and age, and the mode of administration. An effective amount for treating a disorder can easily be determined by empirical methods known to those of ordinary skill in the art, for example by establishing a matrix of dosages and frequencies of administration and comparing a group of experimental units or subjects at each point in the matrix. The exact amount to be administered to a patient will vary depending on the state and severity of the disorder and the physical condition of the patient. A measurable amelioration of any symptom or parameter can be determined by a person skilled in the art or reported by the patient to the physician.

The amount of the agent to be administered can range between about 0.01 and about 25 mg/kg/day, preferably between about 0.1 and about 10 mg/kg/day and most preferably between 0.2 and about 5 mg/kg/day. It will be understood that the pharmaceutical formulations of the invention need not necessarily contain the entire amount of the agent that is effective in treating the disorder, as such effective amounts can be reached by administration of a plurality of doses of such pharmaceutical formulations. In general, an "effective amount" refers to the amount of a pharmaceutical composition administered to improve, inhibit, or ameliorate a disease or disorder or condition of a subject, or a symptom of a disease or disorder, in a clinically relevant manner. Any clinically relevant improvement in the subject is considered sufficient to achieve treatment. Preferably, an amount sufficient to treat is an amount that prevents the occurrence or one or more symptoms of the infection or is an amount that reduces the severity of, or the length of time during which a subject suffers from, or develops, one or more symptoms of the infection relative to a control subject that is not treated with a composition of the invention).

In a preferred embodiment of the invention, the compounds according to formula I are formulated in capsules or tablets, preferably containing 10 to 200 mg of the compounds of the invention, and are preferably administered to a patient at a total daily dose of 10 to 300 mg, preferably 20 to 150 mg and most preferably about 50 mg.

A pharmaceutical composition for parenteral administration contains from about 0.01% to about 100% by weight of the active agents of the invention, based upon 100% weight of total pharmaceutical composition.

Generally, transdermal dosage forms contain from about 0.01% to about 100% by weight of the active agents versus 100% total weight of the dosage form.

The pharmaceutical composition or unit dosage form may be administered in a single daily dose, or the total daily dosage may be administered in divided doses. In addition, co-administration or sequential administration of another compound for the treatment of the disorder may be desirable. To this purpose, the combined active principles are formulated into a simple dosage unit.

For combination treatment where the compounds are in separate dosage formulations, the compounds can be administered concurrently, or each can be administered at staggered intervals. Additional compounds may be administered at specific intervals too. The order of administration will depend upon a variety of factors including age, weight, gender and medical condition of the patient; the severity and aetiology of the disorders to be treated, the route of administration, the renal and hepatic function of the patient, the treatment history of the patient, and the responsiveness of the patient. Determination of the order of administration may be fine-tuned and such fine-tuning is routine in the light of the guidelines given herein.

DESCRIPTION OF THE INVENTION

Synthesis

Compounds of formula I, or indeed those of formulae 1a through 1g, and enantiomers, diastereomers, N-oxides, and pharmaceutically acceptable salts thereof, may be prepared by the general methods outlined hereinafter, said methods constituting a further aspect of the invention.

The compounds of this invention can be prepared by employing reactions as shown in the following schemes, in addition to other standard manipulations that are known in the literature, exemplified in the experimental section or clear to one skilled in the art. The starting materials which are not described herein are either commercially available or may be prepared by employing reactions described in the literature or are clear to one skilled in the art. The following examples are provided so that the invention might be more fully understood, are illustrative only, and should not be construed as limiting.

It will be appreciated by those skilled in the art that it may be desirable to use protected derivatives of intermediates used in the preparation of the compounds according to formula I. Protection and deprotection of functional groups may be performed by methods known in the art (see, for example, Green and Wuts Protective Groups in Organic Synthesis. John Wiley and Sons, New York, 1999).

The abbreviation PG describes a "protecting group" which is introduced to a reactive group before a certain manipulation is carried out, and which is later removed. Examples of PG's for protecting a reactive group include: acetyl-, trifluoracetyl-, benzoyl-, ethoxycarbonyl-, N-tert-butoxycarbonyl—(BOC), N-benzyloxycarbonyl—(Cbz), benzyl-, methoxybenzyl-, 2,4-dimethoxybenzyl- and for amino groups additionally the phthalyl-group for amino-alkylamino or imino groups; N-methoxynethyl—(MOM), N-benzyloxymethyl-(BOM), N-(trimethylsilyl)ethoxymethyl—(SEM), N-tert-butyl-dimethylsiloxymethyl-, N-tert-butyl-dimethylsilyl-(TBDMS), N-triisopropylsilyl—(TIPS), N-benzyl-, N-4-methoxybenzyl (PMB), N-triphenylmethyl—(Tr), N-tert-butoxycarbonyl—(BOC), N-benzyloxycarbonyl—(Cbz) or N-trimethylsilylethylsulfonyl—(SES) for amide groups; methoxy-, benzyloxy-, trimethylsilyl—(TMS), acetyl-, benzoyl-, tert-butyl-, trityl-, benzyl-, or tetrahydropyranyl (THP) groups for hydroxy groups; or trimethylsilyl—(TMS), methyl-ethyl-, tert-butyl-, benzyl-, or tetrahydropyranyl (THP) groups for carboxyl groups.

The compounds of the invention are generally prepared according to the following different schemes. In some cases, the final product may be further modified, for example by manipulation of substituents. These manipulations may include, but are not limited to, reduction, oxidation, alkylation, acylation, and hydrolysis reactions which are commonly known to those skilled in the art. In some cases, the order of carrying out the foregoing reaction schemes may be varied in order to facilitate the reaction or to avoid unwanted reaction products. The following examples are provided so that the invention might be more fully understood. These examples are illustrative only and should not be constructed as limiting the invention in any way.

As shown in Scheme 1 below, commercially available compounds 1 can be selectively converted by nucleophilic aromatic substitution or alternatively by reductive amination into 3-($R_2$-amino)-5-bromopyridine-2-carbonitrile (2) by using consolidated methodologies well known to people skilled in the art. In turn 2 is condensed with the requisite diamines (3) to obtain 2-(4,5-dihydro-1H-imidazol-2-yl)- or 2-(1,4,5,6-tetrahydropyrimidin-2-yl) derivatives of $R_2$—N-5-bromo-pyridin-3-amine N-methyl-pyridin-3-amine (4). In the next step compounds 4 are then cyclized by reactant to afford the corresponding compounds 5, which are finally reacted to produce $R_1$-substituted intermediates directly to obtain compounds falling under the scope of formula 1a or 1e. This last derivatization procedure can be carried out using standard methods such us e.g. Buchwald reactions, acylation reactions, alkylation or any kind of N-derivatization reaction useful to the aim of forming compounds according to formula 1a and 1e, and is very well known to people skilled in the art. The same reaction steps can be rearranged, anticipating or postponing each step in the synthesis without any limitation, e.g. the Buchwald reaction can be carried out as a last step, or alternatively as a first step in the entire procedure.

For Scheme 1 below, the skilled person will appreciate that compounds 4 to 6 illustrate the possibility that the $nR_6$-substituent containing ring may be a five- or six-membered heterocyclic ring comprising two nitrogen atoms, following the reaction with compound 3. This arises when integer m' comprises a value of 1 or 2 and provides for group —$(C)_{m'}$— being a single methylene-bridge carbon atom, or a pair of methylene-bridge carbon atoms in sequence, the heterocyclic ring so-produced being an imidazoline or a pyrimidine derivative respectively. Imidazoline derivatives are illustrated by formula 1a and comprise compounds 1 to 69 as shown in Table 1, and pyrimidine derivatives are illustrated by formula 1e and comprise compounds 141 to 155 as shown in Table 4.

Scheme 1: Production of compounds according to formula 1a and 1e.

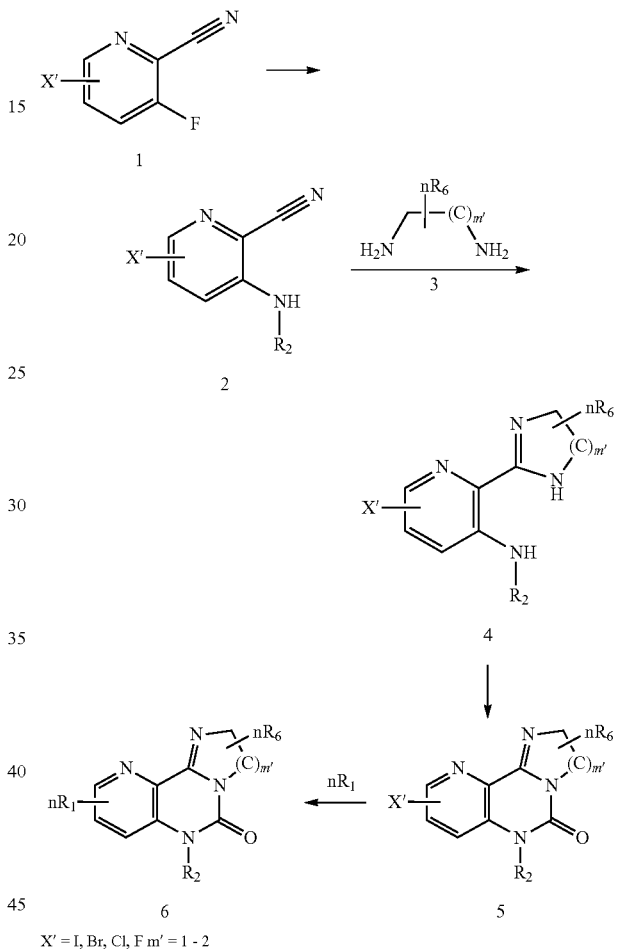

X' = I, Br, Cl, F m' = 1 - 2

As shown in Scheme 2 below, commercially available compounds 1 can be converted by nucleophilic aromatic substitution, or alternatively by reductive amination, with the respective amino or aldehyde derivatives into methyl 3-($R_2$-amino)-5-halopyridine-2-carboxylate (2) by using consolidated methodologies well known to people skilled in the art. In the next step compounds 2 are then cyclized by reactants to afford the corresponding compounds 3, which are reacted with $POCl_3$ to obtain compounds of formulae 4 and 7. In turn 4 is cyclized with the requisite hydrazide derivatives to obtain substituted 3,4,6,8,13-pentazatricyclo[7.4.0.02,6]trideca-1(9),2,4,10,12-pentaen-7-one derivatives (5). In the last step compounds with the halogen derivative (group X') 5 are finally reacted to produce $R_1$-substituted intermediates directly to obtain compounds falling under the scope of formula 1c. This last derivatization procedure can be carried out using standard methods such us e.g. Buchwald reactions, aromatic nucleophilic reactions, acylation reactions, alkylation or any kind of N-derivatization reaction useful to the aim of forming compounds 6 according to formula 1c, and is very well known to people skilled in the art. Scheme 2 also shows that compound 7 is cyclized with the requisite hydrazide derivatives to obtain substituted 2,4,5,7,10-pentazatricyclo[7.4.0.03,7]trideca-1(13),3,5,9,11-pentaen-8-one derivatives (8). In the last step compounds with the halogen derivative (group X') 8 are finally reacted to produce $R_1$-substituted intermediates directly to obtain compounds 9 falling under the scope of formula 1f. This last derivatization procedure can be carried out using standard methods such us e.g. Buchwald reactions, aromatic nucleophilic reactions, acylation reactions, alkylation or any kind of N-derivatization reaction useful to the aim of forming compounds according to formula if, and is very well known to people skilled in the art. The same reaction steps can be rearranged, anticipating or postponing each step in the synthesis without any limitation, e.g. the Buchwald reaction can be carried out as a last step, or alternatively as a first step in the entire procedure.

As shown in Scheme 3 below commercially available compounds 1 can be cyclized by with reactants into 4-amino-6-halo-1H-pyrido[3,2-d]pyrimidin-2-one (2). In the next step compounds 2 are then reacted with the reagent to afford the corresponding compounds 3, which are cyclized with 4 to obtain compounds 5. In turn 5 are finally reacted to produce $R_1$-substituted intermediates directly to obtain compounds falling under the scope of formula 1b. This last derivatization procedure can be carried out using standard methods such us e.g. Buchwald reactions, aromatic nucleophilic reactions, acylation reactions, alkylation or any kind of N-derivatization reaction useful to the aim of forming compounds according to formula 1b, and is very well known to people skilled in the art. The same reaction steps can be rearranged, anticipating or postponing each step in the synthesis without any limitation, e.g. the Buchwald reaction can be carried out as a last step, or alternatively as a first step in the entire procedure.

Scheme 2: Production of compounds according to formula 1c and 1f.

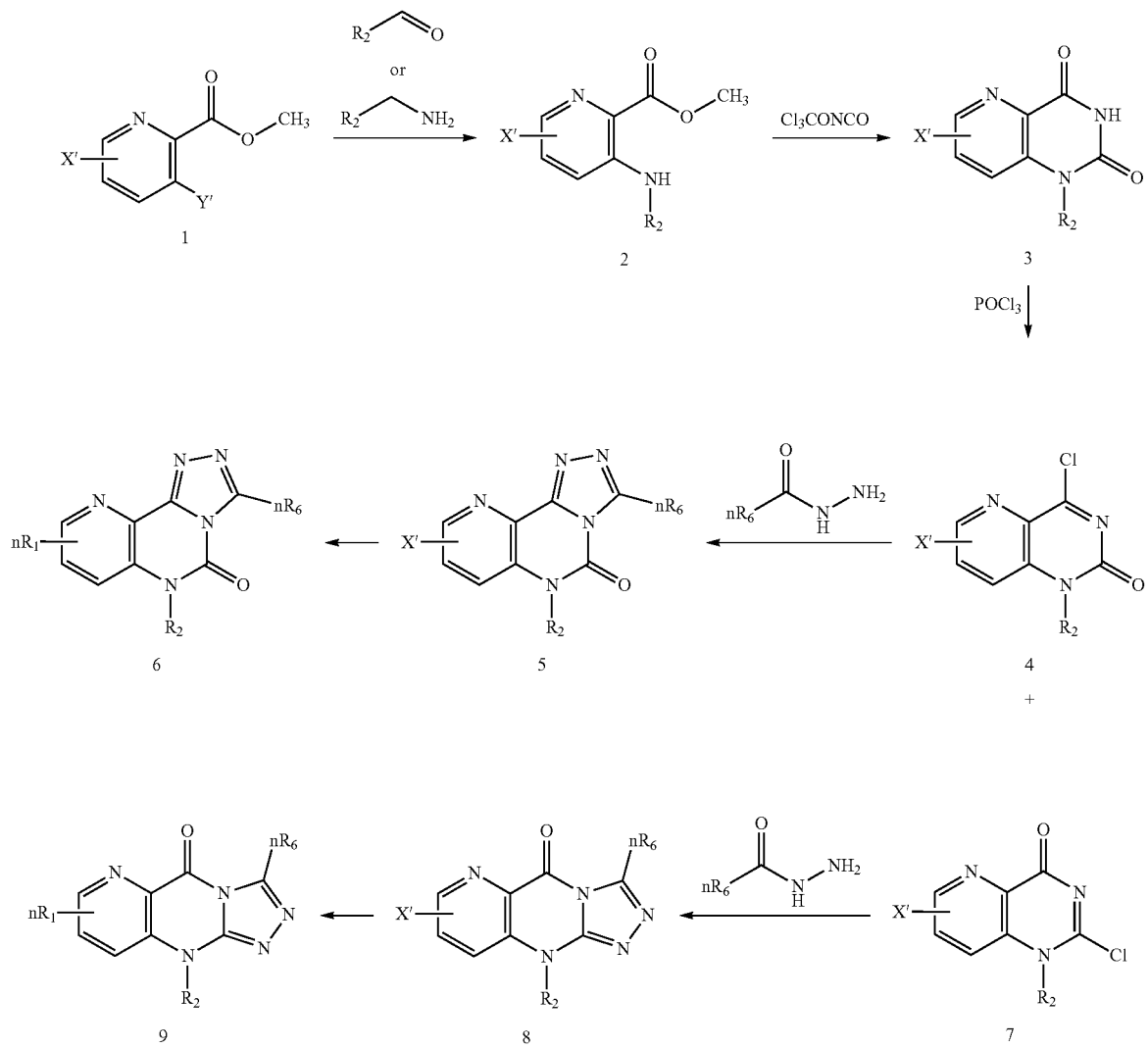

X' = I, Br, Cl, F  Y' = N or F

Scheme 3: Production of compounds according to formula 1b.

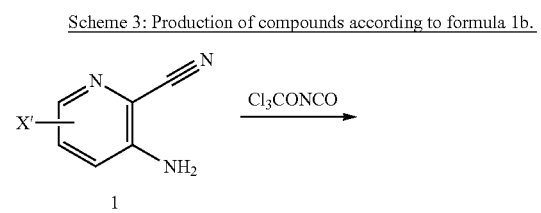

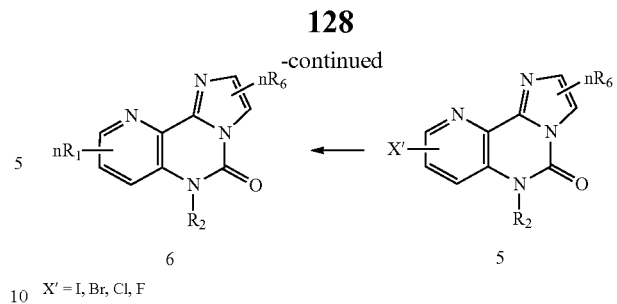

X' = I, Br, Cl, F

As shown in Scheme 4 below commercially available compound 1 can be reacted with isopropanol to afford 5-bromo-2-isopropoxycarbonyl-pyridine-3-carboxylic acid (2). In the next step compounds 2 are then reacted with methyl 2-arylacetate to afford the corresponding compounds 3, which are hydrolysed into 4. In turn 4 is reacted with hydrazine to obtain compounds 5. In the next step 5 is reacted with $POCl_3$ to obtain compounds 6, which are reacted with the requisite hydrazide derivatives affording compounds 7. Compounds 7 are finally reacted to produce $R_1$-substituted intermediates directly to obtain compounds falling under the scope of formula Id. This last derivatization procedure can be carried out using standard methods such us e.g. Buchwald reactions, aromatic nucleophilic reactions, acylation reactions, alkylation or any kind of N-derivatization reaction useful to the aim of forming compounds according to formula Id, and very well known to people skilled in the art. The same reaction steps can be rearranged, anticipating or postponing each step in the synthesis without any limitation, e.g. the Buchwald reaction can be carried out as a last step, or alternatively as a first step in the entire procedure.

Scheme 4: Production of compounds according to formula 1d.

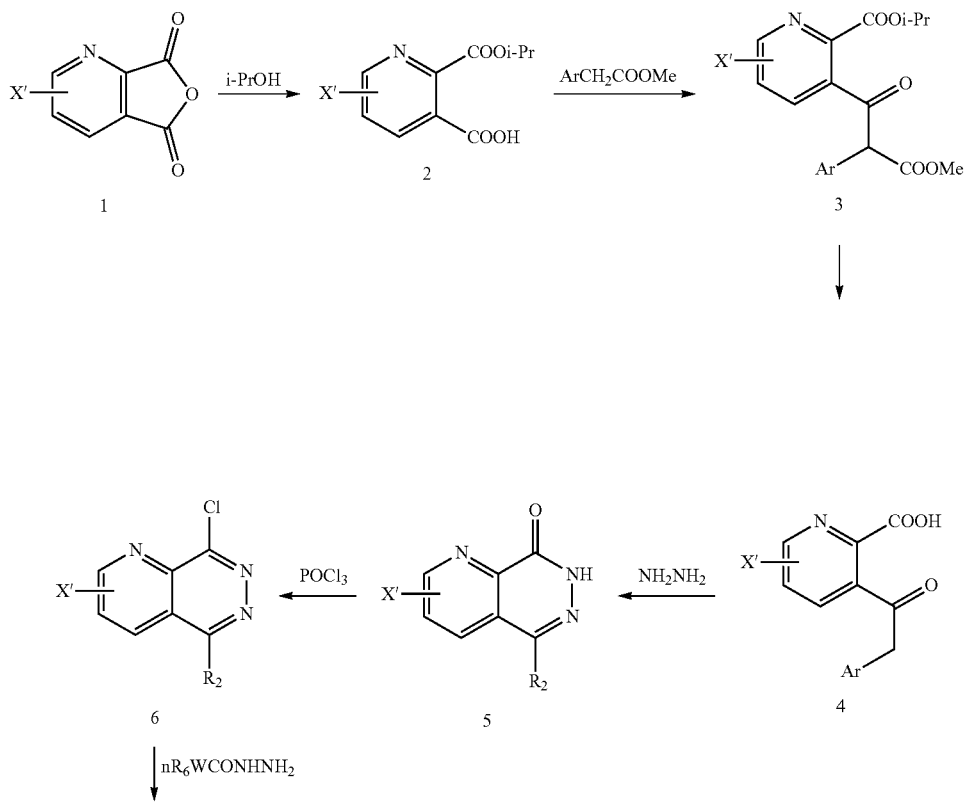

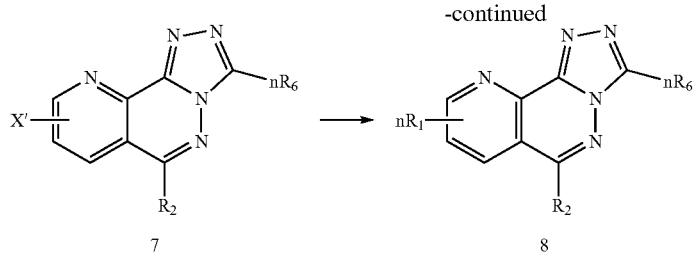

7  →  8

X′ = I, Br, C, Fl

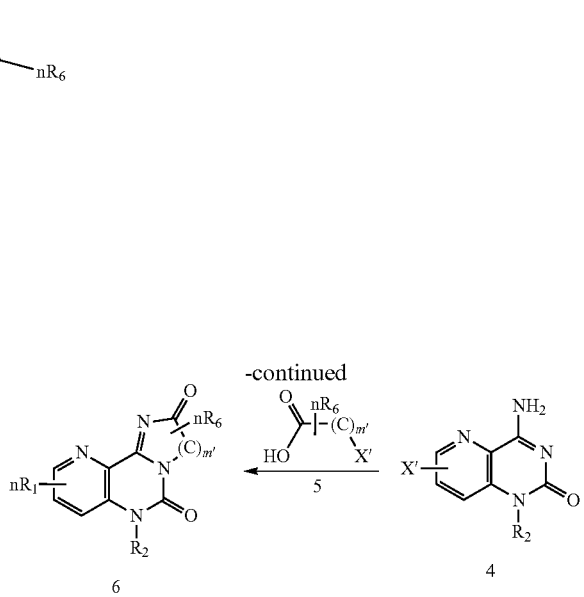

6

X′ = I, Br, Cl, F Y′ = N, I, Br, Cl, F m′ = 1 - 2

As shown in Scheme 5 below, commercially available compounds 1 can be reacted to produce R$_1$-substituted intermediates 2 by standard methods such as e.g. Buchwald reactions, aromatic nucleophilic reactions, alkylation or any kind of N-derivatization reactions useful to the aim of forming compounds of formula 2, and very well known to people skilled in the art. The obtained intermediate 2 can be reacted, according Y′, by standard methods such as e.g. aromatic nucleophilic reactions, reductive amination, Buchwald reactions or any kind of N-derivatization reaction useful to the aim of obtaining the corresponding compounds 3, which can be cyclized into compounds 4 by reaction with trichloroacetyl isocyanate. In turn compounds 4 are condensed with, commercially available or opportunely synthesized, intermediates 5 in order to obtain the appropriately substituted 3,6,8,13-tetrazatricyclo[7.4.0.02,6]trideca-1(9), 2,10,12-tetraene-4,7-dione derivatives 6, falling under the scope of formula 1g. The same reaction steps can be rearranged, anticipating or postponing each step in the synthesis without any limitation, e.g. the Buchwald reaction can be carried out as a last step, or alternatively as a first step in the entire procedure.

Scheme 5: Production of compounds according to formula 1g.

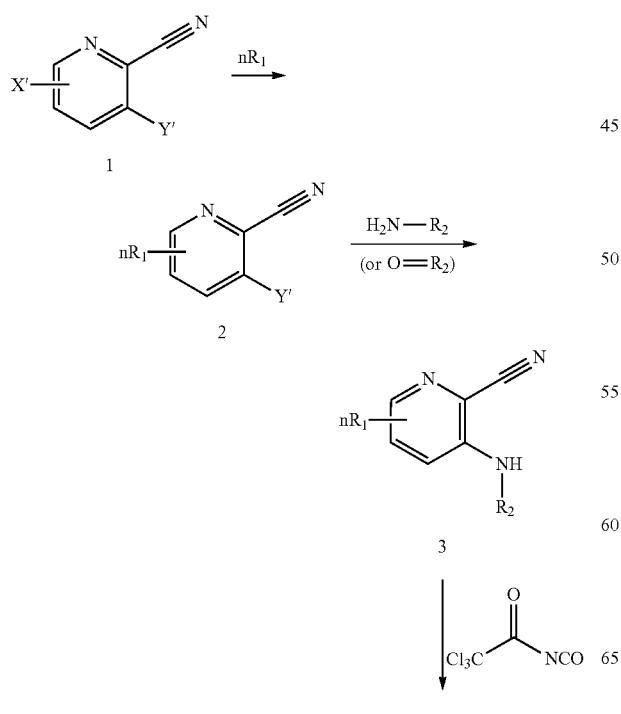

The syntheses of other compounds not currently described in this general description are well documented inside the experimental part of this invention which follows.

The free bases of compounds according to formula I, or indeed those of formulae 1a through 1g, their diastereomers or enantiomers can be converted to the corresponding pharmaceutically acceptable salts under standard conditions well known in the art. For example, the free base is dissolved in a suitable organic solvent, such as methanol, treated with, for example one equivalent of maleic or oxalic acid, one or two equivalents of hydrochloric acid or methanesulphonic acid, and then concentrated under vacuum to provide the corresponding pharmaceutically acceptable salt. The residue can then be purified by recrystallization from a suitable organic solvent or organic solvent mixture, such as methanol/diethyl ether.

The N-oxides of compounds according to formula I, or indeed those of formulae 1a through 1g, can be synthesized by simple oxidation procedures well known to those skilled in the art.

Preparation of Compounds of the General Formula I

Unless otherwise stated, one or more tautomeric forms of compounds of the examples described hereinafter may be prepared in situ and/or isolated. All tautomeric forms of compounds of the examples described hereinafter should be considered to be disclosed.

The invention is illustrated by way of the following examples, in which the following abbreviations may be employed:

AcOH acetic acid
MeCN acetonitrile
Aq. aqueous
BOC tert-butyloxycarbonyl
conc. concentrated
DCM dichloromethane
DCE 1,2-dichloroethane
DIPEA N,N-diisopropylethylamine
DMAc N,N-dimethylacetamide
DMF N,N-dimethylformamide
DMSO dimethyl sulfoxide EI electron ionisation
ESI electrospray ionisation
EtOAc ethyl acetate
EtOH ethanol
HCl hydrochloric acid
HCOOH formic acid
MeOH methanol
MS mass spectrometry
MW molecular weight
NaOH sodium hydroxide
NH$_4$OH ammonium hydroxide (30% ammonia in water)
PE petroleum ether
R$_f$ retention value (from thin layer chromatography)
RT or r.t. room temperature
R$_t$ retention time (from HPLC)
THF tetrahydrofuran
TEA triethylamine
TFA trifluoracetic acid
UPLC ultra high performance liquid chromatography
UPLC-MS UPLC coupled with mass spectrometry The following examples illustrate methods of making some of the compounds of general formula I as described above. These examples are illustrative only and are not intended to limit the scope of the invention. The reagents and starting materials are readily available to those skilled in the art.

Example 1

6-(4-Methoxybenzyl)-8-(morpholin-4-yl)-3-(propan-2-yl)-2,6-dihydroimidazo[1,2-c]pyrido[2,3-e]pyrimidin-5(3H)-one and

Example 18

6-(4-Methoxybenzyl)-8-(morpholin-4-yl)-2-(propan-2-yl)-2,6-dihydroimidazo[1,2-c]pyrido[2,3-e]pyrimidin-5(3H)-one

3-Fluoro-5-morpholinopyridine-2-carbonitrile (Step 1)

To a solution of 1.04 g of 3,5-difluoropyridine-2-carbonitrile (7.46 mmol) in DMAC (5 mL) in a microwave vial 0.65 mL of morpholine (0.65 g, 7.46 mmol) and 2.08 mL of TEA (1.51 g, 14.92 mmol) were added. The mixture was stirred under microwave irradiation at 100° C. for 30 min. After cooling down to room temperature, water was added to the mixture and a white precipitate was obtained. This was washed with water and dried to obtain 1.3 g of 3-fluoro-5-morpholinopyridine-2-carbonitrile as a white solid (Yield 84%).

3-[(4-Methoxyphenyl)methylamino]-5-morpholino-pyridine-2-carbonitrile (Step 2)

To a solution of 0.5 g of 3-fluoro-5-morpholino-pyridine-2-carbonitrile (2.41 mmol) in DMAC (10 mL) were added 1.89 mL of (4-methoxyphenyl)methanamine (1.98 g, 14.48 mmol) and 0.4 mL of TEA (0.29 g 2.89 mmol). The mixture was stirred at 150° C. under MW irradiation for 1 h. After cooling down to room temperature water was added to the mixture. A white solid was obtained, which was washed with water and dried under vacuum to obtain 550 mg (yield 70%) of 3-[(4-methoxyphenyl)methylamino]-5-morpholinopyridine-2-carbonitrile, used in the next step without further purification.

2-(4-Isopropyl-4,5-dihydro-1H-imidazol-2-yl)-N-[(4-methoxyphenyl)methyl]-5-morpholinopyridin-3-amine (Step 3)

To a solution of 300 mg of 3-[(4-methoxyphenyl)methylamino]-5-morpholinopyridine-2-carbonitrile (0.92 mmol) in 5 mL of DMAC in a microwave vial, were added 486 mg of 3-methylbutane-1,2-diamine HCl (2.77 mmol) and 0.77 mL of TEA (561 mg, 5.55 mmol). The vial was sealed and the mixture was heated at 160° C. for 8 h. After cooling down to room temperature, the mixture was diluted with EtOAc and the organic layer was washed with water, brine and dried over anhydrous Na$_2$SO$_4$ and evaporated to dryness to obtain 310 mg of the title product as a yellow oil (81%) used in the next step without further purification.

6-(4-Methoxybenzyl)-8-(morpholin-4-yl)-3-(propan-2-yl)-2,6-dihydroimidazo[1,2-c]pyrido[2,3-e]pyrimidin-5(3H)-one and 6-(4-Methoxybenzyl)-8-(morpholin-4-yl)-2-(propan-2-yl)-2,6-dihydroimidazo[1,2-c]pyrido[2,3-e]pyrimidin-5(3H)-one (Step 4)

To a solution of 300 mg of 2-(4-isopropyl-4,5-dihydro-1H-imidazol-2-yl)-N-[(4-methoxyphenyl)methyl]-5-morpholinopyridin-3-amine (0.73 mmol) in 8 mL of acetonitrile, were added in a microwave vial, 142 mg of carbonyldiimidazole (CDI) (0.88 mmol) and 18 mg of DMAP (0.15 mmol). The vial was sealed and heated under microwave irradiation at 150° C. for 90 min. 1.2 equivalents of CDI and 0.2 equivalents of DMAP, were added and the mixture was heated in the same condition for additional 90 min. The reaction mixture was poured into water, extracted with EtOAc, dried over anhydrous Na$_2$SO$_4$. The solvent was evaporated to dryness and the crude was purified via automated flash chromatography (Biotage Isolera-Dalton, SNAP25 Ultra cartridge) eluting with CHCl$_3$-MeOH 95/5 affording 6-(4-methoxybenzyl)-8-(morpholin-4-yl)-2-(propan-2-yl)-2,6-dihydroimidazo[1,2-c]pyrido[2,3-e]pyrimidin-5(3H)-one (Example 18)

UPLC-MS [M+H]$^+$=436.3

$^1$H NMR (400 MHz, METHANOL-d$_4$) δ ppm 8.15 (d, 1H) 7.18-7.32 (m, 2H) 6.85-6.92 (m, 2H) 6.74 (d, 1H) 5.08-5.26 (m, 2H) 4.11-4.20 (m, 1H) 4.00-4.09 (m, 1H) 3.75-3.82 (m, 5H) 3.74 (s, 3H) 3.16-3.26 (m, 4H) 1.85-2.02 (m, 1H) 1.05 (d, 3H) 0.98 (d, 3H).

A further group of collected fractions afforded after re-purification by Biotage Isolera-Dalton, SNAP10 Ultra cartridge) eluting with a EtOAc-MeOH gradient from 5% to 10% of MeOH 14 mg of the regioisomer 6-(4-methoxybenzyl)-8-(morpholin-4-yl)-3-(propan-2-yl)-2,6-dihydroimidazo[1,2-c]pyrido[2,3-e]pyrimidin-5(3H)-one (Example 1) (yield 4.4%) as colourless oil.

UPLC-MS [M+H]$^+$=436.29

$^1$H NMR (400 MHz, METHANOL-d$_4$) δ ppm 8.23 (d, 1H), 7.25 (m, 2H), 6.92 (m, 2H), 6.80 (d, 1H), 5.25 (AB quartet, 2H), 4.54-4.69 (m, 1H), 3.83-4.13 (m, 2H), 3.80 (m, 4H), 3.78 (s, 3H), 3.25-3.30 (m, 4H), 2.59-2.74 (m, 1H), 1.00 (d, 3H), 0.87 (d, 3H).

Example compounds 2-9, 22, 35, 43, 44, 46, 47 as illustrated in Table 1 were prepared following the procedure described for the compounds of Example 1 but replacing 3,5-dimethoxybenzylamine for (4-methoxyphenyl)methanamine at Step 2 and substituting, if requested, 3-methylbutane-1,2-diamine with the proper 1,2-diamine (purchased from available vendors or synthesised by methods disclosed by the literature) at Step 3. Reported yields are referred to the last step.

Example 2

6-(3,5-Dimethoxybenzyl)-3-methyl-8-(morpholin-4-yl)-2,6-dihydroimidazo[1,2-c]pyrido[2,3-e]pyrimidin-5(3H)-one And

Example 3

6-(3,5-Dimethoxybenzyl)-2-methyl-8-(morpholin-4-yl)-2,6-dihydroimidazo[1,2-c]pyrido[2,3-e]pyrimidin-5(3H)-one Purification of the reaction crude by preparative HPLC afforded Example 2 (11.3%) and Example 3 (22%) as yellow solids.

Example 2: HPLC-MS [M+H]$^+$=438.1 with some contamination of Example 3

$^1$H NMR (400 MHz, CHLOROFORM-d) δ ppm 8.27-8.09 (m, 1H), 6.54 (d, 1H), 6.36 (s, 3H), 5.31 (d, 3H), 5.14 (q, 2H), 4.72 (s, 1H), 4.31 (q, 1H), 3.80 (t, 5H), 3.75 (d, 7H), 3.22 (dd, 4H), 1.52 (dd, 3H).

Example 3: HPLC-MS [M+H]$^+$=438.1

$^1$H NMR (400 MHz, CHLOROFORM-d) δ ppm 8.22 (d, 1H), 6.54 (d, 1H), 6.46-6.30 (m, 3H), 5.28-5.03 (m, 2H), 4.63 (q, 1H), 4.38 (t, 1H), 3.80 (q, 5H), 3.75 (s, 6H), 3.26 (t, 4H), 1.52 (d, 3H).

Example 4

6-(3,5-Dimethoxybenzyl)-8-(morpholin-4-yl)-2-(propan-2-yl)-2,6-dihydroimidazo[1,2-c]pyrido[2,3-e]pyrimidin-5(3H)-one And

Example 9

6-(3,5-Dimethoxybenzyl)-8-(morpholin-4-yl)-3-(propan-2-yl)-2,6-dihydroimidazo[1,2-c]pyrido[2,3-e]pyrimidin-5(3H)-one Purification of the reaction crude by means of a Isolera One (Biotage), cartridge type SNAP50, using a gradient from EtOAC 100% to EtOAc:MeOH 8:2 gave a brown powder, which was then purified on a reverse phase column chromatography, cartridge type SNAP60, using a gradient from NH$_4$HCO$_3$ buffer:MeCN 9:1 to NH$_4$HCO$_3$ buffer:MeCN 3:7 affording a light yellow powder. The sample was then crystallized from acetonitrile and filtered to give Example 4 (white powder, 43.4%). Mother liquors were also recovered as 1:1 mix of regioisomers. Further purification by means of an Isolera One Biotage, cartridge type SNAP25, using a gradient from EtOAc 100% to EtOAc:MeOH 8:2 yielded Example 9 as a pale yellow powder.

Example 4: HPLC-MS [M+H]$^+$=466.23

$^1$H NMR (400 MHz, CHLOROFORM-d) δ ppm 8.17 (d, 1H) 6.58 (d, 1H) 6.41 (d, 2H) 6.34-6.39 ((m, 1H) 4.95-5.29 (m, 2H) 4.16-4.34 (m, 1H) 4.03-4.15 (m, 1H) 3.80-3.86 (m, 5H) 3.77 (s, 6H) 3.14-3.23 (m, 4H) 1.92-2.10 (m, 1H) 0.95-1.20 (m, 6H) Example 9: HPLC-MS [M+H]$^+$=466.23

$^1$H NMR (400 MHz, CHLOROFORM-d) δ ppm 8.13 (d, 1H) 6.57 (d, 1H) 6.37-6.49 (m, 2H) 6.36 (dd, 1H) 4.83-5.36 (m, 2H) 4.55 (ddd, 1H) 3.90-4.18 (m, 2H) 3.77-3.87 (m, 4H) 3.76 (s, 6H) 3.15-3.30 (m, 4H) 2.52-2.82 (m, 1H) 0.74-1.09 (m, 6H)

Example 5

6-(3,5-Dimethoxybenzyl)-2-ethyl-8-(morpholin-4-V)-2,6-dihydroimidazo[1,2-c]pyrido[2,3-e]pyrimidin-5(3H)-one And

Example 6

6-(3,5-Dimethoxybenzyl)-3-ethyl-8-(morpholin-4-yl)-2,6-dihydroimidazo[1,2-c]pyrido[2,3-e]pyrimidin-5(3H)-one Purification of the reaction crude by preparative HPLC afforded Example 5 (19%) and Example 6 (5%).

Example 5: HPLC-MS [M+H]$^+$=452.55

$^1$H NMR (400 MHz, CHLOROFORM-d) δ ppm 8.27 (d, 1H), 6.56 (d, 1H), 6.39 (s, 3H), 5.29-5.05 (m, 2H), 4.51 (m, 1H), 4.36 (t, 1H), 3.92 (dd, 1H), 3.83 (t, 4H), 3.78 (s, 6H), 3.29 (t, 4H), 2.10-1.92 (m, 1H), 1.79 (dt, 1H), 1.10 (t, 3H).

Example 6: HPLC-MS [M+H]$^+$=452.1

Example 7

6-(3,5-Dimethoxybenzyl)-8-(morpholin-4-yl)-2,6-dihydroimidazo[1,2-c]pyrido[2,3-e]pyrimidin-5(3H)-one Pale yellow solid (46%).

HPLC-MS [M+H]$^+$=424.37

$^1$H NMR (400 MHz, DMSO-d$_6$) δ ppm 8.17 (d, 1H) 6.79 (d, 1H) 6.50 (d, 2H) 6.39 (t, 1H) 5.15 (s, 2H) 3.86-4.10 (m, 4H) 3.60-3.78 (m, 10H) 3.22-3.28 (m, 4H)

Example 8

6-(3,5-Dimethoxybenzyl)-2,3-dimethyl-8-(morpholin-4-yl)-2,6-dihydroimidazo[1,2-c]pyrido[2,3-e]pyrimidin-5(3H)-one Purified by preparative TLC using MeOH in DCM as eluent (0→5%). Yield: 29.6%

HPLC-MS [M+H]$^+$=452.6

$^1$H NMR (300 MHz, CHLOROFORM-d) δ ppm 8.13 (d, 1H), 6.55 (d, 1H), 6.37 (m, 3H), 5.13 (s, 2H), 4.65 (dt, 1H), 4.53-4.40 (m, 1H), 3.81 (t, 4H), 3.75 (s, 7H), 3.18 (t, 4H), 1.45 (d, 3H), 1.36 (d, 3H).

Example 22

6-(3,5-Dimethoxybenzyl)-2-(2-methylpropyl)-8-(morpholin-4-yl)-2,6-dihydroimidazo[1,2-c]pyrido[2,3-e]pyrimidin-5(3H)-one And

Example 35

6-(3,5-Dimethoxybenzyl)-3-(2-methylpropyl)-8-(morpholin-4-yl)-2,6-dihydroimidazo[1,2-c]pyrido[2,3-e]pyrimidin-5(3H)-one Purification of the reaction crude by preparative HPLC afforded Example 22 (16%) and Example 35 (11.7%).
Example 22: HPLC-MS [M+H]$^+$=480.24
Example 35: HPLC-MS [M+H]$^+$=480.34

Example 43

2-Cyclohexyl-6-(3,5-dimethoxybenzyl)-8-(morpholin-4-yl)-2,6-dihydroimidazo[1,2-c]pyrido[2,3-e]pyrimidin-5(3H)-one And

Example 44

3-Cyclohexyl-6-(3,5-dimethoxybenzyl)-8-(morpholin-4-yl)-2,6-dihydroimidazo[1,2-c]pyrido[2,3-e]pyrimidin-5(3H)-one Purification of the reaction crude by preparative HPLC afforded Example 43 (56%) and Example 44 (8.7%).
Example 43: HPLC-MS [M+H]$^+$=506.41
Example 44: HPLC-MS [M+H]$^+$=506.35

Example 46

6-(3,5-Dimethoxybenzyl)-8-(morpholin-4-yl)-2-phenyl-2,6-dihydroimidazo[1,2-c]pyrido[2,3-e]pyrimidin-5(3H)-one And

Example 47

6-(3,5-Dimethoxybenzyl)-8-(morpholin-4-V)-3-phenyl-2,6-dihydroimidazo[1,2-c]pyrido[2,3-e]pyrimidin-5(3H)-one Purification of the reaction crude by preparative HPLC afforded Example 46 (26.6%) and Example 47 (2.8%).
Example 46: HPLC-MS [M+H]$^+$=500.38
Example 47: HPLC-MS [M+H]$^+$=500.26

Examples 10-14, 25, 26, 30, 31, 36, 40, 41, 45, 50, 54, 55, 61-63 as illustrated in Table 1 were prepared following the procedure described for Example 1 but replacing 4-chlorobenzylamine for (4-methoxyphenyl)methanamine at Step 2 and substituting, if requested, 3-methylbutane-1,2-diamine with the proper 1,2-diamine (purchased from available vendors or synthesised by methods disclosed by the literature) at Step 3. Reported yields are referred to the last step.

Example 10

6-(4-Chlorobenzyl)-2-cyclopropyl-8-(morpholin-4-yl)-2,6-dihydroimidazo[1,2-c]pyrido[2,3-e]pyrimidin-5(3H)-one And

Example 12

6-(4-Chlorobenzyl)-3-cyclopropyl-8-(morpholin-4-yl)-2,6-dihydroimidazo[1,2-c]pyrido[2,3-e]pyrimidin-5(3H)-one The crude was purified by flash chromatography using MeOH in DCM (0 to 5%), then by preparative HPLC giving 6.6% of Example 10 and 2% of Example 12.
Example 10: HPLC-MS [M+H]$^+$=438.06
$^1$H NMR (300 MHz, CHLOROFORM-d) δ ppm 8.17 (d, 1H), 7.38-7.31 (m, 2H), 7.26-7.16 (m, 2H), 6.46 (d, 1H), 5.31-5.06 (m, 2H), 4.31-4.16 (m, 1H), 3.99-3.86 (m, 2H), 3.87-3.80 (m, 4H), 3.19 (dd, 4H), 1.07 (dd, 1H), 0.74-0.52 (m, 3H), 0.45 (q, 1H).
Example 12: HPLC-MS [M+H]$^+$=438.11

Example 11

6-(4-Chlorobenzyl)-2-(methoxymethyl)-8-(morpholin-4-yl)-2,6-dihydroimidazo[1,2-c]pyrido[2,3-e]pyrimidin-5(3H)-one And

Example 13

6-(4-Chlorobenzyl)-3-(methoxymethyl)-8-(morpholin-4-yl)-2,6-dihydroimidazo[1,2-c]pyrido[2,3-e]pyrimidin-5(3H)-one The crude was purified by flash chromatography using MeOH in DCM (0 to 5%), then by preparative HPLC giving 5% of Example 11 and 5% of Example 13.
Example 11: HPLC-MS [M+H]$^+$=442.05
$^1$H NMR (300 MHz, CHLOROFORM-d) δ ppm 8.82 (d, 1H), 7.37 (d, 1H), 7.23-7.15 (m, 2H), 6.90-6.81 (m, 2H), 4.41 (s, 2H), 3.95-3.84 (m, 4H), 3.78 (s, 3H), 3.73-3.63 (m, 1H), 3.31-3.16 (m, 4H), 1.57 (d, 6H).
Example 13: HPLC-MS [M+H]$^+$=442.12

Example 14

6-(4-Chlorobenzyl)-8-(morpholin-4-yl)-2-(propan-2-yl)-2,6-dihydroimidazo[1,2-c]pyrido[2,3-e]pyrimidin-5(3H)-one And

Example 162

6-(4-Chlorobenzyl)-8-(morpholin-4-yl)-3-(propan-2-yl)-2,6-dihydroimidazo[1,2-c]pyrido[2,3-e]pyrimidin-5(3H)-one The crude was purified via automated flash chromatography (Biotage Isolera-Dalton), SNAP25 Ultra cartridge, eluting with isocratic CHCl₃-MeOH 95/5. Two group of fractions enriched in each regioisomer were isolated. Each group was re-purified with a SNAP10 Ultra cartridge eluting with EtOAc-MeOH gradient from 5% to 10% affording Example 14 as a pale yellow solid (50%) and Example 162 as a pale yellow solid (3.8%).

Example 14: $^1$H NMR (400 MHz, DMSO-d$_6$) δ ppm 8.16 (d, 1H) 7.32-7.45 (m, 4H) 6.73 (d, 1H) 5.12-5.33 (m, 2H) 3.91-4.05 (m, 2H) 3.71 (t, 4H) 3.52-3.65 (m, 1H) 3.24 (dd, 4H) 1.65-1.86 ((m, 1H) 0.99 (d, 3H) 0.92 (d, 3H)

UPLC-MS [M+H]$^+$=440.24

Example 162

UPLC-MS [M+H]$^+$=440.28
$^1$H NMR (400 MHz, DMSO-d6) δ ppm 8.17 (d, 1H) 7.38-7.45 (m, 2H) 7.30-7.35 (m, 2H) 6.76 (d, 1H) 5.17-5.33 (m, 2H) 4.35-4.46 (m, 1H) 3.87-3.96 (m, 1H) 3.77 (dd, 1H) 3.70 (t, 4H) 3.20-3.28 (m, 4H) 2.53 (br d, 1H) 0.89 (d, 3H) 0.74 (d, 3H)

Example 25

6-(4-Chlorobenzyl)-2-cyclohexyl-8-(morpholin-4-yl)-2,6-dihydroimidazo[1,2-c]pyrido[2,3-e]pyrimidin-5(3H)-one And

Example 26

6-(4-Chlorobenzyl)-3-cyclohexyl-8-(morpholin-4-yl)-2,6-dihydroimidazo[1,2-c]pyrido[2,3-e]pyrimidin-5(3H)-one Purification of the reaction crude by preparative HPLC afforded Example 25 (83%) and Example 26 (12%) as waxy yellow solids.
Example 25: HPLC-MS [M+H]$^+$=480.4
Example 26: HPLC-MS [M+H]$^+$=480.4

Example 30

6-(4-Chlorobenzyl)-2-(2-methylpropyl)-8-(morpholin-4-yl)-2,6-dihydroimidazo[1,2-c]pyrido[2,3-e]pyrimidin-5(3H)-one And

Example 31

6-(4-Chlorobenzyl)-3-(2-methylpropyl)-8-(morpholin-4-yl)-2,6-dihydroimidazo[1,2-c]pyrido[2,3-e]pyrimidin-5(3H)-one Purification of the reaction crude by preparative HPLC afforded Example 30 (59%) and Example 31 (15%) as waxy yellow solids.
Example 30: HPLC-MS [M+H]$^+$=454.46
Example 31: HPLC-MS [M+H]$^+$=454.38

Example 36

6-(4-Chlorobenzyl)-8-(morpholin-4-yl)-2-phenyl-2,6-dihydroimidazo[1,2-c]pyrido[2,3-e]pyrimidin-5(3H)-one And

Example 45

6-(4-Chlorobenzyl)-8-(morpholin-4-yl)-3-phenyl-2,6-dihydroimidazo[1,2-c]pyrido[2,3-e]pyrimidin-5(3H)-one Purification of the reaction crude by preparative HPLC afforded Example 36 and Example 45 as yellow waxy solids.
Example 36: HPLC-MS [M+H]$^+$=474.3
Example 45: HPLC-MS [M+H]$^+$=474.3

Example 40

6-(4-Chlorobenzyl)-8-(morpholin-4-yl)-2',3',5',6'-tetrahydrospiro[imidazo[1,2-c]pyrido[2,3-e]pyrimidine-2,4'-pyran]-5(6H)-one And

Example 41

6-(4-Chlorobenzyl)-8-(morpholin-4-yl)-2,2',3',5',6,6'-hexahydro-5H-spiro[imidazo[1,2-c]pyrido[2,3-e]pyrimidine-3,4'-pyran]-5-one Purification of the reaction crude by preparative HPLC afforded Example 40 (53%) and
Example 41 (16.2%) as yellow waxy solids.
Example 40: UPLC-MS [M+H]$^+$=468.4
Example 41: UPLC-MS [M+H]$^+$=468.4

Example 50

6-(4-Chlorobenzyl)-2-ethyl-8-(morpholin-4-yl)-2,6-dihydroimidazo[1,2-c]pyrido[2,3-e]pyrimidin-5(3H)-one Purification of the reaction crude by preparative HPLC afforded Example 50 (12.7%) as yellow waxy solid.
Example 41: UPLC-MS [M+H]$^+$=426.5

Example 54

6-(4-Chlorobenzyl)-8-(morpholin-4-yl)-2-(morpholin-4-ylcarbonyl)-2,6-dihydroimidazo[1,2-c]pyrido[2,3-e]pyrimidin-5(3H)-one And

Example 55

6-(4-Chlorobenzyl)-8-(morpholin-4-yl)-3-(morpholin-4-ylcarbonyl)-2,6-dihydroimidazo[1,2-c]pyrido[2,3-e]pyrimidin-5(3H)-one Purification of the reaction crude by preparative HPLC afforded Example 54 (1.75%) and 55 (1%) as yellow waxy solids.
Example 54: UPLC-MS [M+H]$^+$=511.32
Example 55: UPLC-MS [M+H]$^+$=511.25

Example 61

6-(4-Chlorobenzyl)-2-(cyclohexylmethyl)-8-(morpholin-4-yl)-2,6-dihydroimidazo[1,2-c]pyrido[2,3-e]pyrimidin-5(3H)-one Purification of the reaction crude by preparative HPLC afforded Example 61 (12%) as yellow waxy solid.

Example 61: UPLC-MS [M+H]$^+$=494.38

Example 62

6-(4-Chlorobenzyl)-2-(3-methylbutyl)-8-(morpholin-4-yl)-2,6-dihydroimidazo[1,2-c]pyrido[2,3-e]pyrimidin-5(3H)-one And

Example 63

6-(4-Chlorobenzyl)-3-(3-methylbutyl)-8-(morpholin-4-yl)-2,6-dihydroimidazo[1,2-c]pyrido[2,3-e]pyrimidin-5(3H)-one Purified by flash chromatography using MeOH in DCM (gradient from 0 to 10%) as an eluent followed by preparative HPLC affording Example 62 (25%) and Example 63 (8.8%).

Compound 62: HPLC-MS [M+H]$^+$=468.21

Compound 63: HPLC-MS [M+H]$^+$=468.28

Examples 23, 24, 28, 29, 32-34, 37, 38, 52, 53, 56, 57, 65, 66, 67 as illustrated in Table 1 were prepared following the procedure described for Example 1 but replacing 3-methylbutane-1,2-diamine with the proper 1,2-diamine (purchased from available vendors or synthesised by method disclosed by the literature) at Step 3. Reported yields are referred to the last step.

Example 23

2-Cyclohexyl-6-(4-methoxybenzyl)-8-(morpholin-4-yl)-2,6-dihydroimidazo[1,2-c]pyrido[2,3-e]pyrimidin-5(3H)-one And

Example 24

3-Cyclohexyl-6-(4-methoxybenzyl)-8-(morpholin-4-yl)-2,6-dihydroimidazo[1,2-c]pyrido[2,3-e]pyrimidin-5(3H)-one Purification of the reaction crude by preparative HPLC afforded Example 23 (7.4%) and Example 24 (2.4%) as yellow waxy solid.

Compound 23: HPLC-MS [M+H]$^+$=476.48

Compound 24: HPLC-MS [M+H]$^+$=476.39

Example 28

6-(4-Methoxybenzyl)-8-(morpholin-4-yl)-2-phenyl-2,6-dihydroimidazo[1,2-c]pyrido[2,3-e]pyrimidin-5(3H)-one And

Example 29

6-(4-Methoxybenzyl)-8-(morpholin-4-yl)-3-phenyl-2,6-dihydroimidazo[1,2-c]pyrido[2,3-e]pyrimidin-5(3H)-one Purification of the reaction crude by preparative HPLC afforded Example 28 (5.9%) and Example 29 (5.1%) as yellow waxy solid.

Compound 28: HPLC-MS [M+H]$^+$=470.46

Compound 29: HPLC-MS [M+H]$^+$=470.39

Example 32

2-tert-Butyl-6-(4-methoxybenzyl)-8-(morpholin-4-yl)-2,6-dihydroimidazo[1,2-c]pyrido[2,3-e]pyrimidin-5(3H)-one Purification of the reaction crude by preparative HPLC afforded Example 32 (6.6%).

HPLC-MS [M+H]$^+$=450.48

$^1$H NMR (300 MHz, CHLOROFORM-d) δ ppm 8.16 (d, 1H), 7.23-7.14 (m, 2H), 6.93-6.83 (m, 2H), 6.56 (d, 1H), 5.28-5.01 (m, 2H), 4.23-3.97 (m, 2H), 3.90 (dd, 1H), 3.85-3.74 (m, 7H), 3.24-3.10 (m, 4H), 1.03 (s, 9H).

Example 33

2-Cyclobutyl-6-(4-methoxybenzyl)-8-(morpholin-4-yl)-2,6-dihydroimidazo[1,2-c]pyrido[2,3-e]pyrimidin-5(3H)-one Purification of the reaction crude by preparative HPLC afforded Example 33 (5.2%).

HPLC-MS [M+H]$^+$=448.13

$^1$H NMR (300 MHz, CHLOROFORM-d) δ ppm 8.14 (d, 1H), 7.18 (d, 2H), 6.93-6.82 (m, 2H), 6.55 (d, 1H), 5.24-5.04 (m, 2H), 4.49-4.35 (m, 1H), 4.20-4.07 (m, 1H), 3.86-3.75 (m, 7H), 3.71 (dd, 1H), 3.24-3.12 (m, 4H), 2.63-2.53 (m, 1H), 2.20-1.85 (m, 6H).

Example 34

2-(2,2-Dimethylpropyl)-6-(4-methoxybenzyl)-8-(morpholin-4-yl)-2,6-dihydroimidazo[1,2-c]pyrido[2,3-e]pyrimidin-5(3H)-one Purification of the reaction crude by preparative HPLC afforded Example 34 (10.4%)

HPLC-MS [M+H]$^+$464.14

$^1$H NMR (300 MHz, CHLOROFORM-d) δ ppm 8.16 (d, 1H), 7.24-7.18 (m, 2H), 6.92-6.86 (m, 2H), 6.57 (d, 1H), 5.17 (s, 2H), 4.47-4.36 (m, 1H), 4.35-4.27 (m, 1H), 3.86-3.79 (m, 7H), 3.78-3.70 (m, 1H), 3.24-3.16 (m, 4H), 2.12 (dd, 1H), 1.54 (dd, 1H), 1.04 (s, 9H).

Example 37

6-(4-Methoxybenzyl)-2-(2-methylpropyl)-8-(morpholin-4-yl)-2,6-dihydroimidazo[1,2-c]pyrido[2,3-e]pyrimidin-5(3H)-one And

Example 38

6-(4-methoxybenzyl)-3-(2-methylpropyl)-8-(morpholin-4-yl)-2,6-dihydroimidazo[1,2-c]pyrido[2,3-e]pyrimidin-5(3H)-one Purification of the reaction crude by preparative HPLC afforded Example 37 (66.6%) and Example 38 (15.9%) as yellow waxy solid.

Compound 37: HPLC-MS [M+H]$^+$=450.20
Compound 38: HPLC-MS [M+H]$^+$=450.38

Example 52

2-Ethyl-6-(4-methoxybenzyl)-8-(morpholin-4-yl)-2,6-dihydroimidazo[1,2-c]pyrido[2,3-e]pyrimidin-5(3H)-one And

Example 53

3-Ethyl-6-(4-methoxybenzyl)-8-(morpholin-4-yl)-2,6-dihydroimidazo[1,2-c]pyrido[2,3-e]pyrimidin-5(3H)-one Purification of the reaction crude by preparative HPLC afforded Example 52 (26.6%) and Example 53 (3%) as yellow waxy solid.

Compound 52: HPLC-MS [M+H]$^+$=422.28
Compound 53: HPLC-MS [M+H]$^+$=422.36

Example 56

6-(4-Methoxybenzyl)-8-(morpholin-4-yl)-2-(2,2,2-trifluoroethyl)-2,6-dihydroimidazo[1,2-c]pyrido[2,3-e]pyrimidin-5(3H)-one Purification of the reaction crude by flash chromatography (MeOH in DCM (gradient 0→10%) as an eluent followed by preparative HPLC afforded Example 56 (10.4%).

HPLC-MS [M+H]$^+$=476.14

$^1$H NMR (300 MHz, CHLOROFORM-d) δ ppm 8.14 (s, 1H), 7.21-7.15 (m, 2H), 6.91-6.81 (m, 2H), 6.56 (s, 1H), 5.21-5.07 (m, 2H), 4.73-4.58 (m, 1H), 4.38-4.27 (m, 1H), 3.96-3.86 (m, 1H), 3.84-3.76 (m, 7H), 3.23-3.14 (m, 4H), 3.00-2.87 (m, 1H), 2.46-2.28 (m, 1H).

Example 57

2-(tert-Butoxymethyl)-6-(4-methoxybenzyl)-8-(morpholin-4-yl)-2,6-dihydroimidazo[1,2-c]pyrido[2,3-e]pyrimidin-5(3H)-one And

Example 67

3-(tert-Butoxymethyl)-6-(4-methoxybenzyl)-8-(morpholin-4-yl)-2,6-dihydroimidazo[1,2-c]pyrido[2,3-e]pyrimidin-5(3H)-one Purification of the reaction crude by flash chromatography (MeOH in DCM (gradient 0→10%) as an eluent followed by preparative HPLC afforded Example 57 (14.8%) and Example 67 (3.5%).

Compound 57: HPLC-MS [M+H]$^+$=480.39
$^1$H NMR (300 MHz, CHLOROFORM-d) δ ppm 8.13 (d, 1H), 7.23-7.15 (m, 2H), 6.90-6.83 (m, 2H), 6.55 (d, 1H), 5.25-5.07 (m, 2H), 4.60-4.47 (m, 1H), 4.22-4.11 (m, 1H), 4.07-3.97 (m, 1H), 3.86-3.76 (m, 7H), 3.40-3.32 (m, 1H), 3.21-3.14 (m, 4H), 1.20 (s, 9H). Compound 67: HPLC-MS [M+H]$^+$=480.26

Example 65

6-(4-Methoxybenzyl)-2-(2-methoxyethyl)-8-(morpholin-4-yl)-2,6-dihydroimidazo[1,2-c]pyrido[2,3-e]pyrimidin-5(3H)-one And

Example 66

6-(4-Methoxybenzyl)-3-(2-methoxyethyl)-8-(morpholin-4-yl)-2,6-dihydroimidazo[1,2-c]pyrido[2,3-e]pyrimidin-5(3H)-one Purification of the reaction crude by flash chromatography (MeOH in DCM (gradient 0→10%) as an eluent followed by preparative HPLC afforded Example 65 (16.6%) and Example 66 (8.4%).

Compound 65: HPLC-MS [M+H]$^+$=452.38
Compound 66: HPLC-MS [M+H]$^+$=452.27

Example 15

6-(4-Chlorobenzyl)-8-(2-oxa-6-azaspiro[3.3]heptan-6-yl)-2-(propan-2-yl)-2,6-dihydroimidazo[1,2-c]pyrido[2,3-e]pyrimidin-5(3H)-one 5-Bromo-2-(4-isopropyl-4,5-dihydro-1H-imidazol-2-yl)pyridin-3-amine (Step 1)

In two 20 mL sealed vials were charged 3-amino-5-bromopyridine-2-carbonitrile (1.23 g, 6.18 mmol), 3-methylbutane-1,2-diamine (1.262 g, 12.36 mmol) and carbon disulfide (0.093 mL, 1.545 mmol) dissolved in DMA (0.50 mL). The reaction mixture was heated at 120° C. for 1 h, cooled to r.t., taken up with EtOAc. The organic solvent was washed with water twice, separated and dried over Na$_2$SO$_4$, evaporated to dryness affording a crude which was purified by column chromatography on silica with PE/EtOAc 9/1 yielding the title Example (1.2 g, 68.58%, 100% purity).

8-bromo-3-(propan-2-yl)-2,6-dihydroimidazo[1,2-c]
pyrido[2,3-e]pyrimidin-5(3H)-one and 8-bromo-2-(propan-2-yl)-2,6-dihydroimidazo[1,2-c]
pyrido[2,3-e]pyrimidin-5(3H)-one (Step 2)

In a 20 mL microwave vial 5-bromo-2-(4-isopropyl-4,5-dihydro-1H-imidazol-2-yl)pyridin-3-amine (1.2 g, 4.24 mmol) e carbonyldiimidazole (2.061 g, 12.713 mmol) dissolved in acetonitrile (10 mL) were heated in a microwave vial at 100° C. for 2 h. A precipitate was formed which was filtered after cooling to r.t., washing with MeCN (4 ml) on the filter. After double trituration with DCM (5 ml), the mother liquors were combined, evaporated to dryness, extracted with EtOAc, washing with water, drying over sodium sulphate, and evaporated again triturating the residue with DCM twice (3 mL). The collected precipitated amounted to 1.2 g of white solid of 8-bromo-2-(propan-2-yl)-2,6-dihydroimidazo[1,2-c]pyrido[2,3-e]pyrimidin-5(3H)-one (91.59% yield) and 0.16 g of the isomer from the surfactants.

8-Bromo-6-(4-chlorobenzyl)-2-(propan-2-yl)-2,6-dihydroimidazo[1,2-c]pyrido[2,3-e]pyrimidin-5(3H)-one (Step 3)

8-bromo-2-(propan-2-yl)-2,6-dihydroimidazo[1,2-c]pyrido[2,3-e]pyrimidin-5(3H)-one (700 mg, 2.26 mmol). were dissolved in 10 mL of DMF under stirring. 1-(bromomethyl)-4-chlorobenzene (697.87 mg, 3.40 mmol) was added and the reaction mixture was stirred for 5 min, then sodium hydride (135.85 mg, 3.396 mmol) in 1 ml di DMF dry was added. After overnight stirring, the reaction was quenched with water, extracted with EtOAc two times. EtOAc was dried over sodium sulphate, filtered and evaporated to dryness affording a crude which was purified by column chromatography on silica eluting with PE/EtOAc 7/3 affording 630 mg (64.15% yield) of title compound.

6-(4-Chlorobenzyl)-8-(2-oxa-6-azaspiro[3.3]heptan-6-yl)-2-(propan-2-yl)-2,6-dihydroimidazo[1,2-c]
pyrido[2,3-e]pyrimidin-5(3H)-one (Step 4)

In a microwave 2 ml vial was dissolved in 1,4-dioxane (0.50 mL), the products from Step 4 (50 mg, 0.115 mmol), caesium carbonate (75.12 mg, 0.23 mmol) and Xantphos (16.01 mg, 0.028 mmol). Argon was bubbled inside the reaction vessel, then was added 2-oxa-6-azaspiro[3.3]heptane oxalate (24.93 mg, 0.087 mmol) followed by 0.75 mg of $Cs_2CO_3$ and by $Pd(OAc)_2$ (4.14 mg, 0.018 mmol). The mixture was stirred at 100° C. overnight, cooled and filtered on PTFTE filter washing with MeOH. Dilution of the filtrate with EtOAc, washing with brine, drying on $Na_2SO_4$ and evaporating to dryness gave a crude purified by preparative HPLC in $H_2O$ (+0.1% $NH_3$)/ACN affording the title product (23 mg, 44.15% yield).

HPLC-MS $[M+H]^+$=452.12

The following Examples were prepared as reported for the compound of Example 15 described before replacing the proper amine at the last step:

Example 16

6-(4-Chlorobenzyl)-8-(4-methoxypiperidin-1-yl)-2-(propan-2-yl)-2,6-dihydroimidazo[1,2-c]pyrido[2,3-e]pyrimidin-5(3H)-one From 4-methoxypiperidine. Yield: 22.4%.
HPLC-MS $[M+H]^+$=468.16

Example 17

6-(4-Chlorobenzyl)-8-[3-(methoxymethyl)azetidin-1-yl]-2-(propan-2-yl)-2,6-dihydroimidazo[1,2-c]
pyrido[2,3-e]pyrimidin-5(3H)-one From 3-(methoxymethyl)azetidine. Yield: 33.52%.
HPLC-MS $[M+H]^+$=454.32

Example 51

6-(4-Chlorobenzyl)-8-(4-hydroxypiperidin-1-yl)-2-(propan-2-yl)-2,6-dihydroimidazo[1,2-c]pyrido[2,3-e]pyrimidin-5(3H)-one From 4-Hydroxypiperidine. Yield: 10.1%.
HPLC-MS $[M+H]^+$=454.12

The following Examples were prepared as reported for Example 15 replacing the proper alkylating reagent at Step 3 and the proper amine at the last step:

Example 19

6-(4-Methoxybenzyl)-8-(2-oxa-6-azaspiro[3.3]heptan-6-yl)-2-(propan-2-yl)-2,6-dihydroimidazo[1,2-c]
pyrido[2,3-e]pyrimidin-5(3H)-one From 2-oxa-6-azaspiro[3.3]heptane oxalate. Yield: 43.85%
HPLC-MS $[M+H]^+$=448.46

Example 20

8-[4-(Hydroxymethyl)piperidin-1-yl]-6-(4-methoxybenzyl)-2-(propan-2-yl)-2,6-dihydroimidazo[1,2-c]
pyrido[2,3-e]pyrimidin-5(3H)-one From 4-piperidylmethanol. Yield: 10.58%.
HPLC-MS $[M+H]^+$=464.41

Example 21

8-[4-(Dimethylamino)piperidin-1-yl]-6-(4-methoxybenzyl)-2-(propan-2-yl)-2,6-dihydroimidazo[1,2-c]
pyrido[2,3-e]pyrimidin-5(3H)-one From N,N-dimethylpiperidin-4-amine. Yield: 30.88%.
HPLC-MS $[M+H]^+$=477.58

The following Examples were prepared as reported for Example 15 replacing the diamine at step 1, the proper alkylating reagent at Step 3 and the proper amine at the last step.

Example 27

2-Ethyl-6-(4-methoxybenzyl)-8-[(3R)-3-methoxy-pyrrolidin-1-yl]-2,6-dihydroimidazo[1,2-c]pyrido[2,3-e]pyrimidin-5(3H)-one From [(3R)-3-methoxypyrrolidine. Yield: 95%.
HPLC-MS [M+H]$^+$=436.39

Example 39

2-Ethyl-6-(4-methoxybenzyl)-8-[3-(methoxymethyl)azetidin-1-yl]-2,6-dihydroimidazo[1,2-c]pyrido[2,3-e]pyrimidin-5(3H)-one From 3-(methoxymethyl)azetidine. Yield: 36.8%.
HPLC-MS [M+H]$^+$=436.38

The following Examples were prepared as reported for Example 15 replacing the proper alkylating reagent at Step 3 and the proper amine at the last step.

Example 42

8-(4-Aminopiperidin-1-yl)-6-(3,5-dimethoxybenzyl)-2-(propan-2-yl)-2,6-dihydroimidazo[1,2-c]pyrido[2,3-e]pyrimidin-5(3H)-one From piperidin-4-amine. Yield: 10.6%.
HPLC-MS [M+H]$^+$=479.35

Example 49

6-(3,5-Dimethoxybenzyl)-2-(propan-2-yl)-8-(tetrahydro-2H-pyran-4-ylamino)-2,6-dihydroimidazo[1,2-c]pyrido[2,3-e]pyrimidin-5(3H)-one From tetrahydropyran-4-amine. Yield: 28.5%.
HPLC-MS [M+H]$^+$=480.38

Example 48

6-(4-Chlorobenzyl)-8-hydroxy-2-(propan-2-yl)-2,6-dihydroimidazo[1,2-c]pyrido[2,3-e]pyrimidin-5(3H)-one In a microwave vial a solution of 8-bromo-6-(4-chlorobenzyl)-2-(propan-2-yl)-2,6 dihydroimidazo[1,2-c]pyrido[2,3-e]pyrimidin-5(3H)-one (see Example 15—step 3) (50 mg, 0.116 mmol), copper (Z)-4-hydroxypent-3-en-2-one (0.152 mg, 0.0006 mmol), N,N'-bis(4-hydroxy-2,6-dimethyl-phenyl)oxamide (0.1893 mg, 0.0006 mmol) and lithium hydroxide hydrate (10.158 mg, 0.242 mmol) in a mixture of DMSO (0.09 ml) and water (0.03 ml) was heated in sand bath at 80° C. for 16 hours. Then water and ethyl acetate were added, the two liquid phases were separated and the aqueous layer was extracted with ethyl acetate (2×5 ml). The crude was purified by reverse phase column chromatography eluting with NH$_4$HCO$_3$ water (0.5% HCOOH)/acetonitrile gradient starting from 70:30 to 30:70. 10 mg of Example 48 were collected as white powder. (Yield=23%)
UPLC-MS [M+H]$^+$=371.05

Example 58

6-(3,5-Dimethoxybenzyl)-5-oxo-2-(propan-2-yl)-N-(tetrahydro-2H-pyran-4-yl)-2,3,5,6-tetrahydroimidazo[1,2-c]pyrido[2,3-e]pyrimidine-8-carboxamide In a microwave vial a solution of 8-bromo-6-(3,5-dimethoxybenzyl)-2-(propan-2-yl)-2,6-dihydroimidazo[1,2-c]pyrido[2,3-e]pyrimidin-5(3H)-one (prepared following the procedure described for Example 15—step 3, replacing 1-(bromomethyl)-4-chlorobenzene with 1-(bromomethyl)-4-(3,5-dimethoxybenzene) (35 mg, 0.076 mmol), hydroxy-cesium hydrate (127.96 mg, 0.762 mmol), Xantphos (4.41 mg, 0.0076 mmol), palladium(II) diacetate (0.428 mg, 0.002 mmol) and tetrahydropyran-4-amine (0.008 mL, 0.076 mmol) in a mixture of toluene (0.45 mL), DMSO (0.200 mL) and chloroform (0.018 mL, 0.229 mmol) was heated in sand bath at 80° C. for 16 hours. Then water and ethyl acetate were added, the two liquid phases were separated and the aqueous layer was extracted with ethyl acetate (2×5 ml). The crude was purified by reverse phase column chromatography eluting with a NH$_4$HCO$_3$ water (0.1% NH3)/acetonitrile gradient starting from 70:30 to 30:70. 5.4 mg of the compound of Example 58 were collected as white powder. (Yield=14%)
UPLC-MS [M+H]$^+$=508.2

Example 59

6-(3,5-Dimethoxybenzyl)-5-oxo-2-(propan-2-yl)-2,3,5,6-tetrahydroimidazo[1,2-c]pyrido[2,3-e]pyrimidine-8-carboxylic Acid During the purification of Example 58 on reverse phase column chromatography 1.6 mg of the compound of Example 59 was isolated as white powder (Yield: 4.4%)
UPLC-MS [M+H]$^+$=425.29

Example 60

6-(3,5-Dimethoxybenzyl)-8-(morpholin-4-ylcarbonyl)-2-(propan-2-yl)-2,6-dihydroimidazo[1,2-c]pyrido[2,3-e]pyrimidin-5(3H)-one Example 60 was prepared as described for Example 58 replacing tetrahydropyran-4-amine with morpholine. 3.8 mg of a white powder was isolated. (Yield: 10%)
UPLC-MS [M+H]$^+$=494.3

Example 64

6-(4-Chlorobenzyl)-3-(2-methylpropyl)-8-(morpholin-4-yl)imidazo[1,2-c]pyrido[2,3-e]pyrimidine-2,5(3H,6H)-dione 3-[(4-Chlorobenzyl)amino]-5-(morpholin-4-yl)pyridine-2-carbonitrile (Step 1)

Prepared following the procedure reported for Example 1—Step 2 replacing 4-chlorobenzylamine for 4-methoxybenzylamine (Yield: 80%, white solid).

4-Amino-1-(4-chlorobenzyl)-7-(morpholin-4-yl)pyrido[3,2-d]pyrimidin-2(1H)-one (Step 2)

To a solution of [(4-chlorobenzyl)amino]-5-(morpholin-4-yl)pyridine-2-carbonitrile (0.912 mmol, 300 mg) in THF anhydrous (10 mL) stirred at 0° C. under N₂ atm, trichloroacetyl isocyanate (0.9124 mmol, 171.9 mg, 0.109 mL) was added dropwise. The reaction mixture was stirred at r.t. till on UPLC-MS and formation of carbonyl intermediate was complete (M=517). The reaction was quenched at 0° C. with excess MeOH and the solvents evaporated under reduced pressure. The residue was rinsed with 7M ammonia solution in MeOH (28 mmol, 4 mL) and stirred overnight. The white precipitate was filtered and washed with cold methanol affording the title Example (0.538 mmol, 200 mg) isolated as a white solid (Yield: 59%).

6-(4-Chlorobenzyl)-3-(2-methylpropyl)-8-(morpholin-4-yl)imidazo[1,2-c]pyrido[2,3-e]pyrimidine-2,5(3H,6H)-dione (Step 3)

To a solution of 2-bromo-3,3-dimethyl-butanoic acid (1.076 mmol, 209.8 mg) in toluene (3 mL) oxalyl chloride (1.345 mmol, 170.7 mg, 0.11 mL) and two drops of DMF were added and the solution was stirred at room temperature for 3 hours. The solvent was evaporated to dryness and the residue was dissolved in DMA (1 mL) and added to a solution of 4-amino-1-[(4-chlorophenyl)methyl]-7-morpholino-pyrido[3,2-d]pyrimidin-2-one (from step 2) (0.269 mmol, 100 mg) and DIPEA (3.23 mmol, 371.9 mg, 0.493 mL) and the reaction mixture stirred at room temperature overnight, then heated at 120° C. for 3 hours. The reaction mixture was then poured into water, extracted with DCM, dried over Na₂SO₄ and the solvent was evaporated to dryness. The crude was purified via preparative HPLC giving Example 64 (yield: 5.3%).

HPLC-MS [M+H]⁺=468.1

Example 68

3-tert-Butyl-6-(4-chlorobenzyl)-8-(morpholin-4-yl)imidazo[1,2-c]pyrido[2,3-e]pyrimidine-2,5(3H,6H)-dione The reaction was performed using 2-bromo-4-methylpentanoic acid instead of 2-bromo-3,3-dimethyl-butanoic acid in step 3 of Example 64. The reaction mixture was then poured into water, extracted with EtOAc, dried over Na₂SO₄ and the solvent was evaporated to dryness. The crude was purified via automated flash chromatography (Biotage Isolera-Dalton), SNAP10 Cartridge, eluting with isocratic CHCl₃/MeOH 95/5. The title Example was isolated as a pale yellow solid. (Yield: 17%)

UPLC-MS [M+H]⁺=468.32

¹H NMR (400 MHz, DMSO-d6) δ ppm 8.42 (m, 1H) 7.40 (m, 4H) 6.82 (m, 1H) 5.37 (m, 2H) 4.24 (m, 1H) 3.67-3.78 (m, 4H) 3.41-3.51 (m, 4H) 1.02 (m, 9H)

Example 69

3-tert-Butyl-6-(4-methoxybenzyl)-8-(morpholin-4-yl)imidazo[1,2-c]pyrido[2,3-e]pyrimidine-2,5(3H,6H)-dione The title Example was prepared following the procedure described for Example 64 starting from the compound of Example 1-Step 2 (3-[(4-methoxyphenyl)methylamino]-5-morpholino-pyridine-2-carbonitrile) instead of 3-[(4-chlorobenzyl)amino]-5-(morpholin-4-yl)pyridine-2-carbonitrile (Example 64—Step 1) and using 2-bromo-4-methyl-pentanoic acid instead of 2-bromo-3,3-dimethyl-butanoic acid at the last step.

UPLC-MS [M+H]⁺=464.87

¹H NMR (400 MHz, DMSO-d6) δ ppm 8.41 (m, 1H) 7.32 (m, 2H) 6.85-6.93 (m, 3H) 5.30 (m, 2H) 4.26 ((m, 1H) 3.68-3.77 (m, 7H) 3.41-3.49 (m, 4H) 1.03 (m, 9H).

[M+1]⁺=464.38

Example 70

6-[(3,5-Dimethoxyphenyl)methyl]-2,3-dimethyl-8-{[(oxetan-3-yl)methyl]amino}imidazo[1,2-c]pyrido[2,3-e]pyrimidin-5(6H)-one 4-Amino-7-bromo-1H-pyrido[3,2-d]pyrimidin-2-one (Step 1)

To a solution at 0° C. of 1 g of 3-amino-5-bromopyridine-2-carbonitrile (5.05 mmol) in 15 mL of THF anhydrous, 0.60 mL of 2,2,2-trichloroacetylisocyanate (0.95 g, 5.05 mmol) were added dropwise under nitrogen atmosphere. The reaction mixture was stirred at r.t. and monitored by TLC to completeness. The reaction was quenched at 0° C. with MeOH and the solvents evaporated under reduced pressure. The residue was rinsed with 8 mL of 7M ammonia solution in MeOH (56 mmol) and stirred overnight. The white precipitate was filtered, washed with MeOH and dried in an oven at 60° C. under vacuum to give 1.13 g of the desired product (yield 93%) as white solid that was used for the next step without further purification.

¹H NMR (400 MHz, DMSO-d₆) δ ppm 10.75 (s, 1H), 8.43 (s, 1H), 8.05 (s, 1H), 7.94 (s, 1H), 7.68 (s, 1H).

4-Amino-7-bromo-1-[(3,5-dimethoxyphenyl)methyl]pyrido[3,2-d]pyrimidin-2-one (Step 2)

To a solution of 1 g of 4-amino-7-bromo-1H-pyrido[3,2-d]pyrimidin-2-one (4.15 mmol) in 40 mL of anhydrous DMF under N2 atm was added, 182.52 mg of NaH 60% dispersion in oil (4.56 mmol) and the mixture was stirred at r.t. for 30 min. Afterwards, 1.15 g of 1-(bromomethyl)-3,5-dimethoxybenzene (4.98 mmol) were added and the mixture was stirred at r.t. overnight. The solid formed during the reaction was filtered and washed with a small portion of DMF and water. The crude was grinded with DCM and the suspension filtered affording 1.2 g of the desired product (yield 74%) as pale yellow solid, which was used fort the next step without further purification.

8-Bromo-6-(3,5-dimethoxybenzyl)-2,3-dimethylimidazo[1,2-c]pyrido[2,3-e]pyrimidin-5(6H)-one (Step 3)

A solution of 700 mg of 4-amino-7-bromo-1-[(3,5-dimethoxyphenyl)methyl]pyrido[3,2-d]pyrimidin-2-one (1.79 mmol) and 0.38 mL of 3-bromobutan-2-one (540 mg, 3.58 mmol, 2 equiv) in 4 mL of DMAc was stirred in a MW oven at 160° C. for 45 min. The reaction mixture was cooled to r.t., poured into water and extracted with EtOAc. The organic layer was washed with water, dried over Na₂SO₄ anhydrous, the solvent was evaporated to dryness. The resulting crude was purified via automated flash chromatography (Biotage Isolera-Dalton, SNAP 25 cartridge) eluting with a gradient from 30% PE/EtOAc from to 100% EtOAc to obtain 260 mg of the desired product (yield 33%) as a pale yellow solid.

6-[(3,5-Dimethoxyphenyl)methyl]-2,3-dimethyl-8-{[(oxetan-3-yl)methyl]amino}imidazo[1,2-c]pyrido[2,3-e]pyrimidin-5(6H)-one (Step 4)

In a microwave vial 120 mg of 8-bromo-6-(3,5-dimethoxybenzyl)-2,3-dimethylimidazo[1,2-c]pyrido[2,3-e]pyrimidin-5(6H)-one (0.27 mmol) and 35.4 mg of oxetan-3-ylmethanamine (0.41 mmol) were dissolved in 4 mL of 1,4-dioxane. The solution was purged with $N_2$ and, after 5 minutes, 12.15 mg of palladium(II) acetate (0.054 mmol), 62.65 mg of Xantphos (0.108 mmol) and 176.4 mg of cesium carbonate (0.54 mmol) were added and the mixture was stirred in a microwave oven at 150° C. for 1 h. The reaction was poured into water and extracted with EtOAc. The organic layer was dried over anhydrous $Na_2SO_4$, filtered and evaporated to dryness. The crude residue was purified by means of a Biotage Isolera One instrument, cartridge type SNAP10, using a gradient from EtOAc 100% to EtOAc:MeOH 95:5, to obtain 100 mg of the desired product (yield 82%).

UPLC-MS $[M+H]^+$=450.30

$^1$H NMR (400 MHz, CHLOROFORM-d) δ ppm 8.01 (d, 1H), 6.53 (d, 1H), 6.26-6.46 (m, 3H), 5.35 (s, 2H), 4.82 (dd, 2H), 4.35 (br s, 1H), 4.39 (dd, 2H), 3.75 (s, 6H), 3.28-3.46 (m, 2H), 3.03-3.22 (m, 1H), 2.68 (s, 3H), 2.34 (s, 3H).

Example 71

2-(2-Methylpropyl)imidazo[1,2-c]pyrido[2,3-e]pyrimidin-5(6H)-one

4-Amino-1H-pyrido[3,2-d]pyrimidin-2-one (Step 1)

4-amino-1H-pyrido[3,2-d]pyrimidin-2-one was synthesised following a literature procedure starting from 3-aminopyridine-2-carbonitrile.

2-(2-Methylpropyl)imidazo[1,2-c]pyrido[2,3-e]pyrimidin-5(6H)-one (Step 2)

The title Example was prepared following the procedure described in step 3 of Example 70 replacing 3-bromobutan-2-one with 1-bromo-4-methyl-pentan-2-one.

Pale yellow solid (47%)

UPLC-MS $[M+H]^+$=243.05

Example 72

6-[(4-Methylphenyl)methyl]-2-(2-methylpropyl)imidazo[1,2-c]pyrido[2,3-e]pyrimidin-5(6H)-one The title example was prepared following the procedure described in step 2 of Example 70 replacing 1-(bromomethyl)-3,5-dimethoxybenzene with 1-(bromomethyl)-4-methylbenzene. Pale yellow solid (41%)

UPLC-MS $[M+H]^+$=347.16

Example 73

6-[(4-Chlorophenyl)methyl]-2-(2-methylpropyl)-8-(2-oxa-6-azaspiro[3.3]heptan-6-yl)imidazo[1,2-c]pyrido[2,3-e]pyrimidin-5(6H)-one 4-Amino-7-bromo-1-[(4-chlorophenyl)methyl]pyrido[3,2-d]pyrimidin-2-one (Step 1)

NaH (60 mg, 1.2 equiv.) and 4-amino-7-bromo-1H-pyrido[3,2-d]pyrimidin-2-one (Example 70—Step 1, 300 mg, 1.0 eq.) were placed in dry Schlenk flask and diluted with DMF (8 mL). The reaction mixture was stirred at r.t. for 30 min (yellowish slurry that becomes clear red). Then a solution of 1-(bromomethyl)-4-chlorobenzene (333 mg, 1.3 equiv.) in DMF (4 mL) was added dropwise and the reaction was stirred for 30 min at r.t., then for 3 h at 80° C. The reaction mixture was allowed to cool to r.t. and after 30 min was filtered. Then water (50 mL) was added to the filtrate which was stirred at r.t. overnight. A solid was collected by filtration and washed with DCM (2×5 mL).

$^1$H NMR (400 MHz, DMSO-$d_6$) δ ppm 8.48 (s, 1H), 8.20 (s, 1H), 8.10 (s, 1H), 7.99 (s, 1H), 7.37 (m, 4H).

8-Bromo-6-(4-chlorobenzyl)-2-(2-methylpropyl)imidazo[1,2-c]pyrido[2,3-e]pyrimidin-5(6H)-one (Step 2)

To a solution of 4-amino-7-bromo-1-[(4-chlorophenyl)methyl]pyrido[3,2-d]pyrimidin-2-one (250 mg, 1 eq.) in DMA (4.5 mL) 1-chloro-4-methylpentan-2-one (134.60 µL, 2 eq.) was added. The mixture was stirred under microwave irradiation for 75 min at 150° C. Water was added and the resulting emulsion was extracted with dichloromethane. The combined organic extracts were purified with flash chromatography.

6-[(4-Chlorophenyl)methyl]-2-(2-methylpropyl)-8-(2-oxa-6-azaspiro[3.3]heptan-6-yl)imidazo[1,2-c]pyrido[2,3-e]pyrimidin-5(6H)-one (Step 3)

A solution of 8-bromo-6-(4-chlorobenzyl)-2-(2-methylpropyl)imidazo[1,2-c]pyrido[2,3-e]pyrimidin-5(6H)-one (60 mg, 1 eq) Xantphos (9.3 mg, 0.12 eq) cesium carbonate (88 mg, 2 eq) and 2-oxa-6-azaspiro[3.3]heptane (13.3 mg, 1 eq) in 1,4-dioxane (1 mL) was degassed in sonic bath and purged with argon in a reactor equipped with septum. Then palladium acetate was added and the reaction mixture was stirred at 90° C. overnight. The solvent was removed under reduced pressure and the crude was purified by flash chromatography. The combined fractions were dried under reduced pressure and the resulting residue was purified by crystallization (diethyl ether/dichloromethane) to obtain the desired product (48 mg, yield 76.9%).

HPLC-MS $[M+H]^+$=463.9

$^1$H NMR (400 MHz, CHLOROFORM-d) δ ppm 7.88 (d, 1H), 7.54 (d, 1H), 7.36 (d, 2H), 7.22 (d, 2H), 6.28 (d, 1H), 5.44 (s, 2H), 4.86 (s, 4H), 4.11 (s, 4H), 2.64 (dd, 2H), 2.23 (dq, 1H), 1.01 (d, 6H).

Example 70—Alternative Procedure

6-[(3,5-Dimethoxyphenyl)methyl]-2,3-dimethyl-8-{[(oxetan-3-yl)methyl]amino}imidazo[1,2-c]pyrido[2,3-e]pyrimidin-5(6H)-one Example 70 as illustrated in Table 2 was prepared following the procedure described for Example 73 but replacing 1-(bromomethyl)-4-chlorobenzene with 1-(bromomethyl)-3,5-dimethoxybenzene at step 1, 1-chloro-4-methylpentan-2-one with 3-bromobutan-2-one at step 2 and 2-oxa-6-azaspiro[3.3]heptane with oxetan-3-ylmethanamine at step 3 (yield 60%). UPLC-MS $[M+H]^+$=450.39

$^1$H NMR (400 MHz, DMSO-$d_6$) δ ppm 7.95 (d, 1H) 6.61-6.71 (m, 2H) 6.48 (d, 2H) 6.40-6.45 (m, 1H) 5.34 (s, 2H) 4.60 (dd, 2H) 4.24 (t, 2H) 3.70 (s, 6H) 3.35 (dd, 2H) 2.96-3.12 (m, 1H) 2.58 (s, 3H) 2.21 (s, 3H)

Example 74

6-[(3,5-Dimethoxyphenyl)methyl]-2-(2-methylpropyl)-8-(morpholin-4-yl)imidazo[1,2-c]pyrido[2,3-e]pyrimidin-5(6H)-one Example 74 as illustrated in Table 2 was prepared following the procedure described for Example 73 but replacing 1-(bromomethyl)-4-chlorobenzene with 1-(bromomethyl)-3,5-dimethoxybenzene at step 1 and 2-oxa-6-azaspiro[3.3]heptane with morpholine at step 3 (yield 49%).

UPLC-MS [M+H]$^+$=478.30

$^1$H NMR (400 MHz, CHLOROFORM-d) δ ppm 8.35 (d, 1H) 7.57 (s, 1H) 6.89 (d, 1H) 6.41-6.48 (m, 2H) 6.33-6.41 (m, 1H) 5.43 (s, 2H) 3.81-3.93 (m, 4H) 3.76 (s, 6H) 3.14-3.27 (m, 4H) 2.67 (d, 2H) 2.24 (dquin, 1H) 1.02 (d, 6H)

Example 75

6-[(4-Chloro-2,6-difluorophenyl)methyl]-2-(2-methylpropyl)-8-(morpholin-4-yl)imidazo[1,2-c]pyrido[2,3-e]pyrimidin-5(6H)-one Example 75 as illustrated in Table 2 was prepared following the procedure described for Example 73 but replacing 1-(bromomethyl)-4-chlorobenzene with 2-(bromomethyl)-5-chloro-1,3-difluorobenzene at step 1 and 2-oxa-6-azaspiro[3.3]heptane with morpholine at step 3 (yield 28%).

HPLC-MS [M+H]$^+$=487.9

$^1$H NMR (400 MHz, CHLOROFORM-d) δ ppm 8.32 (d, 1H), 7.53 (s, 1H), 6.96 (m, 2H), 6.87 (d, 1H), 5.59 (s, 2H), 3.89 (dd, 4H), 3.26 (dd, 4H), 2.62 (d, 2H), 2.27-2.12 (m, 1H), 0.98 (d, 6H).

Examples 76 and 77

6-[(3,5-Dimethoxyphenyl)methyl]-2-ethyl-3-methyl-8-{[(oxetan-3-yl)methyl]amino}imidazo[1,2-c]pyrido[2,3-e]pyrimidin-5(6H)-one And 6-[(3,5-Dimethoxyphenyl)methyl]-3-ethyl-2-methyl-8-{[(oxetan-3-yl)methyl]amino}imidazo[1,2-c]pyrido[2,3-e]pyrimidin-5(6H)-one Examples 76 and 77 as illustrated in Table 2 were prepared following the procedure described for Example 70 but replacing at step 3 3-bromobutan-2-one with 2-bromopentan-3-one (yield 33%).

Preparative HPLC purification afforded 7.2 mg of Example 76 and 5.2 mg of Example 77.

Example 76

HPLC-MS [M+H]$^+$=464.7

$^1$H NMR (400 MHz, CHLOROFORM-d) δ ppm 8.02 (d, 1H), 6.53 (d, 1H), 6.39 (s, 3H), 5.35 (s, 2H), 4.91-4.74 (m, 2H), 4.40 (t, 2H), 3.77 (s, 6H), 3.41 (d, 2H), 3.17-3.08 (m, 1H), 2.78-2.65 (m, 5H), 1.33 (t, 3H).

Example 77

HPLC-MS [M+H]$^+$=464.7

NMR: $^1$H NMR (400 MHz, CHLOROFORM-d) δ ppm 8.04 (d, 1H), 6.55 (d, 1H), 6.39 (s, 3H), 5.37 (s, 2H), 4.91-4.77 (m, 2H), 4.41 (t, 2H), 3.77 (s, 6H), 3.43 (d, 2H), 3.13 (m, 3H), 2.37 (s, 3H), 1.30 (t, 3H).

Example 78

6-(4-Methoxybenzyl)-2-(2-methylpropyl)-8-(morpholin-4-yl)imidazo[1,2-c]pyrido[2,3-e]pyrimidin-5(6H)-one Example 78 as illustrated in Table 2 was prepared following the procedure described for Example 73 but replacing 1-(bromomethyl)-4-chlorobenzene with 1-(bromomethyl)-4-methoxybenzene at step 2 and 2-oxa-6-azaspiro[3.3]heptane with morpholine at step 3 (yield 67%).

UPLC-MS [M+H]$^+$=448.40

$^1$H NMR (400 MHz, CHLOROFORM-d) δ ppm 8.36 (d, 1H) 7.58 (s, 1H) 7.23 (d, 2H) 6.85-6.97 (m, 3H) 5.45 (s, 2H) 3.84-3.92 (m, 4H) 3.81 (s, 3H) 3.16-3.27 (m, 4H) 2.69 (d, 2H) 2.24 (dquin, 1H) 1.02 (d, 6H).

Example 79

6-(3,5-Dimethoxybenzyl)-3-methyl-8-(morpholin-4-yl)-2-(propan-2-yl)imidazo[1,2-c]pyrido[2,3-e]pyrimidin-5(6H)-one Example 79 as illustrated in Table 2 was prepared following the procedure described for Example 70 but replacing 3-bromobutan-2-one with 2-bromo-4-methylpentan-3-one at step 3 and 2-oxa-6-azaspiro[3.3]heptane with morpholine at step 4 (yield 56%).

HPLC-MS [M+H]$^+$=477.9

$^1$H NMR (400 MHz, CHLOROFORM-d) δ ppm 8.30 (d, 1H), 6.80 (d, 1H), 6.41-6.34 (m, 3H), 5.34 (s, 2H), 3.86-3.80 (m, 4H), 3.74 (s, 5H), 3.15 (dd, 4H), 3.13-3.03 (m, 1H), 2.70 (d, 3H), 1.37 (d, 6H).

Example 80

6-(3,5-Dimethoxybenzyl)-8-[4-(hydroxyacetyl)piperazin-1-yl]-2-(2-methylpropyl)imidazo[1,2-c]pyrido[2,3-e]pyrimidin-5(6H)-one Example 80 as illustrated in Table 2 was prepared following the procedure described for Example 73 but replacing 1-(bromomethyl)-4-chloro-benzene for 1-(bromomethyl)-3,5-dimethoxy-benzene at step 1 and 2-oxa-6-azaspiro[3.3]heptane with 2-hydroxy-1-piperazin-1-ylethanone at step 3 (yield 16%)

HPLC-MS [M+H]$^+$=535.2

$^1$H NMR (400 MHz, CHLOROFORM-d) δ ppm 8.35 (d, 1H), 7.58 (s, 1H), 6.91 (d, 1H), 6.40 (s, 3H), 5.44 (s, 2H), 4.23 (s, 2H), 3.84 (t, 2H), 3.77 (s, 6H), 3.54 (s, 1H), 3.46 (t, 2H), 3.28 (dt, 4H), 2.70-2.62 (m, 2H), 2.23 (dt, 1H), 1.01 (d, 6H).

Example 81

6-(3,5-Dimethoxybenzyl)-2,3-dimethyl-8-(2-oxa-6-azaspiro[3.3]heptan-6-yl)imidazo[1,2-c]pyrido[2,3-e]pyrimidin-5(6H)-one Example 81 as illustrated in Table 2 was prepared following the procedure described for Example 70 but replacing 2-oxa-6-azaspiro[3.3]heptane for oxetan-3-ylmethylamine at step 4 (yield 27.5%)

HPLC-MS [M+H]$^+$=462.1

$^1$H NMR (400 MHz, CHLOROFORM-d) δ ppm 8.13 (s, 1H), 7.80 (s, 1H), 6.36 (s, 2H), 6.31 (d, J=2.1 Hz, 1H), 5.31 (s, 2H), 4.83 (s, 4H), 4.08 (s, 4H), 3.75 (s, 6H), 2.66 (s, 3H), 2.33 (s, 3H).

Example 82

6-(3,5-Dimethoxybenzyl)-2,3-dimethyl-8-(morpholin-4-yl)imidazo[1,2-c]pyrido[2,3-e]pyrimidin-5(6H)-one Example 82 as illustrated in Table 2 was prepared following the procedure described for Example 70 but replacing morpholine for oxetan-3-ylmethylamine at step 4. (Yield 16.6%).
HPLC-MS [M+H]$^+$=450.1
$^1$H NMR (400 MHz, CHLOROFORM-d) δ ppm 8.30 (d, 1H), 6.82 (d, 1H), 6.39 (q, 3H), 5.37 (s, 2H), 3.90-3.83 (m, 4H), 3.76 (s, 6H), 3.24-3.16 (m, 4H), 2.70 (d, 3H), 2.37 (d, 3H).

Example 83

6-(3,5-Dimethoxybenzyl)-3-methyl-8-[(oxetan-3-ylmethyl)amino]-2-(propan-2-yl)imidazo[1,2-e]pyrido[2,3-e]pyrimidin-5(6H)-one Example 83 as illustrated in Table 2 was prepared following the procedure described for Example 70 but replacing 3-bromobutan-2-one with 2-bromo-4-methyl-pentan-3-one at step 3 (yield 19.7%).
HPLC-MS [M+H]$^+$=478.6
$^1$H NMR (400 MHz, CHLOROFORM-d) δ ppm 8.15 (s, 1H), 6.50 (s, 1H), 6.37 (s, 3H), 5.34 (s, 2H), 4.82 (dd, 2H), 4.39 (t, 2H), 3.76 (s, 6H), 3.39 (d, 2H), 3.21-3.08 (m, 3H), 2.70 (s, 3H), 1.40 (d, 6H).

Example 84

8-(4-Acetylpiperazin-1-yl)-6-(3,5-dimethoxybenzyl)-3-methyl-2-(propan-2-yl)imidazo[1,2-c]pyrido[2,3-e]pyrimidin-5(6H)-one Example 84 as illustrated in Table 2 was prepared following the procedure described for Example 70 but replacing 3-bromobutan-2-one with 2-bromo-4-methylpentan-3-one at step 3 and 1-piperazin-1-ylethanone for oxetan-3-ylmethylamine at step 4 (yield 49%).
HPLC-MS [M+H]$^+$=519.2
$^1$H NMR (400 MHz, CHLOROFORM-d) δ ppm 8.34 (d, 1H), 6.82 (d, 1H), 6.39 (s, 3H), 5.37 (s, 2H), 3.77 (m, 8H), 3.64 (t, 2H), 3.30 (d, 2H), 3.18 (t, 2H), 3.16-3.10 (m, 1H), 2.73 (s, 3H), 2.16 (s, 3H), 1.41 (d, 6H).

Example 85

6-(3,5-Dimethoxybenzyl)-8-(4-methoxypiperidin-1-yl)-2,3-dimethylimidazo[1,2-c]pyrido[2,3-e]pyrimidin-5(6H)-one Example 85 as illustrated in Table 2 was prepared following the procedure described for Example 70 but replacing 4-methoxypiperidine for oxetan-3-ylmethylamine at step 4.
HPLC-MS [M+H]$^+$=478.2
$^1$H NMR (400 MHz, CHLOROFORM-d) δ ppm 8.36 (s, 1H), 6.81 (s, 1H), 6.43-6.36 (m, 3H), 5.36 (s, 2H), 3.77 (s, 6H), 3.57-3.40 (m, 5H), 3.39 (m, 3H), 3.13 (m, 2H), 2.70 (s, 3H), 2.43 (s, 3H), 1.93 (m, 2H).

Example 86

5-(3,5-Dimethoxybenzyl)-8,9-dimethyl-3-(morpholin-4-yl)imidazo[1,2-c]pteridin-6(5H)-one 3-Chloro-5-morpholinopyrazine-2-carbonitrile (Step 1)

To a mixture of morpholine (12.5 mg, 0.144 mmol) and DIPEA (27.9 mg, 0.216 mmol) in 1 ml of dry THF was added two portion of 3,5-dichloropyrazine-2-carbonitrile (24.9 mg, 0.144 mmol). The reaction was stirred for 2 hours at rt. The solvent was removed under reduced pressure and the residue was suspended in ethyl acetate. The organic layer was washed with a 1M HCl solution, a saturated aqueous solution of sodium bicarbonate and brine. The organic phase was dried over Na$_2$SO$_4$ and concentrated in vacuo. The crude product was used in the next step without any further purification.

3-[(3,5-Dimethoxyphenyl)methylamino]-5-morpholinopyrazine-2-carbonitrile (Step 2)

A solution of 3-chloro-5-morpholinopyrazine-2-carbonitrile (31 mg, 0.138 mmol), DIPEA (21.4 mg, 0.166 mmol) and (3,5-dimethoxyphenyl)methanamine (1.2 eq) in 1,4-dioxane (1 ml) was stirred overnight at 100° C. The solvent was removed under reduced pressure and the residue was suspended in ethyl acetate. The organic layer was washed with water and brine.
The organic phase was dried over Na$_2$SO$_4$ and concentrated in vacuo. The crude product was used in the next step without any further purification.

4-Amino-1-[(3,5-dimethoxyphenyl)methyl]-7-morpholinopteridin-2-one (Step 3)

To an ice-cooled solution of 3-[(3,5-dimethoxyphenyl)methylamino]-5-morpholinopyrazine-2-carbonitrile (22 mg, 0.142 mmol) in dry THF (1 ml) trichoroacetylisocyanate (1.5 eq.) was added dropwise. The reaction mixture was allowed to warm to rt and the stirring was continued until full conversion of substrate was observed (TLC, 40% ethyl acetate in hexane). The mixture was cooled, methanol (1 ml) was added carefully and the resulting mixture was stirred for 30 minutes. The solvent was removed under reduced pressure and the resulting residue was diluted with 7.7 M methanolic solution of NH$_3$ (2 ml) and stirred overnight at rt. The resulting white-off solid precipitated was filtered, washed with ice-cold-methanol and dried under reduced pressure. (Yield 12%)

5-(3,5-dimethoxybenzyl)-8,9-dimethyl-3-(morpholin-4-yl)imidazo[1,2-c]pteridin-6(5H)-one (Step 4)

To a solution of 4-amino-1-[(3,5-dimethoxyphenyl)methyl]-7-morpholinopteridin-2-one (50 mg, 1 eq.) in DMA (0.5 mL) 3-bromobutan-2-one (26.7 μL 2 eq.) was added. The mixture was stirred under microwave irradiation for 75 min at 150° C. Water was added and the resulting emulsion was extracted with dichloromethane. The combined organic extracts were dried under reduced pressure and the desired product was isolated via preparative TLC (yield 20%).
HPLC-MS [M+H]$^+$=451.1

¹H NMR (400 MHz, CHLOROFORM-d) δ ppm 8.07 (s, 1H), 6.51 (d, 2H), 6.35 (d, 1H), 5.45 (s, 2H), 3.84-3.79 (m, 4H), 3.74 (s, 6H), 3.71-3.66 (m, 4H), 2.65 (s, 3H), 2.32 (s, 3H).

Example 87

6-(3,5-Dimethoxybenzyl)-8-(4-methoxypiperidin-1-yl)-3-methyl-2-(propan-2-yl)imidazo[1,2-c]pyrido[2,3-e]pyrimidin-5(6H)-one Example 87 as illustrated in Table 2 was prepared following the procedure described for Example 70 but replacing 3-bromobutan-2-one with 2-bromo-4-methylpentan-3-one at step 3 and oxetan-3-ylmethylamine with 4-methoxypiperidine at step 4 (yield 31%).
HPLC-MS [M+H]⁺=506.2
¹H NMR (400 MHz, CHLOROFORM-d) δ ppm 8.33 (d, 1H), 6.84 (d, 1H), 6.45-6.34 (m, 3H), 5.36 (s, 2H), 3.76 (s, 6H), 3.53-3.41 (m, 3H), 3.39 (s, 3H), 3.18-3.04 (m, 3H), 2.72 (s, 3H), 1.94 (t, 2H), 1.76-1.64 (m, 2H), 1.39 (d, 6H).

Example 88

6-(3,5-Dimethoxybenzyl)-8-[3-(methoxymethyl)azetidin-1-yl]-3-methyl-2-(propan-2-yl)imidazo[1,2-c]pyrido[2,3-e]pyrimidin-5(6H)-one Example 88 as illustrated in Table 2 was prepared following the procedure described for Example 70 but replacing 3-bromobutan-2-one with 2-bromo-4-methyl-pentan-3-one at step 3 and oxetan-3-ylmethylamine with 3-(methoxymethyl)azetidine at step 4 (yield 16%).
HPLC-MS [M+H]⁺=492.2
¹H NMR (400 MHz, CHLOROFORM-d) δ ppm 7.84 (d, 1H), 6.38 (s, 3H), 6.30 (d, 1H), 5.32 (s, 2H), 3.99 (t, 2H), 3.85-3.66 (m, 8H), 3.60 (d, 2H), 3.41 (s, 3H), 3.13-2.97 (m, 2H), 2.70 (s, 3H), 1.39 (d, 6H).

Example 89

6-(4-Methoxybenzyl)-3-methyl-8-(morpholin-4-yl)-2-(propan-2-yl)imidazo[1,2-c]pyrido[2,3-e]pyrimidin-5(6H)-one Example 89 as illustrated in Table 2 was prepared following the procedure described for Example 73 but replacing 1-(bromomethyl)-4-chlorobenzene with 1-(bromomethyl)-4-methoxybenzene at step 1, 1-chloro-4-methylpentan-2-one with 2-bromo-4-methylpentan-3-one at step 2 and 2-oxa-6-azaspiro[3.3]heptane with morpholine at step 4 (yield 21%).
UPLC-MS [M+H]⁺=448.32
¹H NMR (400 MHz, CHLOROFORM-d) δ ppm 8.35 (br d, 1H) 7.17-7.25 (m, 2H) 6.87-6.98 (m, 2H) 6.82 (d, 1H) 5.39 (s, 2H) 3.83-3.94 (m, 4H) 3.81 (s, 3H) 3.20 (dd, 4H) 3.10-3.17 (m, 1H) 2.74 (s, 3H) 1.42 (d, 6H).

Example 90

6-(4-Chlorobenzyl)-3-methyl-8-(morpholin-4-yl)-2-(propan-2-yl)imidazo[1,2-c]pyrido[2,3-e]pyrimidin-5(6H)-one Example 90 as illustrated in Table 2 was prepared following the procedure described for Example 73 but replacing 1-chloro-4-methyl-pentan-2-one with 2-bromo-4-methyl-pentan-3-one at step 2 and 2-oxa-6-azaspiro[3.3]heptane with morpholine at step 4 (yield 49.6%).
HPLC-MS [M+H]⁺=452.5
¹H NMR (400 MHz, CHLOROFORM-d) δ ppm 8.32 (d, 1H), 7.33 (d, 2H), 7.21 (d, 2H), 6.69 (d, 1H), 5.39 (s, 2H), 3.90-3.81 (m, 4H), 3.22-3.13 (m, 4H), 3.13-3.02 (m, 1H), 2.71 (s, 3H), 1.39 (d, 6H).

Example 91

6-(4-Chlorobenzyl)-3-methyl-8-(2-oxa-6-azaspiro[3.3]heptan-6-yl)-2-(propan-2-yl)imidazo[1,2-c]pyrido[2,3-e]pyrimidin-5(6H)-one Example 91 as illustrated in Table 2 was prepared following the procedure described for Example 73 but replacing 1-chloro-4-methylpentan-2-one with 2-bromo-4-methylpentan-3-one at step 2 (yield 24%).
HPLC-MS [M+H]⁺=464.5
¹H NMR (400 MHz, CHLOROFORM-d) δ ppm 7.85 (d, 1H), 7.35 (d, 2H), 7.21 (d, 2H), 6.22 (d, 1H), 5.38 (s, 2H), 4.86 (s, 4H), 4.09 (s, 4H), 3.10 (m, 1H), 2.70 (s, 3H), 1.39 (d, 6H).

Example 92

6-(4-Methoxybenzyl)-8-[3-(methoxymethyl)azetidin-1-yl]-3-methyl-2-(propan-2-yl)imidazo[1,2-c]pyrido[2,3-e]pyrimidin-5(6H)-one Example 92 as illustrated in Table 2 was prepared following the procedure described for Example 73 but replacing 1-chloro-4-methylpentan-2-one with 2-bromo-4-methylpentan-3-one at step 2 and 2-oxa-6-azaspiro[3.3]heptane with 3-(methoxymethyl)azetidine at step 4 (yield 5%)
UPLC-MS [M+H]⁺=462.27
¹H NMR (400 MHz, CHLOROFORM-d) □ 7.85 (d, 1H) 7.21 (d, 2H) 6.79-7.00 (m, 2H) 6.26-6.42 ((m, 1H) 5.34 (s, 2H) 4.00 (t, 2H) 3.80 (s, 3H) 3.69-3.78 (m, 2H) 3.61 (d, 2H) 3.41 (s, 3H) 2.95-3.20 (m, 2H) 2.72 (s, 3H) 1.40 (d, 6H)

Example 93

6-(4-Methoxybenzyl)-3-methyl-8-(2-oxa-6-azaspiro[3.3]heptan-6-yl)-2-(propan-2-yl)imidazo[1,2-c]pyrido[2,3-e]pyrimidin-5(6H)-one Example 93 as illustrated in Table 2 was prepared following the procedure described for Example 73 but replacing 1-(bromomethyl)-4-chlorobenzene with 1-(bromomethyl)-4-methoxybenzene at step 1 and 1-chloro-4-methylpentan-2-one with 2-bromo-4-methylpentan-3-one at step 2 (yield 45%).
UPLC-MS [M+H]⁺=460.38
¹H NMR (400 MHz, DMSO-d₆) □ 7.76 (d, 1H) 7.25-7.38 (m, 2H) 6.86-6.94 (m, 2H) 6.62 (d, 1H) 5.36 (s, 2H) 4.72 (s, 4H) 4.11 (s, 4H) 3.72 (s, 3H) 3.05 (spt, 1H) 2.78 (s, 1H) 2.61 (s, 3H) 1.24 (d, 5H)

Example 94

6-(4-Chlorobenzyl)-8-[(4-hydroxypiperidin-1-yl)carbonyl]-3-methyl-2-(propan-2-yl)imidazo[1,2-c]pyrido[2,3-e]pyrimidin-5(6H)-one Example 94 as illustrated in Table 2 was prepared following the procedure described for Example 73 until the step 2 but replacing 1-chloro-4-methylpentan-2-one with 2-bromo-4-methylpentan-3-one. Step 4 was performed as described below:

6-(4-Chlorobenzyl)-8-[(4-hydroxypiperidin-1-yl)carbonyl]-3-methyl-2-(propan-2-yl)imidazo[1,2-c]pyrido[2,3-e]pyrimidin-5(6H)-one (Step 4)

The reaction was performed in a two chamber flask. 8-bromo-6-(4-chlorobenzyl)-3-methyl-2-(propan-2-yl)imidazo[1,2-c]pyrido[2,3-e]pyrimidin-5(6H)-one (50 mg, 0.112 mmol), piperidin-4-ol (13.6 mg, 0.135 mmol), Xantphos (3.2 mg, 0.006 mmol) and caesium carbonate (109.6 mg, 0.337 mmol) were introduced in chamber A and diluted with toluene (1 ml) under argon atmosphere. Methanesulfonyl chloride (77 mg, 0.673 mmol) and formic acid (31 mg, 0.673 mmol) were placed in chamber B and diluted with toluene (0.6 ml) under argon atmosphere. The flask was evacuated and backfilled with 3 cycles of argon. Palladium acetate (1.3 mg, 0.006 mmol) was added to chamber A and the flask was sealed. A solution of TEA (136 mg, 1.346 mmol) in toluene was injected into chamber B. A vigorous reaction took place.

The mixture was stirred at rt for 2 minutes and then heated at 100° C. overnight. The desired product was isolated via pTLC (5% Methanol/dichloromethane). (Yield 39.7%).

HPLC-MS [M+H]$^+$=494.8

$^1$H NMR (300 MHz, CHLOROFORM-d) δ ppm 8.60 (d, 1H), 7.50 (d, 1H), 7.35-7.29 (m, 2H), 7.19 (d, 2H), 5.44 (s, 2H), 4.20-3.89 (m, 3H), 3.55-3.38 (m, 2H), 3.18-3.02 (m, 2H), 2.74 (s, 3H), 1.80-1.55 (m, 4H), 1.38 (d, 6H).

Example 95

6-(4-Chlorobenzyl)-N-(2-hydroxyethyl)-3-methyl-5-oxo-2-(propan-2-yl)-5,6-dihydroimidazo[1,2-c]pyrido[2,3-e]pyrimidine-8-carboxamide Example 95 as illustrated in Table 2 was prepared following the procedure described for Example 94 but replacing piperidin-4-ol with 2-aminoethanol at step 4. (Yield 13%)

HPLC-MS [M+H]$^+$=454.7

$^1$H NMR (300 MHz, CHLOROFORM-d) δ ppm 8.86 (s, 1H), 8.12 (s, 1H), 7.32 (d, 2H), 7.25 (d, 2H), 5.45 (s, 2H), 3.86 (s, 2H), 3.66 (s, 2H), 3.20-3.04 (m, 1H), 2.76 (s, 3H), 1.35 (d, 6H).

Example 96

3-tert-Butyl-6-(4-methoxybenzyl)-8-(morpholin-4-yl)pyrido[2,3-e][1,2,4]triazolo[4,3-c]pyrimidin-5(6H)-one

Methyl 5-bromo-3-[(4-methoxyphenyl)methylamino]pyridine-2-carboxylate (Step 1)

To a solution of methyl 3-fluoro-5-bromopyridine-2-carboxylate (3.0 g, 12.82 mmol) and (4-methoxyphenyl)methanamine (2.286 g, 2.17 mL, 16.66 mmol) in 60 ml of acetonitrile, ethyldiisopropylamine (3.313 g, 4.39 mL, 25.64 mmol) was added and the mixture was stirred at reflux for 4 hours. After cooling down to room temperature, acetonitrile was removed under vacuum. The crude was dissolved in ethyl acetate. The organic solution was washed with water and brine, dried over Na$_2$SO$_4$, filtered and evaporated to dryness. 4.33 g of methyl 5-bromo-3-[(4-methoxyphenyl)methylamino]pyridine-2-carboxylate as white powder was collected and used in the next step without any further purification.

7-Bromo-1-[(4-methoxyphenyl)methyl]pyrido[3,2-d]pyrimidine-2,4-dione (Step 2)

To a stirred solution of methyl 5-bromo-3-[(4-methoxyphenyl)methylamino]pyridine-2-carboxylate in 35 ml of DCM, 2,2,2-trichloroacetyl isocyanate (7.12 mmol, 0.85 ml, 1.34 g) was added. The reaction was stirred at room temperature for 18 hours. Then the solvent was evaporated and sodium methoxide (11.8 g, 12.4 ml, 54.4 mmol) was added. The suspension was heated at 60° C. for 1 hour. After cooling down to room temperature, to the mixture was added water and glacial acetic acid until complete dissolution (pH=4-5). The aqueous layer was extracted with dichloromethane (3 times) and the organic phases were dried over Na$_2$SO$_4$, filtered and evaporated. 1.96 g of 7-bromo-1-[(4-methoxyphenyl)methyl]pyrido[3,2-d]pyrimidine-2,4-dione was collected and used in the next step without any further purification.

7-Bromo-4-chloro-1-[(4-methoxyphenyl)methyl]pyrido[3,2-d]pyrimidin-2-one (Step 3)

Under nitrogen atmosphere, a solution of 7-bromo-1-[(4-methoxyphenyl)methyl]pyrido[3,2-d]pyrimidine-2,4-dione (0.475 g, 1.311 mmol) and diisopropylethylamine (0.508 g, 0.673 mL, 3.93 mmol) in POCl$_3$ (16.090 g, 9.63 mL, 104.9 mmol) was stirred at 50° C. for 3 hours. After cooling down to room temperature, the solvent was removed and the residue was diluted with 1,4-dioxane and the mixture evaporated (3 times). 500 mg of 7-bromo-4-chloro-1-[(4-methoxyphenyl)methyl]pyrido[3,2-d]pyrimidin-2-one as a crude dark oil was collected and used in the next step without any further purification.

8-Bromo-3-tert-butyl-6-(4-methoxybenzyl)pyrido[2,3-e][1,2,4]triazolo[4,3-c]pyrimidin-5(6H)-one (Step 4)

A solution of 7-bromo-4-chloro-1-[(4-methoxyphenyl)methyl]pyrido[3,2-d]pyrimidin-2-one (2.89 g, 7.593 mmol) and 2,2-dimethylpropanidrazide (1.764 g, 15.19 mmol) in 40 ml of 1,4-dioxane was stirred at 90° C. for 2 hours. Then water and ethyl acetate were added into. The two phases were separated, the organic layer was dried over Na$_2$SO$_4$, filtered and evaporated to dryness. The crude was purified by means of a Biotage Isolera One, cartridge type SNAP50, using a gradient from petroleum ether:ethyl acetate=1:1 to petroleum ether:ethyl acetate=1:9. 1.1 g of the desired product as a light yellow powder was collected.

3-tert-Butyl-6-(4-methoxybenzyl)-8-(morpholin-4-yl)pyrido[2,3-e][1,2,4]triazolo[4,3-c]pyrimidin-5(6H)-one (Step 5)

In a microwave vial a solution of 8-bromo-3-tert-butyl-6-(4-methoxybenzyl)pyrido[2,3-e][1,2,4]triazolo[4,3-c]pyrimidin-5(6H)-one (155 mg, 0.35 mmol) and morpholine (45.80 mg, 45.8 µl, 0.5257 mmol,) in 1,4-dioxane (2 ml) was purged with nitrogen; after 5 minutes palladium(II) acetate (15.73 mg, 0.07 mmol), xantphos (81.11 mg, 0.140 mmol,) and cesium carbonate (228.4 mg, 0.70 mmol) were added and the mixture was heated in a sand bath at 80° C. for 4 h. After cooling down to room temperature, water and ethyl acetate were added, the two liquid phases were separated and the aqueous layer was extracted with ethyl acetate (2×). The combined organic phases were dried over $Na_2SO_4$, filtered and evaporated. The crude residue was purified by means of a Biotage Isolera One, cartridge type SNAP25, using a gradient from ethyl acetate 100% to ethyl acetate: methanol 9:1. The fractions collected were further purified by reverse phase column chromatography eluting with a gradient from aqueous ammonium bicarbonate buffer:acetonitrile 8:2 to 1:1. 15 mg of 3-tert-butyl-6-(4-methoxybenzyl)-8-(morpholin-4-yl)pyrido[2,3-e][1,2,4]triazolo[4,3-c]pyrimidin-5(6H)-one as white powder, was collected.

UPLC-MS $[M+H]^+$=449.26

$^1$H NMR (400 MHz, DMSO-d6) δ ppm 8.38 (d, 1H), 7.34 (m, 2H), 7.08 (d, 1H), 6.90 (m, 2H), 5.45 (s, 2H), 3.73-3.79 (m, 4H), 3.72 (s, 3H), 3.31-3.34 (m, 4H), 1.58 (s, 9H).

Example 96—Alternative Procedure

3-[(4-Methoxyphenyl)methylamino]-5-morpholino-pyridine-2-carboxamide (Step 1)

To an ice bath cooled solution of 3-[(4-methoxyphenyl)methylamino]-5-morpholino-pyridine-2-carbonitrile (Example 1, Step 2, 46.24 mmol, 15 g) in DMSO (400 mL) 1M sodium hydroxide solution (27.74 mL) was added followed by hydrogen peroxide (30-35%) (55.49 mmol, 5.67 mL) and the mixture was stirred at room temperature for 3 hours. Then water and EtOAc were added, the two phases were separated, the aqueous layer was extracted with EtOAc and the combined organic layers were dried over $Na_2SO_4$, filtered and evaporated to dryness. The crude product was crystallized from acetonitrile affording 3-[(4-methoxyphenyl)methylamino]-5-morpholinopyridine-2-carboxamide (12 g) which was isolated as a brown solid. Yield: 75%.

1-[(4-Methoxyphenyl)methyl]-7-morpholinopyrido[3,2-d]pyrimidine-2,4-dione (Step 2)

To a solution of 3-[(4-methoxyphenyl)methylamino]-5-morpholinopyridine-2-carboxamide (7.6 mmol, 2.6 g) in THF anhydrous (30 mL) under nitrogen atmosphere, sodium hydride (7.6 mmol, 0.30 g) was added and the reaction solution was stirred at room temperature for 15 minutes. Then the mixture was cooled at 0-4° C. and ethyl chloroformate (38 mmol, 3.6 mL) was added dropwise. The reaction mixture was heated at reflux for 9 hours. The mixture was cooled to 0° C. and 60% sodium hydride (1.5 g) was added, the reaction was heated at reflux for further 6 hours The mixture was then cooled to 0-4° C., water was slowly added and the pH was adjusted around 8-9. A precipitate was filtered to give 1-[(4-methoxyphenyl)methyl]-7-morpholino-pyrido[3,2-d]pyrimidine-2,4-dione (4.89 mmol, 1.8 g) which was used for the next step without further purification. Yield: 64%

Alternative Preparation: 1-[(4-Methoxyphenyl)methyl]-7-morpholinopyrido[3,2-d]pyrimidine-2,4-dione (Step 2)

This intermediate has been alternatively prepared from 7-bromo-1-[(4-methoxyphenyl)methyl]pyrido[3,2-d]pyrimidine-2,4-dione (Step 3 of Example 96 main procedure) by Buchwald reaction with morpholine as described in step 5 of the main procedure.

4-Chloro-1-[(4-4-methoxyphenyl)methyl]-7-morpholino-pyrido[3,2-d]pyrimidin-2-one (Step 3)

To a suspension of 1-[(4-methoxyphenyl)methyl]-7-morpholinopyrido[3,2-d]pyrimidine-2,4-dione (2.24 mmol, 834 mg) in ethyldiisopropylamine (1.15 mL), $POCl_3$ (10 mL) was added and the resulting mixture was stirred at 50° C. for 20 min and cooled to r.t. The liquid was evaporated, rinsed with dioxane and evaporated to give 4-chloro-1-[(4-4-methoxyphenyl)methyl]-7-morpholino-pyrido[3,2-d]pyrimidin-2-one used for the next step without further purification 3-tert-Butyl-6-(4-methoxybenzyl)-8-(morpholin-4-yl)pyrido[2,3-e][1,2,4]triazolo[4,3-c]pyrimidin-5(6H)-one (Step 4)

To a solution of 4-chloro-1-[(4-methoxyphenyl)methyl]-7-morpholino-pyrido[3,2-d]pyrimidin-2-one (0.87 g, 2.224 mmol) in dioxane (15 mL) 2-methylpropanehydrazide (0.4543 g, 4.448 mmol) was added and the reaction mixture was stirred 4 hours at 80° C., cooled to r.t., poured into water and extracted with EtOAc. The organic phase was washed with water, dried over $Na_2SO_4$ and the solvent was evaporated to dryness to give the crude that was purified via automated flash chromatography eluting with EtOAc-MeOH gradient from 10:0 to 8:2 to give Example 97, mg 335. Yield 34%.

UPLC-MS $[M+H]^+$=449.05

Examples 97-100, 102-105, 108 were prepared following the procedure reported above for Example 96—alternative procedure starting from either 1-[(4-methoxyphenyl)methyl]-7-morpholinopyrido[3,2-d]pyrimidine-2,4-dione or from 1-[(4-chlorophenyl)methyl]-7-morpholinopyrido[3,2-d]pyrimidine-2,4-dione (similarly prepared) and using the proper hydrazide (purchased from available vendors or synthesised by method disclosed by the literature) at step 4 in place of pivaloyl hydrazide.

Example 97

6-(4-Methoxybenzyl)-8-(morpholin-4-yl)-3-(propan-2-yl)pyrido[2,3-e][1,2,4]triazolo[4,3-c]pyrimidin-5(6H)-one From 2-methylpropanehydrazide.
HPLC-MS $[M+H]^+$=507.10
$^1$H NMR (300 MHz, CHLOROFORM-d) δ ppm 8.37 (d, 1H), 7.22 (d, 2H), 6.91 (d, 2H), 6.83 (d, 1H), 5.38 (s, 2H), 4.10-4.00 (m, 1H), 3.88 (dd, 4H), 3.82 (s, 3H), 3.29-3.19 (m, 4H), 1.56-1.52 (m, 6H).

Example 98

6-(4-Methoxybenzyl)-8-(morpholin-4-yl)-3-[(tetrahydro-2H-pyran-4-yloxy)methyl]pyrido[2,3-e][1,2,4]triazolo[4,3-c]pyrimidin-5(6H)-one From 2-(tetrahydro-2H-pyran-4-yloxy)acetohydrazide.
HPLC-MS $[M+H]^+$=507.36
$^1$H NMR (300 MHz, CHLOROFORM-d) δ ppm 8.38 (d, 1H), 7.23 (d, 2H), 6.95-6.88 (m, 2H), 6.85 (d, 1H), 5.40 (s, 2H), 5.23 (s, 2H), 3.98 (dt, 2H), 3.96-3.82 (m, 5H), 3.82 (s, 3H), 3.56-3.41 (m, 2H), 3.26 (dd, 4H), 2.06-1.93 (m, 2H), 1.79-1.64 (m, 2H).

Example 99

6-(4-Chlorobenzyl)-8-(morpholin-4-yl)-3-(propan-2-yl)pyrido[2,3-e][1,2,4]triazolo[4,3-c]pyrimidin-5(6H)-one From 2-methylpropanehydrazide.
HPLC-MS [M+H]⁺=439.05
¹H NMR (300 MHz, CHLOROFORM-d) δ ppm 8.36 (d, 1H), 7.40-7.31 (m, 2H), 7.20 (d, 2H), 6.68 (d, 1H), 5.39 (s, 2H), 3.99 (m, 1H), 3.90-3.79 (m, 4H), 3.26-3.14 (m, 4H), 1.53 (d, 6H).

Example 100

6-(4-Chlorobenzyl)-8-(morpholin-4-yl)-3-(pyridin-3-ylmethyl)pyrido[2,3-e][1,2,4]triazolo[4,3-c]pyrimidin-5(6H)-one From 3-pyridylacetohydrazide.
HPLC-MS [M+H]⁺=488.02

Example 102

6-(4-Chlorobenzyl)-3-(1-methylcyclopropyl)-8-(morpholin-4-yl)pyrido[2,3-e][1,2,4]triazolo[4,3-c]pyrimidin-5(6H)-one From 1-methylcyclopropanecarbohydrazide.
HPLC-MS [M+H]⁺=451.07
¹H NMR (300 MHz, CHLOROFORM-d) δ ppm 8.35 (d, 1H), 7.39-7.32 (m, 2H), 7.23-7.17 (m, 2H), 6.68 (d, 1H), 5.41 (s, 2H), 3.91-3.81 (m, 4H), 3.25-3.16 (m, 4H), 1.38-1.25 (m, 5H), 0.98-0.91 (m, 2H).

Example 103

2-[6-(4-Chlorobenzyl)-8-(morpholin-4-yl)-5-oxo-5,6-dihydropyrido[2,3-e][1,2,4]triazolo[4,3-c]pyrimidin-3-yl]-N-(propan-2-yl)acetamide From 3-hydrazinyl-3-oxo-N-(propan-2-yl)propanamide.
HPLC-MS [M+H]⁺=496.1
¹H NMR (300 MHz, CHLOROFORM-d) δ ppm 8.39-8.35 (m, 1H), 7.35 (d, 2H), 7.20 (d, 2H), 6.69 (d, 1H), 6.30 (brs, 1H), 5.37 (s, 2H), 4.35 (s, 2H), 4.15-4.06 (m, 1H), 3.86 (t, 4H), 3.23 (t, 4H), 1.17 (d, 6H).

Example 104

6-(4-Methoxybenzyl)-3-(2-methylpropyl)-8-(morpholin-4-yl)pyrido[2,3-e][1,2,4]triazolo[4,3-c]pyrimidin-5(6H)-one From 3-methylbutanehydrazide.
HPLC-MS [M+H]⁺=449.26

Example 105

6-(4-Chlorobenzyl)-3-[(2-hydroxypyridin-3-yl)methyl]-8-(morpholin-4-yl)pyrido[2,3-e][1,2,4]triazolo[4,3-c]pyrimidin-5(6H)-one From 3-(2-hydroxypyridyl)acetohydrazide.
HPLC-MS [M+H]⁺=504.00
¹H NMR (300 MHz, CHLOROFORM-d) δ ppm 12.00 (br, 1H), 8.38 (d, 1H), 7.46 (d, J=6.6 Hz, 1H), 7.37-7.28 (m, 3H), 7.26-7.20 (m, 2H), 6.74 (d, 1H), 6.20 (t, 1H), 5.50 (s, 2H), 4.26 (s, 2H), 3.88-3.82 (m, 4H), 3.28-3.21 (m, 4H).

Example 108

6-(4-Chlorobenzyl)-3-(2-methylpropyl)-8-(morpholin-4-yl)pyrido[2,3-e][1,2,4]triazolo[4,3-c]pyrimidin-5(6H)-one From 3-methylbutanehydrazide.
HPLC-MS [M+H]⁺=453.87

Example 101

6-(3,5-Dimethoxybenzyl)-3-methyl-8-(morpholin-4-yl)pyrido[2,3-e][1,2,4]triazolo[4,3-c]pyrimidin-5(6H)-one Prepared as described for Example 96 standard procedure using 3,5-dimethoxyphenylmethanamine instead of (4-methoxyphenyl)methanamine at step 1 and acetohydrazide instead of 2,2-dimethylpropanehydrazide at step 4.
HPLC-MS [M+H]⁺=[M+H]⁺=437.28
¹H NMR (400 MHz, CHLOROFORM-d) δ ppm 8.37 (d, 1H), 6.88 (d, 1H), 6.41 (d, 2H), 6.37 (t, 1H), 5.46 (s, 2H), 3.90-3.81 (m, 4H), 3.74 (s, 6H), 3.31-3.21 (m, 4H), 2.65 (s, 3H).

Example 106

6-(4-Chlorobenzyl)-3-[(2-methylpyridin-3-yl)methyl]-8-(morpholin-4-yl)pyrido[2,3-e][1,2,4]triazolo[4,3-c]pyrimidin-5(6H)-one To a solution of 4-chloro-1-[(4-chlorophenyl)methyl]-7-morpholinopyrido[3,2-d]pyrimidin-2-one prepared as described above for analogues (0.608 mmol, 237 mg) in dioxane (5 mL) 2-(2-methyl-3-pyridyl)acetohydrazide (0.67 mmol, 88 mg) was added and the reaction mixture was stirred at r.t. for 1 hour poured into water and extracted with EtOAc. The organic phase was washed with water, dried over Na₂SO₄ and the solvent was evaporated to dryness. The residue was solved in THF (5 mL) and Burgess reagent (0.217 g, 1.5 equiv.) was added and the reaction mixture stirred at r.t. overnight, poured into water and extracted with EtOAc. The organic phase was washed with water, dried over Na₂SO₄ and the solvent was evaporated to dryness to give the crude. The crude was purified via automated flash chromatography (Biotage-Isolera Dalton), eluting with a EtOAc-MeOH gradient from 10:0 to 8:2 and by SNAP30-C18 Cartridge, eluting with a H₂O-ACN gradient from 8:2 to 2:8 to give 6-(4-chlorobenzyl)-3-[(2-methylpyridin-3-yl)methyl]-8-(morpholin-4-yl)pyrido[2,3-e][1,2,4]triazolo[4,3-c]pyrimidin-5(6H)-one, mg 41. Yield 14%.
HPLC-MS [M+H]⁺=502.10
¹H NMR (300 MHz, CHLOROFORM-d) δ ppm 8.40 (dd, 1H), 8.36 (d, 1H), 7.47 (d, 1H), 7.39-7.31 (m, 2H), 7.14 (d, 2H), 7.06 (dd, 1H), 6.66 (d, 1H), 5.33 (s, 2H), 4.74 (s, 2H), 3.85 (dd, 4H), 3.21 (dd, 4H), 2.71 (s, 3H).

By the same procedure described in Example 106, the following Examples 107, 109, 110 were prepared replacing the proper hydrazide for 2-(2-methyl-3-pyridyl)acetohydrazide

Example 107

6-(4-chlorobenzyl)-3-(1-ethyl-1H-pyrazol-5-yl)-8-(morpholin-4-yl)pyrido[2,3-e][1,2,4]triazolo[4,3-c]pyrimidin-5(6H)-one From 2-ethylpyrazole-3-carbohydrazide.
HPLC-MS [M+H]$^+$=491.10
$^1$H NMR (300 MHz, CHLOROFORM-d) δ ppm 8.38 (d, 1H), 7.53 (d, 1H), 7.37-7.29 (m, 2H), 7.20 (d, 2H), 6.92 (d, 1H), 6.69 (d, 1H), 5.40 (s, 2H), 4.32 (q, 2H), 3.91-3.80 (m, 4H), 3.25-3.19 (m, 4H), 1.57 (t, 3H).

Example 109

6-(4-Chlorobenzyl)-3-(1-ethyl-1H-pyrazol-3-yl)-8-(morpholin-4-yl)pyrido[2,3-e][1,2,4]triazolo[4,3-c]pyrimidin-5(6H)-one From 1-ethylpyrazole-3-carbohydrazide.
HPLC-MS [M+H]$^+$=491.12

Example 110

6-(4-Chlorobenzyl)-3-(3,5-dimethyl-1,2-oxazol-4-yl)-8-(morpholin-4-yl)pyrido[2,3-e][1,2,4]triazolo[4,3-c]pyrimidin-5(6H)-one From 3,5-dimethylisoxazole-4-carbohydrazide.
HPLC-MS [M+H]$^+$=492.05

Example 111

3-tert-Butyl-6-(4-chlorobenzyl)-8-(morpholin-4-yl)pyrido[2,3-d][1,2,4]triazolo[4,3-b]pyridazine

5-Bromo-2-isopropoxycarbonylpyridine-3-carboxylic Acid (Step 1)

A suspension of 3-bromofuro[3,4-b]pyridine-5,7-dione (15.2 g, 66.67 mmol) in 150 ml of isopropanol was stirred at rt overnight. A clear brown solution was obtained. The solvent was removed to dryness and the crude was purified by column chromatography eluting with dichloromethane:methanol=10:1. 13.7 g of the desired Example were obtained (yield: 71%).

Isopropyl 5-bromo-3-[2-(4-chlorophenyl)-3-methoxy-3-oxo-propanoyl]pyridine-2-carboxylate (Step 2)

To a solution of 5-bromo-2-isopropoxycarbonylpyridine-3-carboxylic acid (1 g, 3.5 mmol) in anhydrous DMF (10 ml) carbodiimidazole (732 mg, 4.5 mmol) was added and the reaction mixture was stirred overnight at 50° C. After cooling to rt, methyl 2-(4-chlorophenyl)acetate (628 mg, 3.8 mmol) was added, the mixture was cooled to −40° C. and NaH (487 mg, 4.5 mmol, 60% oil suspension) was added in four portion. The reaction mixture was stirred for 1 hour at −25° C., for 1 hour at 0° C. and for 2 hours at rt until reaction was completed. The mixture was quenched with 75 ml of water and neutralized with 2M HCl. The aqueous layers were extracted with ethyl acetate (3×200 ml). The organic phase was washed with water and brine, dried over Na$_2$SO$_4$, filtered and concentrated under vacuum. 2 g of the desired product were obtained (yield 66%).

5-Bromo-3-[2-(4-chlorophenyl)acetyl]pyridine-2-carboxylic Acid (Step 3)

To a solution of Isopropyl 5-bromo-3-[2-(4-chlorophenyl)-3-methoxy-3-oxo-propanoyl]pyridine-2-carboxylate (1.5 g, 3.45 mmol) in dioxane (75 ml) 6 M HCl (8 ml) was added and the mixture was stirred at 80° C. for 2 days. The mixture was concentrated under vacuum and neutralized with sodium acetate. The aqueous phase was extracted with ethyl acetate (3×100 ml), organic layers were dried over MgSO$_4$, filtered and evaporated to dryness under vacuum. 906 mg of the desired Example were obtained (yield 74%).

3-Bromo-5-[(4-chlorophenyl)methyl]-7H-pyrido[2,3-d]pyridazin-8-one (Step 4)

To a solution of 5-bromo-3-[2-(4-chlorophenyl)acetyl]pyridine-2-carboxylic acid (906 mg, 2.7 mmol) in 20 ml of ethanol, hydrazine monohydrate (203 mg, 4.1 mmol) was added. The mixture was stirred at 60° C. for 24 hours. Ethanol was evaporated and the crude was diluted with water and extracted with ethyl acetate (3×100 ml). The organic layers were washed with brine and dried over MgSO$_4$ anhydrous, filtered and evaporated to dryness. The crude was purified by silica gel column chromatography eluting with ethyl acetate/hexane gradient starting from 0:100 to 100:0. 350 mg of the desired product were obtained (yield 37%).

3-Bromo-8-chloro-5-[(4-chlorophenyl)methyl]pyrido[2,3-d]pyridazine (Step 5)

3-Bromo-5-[(4-chlorophenyl)methyl]-7H-pyrido[2,3-d]pyridazin-8-one (760 mg, 2.17 mmol) and ethyldiisopropylamine (840.5 mg, 1.11 ml, 6.50 mmol) were placed in a dry flask with POCl$_3$ (26.590 g, 15.9 ml, 173.4 mmol). The mixture was stirred at 50° C. for 3 hours. After cooling down to room temperature, the solvent was removed and the residue was diluted with 1,4-dioxane and the mixture evaporated (repeated three times). 2.5 g of the desired product as a dark oil was obtained and used in the next step without any further purification.

8-Bromo-3-tert-butyl-6-(4-chlorobenzyl)pyrido[2,3-d][1,2,4]triazolo[4,3-b]pyridazine (Step 6) (Example 112)

A solution of 3-bromo-8-chloro-5-[(4-chlorophenyl)methyl]pyrido[2,3-d]pyridazine (760 mg, 2.06 mmol) and 2,2-dimethylpropanehydrazide (717.7 mg, 6.18 mmol) in 1,4-dioxane (20 ml) was stirred at 60° C. for 2 hours, then at room temperature overnight. The solvent was removed under vacuum, water and ethyl acetate were added. The organic layer was separated, dried over Na$_2$SO$_4$ anhydrous, filtered and evaporated to dryness. The obtained crude was purified by Biotage Isolera One, cartridge type SNAP50, eluting with a gradient from petroleum ether: ethyl acetate 1:1 to Ethyl Acetate 100%. 560 mg of Example 136 were collected as an orange powder (Yield: 63%)
UPLC-MS [M+H]$^+$=430.16-432.23
$^1$H NMR (400 MHz, DMSO-d$_6$) δ ppm 9.29 (d, 1H) 8.98 (d, 1H) 7.42 (s, 4H) 4.65 (s, 2H) 1.43 (s, 9H)

3-tert-Butyl-6-(4-chlorobenzyl)-8-(morpholin-4-yl)pyrido[2,3-d][1,2,4]triazolo[4,3-b]pyridazine (Step 7)

In a microwave vial a solution of 8-bromo-3-tert-butyl-6-(4-chlorobenzyl)pyrido[2,3-d][1,2,4]triazolo[4,3-b]pyridazine (50 mg, 0.116 mmol) and morpholine (15.17 mg, 0.17 mmol) in 1,4-dioxane (2 ml) was purged with N$_2$; after 5 minutes palladium(II) acetate (5.212 mg, 0.023 mmol), xantphos (26.87 mg, 0.0464 mmol) and cesium carbonate (75.65 mg, 0.232 mmol) were added and the mixture was heated in a sand bath at 80° C. for 2 hours. Then water and ethyl acetate were added, the two liquid phases were separated and the aqueous layer was extracted with ethyl acetate (2×25 ml). The organic phase was dried over Na$_2$SO$_4$ anhydrous, filtered and evaporated to dryness. The crude residue was purified by means of a Biotage Isolera One, cartridge type SNAP10, using a gradient from ethyl acetate-methanol 100:0 to ethyl acetate-methanol 80:20. Collected fractions gave 24 mg of the desired product as yellow powder which were purified again on a reverse phase column chromatography using a gradient NH$_4$HCO$_3$ buffer-MeCN starting from 7:3 to NH$_4$HCO$_3$ buffer-MeCN 3:7. 11 mg of Example 137 were collected as yellow powder. (Yield: 21%).

UPLC-MS [M+H]$^+$=437.28

$^1$H NMR (400 MHz, CHLOROFORM-d) δ ppm 8.88 (d, 1H), 7.32-7.39 (m, 3H), 7.23 (d, 2H), 4.46 (s, 2H), 3.89-3.98 (m, 4H), 3.27-3.36 (m, 4H), 1.62 (s, 9H).

Examples 113-115, 117, 137 (Table 3) were prepared following the procedure described for Example 111 but replacing methyl 2-(4-chlorophenyl)acetate with methyl 2-(4-methylphenyl)acetate at step 2 and substituting 2,2-dimethylpropanhydrazide with 2-cyclohexylacetohydrazide or acetohydrazide or 2-methylpropanehydrazide (synthesised by method disclosed by the literature or purchased from available vendors) at Step 6. Morpholine was replaced by the proper amine (purchased from available vendors) at Step 7.

Example 113

N-(2-Methoxyethyl)-3-methyl-6-(4-methylbenzyl)pyrido[2,3-d][1,2,4]triazolo[4,3-b]pyridazin-8-amine Yellow solid. Yield: 8%.
UPLC-MS [M+H]$^+$=440.28
$^1$H NMR (400 MHz, CHLOROFORM-d) δ ppm 8.73-8.57 (m, 1H), 7.21-7.03 (m, 5H), 4.42 (s, 2H), 3.59 (t, 2H), 3.38 (d, 3H), 3.28 (t, 2H), 2.84 (s, 3H), 2.31 (s, 3H).

Example 114

3-Methyl-6-(4-methylbenzyl)-N-(oxetan-3-ylmethyl)pyrido[2,3-d][1,2,4]triazolo[4,3-b]pyridazin-8-amine Yield: 10%.
UPLC-MS [M+H]$^+$=375.25
$^1$H NMR (400 MHz, Methanol-d4) δ ppm 8.52 (d, 1H), 7.46-6.85 (m, 5H), 4.79 (dd, 2H), 4.53 (s, 2H), 4.42 (t, 2H), 3.45 (d, 2H), 3.13 (m, 1H), 2.81 (s, 3H), 2.33 (s, 3H).

Example 115

6-(4-Methylbenzyl)-8-(morpholin-4-yl)-3-(propan-2-yl)pyrido[2,3-d][1,2,4]triazolo[4,3-b]pyridazine Yield: 4%.
UPLC-MS [M+H]$^+$=403.46
$^1$H NMR (400 MHz, CHLOROFORM-d) δ ppm 8.83 (s, 1H), 7.40 (d, 1H), 7.16 (q, J=8.2 Hz, 4H), 4.45 (s, 2H), 4.03-3.80 (m, 4H), 3.71 (dt, 1H), 3.35-3.14 (m, 4H), 2.34 (s, 3H), 1.60 (d, 6H).

Example 117

6-(4-Methylbenzyl)-8-(morpholin-4-yl)-3-(tetrahydro-2H-pyran-4-ylmethyl)pyrido[2,3-d][1,2,4]triazolo[4,3-b]pyridazine Yield: 6%.
UPLC-MS [M+H]$^+$=459.1

Examples 116 and 118-121 as illustrated in Table 3 were prepared following the procedure described for Example 111 but replacing methyl 2-(4-chlorophenyl)acetate with methyl 2-(3,5-dimethoxyphenyl)acetate at step 2 and substituting 2,2-dimethylpropanidrazide with the proper hydrazide (purchased from available vendors or synthesised by method disclosed by the literature) at Step 6. Morpholine was in case replaced by the proper amine (purchased from available vendors) at Step 7. Reported yields are referred to the last step.

Example 116

6-(3,5-Dimethoxybenzyl)-3-(2-methylpropyl)-8-(morpholin-4-yl)pyrido[2,3-d][1,2,4]triazolo[4,3-b]pyridazine Yield: 5%.
UPLC-MS [M+H]$^+$=463.2

Example 118

6-(3,5-Dimethoxybenzyl)-N-(2-methoxyethyl)-3-(2-methylpropyl)pyrido[2,3-d][1,2,4]triazolo[4,3-b]pyridazin-8-amine Yield: 5%.
UPLC-MS [M+H]$^+$=451.3

Example 119

6-(3,5-Dimethoxybenzyl)-8-(morpholin-4-yl)-3-[(propan-2-yloxy)methyl]pyrido[2,3-d][1,2,4]triazolo[4,3-b]pyridazine Yield: 18%.
UPLC-MS [M+H]$^+$=479.2

Example 120

6-(3,5-dimethoxybenzyl)-8-(morpholin-4-yl)-3-(prop-1-en-2-yl)pyrido[2,3-d][1,2,4]triazolo[4,3-b]pyridazine Yield: 17%.
UPLC-MS [M+H]$^+$=447.2
$^1$H NMR (400 MHz, CHLOROFORM-d) δ ppm 8.88 (d, 1H), 7.46 (d, 1H), 6.65 (s, 1H), 6.44 (d, 2H), 6.38 (t, 1H), 5.71-5.63 (m, 1H), 4.44 (s, 2H), 4.01-3.86 (m, 4H), 3.76 (s, 6H), 3.39-3.22 (m, 4H), 2.51 (s, 3H).

Example 121

6-(3,5-Dimethoxybenzyl)-8-[3-(methoxymethyl)azetidin-1-yl]-3-(2-methylpropyl)pyrido[2,3-d][1,2,4]triazolo[4,3-b]pyridazine Yield: 9%.
UPLC-MS [M+H]$^+$=477.2

Examples 122-125, 130 as illustrated in Table 3 were prepared following the procedure described for Example 111 but replacing methyl 2-(4-chlorophenyl)acetate with methyl 2-(4-methoxyphenyl)acetate at step 2 and substituting 2,2-dimethylpropanhydrazide with the proper hydrazide (synthesised by method disclosed by the literature or purchased from available vendors) at Step 6. Morpholine was in case replaced by the proper amine (purchased from available vendors) at Step 7. Reported yields are referred to the last step.

Example 122

6-(4-Methoxybenzyl)-8-(morpholin-4-yl)-3-(propan-2-yl)pyrido[2,3-d][1,2,4]triazolo[4,3-b]pyridazine Yield: 10%.
UPLC-MS [M+H]$^+$=419.15
$^1$H NMR (300 MHz, CHLOROFORM-d) δ ppm 8.82 (d, 1H), 7.37 (d, 1H), 7.23-7.15 (m, 2H), 6.90-6.81 (m, 2H), 4.41 (s, 2H), 3.95-3.84 (m, 4H), 3.78 (s, 3H), 3.73-3.63 (m, 1H), 3.31-3.16 (m, 4H), 1.57 (d, 6H).

Example 123

3-tert-Butyl-6-(4-methoxybenzyl)-8-(morpholin-4-yl)pyrido[2,3-d][1,2,4]triazolo[4,3-b]pyridazine Yield: 31%.
UPLC-MS [M+H]$^+$=433.08

Example 124

6-(4-Methoxybenzyl)-8-[3-(methoxymethyl)azetidin-1-yl]-3-(2-methylpropyl)pyrido[2,3-d][1,2,4]triazolo[4,3-b]pyridazine Yield: 30%.
UPLC-MS [M+H]$^+$=447.17
$^1$H NMR (300 MHz, CHLOROFORM-d) δ ppm 8.82 (d, 1H), 7.39 (d, 1H), 7.18 (d, 2H), 6.86 (d, 2H), 4.40 (s, 2H), 3.96-3.83 (m, 4H), 3.78 (s, 3H), 3.33-3.19 (m, 4H), 1.63 (s, 9H).

Example 125

6-(4-Methoxybenzyl)-8-(morpholin-4-yl)-3-(tetrahydro-2H-pyran-4-ylmethyl)pyrido[2,3-d][1,2,4]triazolo[4,3-b]pyridazine Yield: 7%.
UPLC-MS [M+H]$^+$=475.14

Example 130

6-(4-Methoxybenzyl)-8-(2-oxa-6-azaspiro[3.3]heptan-6-yl)-3-(tetrahydro-2H-pyran-4-ylmethyl)pyrido[2,3-d][1,2,4]triazolo[4,3-b]pyridazine Yield: 6%.
UPLC-MS [M+H]$^+$=487.11
$^1$H NMR (300 MHz, CHLOROFORM-d) δ ppm 8.33 (d, 1H), 7.20-7.14 (m, 2H), 6.92 (d, 1H), 6.89-6.83 (m, 2H), 4.87 (s, 4H), 4.37 (s, 2H), 4.17 (s, 4H), 3.94 (d, 2H), 3.78 (s, 3H), 3.46-3.32 (m, 2H), 3.16 (d, 2H), 2.34-2.23 (m, 1H), 1.75-1.43 (m, 4H).

Example 137

3-(Cyclohexylmethyl)-6-(4-methylbenzyl)-8-(morpholin-4-yl)pyrido[2,3-d][1,2,4]triazolo[4,3-b]pyridazine Yield: 26%.
UPLC-MS [M+H]$^+$=457.10
$^1$H NMR (400 MHz, CHLOROFORM-d) δ ppm 8.83 (d, 1H), 7.40 (d, 1H), 7.16 (q, 4H), 4.44 (s, 2H), 3.97-3.84 (m, 4H), 3.32-3.22 (m, 4H), 3.14 (d, 2H), 2.34 (s, 3H), 2.06 (ddd, 1H), 1.74 (m, 6H), 1.23-1.07 (m, 4H)

The compound of Example 134 was obtained as a by-product from the purification by flash chromatography of Example 125

Example 134

(4-Methoxyphenyl)[8-(morpholin-4-yl)-3-(tetrahydro-2H-pyran-4-ylmethyl)pyrido[2,3-d][1,2,4]triazolo[4,3-b]pyridazin-6-yl]methanone Yield: 4%.
UPLC-MS [M+H]$^+$=489.23

Examples 126-129, 132 and 133, 138, 140 as illustrated in Table 3 were prepared following the procedure described for Example 111 but replacing 2,2-dimethylpropanidrazide with the proper hydrazide (purchased from available vendors or synthesized by method disclosed by the literature) at Step 6. Morpholine was in case replaced by the proper amine (purchased from available vendors) at Step 7. Reported yield is referred to the last step.

Example 126

6-(4-Chlorobenzyl)-8-(morpholin-4-yl)-3-(tetrahydro-2H-pyran-4-ylmethyl))pyrido[2,3-d][1,2,4]triazolo[4,3-b]pyridazine Yield: 17%
UPLC-MS [M+H]$^+$=479.08
$^1$H NMR (300 MHz, CHLOROFORM-d) δ ppm 8.85 (d, 1H), 7.36-7.28 (m, 3H), 7.20 (d, 2H), 4.45 (s, 2H), 4.02-3.83 (m, 6H), 3.45-3.32 (m, 2H), 3.32-3.23 (m, 4H), 3.15 (d, 2H), 2.36-2.21 (m, 1H), 1.75-1.61 (m, 2H), 1.57-1.39 (m, 2H).

Example 127

6-(4-Chlorobenzyl)-8-(morpholin-4-yl)-3-(propan-2-yl)pyrido[2,3-d][1,2,4]triazolo[4,3-b]pyridazine White powder. Yield: 18%.
UPLC-MS [M+H]$^+$=423.08

Example 128

6-(4-Chlorobenzyl)-8-[3-(methoxymethyl)azetidin-1-yl]-3-(2-methylpropyl)pyrido[2,3-d][1,2,4]triazolo[4,3-b]pyridazine Yield: 16%.
UPLC-MS [M+H]$^+$=451.12

Example 129

6-(4-Chlorobenzyl)-8-(2-oxa-6-azaspiro[3.3]heptan-6-yl)-3-(tetrahydro-2H-pyran-4-ylmethyl)pyrido[2,3-d][1,2,4]triazolo[4,3-b]pyridazine White powder. Yield: 2%.
UPLC-MS [M+H]$^+$=491.1
$^1$H NMR (300 MHz, CHLOROFORM-d) δ ppm 8.45-8.32 (m, 1H), 7.36-7.29 (m, 2H), 7.21-7.15 (m, 2H), 6.83 (d, 1H), 4.87 (s, 4H), 4.41 (s, 2H), 4.20 (s, 4H), 4.01-3.91 (m, 2H), 3.41-3.32 (m, 2H), 3.13 (d, 2H), 2.28-2.18 (m, 1H), 1.70-1.60 (m, 2H), 1.57-1.43 (m, 2H).

Example 132

6-(4-Chlorobenzyl)-8-(morpholin-4-yl)-3-[1-(tetrahydro-2H-pyran-4-yl)ethyl]pyrido[2,3-d][1,2,4]triazolo[4,3-b]pyridazine Yield: 6%.
UPLC-MS [M+H]$^+$=493.13
$^1$H NMR (300 MHz, CHLOROFORM-d) δ ppm 8.85 (d, 1H), 7.37-7.29 (m, 3H), 7.24-7.16 (m, 2H), 4.44 (s, 2H), 4.05-3.97 (m, 1H), 3.94-3.82 (m, 5H), 3.44-3.21 (m, 7H), 2.21-2.11 (m, 1H), 1.87-1.75 (m, 1H), 1.49 (d, 3H), 1.41 (dt, 3H).

Example 133

6-(4-Chlorobenzyl)-3-(2-methylpropyl)-8-(morpholin-4-yl)pyrido[2,3-d][1,2,4]triazolo[4,3-b]pyridazine Yield: 7%.
UPLC-MS [M+H]$^+$=437.15
$^1$H NMR (300 MHz, CHLOROFORM-d) δ ppm 8.85 (d, 1H), 7.34-7.28 (m, 3H), 7.23-7.17 (m, 2H), 4.44 (s, 2H), 3.95-3.86 (m, 4H), 3.29-3.22 (m, 4H), 3.09 (d, 2H), 2.45-2.27 (m, 1H), 1.03 (d, 6H).

Example 138 tert-Butyl {1-[3-tert-butyl-6-(4-chlorobenzyl)pyrido[2,3-d][1,2,4]triazolo[4,3-b]pyridazin-8-yl]piperidin-4-yl}carbamate Yellow powder. Yield: 49%.
UPLC-MS [M+H]$^+$=550.27
$^1$H NMR (400 MHz, DMSO-d6) δ ppm 8.96 (d, 1H) 7.75 (d, 1H) 7.42 (d, 3H) 6.88 (br d, 1H) 4.60 (s, 2H) 3.93-4.13 (m, 3H) 3.53 (s, 1H) 2.96-3.15 (m, 2H) 1.81-1.95 (m, 2H) 1.43 (d, 20H)

Example 140

1-[3-tert-Butyl-6-(4-chlorobenzyl)pyrido[2,3-d][1,2,4]triazolo[4,3-b]pyridazin-8-yl]piperidin-4-ol White powder. Yield: 3%.
UPLC-MS [M+H]$^+$=451.24
$^1$H NMR (400 MHz, CHLOROFORM-d) 8.88 (m, 1H) 7.32-7.39 (m, 2H) 7.19-7.27 (m, 2H) 4.45 (m, 2H) 4.08-4.20 ((m, 1H) 4.03 ((m, 1H) 3.60-3.74 (m, 2H) 3.20 (m, 2H) 2.07 (m, 1H) 1.65-1.79 (m, 5H) 1.61 (m, 8H)

Example 131

(4-Chlorophenyl){8-(morpholin-4-yl)-3-[2-(tetrahydro-2H-pyran-4-yl)ethyl]pyrido[2,3-d][1,2,4]triazolo[4,3-b]pyridazin-6-yl}methanone And

Example 135

(4-Chlorophenyl){8-(morpholin-4-yl)-3-[2-(tetrahydro-2H-pyran-4-1)ethyl]pyrido[2,3-d][1,2,4]triazolo[4,3-b]pyridazin-6-yl}methanol The above compounds (Table 3) were isolated as by products during an attempt of synthesis of 6-(4-chlorobenzyl)-8-(morpholin-4-yl)-3-[2-(tetrahydro-2H-pyran-4-yl)ethyl]pyrido[2,3-d][1,2,4]triazolo[4,3-b]pyridazine following the procedure described for Example 111 but replacing 2,2-dimethylpropanhydrazide with 3-tetrahydropyran-4-yl-propanehydrazide (synthesised by method disclosed by the literature) at Step 6.

Example 131

Yield: 7%.
UPLC-MS [M+H]$^+$=507.11
$^1$H NMR (300 MHz, CHLOROFORM-d) δ ppm δ 8.95 (d, 1H), 8.02-7.96 (m, 2H), 7.70 (d, 1H), 7.56-7.51 (m, 2H), 3.98-3.84 (m, 6H), 3.45-3.24 (m, 6H), 3.20-3.09 (m, 2H), 1.95-1.77 (m, 2H), 1.69-1.29 (m, 5H).

Example 135

Yield: 3%.
UPLC-MS [M+H]$^+$=509.09

Example 136

3-(Cyclohexylmethyl)-6-[(4-methylphenyl)methyl]pyrido[2,3-d][1,2,4]triazolo[4,3-b]pyridazine This compound was prepared following the procedure described for Example 112 but replacing 3-bromofuro[3,4-b]pyridine-5,7-dione with furo[3,4-b]pyridine-5,7-dione at Step 1, methyl 2-(4-chlorophenyl)acetate for methyl 2-(4-methylphenyl)acetate at Step 2, and substituting 2,2-dimethylpropanhydrazide with the proper hydrazide (synthesised by method disclosed by the literature) at Step 6. Yield: 27%.
UPLC-MS [M+H]$^+$=372.4

Example 139

1-[3-tert-Butyl-6-(4-chlorobenzyl)pyrido[2,3-d][1,2,4]triazolo[4,3-b]pyridazin-8-yl]piperidin-4-amine To an ice bath cooled solution of Example 138 (60 mg, 0.109 mmol) in CHCl3 (1 mL) Trifluoroacetic Acid (2.181 mmol, 248.7 mg, 0.168 mL) was added and the resulting mixture was stirred at room temperature for 2 days. Then, chloroform and excess TFA were removed under reduced pressure. 2N NaOH solution and DCM were added, the two phases were separated and the aqueous layer was extracted with DCM. The combined organic phases were washed with brine, dried over Na$_2$SO$_4$, filtered and evaporated. 39 mg of the compound of Example 139 were collected as a yellow powder (yield: 79%).

UPLC-MS [M+H]$^+$=450.25

$^1$H NMR (400 MHz, DMSO-d$_6$) δ ppm 8.96 (d, 1H) 7.73 (d, 1H) 7.33-7.49 (m, 4H) 4.60 (s, 2H) 3.90-4.05 (m, 2H) 2.96-3.11 (m, 2H) 2.77-2.91 (m, 1H) 1.69-1.88 (m, 4H) 1.44 (s, 9H) 1.19-1.36 (m, 2H)

Example 147

5-(3,5-Dimethoxybenzyl)-9,9-dimethyl-3-(morpholin-4-yl)-5,8,9,10-tetrahydro-6H-pyrido[2,3-e]pyrimido[1,2-c]pyrimidin-6-one 5-Bromo-2-(5,5-dimethyl-4,6-dihydro-1H-pyrimidin-2-yl)pyridin-3-amine (Step 1)

3-amino-5-bromo-pyridine-2-carbonitrile (500 mg, 2.52 mmol), 2,2-dimethylpropane-1,3-diamine (774 mg, 7.57 mmol) and DMAc (5 ml) were placed in a microwave vial. The vial was sealed and the reaction was heated at 160° C. in a sand bath and stirred overnight. The reaction was cooled to rt, water was added and a solid which precipitated was obtained. The pale yellow solid was filtered, washed with water and dried in an oven at 60° C. under vacuum to give 700 mg of the desired product (yield 98%), used in the next step without further purification.

3-Bromo-9,9-dimethyl-5,8,9,10-tetrahydro-6H-pyrido[2,3-e]pyrimido[1,2-c]pyrimidin-6-one (Step 2, Example 142)

5-Bromo-2-(5,5-dimethyl-4,6-dihydro-1H-pyrimidin-2-yl)pyridin-3-amine (700 mg, 2.47 mmol) was dissolved in 15 mL of acetonitrile. After addition of carbonyldiimidazole (481 mg, 2.96 mmol) the resulting mixture was heated at 80° C. overnight. The reaction was cooled at rt. A solid precipitate was obtained, filtered and washed with acetonitrile. The crude product (700 mg, yield 91%), isolated as a yellowish solid, was used in the next step without any further purification.

HPLC-MS [M+H]$^+$=310.08.

3-Bromo-5-(3,5-dimethoxybenzyl)-9,9-dimethyl-5,8,9,10-tetrahydro-6H-pyrido[2,3-e]pyrimido[1,2-c]pyrimidin-6-one (Step 3, Example 146)

To a solution of 3-Bromo-9,9-dimethyl-5,8,9,10-tetrahydro-6H-pyrido[2,3-e]pyrimido[1,2-]pyrimidin-6-one (150 mg, 0.485 mml) in 5 mL of DMF anhydrous, under nitrogen atmosphere, NaH 60% (23.287 mg, 0.5822 mmol) was added and the mixture stirred at rt for 30 minutes. Afterwards, 1-(bromomethyl)-3,5-dimethoxybenzene (123.33 mg, 0.534 mmol) was added and the mixture was stirred at rt overnight. The obtained precipitate was filtrated and washed with a small portion of DMF. Water was added to the filtrate and the resulting solid was obtained. The crude product was grinded with DCM and the suspension filtrated affording the 120 mg of the desired product (yield 54%) as a pale yellow solid that was used in the next step without purification.

HPLC-MS [M+H]$^+$=460.58

5-(3,5-Dimethoxybenzyl)-9,9-dimethyl-3-(morpholin-4-yl)-5,8,9,10-tetrahydro-6H-pyrido[2,3-e]pyrimido[1,2-c]pyrimidin-6-one (Step 4)

In a microwave vial, to a solution purged with N$_2$ of 3-Bromo-5-(3,5-dimethoxybenzyl)-9,9-dimethyl-5,8,9,10-tetrahydro-6H-pyrido[2,3-e]pyrimido[1,2-c]pyrimidin-6-one (120 mg, 0.2613 mmol) and morpholine (34.14 mg, 0.3919 mmol), in 3 ml of 1,4-dioxane, after 5 minutes was added palladium(II) acetate (11.73 mg, 0.052 mmol), XantPhos (60.47 mg, 0.10 mmol) and cesium carbonate (170 mg, 0.52 mmol). The mixture was stirred in microwave oven at 150° C. for 2 hours, cooled to RT, poured into water and extracted with EtOAc. The organic layer was washed with water, dried over Na$_2$SO$_4$ anhydrous, and the solvent was evaporated to give the crude that was purified via automated flash chromatography (Isolera, SNAP10) eluted with EtOAc/MeOH—NH$_3$ gradient from 5 to 20%. The desired product (70 mg) was isolated as a pale yellow solid. (Yield 57%).

UPLC-MS [M+H]$^+$=466.32

$^1$H NMR (400 MHz, DMSO-d$_6$) δ ppm 8.22 (d, 1H), 6.85 (d, 1H), 6.49 (d, 2H), 6.40 (dd, 1H), 5.25 (s, 2H), 3.70-3.76 (m, 4H), 3.70 (s, 6H), 3.62 (s, 2H), 3.30-3.34 (m, 4H), 3.27 (s, 2H), 1.01 (s, 6H).

The following compounds of Examples 141, 144-146 and 148-155 as illustrated in Table 4 were prepared in a similar manner as described below:

Example 141

9,9-Dimethyl-5-[(4-methylphenyl)methyl]-3-{[(oxetan-3-yl)methyl]amino}-5,8,9,10-tetrahydro-6H-pyrido[2,3-e]pyrimido[1,2-c]pyrimidin-6-one 3-Bromo-9,9-dimethyl-5-(4-methylbenzyl)-5,8,9,10-tetrahydro-6H-pyrido[2,3-e]pyrimido[1,2-c]pyrimidin-6-one (Step 1)

The title Example was synthesized as the Compound of Example 146 (Example 147—Step 3) using 1-(bromomethyl)-4-methylbenzene instead of 1-(bromomethyl)-3,5-dimethoxybenzene to give the title Example.

9,9-Dimethyl-5-[(4-methylphenyl)methyl]-3-{[(oxetan-3-yl)methyl]amino}-5,8,9,10-tetrahydro-6H-pyrido[2,3-e]pyrimido[1,2-c]pyrimidin-6-one (Step 2)

The title Example was prepared following the procedure described for the compound of Example 147 substituting morpholine with the proper amine (purchased from available vendors). Yield 11%.

$^1$H NMR (400 MHz, CHLOROFORM-d) δ ppm 7.97 (d, 1H), 7.13 (s, 4H), 6.28 (d, 1H), 5.20 (s, 2H), 4.76 (dd, 2H), 4.34 (t, 2H), 3.66 (s, 2H), 3.43 (s, 2H), 3.33 (dd, 2H), 3.08 (q, 1H), 2.32 (s, 3H), 1.06 (s, 6H).

HPLC-MS [M+H]$^+$=491.9

Example 144

5-(3,5-Dimethoxybenzyl)-3-[(2-hydroxyethyl)amino]-9,9-dimethyl-5,8,9,10-tetrahydro-6H-pyrido[2,3-e]pyrimido[1,2-c]pyrimidin-6-one The title Example was synthesized as described for the compound of Example 147 using ethanolamine instead of morpholine at step 4. Yield 4%.

HPLC-MS [M+H]$^+$=439.9

$^1$H NMR (400 MHz, CHLOROFORM-d) δ ppm 7.88 (s, 1H), 6.41-6.32 (m, 4H), 5.16 (s, 2H), 3.75 (s, 9H), 3.65 (s, 2H), 3.43 (s, 2H), 3.20 (q, 2H), 1.06 (s, 6H).

Example 148

3-Bromo-5-(4-chlorobenzyl)-9,9-dimethyl-5,8,9,10-tetrahydro-6H-pyrido[2,3-e]pyrimido[1,2-c]pyrimidin-6-one The title Example was synthesized as described for the compound of Example 146 (Example 147—step 3) using 1-chloro-4-(chloromethyl)benzene instead of 1-(bromomethyl)-3,5-dimethoxybenzene. Yield 4%.
HPLC-MS [M+H]$^+$=434.91

Examples 143 and 149 as illustrated in Table 4 were prepared following the procedure described for the compound of Example 147—step 4 starting from the compound of Example 148 and substituting morpholine with the proper amine (purchased from available vendors).

Example 143

5-(4-Chlorobenzyl)-3-[(2-hydroxyethyl)amino]-9,9-dimethyl-5,8,9,10-tetrahydro-6H-pyrido[2,3-e]pyrimido[1,2-c]pyrimidin-6-one Yield 11%.
$^1$H NMR (400 MHz, CHLOROFORM-d) δ ppm 8.17 (d, 1H), 7.84 (s, 1H), 7.31 (d, 2H), 7.26 (d, 2H), 6.31 (d, 1H), 5.29 (s, 2H), 3.88 (m, 2H), 3.70 (s, 2H), 3.49 (s, 2H), 3.15 (m, 3H), 1.16 (s, 6H).
[M+H]$^+$=413.9

Example 149

5-(4-Chlorobenzyl)-3-[3-(methoxymethyl)azetidin-1-yl]-9,9-dimethyl-5,8,9,10-tetrahydro-6H-pyrido[2,3-e]pyrimido[1,2-c]pyrimidin-6-one Yield 32%.
$^1$H NMR (400 MHz, DMSO-d6) δ ppm 7.62 (d, 1H) 7.38-7.47 (m, 2H) 7.28-7.36 (m, 2H) 6.26 (d, 1H) 5.24 (s, 2H) 3.94 (t, 2H) 3.64 (dd, 2H) 3.56 (s, 2H) 3.50 (d, 2H) 3.27 (s, 3H) 3.22-3.26 (m, 2H) 2.89-3.01 (m, 1H) 0.98 (s, 6H)
HPLC-MS [M+H]$^+$=455.56

Example 145

5-(3,5-Dimethoxybenzyl)-9-methyl-3-(morpholin-4-yl)-5,8,9,10-tetrahydro-6H-pyrido[2,3-e]pyrimido[1,2-c]pyrimidin-6-one 3-Bromo-9-methyl-5,8,9,10-tetrahydro-6H-pyrido[2,3-e]pyrimido[1,2-c]pyrimidin-6-one (Step 1)

The title Example was prepared following the procedure described for the compound of Example 142 substituting 2,2-dimethylpropane-1,3-diamine with the proper diamine (purchased from available vendors) at Step 1—Example 147.

3-Bromo-5-(3,5-dimethoxybenzyl)-9-methyl-5,8,9,10-tetrahydro-6H-pyrido[2,3-e]pyrimido[1,2-c]pyrimidin-6-one (Step 2)

The title Example was synthesized as Example 146 (Example 147—step 3) using 1-(bromomethyl)toluene instead of 1-(bromomethyl)-3,5-dimethoxybenzene.

5-(3,5-Dimethoxybenzyl)-9-methyl-3-(morpholin-4-yl)-5,8,9,10-tetrahydro-6H-pyrido[2,3-e]pyrimido[1,2-c]pyrimidin-6-one The title Example was synthesized as Example 147—step 4.
$^1$H NMR (400 MHz, CHLOROFORM-d) δ ppm 8.15 (d, 1H), 6.55 (d, 1H), 6.36 (dd, 3H), 5.33-4.97 (m, 2H), 4.48-4.22 (m, 1H), 4.00-3.85 (m, 1H), 3.80 (t, 4H), 3.75 (s, 6H), 3.30-3.21 (m, 2H), 3.15 (t, 4H), 2.06 (d, 1H), 1.10 (d, 3H).
Yield 15%.
HPLC-MS [M+H]$^+$=452.5

Examples 150 and 151 were prepared following the procedure described for the Compound of Example 1 starting from 3-[(3,5-dimethoxyphenyl)methylamino]-5-morpholinopyridine-2-carbonitrile prepared as described in Example 1—Step 2 replacing 4-methoxybenxyl chloride with 3,5-dimethoxybenzyl chloride and replacing at step 3 3-methylbutane-1,2-diamine with the proper 1,3-diamine. Purification by preparative HPLC afforded.

Example 150

5-(3,5-Dimethoxybenzyl)-10-ethyl-3-(morpholin-4-yl)-5,8,9,10-tetrahydro-6H-pyrido[2,3-e]pyrimido[1,2-c]pyrimidin-6-one Yield 4%.
HPLC-MS [M+H]$^+$=512.5

Example 151

5-(3,5-Dimethoxybenzyl)-8-ethyl-3-(morpholin-4-yl)-5,8,9,10-tetrahydro-6H-pyrido[2,3-e]pyrimido[1,2-c]pyrimidin-6-one Yield 27%.
HPLC-MS [M+H]$^+$=512.2

Examples 152 and 153 were prepared following the procedure described for the compound of Example 1 replacing at step 3 3-methylbutane-1,2-diamine with the proper 1,3-diamine. Purification by preparative HPLC afforded:

Example 152

10-Ethyl-5-(4-methoxybenzyl)-3-(morpholin-4-yl)-5,8,9,10-tetrahydro-6H-pyrido[2,3-e]pyrimido[1,2-c]pyrimidin-6-one Yield 17%.
HPLC-MS [M+H]$^+$=482.4

Example 153

8-Ethyl-5-(4-methoxybenzyl)-3-(morpholin-4-yl)-5,8,9,10-tetrahydro-6H-pyrido[2,3-e]pyrimido[1,2-c]pyrimidin-6-one Yield 4%.
HPLC-MS [M+H]$^+$=482.7

Examples 154 and 155 were prepared following the procedure described for the compound of Example 1 starting from 3-[(4-chlorophenyl)methylamino]-5-morpholinopyridine-2-carbonitrile prepared as described in Example 1—Step 2 replacing 4-chlorobenzyl chloride with 3,5-dimethoxybenzyl chloride and replacing at step 3 3-methylbutane-1,2-diamine with the proper 1,3-diamine. Purification by preparative HPLC afforded:

Example 154

5-(4-Chlorobenzyl)-10-ethyl-3-(morpholin-4-yl)-5,8,9,10-tetrahydro-6H-pyrido[2,3-e]pyrimido[1,2-c]pyrimidin-6-one Yield 6%.
HPLC-MS [M+H]$^+$=487.4

Example 155

5-(4-Chlorobenzyl)-8-ethyl-3-(morpholin-4-yl)-5,8,9,10-tetrahydro-6H-pyrido[2,3-e]pyrimido[1,2-c]pyrimidin-6-one Yield 4%
HPLC-MS [M+H]$^+$=487.4

Example 156

6-(4-Methoxybenzyl)-2-(2-methylpropyl)-8-(morpholin-4-yl)pyrido[2,3-e][1,2,4]triazolo[1,5-c]pyrimidin-5(6H)-one During column chromatography purification of step 6 of Example 104, the title compound was also isolated as a white powder. Yield: 2%.
UPLC-MS [M+H]$^+$=449.34

Example 157

2-tert-Butyl-6-(4-methoxybenzyl)-8-(morpholin-4-yl)pyrido[2,3-e][1,2,4]triazolo[1,5-c]pyrimidin-5(6H)-one During column chromatography purification of step 6 of the compound of Example 96 the title compound was also isolated as a white powder (yield 7%).
UPLC-MS [M+H]$^+$=449.26
$^1$H NMR (400 MHz, DMSO-d6) δ ppm 8.44 (d, 1H) 7.34 (d, 2H) 7.12 (d, 1H) 6.89 (d, 2H) 5.51 (s, 2H) 3.73-3.80 (m, 4H) 3.72 (s, 3H) 3.32-3.40 (m, 4H) 1.44 (s, 9H)

Example 158

6-(4-Chlorobenzyl)-9-methoxy-3-(tetrahydro-2H-pyran-4-ylmethyl)pyrimido[4,5-e][1,2,4]triazolo[4,3-c]pyrimidin-5(6H)-one Methyl 5-amino-2-methylsulfanyl-pyrimidine-4-carboxylate (Step 1)

To a solution of 5-amino-2-methylsulfanylpyrimidine-4-carboxylic acid (10.80 mmol, 2 g) in a mixture of dichloromethane (100 mL) and methanol (20 mL) at 0° C. 4-dimethylaminopyridine (8.6393 mmol, 1.056 g) was added followed by (3-dimethylaminopropyl)ethylcarbodiimide·HCl (19.44 mmol, 3.73 g) and the mixture was stirred at 0° C. for 90 min, then at room temperature overnight. The organic layer was washed twice with water, twice with NaHCO$_3$ sat. solution and once with brine and then dried over Na$_2$SO$_4$. The crude was purified by silica gel column chromatography eluting with ethyl acetate/petroleum ether gradient starting from 20:80 to 70:30. 1.5 g of the desired product were obtained as yellow powder (Yield: 70%).

Methyl 5-[(4-chlorophenyl)methylamino]-2-methylsulfanyl-pyrimidine-4-carboxylate (Step 2)

To a mixture of methyl 5-amino-2-methylsulfanyl-pyrimidine-4-carboxylate (3.76 mmol, 750 mg), 4-chlorobenzaldehyde (7.5290 mmol, 1058.3 mg) and acetic acid (7.53 mmol, 0.431 mL, 452.1 mg) in dichloromethane (50 mL) was added portion wise sodium triacetoxy borohydride (11.293 mmol, 2393.5 mg) and the resulting mixture stirred at room temperature for 2 days, adding one equivalent of reducing agent each day. Then the reaction was quenched with water, the two phases were separated and the aqueous layer was extracted with DCM. The combined organic phases were dried over Na$_2$SO$_4$, filtered and evaporated. The crude was purified by silica gel column chromatography eluting with ethyl acetate/petroleum ether gradient starting from 0:100 to 40:60. 1.19 g of the desired product were obtained as yellow oil (Yield: 97%).

5-[(Chlorophenyl)methyl]-2-methoxy-pyrimido[5,4-d]pyrimidine-6,8-dione (Step 3)

To a stirred solution of methyl 5-[(4-chlorophenyl)methylamino]-2-methylsulfanylpyrimidine-4-carboxylate (3.68 mmol, 1.19 g) in DCM, 2,2,2-trichloroacetyl isocyanate (4.01 mmol, 0.477 mL, 0.755 g) was added and the reaction stirred at room temperature overnight. Then the solvent was evaporated and sodium methoxide (36.8 mmol, 8.40 mL, 7.94 g, 25 mass %) was added and the suspension was heated at 60° C. for 1 h. After cooling down to room temperature, acetic acid was added until pH=4-5, then water and DCM were added, the two phases were separated and the aqueous layer was extracted with DCM (3×). The combined organic layers were dried over Na$_2$SO$_4$, filtered and evaporated. A yellow powder was collected, suspended in diethyl ether and filtered to give 670 mg of the desired product as a light yellow powder (57%).

4-Chloro-1-[(4-chlorophenyl)methyl]-6-methoxy-pyrimido[5,4-d]pyrimidin-2-one (Step 4)

Under nitrogen atmosphere, a solution of 5-[(4-chlorophenyl)methyl]-2-methoxy-pyrimido[5,4-d]pyrimidine-6,8-dione (4.67 mmol, 1490 mg) and ethyldiisopropylamine (14.03 mmol, 2.40 mL, 1813 mg) in POCl$_3$ (374.0 mmol, 34.3 mL, 57350 mg) was stirred at 50° C. for 3 h. After cooling down to room temperature, the solvent was removed and the residue was diluted with 1,4 dioxane and the mixture evaporated (repeated three times). 1550 mg of crude desired product were collected as dark oil and used in the next step without any further purification. (98%)

6-(4-Chlorobenzyl)-9-methoxy-3-(tetrahydro-2H-pyran-4-ylmethyl)pyrimido[4,5-e][1,2,4]triazolo[4,3-c]pyrimidin-5(6H)-one (Step 5)

A solution of 4-chloro-1-[(4-chlorophenyl)methyl]-6-methoxypyrimido[5,4-d]pyrimidin-2-one (0.468 mmol, 158 mg) and 2-tetrahydropyran-4-ylacetohydrazide (0.47 mmol, 74 mg) (synthesized by method disclosed by the literature) in 1,4-dioxane (5 mL, 100 mass %) was stirred at room temperature for 30 min. The mixture was then heated at reflux for 1 h. After cooling at room temperature, water and EtOAc were added and the two phases were separated. Water was then extracted with EtOAc and the combined organic phases were dried over Na$_2$SO$_4$, filtered and evaporated. The crude was purified by silica gel column chromatography eluting with methanol/ethyl acetate gradient starting from 0:100 to 10:90. 40 mg of the desired product were obtained as a yellow powder. Yield: 19%.

UPLC-MS [M+H]$^+$=441.16

$^1$H NMR (400 MHz, DMSO-d$_6$) δ ppm 8.76 (s, 1H) 7.45-7.54 (m, 2H) 7.37-7.43 (m, 2H) 5.49 (s, 2H) 4.01 (s, 3H) 3.85 (br dd, 2H) 3.30 (br dd, 2H) 3.21-3.27 (m, 2H) 2.18 (ttd, 1H) 1.65 (br dd, 2H) 1.29-1.44 (m, 2H)

Examples 159-160 as illustrated in Table 5 were prepared following the procedure described in Example 1 substituting (4-methoxyphenyl)methanamine with (4-chlorophenyl)methanamine (purchased from available vendors) at step 2 and replacing 3-methylbutane-1,2-diamine HCl with 4,4,4-trifluorobutane-1,2-diamine (from available vendors) at step 3. Reported yields are referred to final step.

Example 159

6-(4-Chlorobenzyl)-8-morpholino-2-(2,2,2-trifluoroethyl)-2,6-dihydroimidazo[1,2-c]pyrido[2,3-e]pyrimidin-5(3H)-one And Example 160

6-(4-Chlorobenzyl)-8-morpholino-3-(2,2,2-trifluoroethyl)-2,6-dihydroimidazo[1,2-c]pyrido[2,3-e]pyrimidin-5(3H)-one First eluted: Example 159. Yellow sticky solid (yield 35%).

UPLC-MS [M+H]$^+$=480.14

$^1$H NMR (400 MHz, ACETONITRILE-d$_3$+TFA) δ ppm 8.36 (br d, 1H), 7.32-7.45 (m, 4H), 6.62 (d, 1H), 5.35 (s, 2H), 4.85 (m, 1H), 4.63 (t, 1H), 4.23 (m, 1H), 3.73-3.83 (m, 4H), 3.46-3.55 (m, 4H), 2.78-2.97 (m, 2H)

Second eluted: Example 160: yellow sticky solid (yield 25%)

UPLC-MS [M+H]$^+$=480.14

$^1$H NMR (400 MHz, ACETONITRILE-d$_3$) δ ppm 8.35 (d, 1H), 7.34-7.45 (m, 4H), 6.61 (d, 1H), 5.27 (s, 1H), 5.25-5.39 (m, 1H), 5.11-5.19 (m, 1H), 4.39 (t, 1H), 4.11 (m, 1H), 3.73-3.81 (m, 4H), 3.43-3.54 (m, 4H), 3.15-3.29 (m, 1H), 2.81-3.01 (m, 1H).

Example 161

6-(3,5-Dimethoxybenzyl)-2,2-dimethyl-8-(morpholin-4-V1)-2,6-dihydroimidazo[1,2-c]pyrido[2,3-e]pyrimidin-5(3H)-one Prepared following the procedure described for the compounds of Example 1 but replacing 3,5-dimethoxybenzylamine for (4-methoxyphenyl)methanamine at Step 2 and substituting 3-methylbutane-1,2-diamine with the proper 2-methylpropene-1,2-diamine (purchased from available vendors or synthesised by methods disclosed by the literature) at Step 3.

Yellow solid (51.8%).

HPLC-MS [M+H]$^+$=452.70

$^1$H NMR (400 MHz, CHLOROFORM-d) δ ppm 8.12 (d, 1H), 6.55 (d, 1H), 6.37 (dd, 3H), 5.12 (s, 2H), 3.85-3.76 (m, 6H), 3.75 (s, 6H), 3.19-3.12 (m, 4H), 1.46 (s, 6H), 1.26 (d, 9H), 0.92-0.80 (m, 4H).

Examples 163-165 were synthesised as reported for the previous Example 64 using the proper benzyl halogenide, alpha-bromocarboxylic acid and amine (each purchased from available vendors or synthesised by methods disclosed by the literature).

Example 163

6-(4-Methoxybenzyl)-8-(morpholin-4-yl)-3-(propan-2-yl)imidazo[1,2-c]pyrido[2,3-e]pyrimidine-2,5(3H, 6H)-dione Yellow solid. Yield: 36.78%.

$^1$H NMR (400 MHz, DMSO-d$_6$) δ ppm 8.46 (d, 1H) 7.40 (s, 4H) 6.83 (d, 1H) 5.42-5.52 (m, 1H) 5.25-5.38 (m, 1H) 4.41 (d, 1H) 3.72 (t, 4H) 3.39-3.56 (m, 4H) 2.76 (m, 1H) 1.16 (d, 3H) 0.78 (d, 3H)

UPLC-MS [M+H]$^+$=451.21

Example 164

6-(4-Methoxybenzyl)-8-(morpholin-4-yl)-3-(propan-2-yl)imidazo[1,2-c]pyrido[2,3-e]pyrimidine-2,5(3H, 6H)-dione Yellowish solid.

$^1$H NMR (400 MHz, DMSO-d$_6$) δ ppm 8.45 (d, 1H) 7.23-7.36 (m, 2H) 6.85-6.94 (m, 3H) 5.23-5.43 (m, 2H) 4.43 (d, 1H) 3.68-3.76 (m, 7H) 3.39-3.53 (m, 4H) 2.78 (m, 1H) 1.17 (d, 3H) 0.78 (d, 3H)

Example 165

3-tert-Butyl-8-(diethylamino)-6-(4-methoxybenzyl)imidazo[1,2-c]pyrido[2,3-e]pyrimidine-2,5(3H,6H)-dione Yellowish solid $^1$H NMR (400 MHz, DMSO-d$_6$) δ ppm 8.18 (d, 1H) 7.31 (d, 2H) 6.86-6.98 (m, 2H) 6.47 (d, 1H) 5.18-5.41 (m, 2H) 4.24 (s, 1H) 3.71 (s, 3H) 3.38-3.58 (m, 4H) 1.04 (s, 9H) 1.01 (t, 6H)

The compounds of examples 166 and 168 as illustrated in Table 5 were prepared following the procedure described for compound 158 but replacing 2-tetrahydropyran-4-ylacetohydrazide with the proper hydrazide (purchased from available vendors) at Step 5. Reported yields are referred to the last step.

Example 166

6-(4-Chlorobenzyl)-9-methoxy-3-(1-methylcyclopropyl)pyrimido[4,5-e][1,2,4]triazolo[4,3-c]pyrimidin-5(6H)-one Light brown powder. Yield: 4%.

UPLC-MS [M+H]$^+$=397.17

$^1$H NMR (400 MHz, CHLOROFORM-d) δ ppm 8.60 (s, 1H) 7.34-7.45 (m, 2H) 7.21-7.31 (m, 2H) 5.47 (s, 2H) 4.17 (s, 3H) 1.62 (s, 3H) 1.32-1.40 (m, 2H) 0.98-1.07 (m, 2H)

Example 168

3-tert-Butyl-6-(4-chlorobenzyl)-9-methoxypyrimido[4,5-e][1,2,4]triazolo[4,3-c]pyrimidin-5(6H)-one Yellow powder. Yield: 29%
UPLC-MS [M+H]$^+$=399.15
$^1$H NMR (400 MHz, DMSO-d$_6$) δ ppm 8.76 (s, 1H) 7.45-7.51 (m, 2H) 7.37-7.43 (m, 2H) 5.51 (s, 2H) 4.01 (s, 3H) 1.59 (s, 9H)

Examples 167 and 169 as illustrated in Table 5 were prepared following the procedure described for compound 158 but replacing 4-chlorobenzaldehyde with 4-methoxybenzaldehyde at step 2 and substituting 2-tetrahydropyran-4-ylacetohydrazide for the proper hydrazide (purchased from available vendors) at Step 5. Reported yields are referred to the last step.

Example 167

3-tert-Butyl-9-methoxy-6-(4-methoxybenzyl)pyrimido[4,5-e][1,2,4]triazolo[4,3-c]pyrimidin-5(6H)-one Yellow powder. Yield: 17%.
UPLC-MS [M+H]$^+$=395.18
$^1$H NMR (400 MHz, DMSO-d$_6$) δ ppm 8.81 (s, 1H) 7.37 (d, 2H) 6.83-6.96 (m, 2H) 5.45 (s, 2H) 4.00 (s, 3H) 3.73 (s, 3H) 1.60 (s, 9H)

Example 169

9-Methoxy-6-(4-methoxybenzyl)-3-(1-methylcyclopropyl)pyrimido[4,5-e][1,2,4]triazolo[4,3-c]pyrimidin-5(6H)-one Yellow powder. Yield: 42%.
UPLC-MS [M+H]$^+$=393.21
$^1$H NMR (400 MHz, DMSO-d$_6$) δ ppm 8.79 (s, 1H) 7.39 (d, 2H) 6.86-6.98 (m, 2H) 5.45 (s, 2H) 3.99 (s, 3H) 3.73 (s, 3H) 1.52 (s, 3H) 1.18-1.28 (m, 2H) 0.80-0.95 (m, 2H)

Example 170 as illustrated in Table 5 was prepared following the procedure described for compound 158 but replacing 4-chlorobenzaldehyde with 4-methoxybenzaldehyde at step 2. Reported yield is referred to the last step.

Example 170

9-Methoxy-6-(4-methoxybenzyl)-3-(tetrahydro-2H-pyran-4-ylmethyl)pyrimido[4,5-e][1,2,4]triazolo[4,3-c]pyrimidin-5(6H)-one Yellow powder. Yield: 27%.
UPLC-MS [M+H]$^+$=437.19
$^1$H NMR (400 MHz, DMSO-d$_6$) δ ppm 8.80 (s, 1H) 7.38 (d, 2H) 6.82-6.98 (m, 2H) 5.43 (s, 2H) 4.00 (s, 3H) 3.85 (br dd, 2H) 3.73 (s, 3H) 3.29 (br d, 2H) 3.25 (d, 2H) 2.12-2.26 (m, 1H) 1.65 (br dd, 2H) 1.28-1.43 (m, 2H)

Example 172

6-(4-Chlorobenzyl)-2-(1-methylcyclopropyl)-8-(morpholin-4-yl)pyrido[2,3-e][1,2,4]triazolo[1,5-c]pyrimidin-5(6H)-one During the column chromatography purification of step 6 of the compound of Example 102, the compound of Example 172 was also isolated.

Orange powder. Yield 11%.
UPLC-MS [M+H]$^+$=451.25
$^1$H NMR (400 MHz, DMSO-d$_6$) δ ppm 7.69 (d, 1H) 7.39 (s, 4H) 7.09 (d, 1H) 5.29 (s, 2H) 3.74-3.86 (m, 4H) 3.34-3.44 (m, 4H) 1.40 (s, 3H) 1.08-1.17 (m, 2H) 1.04 (s, 2H)

Example 173

3-tert-Butyl-6-[(5-chloropyridin-2-1)methyl]-8-(morpholin-4-yl)pyrido[2,3-e][1,2,4]triazolo[4,3-c]pyrimidin-5(6H)-one Example 173 as illustrated in Table 5 was prepared following the procedure described for the compound of Example 96 replacing (4-methoxyphenyl)methanamine with (5-chloro-2-pyridyl)methanamine (purchased from available vendors) at step 2. Reported yield is referred to final step.

Yellow solid. Yield: 7%.
UPLC-MS [M+H]$^+$=454.21
$^1$H NMR (400 MHz, CHLOROFORM-d) δ ppm 8.54 (d, 1H) 8.38 (d, 1H) 7.72 (dd, 1H) 7.44 (d, 1H) 7.33 (d, 1H) 5.51 (s, 2H) 3.88-3.96 (m, 4H) 3.30-3.41 (m, 4H) 1.69 (s, 9H)

Example 174

6-(4-Methoxybenzyl)-3-(1-methylcyclopropyl)-8-(morpholin-4-yl)pyrido[2,3-e][1,2,4]triazolo[4,3-c]pyrimidin-5(6H)-one Example 174 as illustrated in Table 5 was prepared following the procedure described for the compound of Example 96 replacing 2,2-dimethylpropanehydrazide with 1-methylcyclopropanecarbohydrazide (purchased from available vendors) at step 6. Reported yield is referred to final step.

Yellow solid. Yield: 5%.
UPLC-MS [M+H]$^+$=447.22
$^1$H NMR (400 MHz, CHLOROFORM-d) δ ppm 8.35 (d, 1H) 7.23 (d, 2H) 6.88-6.96 (m, 2H) 6.83 (d, 1H) 5.41 (s, 2H) 3.84-3.92 (m, 4H) 3.82 (s, 3H) 3.20-3.28 (m, 4H) 1.62 (s, 3H) 1.30-1.39 (m, 2H) 0.95-1.03 (m, 2H)

Example 177

3-tert-Butyl-8-(4-hydroxypiperidin-1-yl)-6-(4-methoxybenzyl)pyrido[2,3-e][1,2,4]triazolo[4,3-c]pyrimidin-5(6H)-one Example 177 as illustrated in Table 5 was prepared following the procedure described for the compound of Example 96 (alternative synthesis) replacing morpholine with piperidin-4-ol (purchased from available vendors) at step 5. Reported yield is referred to final step.

Yellow powder. Yield: 2%.
UPLC-MS [M+H]$^+$=463.26
$^1$H NMR (400 MHz, CHLOROFORM-d) δ ppm 8.40 (d, 1H) 7.28 (s, 1H) 6.90-6.93 (m, 1H) 6.85-6.90 (m, 2H) 5.49 (s, 2H) 4.00 (tt, 1H) 3.77-3.84 (m, 4H) 3.57-3.72 (m, 3H) 3.11-3.26 (m, 2H) 1.90-2.04 (m, 3H) 1.66 (ddd, 5H) 1.57 (s, 10H)

During column chromatography purification of step 5 of Example 177, the compounds of Examples 175 and Example 176 were also isolated.

Example 175

2-tert-Butyl-8-(4-hydroxypiperidin-1-yl)-6-(4-methoxybenzyl)pyrido[2,3-e][1,2,4]triazolo[4,3-c]pyrimidin-5(6H)-one Yellow powder. Yield: 7%.
UPLC-MS [M+H]$^+$=463.32
$^1$H NMR (400 MHz, CHLOROFORM-d) δ ppm 8.41 (d, 1H) 7.27 (d, 2H) 6.93 (d, 1H) 6.85-6.91 (m, 2H) 5.49 (s, 2H) 4.00 (tt, 1H) 3.75-3.83 (m, 3H) 3.58-3.70 (m, 2H) 3.10-3.24 (m, 2H) 1.91-2.06 (m, 2H) 1.60-1.73 (m, 3H) 1.51-1.60 (m, 10H)

Example 176

8-Amino-3-tert-butyl-6-(4-methoxybenzyl)pyrido[2,3-e][1,2,4]triazolo[4,3-c]pyrimidin-5(6H)-one Yellow powder. Yield: 7%.
UPLC-MS [M+H]$^+$=379.26
$^1$H NMR (400 MHz, DMSO-d6) δ ppm 7.98 (d, 1H) 7.28 (d, 2H) 6.86-6.98 (m, 3H) 6.78 (d, 1H) 6.20 (s, 2H) 5.27 (s, 2H) 3.73 (s, 4H) 1.49-1.64 (m, 11H)

Example 171 as illustrated in Table 5 was prepared following the procedure described in alternative synthesis for Example 96 (via Buchwald at the final step) substituting (4-methoxyphenyl)methanamine with (4-chlorophenyl)methanamine (purchased from available vendors) at step 1, 2,2-dimethylpropanidrazide with 2-methylpropanehydrazide (purchased from available vendors) at step 4 and replacing morpholine for piperidin-4-ol (purchased from available vendors) at step 5. Reported yield is referred to final step.

Example 171

6-(4-Chlorobenzyl)-8-(4-hydroxypiperidin-1-yl)-3-(propan-2-yl)pyrido[2,3-e][1,2,4]triazolo[4,3-c]pyrimidin-5(6H)-one Yellow powder. Yield: 2%.
UPLC-MS [M+H]$^+$=453.31
$^1$H NMR (400 MHz, CHLOROFORM-d) δ ppm 8.42 (d, 1H) 7.32-7.39 (m, 2H) 7.24-7.28 (m, 2H) 6.77 (d, 1H) 5.53 (s, 2H) 4.01 ((m, 1H) 3.57-3.69 (m, 2H) 3.37 (spt, 1H) 3.18 (ddd, 2H) 1.90-2.04 (m, 2H) 1.61-1.71 (m, 2H) 1.51 (d, 6H)

Example 178

9-tert-Butyl-5-(4-chlorobenzyl)-3-(morpholin-4-yl)[1,2,4]triazolo[1',5':1,6]pyrimido[5,4-c]pyridazin-6(5H)-one Methyl 6-chloro-4-((4-chlorobenzyl)amino)pyridazine-3-carboxylate (Step 1)

(4-Chlorophenyl)methanamine (1.95 mL, 15.94 mmol) and DIPEA (2.78 mL, 15.94 mmol) were added to a stirred solution of methyl 4,6-dichloropyridazine-3-carboxylate (3.0 g, 14.49 mmol) in MeCN (48.3 mL, 0.925 mol) at rt. After 1 h of stirring the precipitate formed was isolated by filtration. The powder was triturated with Et$_2$O containing small amount of DMF to afford the title compound as off-white powder (3.8 g, yield: 84%).

6-Chloro-4-((4-chlorobenzyl)amino)pyridazine-3-carboxamide (Step 2)

Methyl 6-chloro-4-[(4-chlorophenyl)methylamino]pyridazine-3-carboxylate (3.8 g, 12.17 mmol) was treated with a solution of ammonia 7N in MeOH (71.3 mL) at room temperature. The reaction was stirred at 50° C. for 1 h. The volatiles were removed under vacuum to afford the title compound as white solid (2.9 g, yield: 80%).

3-Chloro-5-(4-chlorobenzyl)pyrimido[5,4-c]pyridazine-6,8(5H, 7H)-dione (Step 3)

A stirred solution of 6-chloro-4-((4-chlorobenzyl)amino)pyridazine-3-carboxamide (2.0 g, 6.73 mmol) in DMF (67.0 mL) was treated with sodium hydride 60% dispersion in mineral oil (0.807 g, 20.19 mmol) and CDI (3.3 g, 20.19 mmol) at rt. The reaction mixture was stirred 1 h at rt. The solvent was removed, in the attempt to dissolve the crude material with small DMSO to perform a reverse phase purification a precipitate was formed and isolated by filtration to afford after trituration with MeCN the first amount of the desired product (630 mg). The filtrate was purified with a C18 cartridge (30 gr) and eluted using 1/1 H$_2$O/MeCN to afford the second amount of the desired product (580 mg). The combined fraction afforded the title compound as white solid (1.2 gr, yield: 55%).

3-(tert-Butyl)-8-chloro-6-(4-chlorobenzyl)-[1,2,4]triazolo[4',3':1,6]pyrimido[5,4-c]pyridazin-5(6H)-one (Step 4)

DIPEA (1.1 mL, 6.7 mmol) was added dropwise to a stirred suspension of 3-chlorol-5-[(4-chlorophenyl)methyl]pyrimido[5,4-c]pyridazine-6,8-dione (545 mg, 1.69 mmol) in phosphoryl chloride (30.0 mL) at rt. The reaction mixture was heated at 80° C. for 3 h, monitoring by UPLC (quenching with MeOH the formation of Cl intermediate is observed as methoxy analogue ES$^+$=337). After cooling, volatiles were evaporated and the resulting residue was dissolved in 1,4-dioxane (30.7 mL) and 2,2-dimethylpropanehydrazide (293.88 mg, 2.53 mmol) was added. The stirring was continued 30 min at 50° C. monitoring by UPLC the formation of the open intermediate (ES$^+$=421) and then, at reflux to obtain the ring closure to the triazole. After cooling, the mixture was treated with a saturated solution of NaHCO$_3$ and extracted with EtOAc. The organic phase was washed with brine and dried over Na$_2$SO$_4$ to afford after filtration a residue that was purified by RP chromatography to afford the title compound (160 mg, yield: 23%)

9-tert-Butyl-5-(4-chlorobenzyl)-3-(morpholin-4-yl)[1,2,4]triazolo[1',5':1,6]pyrimido[5,4-c]pyridazin-6(5H)-one (Step 5)

3-(tert-butyl)-8-chloro-6-(4-chlorobenzyl)-[1,2,4]triazolo[4',3':1,6]pyrimido[5,4-c]pyridazin-5(6H)-one (80 mg, 0.20 mmol), Xantphos (27.45 mg, 0.050 mmol), dicesium carbonate (131 mg, 0.40 mmol) were dissolved in degassed 1,4-dioxane (2 mL). Then morpholine (27 QL, 0.30 mmol) and Pd(OAc)$_2$ (7 mg, 0.03 mmol) were added. The mixture was stirred at 100° C. for 1 h, after cooling the reaction was filtered over SolkaFloc and solvent was removed. The crude was purified by RP column chromatography eluting with water+0.1% TFA/ACN+0.1% TFA gradient starting from 8:2 to 1:1. The title compound was obtained as a pale-yellow solid (4 mg, yield: 5%).

UPLC-MS [M+H]$^+$=454.31

$^1$H NMR (400 MHz, DMSO-d$_6$) δ ppm 7.35-7.47 (m, 4H), 6.80 (s, 1H), 5.48 (s, 2H), 3.49-3.76 (m, 8H), 1.44 (s, 9H).

General Procedure for Photoinduced Nickel Catalysed Amination

A vial equipped with a magnetic and PTFE/silicone septum was charged with the proper chloro or bromo intermediate (see below, 1.0 eq), amine (1.5 eq), DABCO (1.8 eq) and 4,4'-Di-t-butyl-2,2'-bipyridine)bis[3,5-difluoro-2-[5-trifluoromethyl-2-pyridinyl-kN)phenyl-kC]iridium (III) hexafluorophosphate (0.020 eq), followed by DMA and a solution of Nickel (2+) chloride-1,2-dimethoxyethane (1:2:1) (0.050 eq) in DMA (0.25 M total). The mixture was rigorously degassed (the vial is first filled with nitrogen, cooled at −78° C. and degassed under vacuum, backfilled with nitrogen and warmed to RT, 3 cycles) and then the vial was sealed with a parafilm strip. The vial was subjected to 365 nm LED irradiation (2 cm distance from 34 W blue LED lamp). The internal temperature upon irradiation was approximately 55° C. (no fan cooling). After 2-4 h the reaction was diluted with EtOAc and washed sequentially with water and brine. The organic phase was dried over Na$_2$SO$_4$, to afford after filtration and solvent removal a residue that was purified by chromatography or RP-HPLC.

Example 179

8-(4-Aminopiperidin-1-yl)-3-tert-butyl-6-(4-chlorobenzyl)[1,2,4]triazolo[4',3':1,6]pyrimido[5,4-c]pyridazin-5(6H)-one Example 179 as illustrated in Table 5 was prepared according to the procedure described for compound 178 but following General procedure for photoinduced Nickel catalysed amination at Step 5 using 3-(tert-butyl)-8-chloro-6-(4-chlorobenzyl)-[1,2,4]triazolo[4',3':1,6]pyrimido[5,4-c]pyridazin-5(6H)-one (70 mg, 0.17 mmol) and N-(4-piperidyl)carbamate (52 mg, 0.26 mmol). After treatment with DCM/TFA (9/1) for 2 h and solvents removal the resulting residue was purified by RP-HPLC to afford the titled compound. Pale yellow solid. Yield: 12%.

UPLC-MS [M+H]$^+$=467.49

$^1$H NMR (400 MHz, DMSO-d$_6$) δ ppm 7.78-7.91 (m, 3H), 7.37-7.48 (m, 4H), 6.79 (s, 1H), 5.45 (s, 2H), 4.45-4.56 (m, 2H), 3.06 (br t, 2H), 1.98 (br d, 2H), 1.55 (s, 9H), 1.37-1.52 (m, 3H)

Example 180

3-tert-Butyl-6-(4-methoxybenzyl)-8-(morpholin-4-yl)[1,2,4]triazolo[4',3':1,6]pyrimido[5,4-c]pyridazin-5(6H)-one The compound of Example 181 as illustrated in Table 5 was prepared following the procedure described in Example 178 substituting (4-chlorophenyl)methanamine with (4-methoxyphenyl)methanamine (purchased from available vendors) at step 1, and performing photoinduced Nickel catalysed amination for the final step, as described in Example 180, replacing morpholine for 4 aminopiperidine. Reported yield is referred to final step.

Pale brown solid. Yield: 21%.

UPLC-MS [M+H]$^+$=450.41

$^1$H NMR (400 MHz, DMSO-d$_6$) δ ppm 7.36 (br d, 2H), 6.91-7.01 (m, 1H), 6.87 (br d, 2H), 5.40 (s, 2H), 3.71-3.85 (m, 4H), 3.70 (s, 7H), 1.55 (s, 9H)

Examples 181-185 as illustrated in Table 5 were prepared following the procedure described in alternative synthesis for Example 96 (via Buchwald at final step) substituting (4-methoxyphenyl)methanamine with the proper amine (synthesized following disclosed literature procedure or purchased from available vendors) at step 1, and replacing morpholine, if the case, with the proper amine (purchased from available vendors) during photoinduced Nickel catalysed amination in final step. Reported yield are referred to final step.

Example 181 tert-Butyl 4-[3-tert-butyl-6-(4-chlorobenzyl)-5-oxo-5,6-dihydropyrido[2,3-e][1,2,4]triazolo[4,3-c]pyrimidin-8-yl]piperazine-1-carboxylate (Step 1)

The compound was prepared according to the general procedure for photoinduced Nickel catalysed amination using 8-bromo-3-(tert-butyl)-6-(4-chlorobenzyl)pyrido[2,3-e][1,2,4]triazolo[4,3-c]pyrimidin-5(6H)-one (80.0 mg, 0.180 mmol) and tert-butylpiperazine-1-carboxylate (50.03 mg, 0.270 mmol) The crude was purified by RP column chromatography eluting with water+0.1% TFA/ACN+0.1% TFA gradient starting from 8:2 to 1:1 to afford the title compound (35 mg, 35% yield).

3-(tert-Butyl)-6-(4-chlorobenzyl)-8-(piperazin-1-yl)pyrido[2,3-e][1,2,4]triazolo[4,3-c]pyrimidin-5(6H)-one (Step 2)

TFA (0.1 mL) was added to a stirred solution of tert-butyl 4-(3-(tert-butyl)-6-(4-chlorobenzyl)-5-oxo-5,6-dihydropyrido[2,3-e][1,2,4]triazolo[4,3-c]pyrimidin-8-yl)piperazine-1-carboxylate (35 mg, 0.060 mmol) in DCM (0.900 mL) at 0° C. The reaction was left to warm up at rt and stirred for 2 h. Volatiles were removed under vacuum and the crude was purified by RP column chromatography eluting with water+0.1% TFA/ACN+0.1% TFA gradient starting from 8:2 to 1:1 to afford the title compound as pale brown powder (19 mg, yield: 66%).

UPLC-MS [M+H]$^+$=452.46

$^1$H NMR (400 MHz, DMSO-d$_6$+TFA) δ ppm 8.91 (br s, 2H), 8.49 (br s, 1H), 7.42 (s, 2H), 7.39 (s, 2H), 7.08 (br s, 1H), 5.55 (br s, 2H), 3.50-3.58 (m, 4H), 3.24 (br s, 4H), 1.55 (br s, 9H)

Example 182

2-(tert-Butyl)-6-(4-chlorobenzyl)-8-(piperazin-1-yl)pyrido[2,3-e][1,2,4]triazolo[1,5-c]pyrimidin-5(6H)-one During the final step, column chromatography purification of the compound of Example 181, the compound of Example 182 was also isolated as white powder (16 mg, yield: 31%).

UPLC-MS [M+H]$^+$=452.31

$^1$H NMR (400 MHz, DMSO-d$_6$) δ ppm 8.78 (br s, 2H), 8.49 (d, 1H), 7.36-7.45 (m, 4H), 7.10 (d, 1H), 5.57 (s, 2H), 3.55-3.70 (m, 4H), 3.15-3.34 (m, 4H), 1.43 (s, 9H).

Example 183

3-(tert-Butyl)-6-(4-chlorobenzyl)-8-(3-methoxypyrrolidin-1-yl)pyrido[2,3-e][1,2,4]triazolo[4,3-c]pyrimidin-5(6H)-one The compound was prepared according to the general procedure for photoinduced Nickel catalysed amination using 8-bromo-3-(tert-butyl)-6-(4-chlorobenzyl)pyrido[2,3-e][1,2,4]triazolo[4,3-c]pyrimidin-5(6H)-one (70 mg, 0.160 mmol) and 3-methoxypyrrolidine (23.77 mg, 0.240 mmol). The crude was purified by RP column chromatography eluting with water+0.1% TFA/ACN+0.1% TFA gradient starting from 8:2 to 1:1 to afford the title compound as pale-yellow solid (13.8 mg, yield 19%)

UPLC-MS [M+H]$^+$=467.42

$^1$H NMR (400 MHz, DMSO-d6) δ ppm 8.19 (d, 1H), 7.37-7.53 (m, 4H), 5.57 (s, 2H), 4.12 (br s, 1H), 3.50 (br s, 3H), 3.32-3.44 (m, 1H), 3.26 (s, 3H), 1.98-2.22 (m, 2H), 1.57 (s, 9H)

Example 184

3-(tert-Butyl)-6-(4-chlorobenzyl)-8-((tetrahydro-2H-pyran-4-yl)amino)pyrido[2,3-e][1,2,4]triazolo[4,3-c]pyrimidin-5(6H)-one The title compound was prepared according to the general procedure for photoinduced Nickel catalysed amination using 8-bromo-3-(tert-butyl)-6-(4-chlorobenzyl)pyrido[2,3-e][1,2,4]triazolo[4,3-c]pyrimidin-5(6H)-one (20 mg, 0.04 mmol) and tetrahydropyran-4-amine (7 QL, 0.07 mmol). The crude was purified by RP column chromatography eluting with water+0.1% TFA/ACN+0.1% TFA gradient starting from 8:2 to 1:1 to afford the title compound as pale-yellow solid (4 mg, yield: 15%)

UPLC-MS [M+H]$^+$=467.20

$^1$H NMR (400 MHz, DMSO-$d_6$) δ ppm 8.09-8.26 (m, 1H), 7.35-7.55 (m, 4H), 6.59 (d, 1H), 5.54 (s, 2H), 3.83 (br d, 2H), 3.53-3.69 (m, 1H), 3.24-3.45 (m, 2H), 1.52-1.66 (m, 11H), 1.12-1.42 (m, 2H).

Example 185

3-tert-Butyl-6-[(5-methylthiophen-2-yl)methyl]-8-(morpholin-4-yl)pyrido[2,3-e][1,2,4]triazolo[4,3-c]pyrimidin-5(6H)-one The title compound was prepared according to the general procedure for photoinduced Nickel catalysed amination using 8-bromo-3-(tert-butyl)-6-((5-methylthiophen-2-yl)methyl)pyrido[2,3-e][1,2,4]triazolo[4,3-c]pyrimidin-5(6H)-one 478-100 (60 mg, 0.132 mmol) as starting material. The crude was purified by RP column chromatography eluting with water+0.1% TFA/ACN+0.1% TFA gradient starting from 8:2 to 4:6 giving the title compound as pale yellow solid (19 mg, yield: 32%)

UPLC-MS [M+H]$^+$=439.19

$^1$H NMR (400 MHz, DMSO-$d_6$) δ ppm 8.42 (d, 1H), 7.36 (d, 1H), 7.10 (d, 1H), 6.66 (m, 1H), 5.60 (s, 2H), 3.70-3.88 (m, 4H), 3.37-3.48 (m, 4H), 2.35 (s, 3H), 1.57 (s, 9H).

Examples 186-188 as illustrated in Table 5 were prepared following the procedure described in alternative synthesis for Example 96 (via Buchwald at final step) substituting (4-methoxyphenyl)methanamine with (4-chlorophenyl) methanamine (purchased from available vendors) in step 1, 2,2-dimethylpropanidrazide with the proper hydrazide (synthesized following disclosed literature procedure or purchased from available vendors) at step 4 and morpholine with the proper amine at step 5. Reported yield are referred to final step.

Example 186

6-(4-Chlorobenzyl)-8-(morpholin-4-yl)-3-(tetrahydro-2H-pyran-4-ylmethyl)pyrido[2,3-e][1,2,4]triazolo[4,3-c]pyrimidin-5(6H)-one Pale yellow solid. Yield: 15%.

UPLC-MS [M+H]$^+$=495.20

$^1$H NMR (400 MHz, DMSO-$d_6$) δ ppm 8.47 (d, 1H) 7.51-7.59 (m, 2H) 7.41-7.50 (m, 2H) 7.07 (d, 1H) 5.56 (s, 2H) 3.93 (dd, 2H) 3.77-3.86 (m, 4H) 3.33-3.48 (m, 6H) 3.26 (d, 2H) 2.19-2.34 (m, 1H) 1.69-1.80 (m, 2H) 1.34-1.50 (m, 2H)

Example 187

8-(4-Acetylpiperazin-1-yl)-6-(4-chlorobenzyl)-3-(propan-2-yl)pyrido[2,3-e][1,2,4]triazolo[4,3-c]pyrimidin-5(6H)-one Pale yellow solid. Yield: 9%.

UPLC-MS [M+H]$^+$=480.24

1H NMR (400 MHz, DMSO-d6) δ ppm 8.45 (d, 1H) 7.35-7.50 (m, 4H) 7.03 (d, 1H) 5.57 (s, 2H) 3.52-3.65 (m, 4H) 3.34-3.48 (m, 4H) 3.18 (spt, 1H) 2.05 (s, 3H) 1.38 (d, 6H)

Example 188

6-(4-Chlorobenzyl)-8-(morpholin-4-yl)-3-[(tetrahydro-2H-pyran-4-yloxy)methyl]pyrido[2,3-e][1,2,4]triazolo[4,3-c]pyrimidin-5(6H)-one Pale yellow solid. Yield 19%.

UPLC-MS [M+H]$^+$=511.21

$^1$H NMR (400 MHz, DMSO-$d_6$) δ ppm 8.41 (d, 1H) 7.31-7.50 (m, 4H) 7.01 (d, 1H) 5.50 (s, 2H) 5.08 (s, 2H) 3.76-3.90 (m, 3H) 3.69-3.75 (m, 4H) 3.25-3.42 (m, 6H) 1.82-1.98 (m, 2H) 1.39-1.57 (m, 2H)

Example 189

3-tert-Butyl-6-(4-methoxybenzyl)-8-(morpholin-4-yl)pyrido[3,4-e][1,2,4]triazolo[4,3-c]pyrimidin-5(6H)-one 6-Chloro-4-[(4-methoxyphenyl)methylamino]pyridine-3-carbonitrile (Step 1)

To a solution of 4,6-dichloropyridine-3-carbonitrile (5.78 mmol, 1000 mg) in MeCN (20 mL) (4-methoxyphenyl) methanamine (8.68 mmol, 1189.4 mg, 1.13 mL) was added and the mixture was stirred at 65° C. for 12 h, a white precipitate was formed. After cooling at room temperature, water and EtAcO were added, the two phases were separated, the organic layer was washed with water and brine, dried over Na$_2$SO$_4$, filtered and evaporated. The crude was purified by silica gel column chromatography eluting with ethyl acetate/petroleum ether gradient starting from 0:100 to 30:70. 513 mg of the desired product were obtained as white powder (yield 32%).

4-[(4-Methoxyphenyl)methylamino]-6-morpholino-pyridine-3-carbonitrile (Step 2)

To a solution of 6-chloro-4-[(4-methoxyphenyl)methylamino]pyridine-3-carbonitrile (1.87 mmol, 513 mg) in NMP (10 mL) in a MW vial, morpholine (2.81 mmol, 244.9 mg, 0.245 mL) was added and the mixture was stirred at 130° C. under microwave irradiation for 2 h (adding 1 equivalent of morpholine after 1 h). After cooling at room temperature, water and EtOAc were added and the two phases were separated. Water was then extracted with EtOAc and the combined organic phases were dried over $Na_2SO_4$, filtered and evaporated. The crude was purified by silica gel column chromatography eluting with ethyl acetate/petroleum ether gradient starting from 20:80 to 50:50. 500 mg of the desired product were obtained as white powder (yield 82%).

4-[(4-Methoxyphenyl)methylamino]-6-morpholino-pyridine-3-carboxamide (Step 3)

To an ice bath cooled solution of 4-[(4-methoxyphenyl)methylamino]-6-morpholino-pyridine-3-carbonitrile (0.669 mmol, 217 mg) in DMSO (5 mL) sodium hydroxide solution (0.401 mmol, 0.4014 mL, 1 mol/L) was added followed by hydrogen peroxide 30% solution (0.803 mmol, 0.082 mL, 91.01 mg) and the mixture was stirred at room temperature for 2 h. Then water and EtOAc were added, the two phases were separated, the aqueous layer was extracted with EtOAc (3×) and the combined organic layers were dried over $Na_2SO_4$, filtered and evaporated. 190 mg of desired product were collected as off-white powder and used in the next step without any further purification (yield 82%).

1-[(4-Methoxyphenyl)methyl]-7-morpholino-pyrido[4,3-d]pyrimidine-2,4-dione (Step 4)

To a solution of 4-[(4-methoxyphenyl)methylamino]-6-morpholino-pyridine-3-carboxamide (0.730 mmol, 250 mg) in DMF (10 mL, 100 mass %), sodium hydride (4.381 mmol, 175.2 mg, 60 mass %) was added, followed by di(imidazol-1-yl)methanone (4.381 mmol, 710.4 mg) and the mixture was stirred at room temperature overnight. Acetic acid was added until pH=3-4, then water was added and a white precipitate was formed. After filtration 220 mg of desired product were collected as white powder (yield=81%).

4-Chloro-1-[(4-methoxyphenyl)methyl]-7-morpholinopyrido[4,3-d]pyrimidin-2-one (Step 5)

1-[(4-methoxyphenyl)methyl]-7-morpholino-pyrido[4,3-d]pyrimidine-2,4-dione (0.271 mmol, 100 mg) under nitrogen atmosphere was suspended in ethyldiisopropylamine (0.814 mmol, 0.139 mL, 105.2 mg) and $POCl_3$ (38 mmol, 3.49 mL, 5827 mg) was added dropwise and the mixture were stirred at 50° C. for 1 h. The mixture was cooled down to room temperature, $POCl_3$ was evaporated under reduced pressure and the residue washed with 1,4 dioxane (3 times). 104 mg of the desired product was collected as crude (dark oil) and used in the next step without any further purification (yield 99%).

3-tert-Butyl-6-(4-methoxybenzyl)-8-(morpholin-4-yl)pyrido[3,4-e][1,2,4]triazolo[4,3-c]pyrimidin-5(6H)-one (Step 6)

A solution of 4-chloro-1-[(4-methoxyphenyl)methyl]-7-morpholino-pyrido[4,3-d]pyrimidin-2-one (0.269 mmol, 104 mg) and 2,2-dimethylpropanehydrazide (0.403 mmol, 47 mg) in 1,4 dioxane (3 ml) was stirred at room temperature for 30 min. The mixture was then heated at reflux for 2 h. After cooling at room temperature, water and EtOAc were added and the two phases were separated. Water was extracted with EtOAc and the combined organic phases were dried over $Na_2SO_4$, filtered and evaporated. The crude residue was solved in dry tetrahydrofuran (5 mL, 100 mass %) and Burgess Reagent (0.864 mmol, 0.206 g) was added and the mixture stirred at room temperature for overnight, water was extracted with EtOAc and the combined organic phases were dried over $Na_2SO_4$, filtered and evaporated. The crude was purified by silica gel column chromatography eluting with ethyl acetate/petroleum ether gradient starting from 50:50 to 100:0. 20 mg of Example 189 were obtained.

White powder. Yield: 16%.
UPLC-MS [M+H]$^+$=449.15
$^1$H NMR (400 MHz, DMSO-d$_6$) δ ppm 8.94 (s, 1H) 7.34 (d, 2H) 6.86-6.96 (m, 2H) 6.54 (s, 1H) 5.41 (s, 2H) 3.72 (s, 3H) 3.64-3.71 (m, 4H) 3.50-3.58 (m, 4H) 1.55 (s, 9H)

Example 190 as illustrated in Table 5 was prepared following the procedure described for compound 189 but replacing 2,2-dimethylpropanehydrazide for 1-methylcyclopropanecarbohydrazide (purchased from available vendors) at Step 6.

Example 190

6-(4-Methoxybenzyl)-3-(1-methylcyclopropyl)-8-(morpholin-4-yl)pyrido[3,4-e][1,2,4]triazolo[4,3-c]pyrimidin-5(6H)-one Powder light yellow. Yield: 25%.
UPLC-MS [M+H]$^+$=447.29
$^1$H NMR (400 MHz, DMSO-d$_6$) δ ppm 8.90 (s, 1H) 7.37 (d, 2H) 6.85-6.94 (m, 2H) 6.52 (s, 1H) 5.40 (s, 2H) 3.72 (s, 3H) 3.63-3.70 (m, 4H) 3.49-3.56 (m, 4H) 1.48 (s, 3H) 1.14-1.19 (m, 2H) 0.79-0.87 (m, 2H)

Example 191 as illustrated in Table 5 was prepared following the procedure described for compound 180 but replacing (4-methoxyphenyl)methanamine for (4-chlorophenyl)methanamine (purchased from available vendors) at Step 1.

Example 191

3-tert-Butyl-6-(4-chlorobenzyl)-8-(morpholin-4-yl)[1,2,4]triazolo[4',3':1,6]pyrimido[5,4-c]pyridazin-5(6H)-one Example 192 as illustrated in Table 5 was prepared following the procedure described for compound in Example 189 substituting (4-methoxyphenyl)methanamine with (4-chlorophenyl)methanamine (purchased from available vendors) in step 1.

Example 192

3-tert-Butyl-6-(4-chlorobenzyl)-8-(morpholin-4-yl)pyrido[3,4-e][1,2,4]triazolo[4,3-c]pyrimidin-5(6H)-one Powder light yellow. Yield: 23%.
UPLC-MS [M+H]$^+$=452.95

Examples 193-194 as illustrated in Table 5 were prepared following the procedure described in Example 1 substituting (4-methoxyphenyl)methanamine with (3,5-dimethoxyphenyl)methanamine (purchased from available vendors) at step 2 and replacing 3-methylbutane-1,2-diamine HCl with 4,4-dimethylpentane-1,2-diamine (from available vendors) at step 3. Reported yields are referred to final step.

Example 193

6-(3,5-Dimethoxybenzyl)-2-(2,2-dimethylpropyl)-8-(morpholin-4-yl)-2,6-dihydroimidazo[1,2-c]pyrido[2,3-e]pyrimidin-5(3H)-one And Example 194

6-(3,5-Dimethoxybenzyl)-3-(2,2-dimethylpropyl)-8-(morpholin-4-yl)-2,6-dihydroimidazo[1,2-c]pyrido[2,3-e]pyrimidin-5(3H)-one First eluted: Example 194. Off-white solid (yield: 25%).
UPLC-MS [M+H]$^+$=494.28
$^1$H NMR (400 MHz, Acetonitrile-d$_3$) δ ppm 8.11 (s, 1H), 6.64 (s, 1H), 6.48 (s, 2H), 6.40 (br s, 1H), 5.13 (br s, 2H), 4.25-4.36 (m, 1H), 4.08-4.23 (m, 1H), 3.75 (s, 10H), 3.53 (br t, 1H), 3.13-3.25 (m, 4H), 1.83 (m, 1H), 1.53 (m, 1H), 1.05 (s, 9H).

Second eluted: Example 195. Pale yellow solid (yield: 13%).
UPLC-MS [M+H]$^+$=494.28
$^1$H NMR (400 MHz, Acetonitrile-d3+TFA) δ ppm 9.63 (br s, 22H), 8.33 (d, 1H), 6.59-6.68 (m, 1H), 6.43-6.50 (m, 3H), 5.15-5.39 (m, 2H), 4.83-5.01 (m, 1H), 4.24-4.40 (m, 1H), 3.84-3.99 (m, 1H), 3.74-3.80 (m, 10H), 3.43-3.52 (m, 4H), 2.13-2.38 (m, 1H), 1.97 (m, 5H), 1.62-1.85 (m, 1H), 1.05 (s, 9H).

Biological Assay: Calcium Fluorescence Measurements

The assay for the human purinergic P2X$_3$ receptor has been adapted to the internal screening instrumentation using the FLEXSTATION as reader and a photoprotein as luminescent readout. The assay consists of CHO-K1 cells recombinantly co-expressing the human P2rx3 receptor and a Ca$^{2+}$ sensitive photoprotein. Cells are maintained in DMEM F-12 (1:1) mixture (LONZA cat. no BE04-687F/U1) supplemented with 9 mL of 100 mM Sodium Pyruvate (LONZA cat. no BE13-115E), 29 mL of 7.5% Sodium Bicarbonate (LONZA cat. no: BE17-613E), 5.5 mL of 1 M Hepes (LONZA cat. no BE17-737E), 5 mL of 100× Penicillin/Streptomycin (LONZA cat. no DE17-602E) and 50 mL of Fetal Bovine Serum (Sigma cat. no F7524), 1 mg/mL G418 (Sigma cat. no G8168) and 5 g/ml puromycin (Sigma cat. no P9620). Standard propagation conditions consist of seeding in a P75 flask twice a week, recovering about 20×106 cells, corresponding to about 80% confluency. Cells were seeded into black-walled clear bottom 96 well plates at a density of 40000 cells/well in a Tyrode's buffer (Standard Tyrode's buffer: in house solution, 130 mM NaCl, 5 mM KCl, 2 mM CaCl2, 5 mM NaHCO3, 1 mM MgCl2, 20 mM HEPES, pH 7.4). After 24 h the culture medium was replaced with 200 μL/well of coelenterazine in Tyrode's buffer (Coelenterazine: from BIOSYNTH (cat. no C-7001). 10 mM stock solution was prepared in DMSO and glutathione and stored at −20° C.). The plates were incubated for 4 hours at 37° C., and injected with 10 μL/well of test compounds at 25× concentration in Tyrode's buffer. After 4 minutes a second injection of 50 μL/well of 5× α,β-Met-ATP in Tyrode's buffer (α,β-Met-ATP: from Tocris (cat. no 3209), was dissolved at 100 mM in water and stored in aliquots at −20° C.) was performed and the signal of the emitted luminescence was recorded by FLEXSTATION III (Molecular Devices). The tested compounds showed an antagonism versus human P2X$_3$ receptor between 1 nM and 10 μM. Example 96 and Example 102 showed an inhibition of 20.7 and 25.5 nM, respectively.

Selected antagonists of human P2X$_3$ receptors expressed as IC$_{50}$ (nM) for some of the compounds of interest, prepared according to the invention, are shown below in Tables 6 to 9.

TABLE 6

Human P2X$_3$ receptor antagonist activity for selected compounds of the invention.

| Compound | h-P2X$_3$ IC$_{50}$ nM |
|---|---|
| 1 | 5216.0 |
| 2 | 1191.0 |
| 3 | 1155.0 |
| 4 | 178.0 |
| 5 | 278.4 |
| 6 | 503.7 |
| 7 | 1643.0 |
| 8 | 636.4 |
| 9 | 74.3 |
| 10 | 241.0 |
| 11 | 357.6 |
| 12 | 427.9 |
| 13 | 1258.0 |
| 14 | 171.9 |
| 15 | 1425.5 |
| 16 | 2233.5 |
| 17 | 690.0 |
| 18 | 300.9 |
| 19 | 5509.5 |
| 20 | 1138.0 |
| 21 | 7193.0 |
| 22 | 142.8 |
| 23 | 506.2 |
| 24 | 515.2 |
| 25 | 388.9 |
| 26 | 468.8 |
| 28 | 375.0 |
| 29 | 367.9 |
| 30 | 350.2 |
| 31 | 228.5 |
| 32 | 123.8 |
| 33 | 219.2 |
| 34 | 408.1 |
| 35 | 793.3 |
| 36 | 245.3 |
| 37 | 677.7 |
| 38 | 2037.5 |
| 39 | 5141.0 |
| 40 | 1047.9 |
| 41 | 3318.5 |
| 42 | 188.6 |
| 43 | 111.8 |
| 44 | 491.0 |
| 45 | 200.5 |
| 46 | 126.8 |
| 47 | 199.0 |
| 49 | 871.7 |
| 50 | 280.1 |
| 51 | 731.0 |
| 52 | 1252.0 |
| 53 | 2068.0 |
| 54 | 1696.0 |
| 55 | 2439.5 |
| 56 | 345.1 |
| 57 | 3285.0 |
| 58 | 9201.0 |
| 60 | 1095.5 |
| 61 | 1076.8 |
| 62 | 720.3 |
| 63 | 298.7 |

TABLE 6-continued

Human P2X$_3$ receptor antagonist activity for selected compounds of the invention.

| Compound | h-P2X$_3$ IC$_{50}$ nM |
|---|---|
| 64 | 108.6 |
| 65 | 1788.5 |
| 66 | 2281.0 |
| 67 | 217.7 |
| 68 | 108.9 |
| 69 | 98.3 |

TABLE 7

Human P2X$_3$ receptor antagonist activity for selected compounds of the invention.

| Example | h-P2X$_3$ IC$_{50}$ nM |
|---|---|
| 70 | 138.9 |
| 72 | 1386.0 |
| 73 | 917.3 |
| 74 | 416.4 |
| 75 | 3506.0 |
| 76 | 381.1 |
| 77 | 238.9 |
| 78 | 631.0 |
| 79 | 53.7 |
| 80 | 1534.0 |
| 81 | 268.6 |
| 82 | 332.4 |
| 83 | 292.5 |
| 84 | 259.1 |
| 85 | 1304.0 |
| 87 | 443.9 |
| 88 | 53.6 |
| 89 | 574.9 |
| 90 | 332.0 |
| 91 | 507.4 |
| 92 | 801.5 |
| 93 | 1009.0 |
| 94 | 8262.0 |
| 95 | 2985.0 |
| 96 | 20.7 |
| 97 | 393.7 |
| 98 | 897.0 |
| 99 | 121.5 |
| 100 | 153.1 |
| 101 | 2442.0 |
| 102 | 25.5 |
| 103 | 810.5 |
| 104 | 734.1 |
| 105 | 655.4 |
| 106 | 40.6 |
| 107 | 1316.7 |
| 108 | 175.4 |
| 109 | 203.4 |
| 110 | 256.6 |

TABLE 8

Human P2X$_3$ receptor antagonist activity for selected compounds of the invention.

| Example | h-P2X$_3$ IC$_{50}$ nM |
|---|---|
| 111 | 101.7 |
| 112 | 1438.5 |
| 115 | 436.6 |
| 116 | 468.6 |
| 117 | 197.4 |
| 118 | 1055.0 |

TABLE 8-continued

Human P2X$_3$ receptor antagonist activity for selected compounds of the invention.

| Example | h-P2X$_3$ IC$_{50}$ nM |
|---|---|
| 119 | 1214.0 |
| 120 | 543.6 |
| 121 | 1151.0 |
| 122 | 1813.5 |
| 123 | 246.2 |
| 124 | 2817.5 |
| 125 | 538.0 |
| 126 | 20.6 |
| 127 | 147.1 |
| 128 | 575.5 |
| 132 | 19.1 |
| 133 | 216.8 |
| 136 | 1788.0 |
| 137 | 234.4 |
| 138 | 3344 |
| 139 | 379.0 |
| 140 | 309.1 |

TABLE 9

Human P2X$_3$ receptor antagonist activity for selected compounds of the invention.

| Example | h-P2X$_3$ IC$_{50}$ nM |
|---|---|
| 143 | 2255 |
| 144 | 2483 |
| 145 | 1783 |
| 147 | 2441 |
| 151 | 937.7 |
| 154 | 1046.4 |
| 155 | 2170.5 |
| 156 | 607.8 |
| 157 | 495.2 |
| 161 | 4294.0 |
| 163 | 277.5 |
| 164 | 188.0 |
| 165 | 701.9 |
| 168 | 1394.8 |
| 171 | 699.7 |
| 173 | 2.59 |
| 174 | 78.5 |
| 176 | 2569.2 |
| 186 | 289.0 |
| 188 | 527.7 |

Statistical Analysis.

The inhibition curves of the tested compounds at cloned P2X$_3$ receptor were determined by nonlinear regression analysis using software Prism 4.0 (Graphpad, San Diego, Calif.). The IC$_{50}$ values and pseudo-Hill slope coefficients were estimated by the program.

What is claimed is:

1. A compound according to formula I:

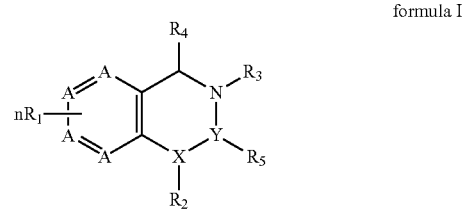

formula I or an enantiomer, diastereomer, N-oxide, or a pharmaceutically acceptable salt or combinations thereof, wherein:

one or two of the A groups comprise nitrogen atoms, and the remaining A groups each comprises carbon atom;

X—Y represents a N—C group;

each $R_1$ independently represents 2-oxa-6-azaspiro[3.3]heptan-6-yl, 3-methoxymethylazetidin-1-yl, 3-methoxypyrrolidin-1-yl, 4-acetylpiperazin-1-yl, 4-aminopiperidin-1-yl, 4-hydroxypiperidin-1-yl, 4-hydroxypiperidin-1-yl-carbonyl, 4-methoxypiperidin-1-yl, 4-morpholinyl, dimethylaminopiperidin-1-yl, hydroxymethylpiperidin-1-yl, morpholin-4-ylcarbonyl, tetrahydro-2H-pyran-4-ylamino or tetrahydro-2H-pyran-4-ylaminocarbonyl, (oxetan-3-ylmethyl)amino, 4-(hydroxyacetyl)piperazin-1-yl;

$R_2$ is an optionally substituted, $C_1$-$C_6$ alkyl group, $C_1$-$C_6$ alkoxy group, $C_4$-$C_{14}$ arylalkyl group, $C_4$-$C_{14}$ heteroarylalkyl group, $C_3$-$C_7$ cycloalkyl group, a mono-, bi- or tricyclic $C_6$-$C_{14}$ aryl group or a mono-, bi- or tricyclic $C_1$-$C_{13}$ heterocyclic group containing from 1 to 5 heteroatoms selected from N, O or S;

groups $R_3$ and $R_4$ are linked to each other to form a five-membered heterocyclic ring containing 2 or 3 nitrogen atoms or a six-membered heterocyclic ring containing 2 nitrogen atoms, substituted with one or more groups $R_6$;

$R_5$ is O double-bonded directly to the X—Y containing ring;

each $R_6$ independently represents a halogen atom selected from F, Cl, Br or I; or an, optionally substituted, carbonyl, oxo, $C_1$-$C_6$ alkyl, $C_1$-$C_6$ alkoxy or $C_3$-$C_7$ cycloalkyl group, an, optionally substituted, mono-, bi- or tricyclic $C_6$-$C_{14}$ aryl group or an, optionally substituted, mono-, bi- or tricyclic $C_1$-$C_{13}$ heterocyclic group containing from 1 to 5 heteroatoms selected from N, O or S or alternatively, two $R_6$ groups are linked to each other to form a group of the formula -(Zp)- wherein p is an integer of from 3 to 5 and each Z independently represents an oxygen atom or an optionally substituted methylene group, provided that no two adjacent Z moieties represent oxygen atoms; and n is an integer independently selected from 0 to 3.

2. The compound according to claim 1 wherein the optional substituents are independently selected from the group consisting of halogen atoms, $C_1$-$C_6$ alkyl, $C_1$-$C_6$ alkoxy, hydroxy, mercapto, nitro, cyano, oxo, halo($C_1$-$C_6$)alkyl, halo($C_1$-$C_6$)alkoxy, $C_1$-$C_6$ alkylthio, $C_1$-$C_6$ alkylsulphonyl, $C_1$-$C_6$ alkylcarbonyl, sulphamoyl, $C_1$-$C_6$ alkylsulphamoyl, di($C_1$-$C_6$)alkylsulphamoyl, ($C_1$-$C_6$) alkoxycarbonyl and ($C_1$-$C_6$)alkylcarbonyl($C_1$-$C_6$)alkyl groups, and from groups of the formulae —NR*R*, —C(=O)—NR*R*, -D, —O-D, —C(=O)-D, —(CH$_2$)q-D, —NR-D, —C(=O)—NR-D, —NR**C(=O)-D and —O—C(=O)-D wherein each R* independently represents a hydrogen atom or a $C_1$-$C_6$ alkyl, $C_1$-$C_6$ alkoxy, $C_1$-$C_6$ alkylcarbonyl, phenyl or benzyl group, R** represents a hydrogen atom or a $C_1$-$C_6$ alkyl group, q is an integer from 1 to 6 and D represents a phenyl group or a $C_1$-$C_8$ heterocyclic group containing from 1 to 3 heteroatoms selected from N, O and S; a $C_1$-$C_6$ cycloalkyl group; each group D being further optionally substituted with from 1 to 3 groups independently selected from halo, hydroxy, cyano, nitro and $C_1$-$C_6$ alkyl, preferably wherein the optional substituents are selected from the groups consisting of halogen atoms and $C_1$-$C_6$ alkyl groups.

3. A compound according to formula I:

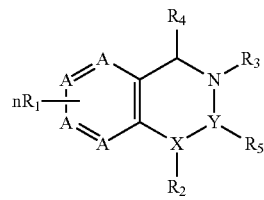

formula I or an enantiomer, diastereomer, N-oxide, or a pharmaceutically acceptable salt or combinations thereof, wherein:

one or two of the A groups comprise nitrogen atoms, and the remaining A groups each comprises carbon atom;

X—Y represents a N—C group;

each $R_1$ independently represents H, morpholinyl, oxetanyl, piperazinyl, piperidinyl, pyranyl, pyrrolidinyl, or derivative thereof, $R_2$ is an optionally substituted, $C_1$-$C_6$ alkyl group, $C_1$-$C_6$ alkoxy group, $C_4$-$C_{14}$ arylalkyl group, $C_4$-$C_{14}$ heteroarylalkyl group, $C_3$-$C_7$ cycloalkyl group, a mono-, bi- or tricyclic $C_6$-$C_{14}$ aryl group or a mono-, bi- or tricyclic $C_1$-$C_{13}$ heterocyclic group containing from 1 to 5 heteroatoms selected from N, O or S;

groups $R_3$ and $R_4$ are linked to each other to form a five-membered heterocyclic ring containing 2 or 3 nitrogen atoms or six-membered heterocyclic ring containing 2 b nitrogen atoms, substituted with one or more groups $R_6$;

$R_5$ is O double-bonded directly to the X—Y containing ring;

each $R_6$ independently represents a halogen atom selected from F, Cl, Br or I; or an, optionally substituted, carbonyl, oxo, $C_1$-$C_6$ alkyl, $C_1$-$C_6$ alkoxy or $C_3$-$C_7$ cycloalkyl group, an, optionally substituted, mono-, bi- or tricyclic $C_6$-$C_{14}$ aryl group or an, optionally substituted, mono-, bi- or tricyclic $C_1$-$C_{13}$ heterocyclic group containing from 1 to 5 heteroatoms selected from N, O or S or alternatively, two $R_6$ groups are linked to each other to form a group of the formula -(Zp)- wherein p is an integer of from 3 to 5 and each Z independently represents an oxygen atom or an optionally substituted methylene group, provided that no two adjacent Z moieties represent oxygen atoms; and n is an integer independently selected from 0 to 3.

4. The compound according to claim 1, wherein $R_2$ is an optionally substituted benzyl group or derivative thereof.

5. The compound according to claim 4, wherein $R_2$ is selected from the group comprising 3,5-dimethoxybenzyl, 4-methoxybenzyl, 4-methylbenzyl, 4-chlorobenzyl or 4-chloro-2,6-difluorobenzyl.

6. The compound according to claim 1, wherein $R_6$ is selected from the group comprising phenyl, (1-phenyl)ethyl, 1-ethyl-1H-pyrazol-3-yl, 1-ethyl-1H-pyrazol-5-yl, (tetrahydro-2H-pyran-4-yl)methyl, (tetrahydro-2H-pyran-4-yloxy)methyl, (tetrahydro-2H-pyran-4-yl)ethyl, 3,5-dimethyl-1,2oxazol-4-yl, 2-hydroxypyridin-3-yl, 2-methylpyridin-3-yl, morpholin-4-yl-carbonyl, pyridin-3-ylmethyl, oxo, methyl, ethyl, iso-propyl, tertiary-butyl, methylpropyl, 2,2-dimethylpropyl, 3-methylbutyl, 2,2,2-trifluoroethyl, methoxymethyl, methoxyethyl, (propan-2-yloxy)methyl, tertiary-butoxymethyl, prop-1-en-2-yl, propan-2-yl-acetamide, cyclopropyl, cyclobutyl, cyclohexyl, or 1-methylcyclopropyl.

7. The compound according to claim 1, wherein -(Zp)- represents a group selected from —O—(CH$_2$)$_2$—O—, —O—(CH$_2$)$_3$—O—, —O—(CH$_2$)$_2$—, —O—(CH$_2$)$_3$—, —CH$_2$—O—CH$_2$—, and —(CH$_2$)$_2$—O—(CH$_2$)$_2$.

8. A pharmaceutical composition comprising a compound according to claim 1 and a pharmaceutically acceptable carrier or diluent.

9. A method for the treatment of chronic pain and cancer pain, overactive bladder, irritable bowel syndrome (IBS) and Burning Mouth Syndrome (BMS) relating to migraines and itches comprising administering to a subject in need of treatment an effective amount of a pharmaceutical composition according to claim 8.

10. A compound according to formula I:

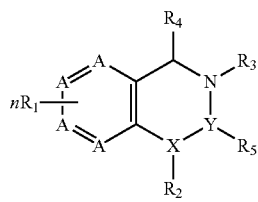

formula I or an enantiomer, diastereomer, N-oxide, or a pharmaceutically acceptable salt or combinations thereof, wherein:
one or two of the A groups comprise nitrogen atoms, and the remaining A groups each comprise a carbon atom;
X—Y represents a N—C group;
each R$_1$ is selected from the group comprising 2-oxa-6-azaspiro[3.3]heptan-6-yl, 3-methoxymethylazetidin-1-yl, 3-methoxypyrrolidin-1-yl, 4-acetylpiperazin-1-yl, 4-aminopiperidin-1-yl, 4-hydroxypiperidin-1-yl, 4-hydroxypiperidin-1-yl-carbonyl, 4-methoxypiperidin-1-yl, 4-morpholinyl, dimethylaminopiperidin-1-yl, hydroxymethylpiperidin-1-yl, morpholin-4-ylcarbonyl, tetrahydro-2H-pyran-4-ylamino or tetrahydro-2H-pyran-4-ylaminocarbonyl;
R$_2$ is an optionally substituted, C$_1$-C$_6$ alkyl group, C$_1$-C$_6$ alkoxy group, C$_4$-C$_{14}$ arylalkyl group, C$_4$-C$_{14}$ heteroarylalkyl group, C$_3$-C$_7$ cycloalkyl group, a mono-, bi- or tricyclic C$_6$-C$_{14}$ aryl group or a mono-, bi- or tricyclic C$_1$-C$_{13}$ heterocyclic group containing from 1 to 5 heteroatoms selected from N, O or S;
groups R$_3$ and R$_4$ are linked to each other to form a five- or six-membered b heterocyclic ring containing from 2 to 3 nitrogen heteroatoms, substituted with one or more groups R$_6$;
R$_5$ is O double-bonded directly to the X—Y containing ring;
each R$_6$ independently represents a halogen atom selected from F, Cl, Br or I; or an, optionally substituted, carbonyl, oxo, C$_1$-C$_6$ alkyl, C$_1$-C$_6$ alkoxy or C$_3$-C$_7$ cycloalkyl group, an, optionally substituted, mono-, bi- or tricyclic C$_6$-C$_{14}$ aryl group or an, optionally substituted, mono-, bi- or tricyclic C$_1$-C$_{13}$ heterocyclic group containing from 1 to 5 heteroatoms selected from N, O or S or alternatively, two R$_6$ groups are linked to each other to form a group of the formula -(Zp)- wherein p is an integer of from 3 to 5 and each Z independently represents an oxygen atom or an optionally substituted methylene group, provided that no two adjacent Z moieties represent oxygen atoms; and
n is an integer independently selected from 0 to 3.

11. The compound according to claim 10, wherein the optional substituents are independently selected from the group consisting of halogen atoms, C$_1$-C$_6$ alkyl, C$_1$-C$_6$ alkoxy, hydroxy, mercapto, nitro, cyano, oxo, halo(C$_1$-C$_6$)alkyl, halo(C$_1$-C$_6$)alkoxy, C$_1$-C$_6$ alkylthio, C$_1$-C$_6$ alkylsulphonyl, C$_1$-C$_6$ alkylcarbonyl, sulphamoyl, C$_1$-C$_6$ alkylsulphamoyl, di(C$_1$-C$_6$)alkylsulphamoyl, (C$_1$-C$_6$) alkoxycarbonyl and (C$_1$-C$_6$)alkylcarbonyl(C$_1$-C$_6$)alkyl groups, and from groups of the formulae —NR*R*, —C(=O)—NR*R*, -D, —O-D, —C(=O)-D, —(CH$_2$)q-D, —NR-D, —C(=O)—NR-D, —NR**C(=O)-D and —O—C(=O)-D wherein each R* independently represents a hydrogen atom or a C$_1$-C$_6$ alkyl, C$_1$-C$_6$ alkoxy, C$_1$-C$_6$ alkylcarbonyl, phenyl or benzyl group, R** represents a hydrogen atom or a C$_1$-C$_6$ alkyl group, q is an integer from 1 to 6 and D represents a phenyl group or a C$_1$-C$_8$ heterocyclic group containing from 1 to 3 heteroatoms selected from N, O and S; a C$_1$-C$_6$ cycloalkyl group; each group D being further optionally substituted with from 1 to 3 groups independently selected from halo, hydroxy, cyano, nitro and C$_1$-C$_6$ alkyl, preferably wherein the optional substituents are selected from the groups consisting of halogen atoms and C$_1$-C$_6$ alkyl groups.

12. The compound according to claim 10, wherein R$_2$ is an optionally substituted benzyl group or derivative thereof.

13. The compound according to claim 12, wherein R$_2$ is selected from the group comprising 3,5-dimethoxybenzyl, 4-methoxybenzyl, 4-methylbenzyl, 4-chlorobenzyl or 4-chloro-2,6-difluorobenzyl.

14. The compound according to claim 10, wherein R$_6$ is selected from the group comprising phenyl, (1-phenyl)ethyl, 1-ethyl-1H-pyrazol-3-yl, 1-ethyl-1H-pyrazol-5-yl, (tetrahydro-2H-pyran-4-yl)methyl, (tetrahydro-2H-pyran-4-yloxy)methyl, (tetrahydro-2H-pyran-4-yl)ethyl, 3,5-dimethyl-1,2oxazol-4-yl, 2-hydroxypyridin-3-yl, 2-methylpyridin-3-yl, morpholin-4-yl-carbonyl, pyridin-3-yl-methyl, oxo, methyl, ethyl, iso-propyl, tertiary-butyl, methylpropyl, 2,2-dimethylpropyl, 3-methylbutyl, 2,2,2-trifluoroethyl, methoxymethyl, methoxyethyl, (propan-2-yloxy)methyl, tertiary-butoxymethyl, prop-1-en-2-yl, propan-2-yl-acetamide, cyclopropyl, cyclobutyl, cyclohexyl, or 1-methylcyclopropyl.

15. The compound according to claim 10, wherein -(Zp)- represents a group selected from —O—(CH$_2$)$_2$—O—, —O—(CH$_2$)$_3$—O—, —O—(CH$_2$)$_2$—, —O—(CH$_2$)$_3$—, —CH$_2$—O—CH$_2$—, and —(CH$_2$)$_2$—O—(CH$_2$)$_2$.

16. The compound according to claim 1, the compound being selected from the group consisting of:
6-(4-methoxybenzyl)-8-(morpholin-4-yl)-3-(propan-2-yl)-2,6-dihydroimidazo[1,2-c]pyrido[2,3-e]pyrimidin-5(3H)-one;
6-(3,5-dimethoxybenzyl)-3-methyl-8-(morpholin-4-yl)-2,6-dihydroimidazo[1,2-c]pyrido[2,3-e]pyrimidin-5 (3H)-one;
6-(3,5-dimethoxybenzyl)-2-methyl-8-(morpholin-4-yl)-2,6-dihydroimidazo[1,2-c]pyrido[2,3-e]pyrimidin-5 (3H)-one;
6-(3,5-dimethoxybenzyl)-8-(morpholin-4-yl)-2-(propan-2-yl)-2,6-dihydroimidazo[1,2-c]pyrido[2,3-e]pyrimidin-5(3H)-one;
6-(3,5-dimethoxybenzyl)-2-ethyl-8-(morpholin-4-yl)-2,6-dihydroimidazo[1,2-c]pyrido[2,3-e]pyrimidin-5 (3H)-one;

6-(3,5-dimethoxybenzyl)-3-ethyl-8-(morpholin-4-yl)-2,6-dihydroimidazo[1,2-c]pyrido[2,3-e]pyrimidin-5(3H)-one;

6-(3,5-dimethoxybenzyl)-8-(morpholin-4-yl)-2,6-dihydroimidazo[1,2-c]pyrido[2,3-e]pyrimidin-5(3H)-one;

6-(3,5-dimethoxybenzyl)-2,3-dimethyl-8-(morpholin-4-yl)-2,6-dihydroimidazo[1,2-c]pyrido[2,3-e]pyrimidin-5(3H)-one;

6-(3,5-dimethoxybenzyl)-8-(morpholin-4-yl)-3-(propan-2-yl)-2,6-dihydroimidazo[1,2-c]pyrido[2,3-e]pyrimidin-5(3H)-one;

6-(4-chlorobenzyl)-2-cyclopropyl-8-(morpholin-4-yl)-2,6-dihydroimidazo[1,2-c]pyrido[2,3-e]pyrimidin-5(3H)-one;

6-(4-chlorobenzyl)-2-(methoxymethyl)-8-(morpholin-4-yl)-2,6-dihydroimidazo[1,2-c]pyrido[2,3-e]pyrimidin-5(3H)-one;

6-(4-chlorobenzyl)-3-cyclopropyl-8-(morpholin-4-yl)-2,6-dihydroimidazo[1,2-c]pyrido[2,3-e]pyrimidin-5(3H)-one;

6-(4-chlorobenzyl)-3-(methoxymethyl)-8-(morpholin-4-yl)-2,6-dihydroimidazo[1,2-c]pyrido[2,3-e]pyrimidin-5(3H)-one;

6-(4-chlorobenzyl)-8-(morpholin-4-yl)-2-(propan-2-yl)-2,6-dihydroimidazo[1,2-c]pyrido[2,3-e]pyrimidin-5(3H)-one;

6-(4-chlorobenzyl)-8-(2-oxa-6-azaspiro[3.3]heptan-6-yl)-2-(propan-2-yl)-2,6-dihydroimidazo[1,2-c]pyrido[2,3-e]pyrimidin-5(3H)-one;

6-(4-chlorobenzyl)-8-(4-methoxypiperidin-1-yl)-2-(propan-2-yl)-2,6-dihydroimidazo[1,2-c]pyrido[2,3-e]pyrimidin-5(3H)-one;

6-(4-chlorobenzyl)-8-[3-(methoxymethyl)azetidin-1-yl]-2-(propan-2-yl)-2,6-dihydroimidazo[1,2-c]pyrido[2,3-e]pyrimidin-5(3H)-one;

6-(4-methoxybenzyl)-8-(morpholin-4-yl)-2-(propan-2-yl)-2,6-dihydroimidazo[1,2-c]pyrido[2,3-e]pyrimidin-5(3H)-one;

6-(4-methoxybenzyl)-8-(2-oxa-6-azaspiro[3.3]heptan-6-yl)-2-(propan-2-yl)-2,6-dihydroimidazo[1,2-c]pyrido[2,3-e]pyrimidin-5(3H)-one;

8-[4-(hydroxymethyl)piperidin-1-yl]-6-(4-methoxybenzyl)-2-(propan-2-yl)-2,6-dihydroimidazo[1,2-c]pyrido[2,3-e]pyrimidin-5(3H)-one;

8-[4-(dimethylamino)piperidin-1-yl]-6-(4-methoxybenzyl)-2-(propan-2-yl)-2,6-dihydroimidazo[1,2-c]pyrido[2,3-e]pyrimidin-5(3H)-one;

6-(3,5-dimethoxybenzyl)-2-(2-methylpropyl)-8-(morpholin-4-yl)-2,6-dihydroimidazo[1,2-c]pyrido[2,3-e]pyrimidin-5(3H)-one;

2-cyclohexyl-6-(4-methoxybenzyl)-8-(morpholin-4-yl)-2,6-dihydroimidazo[1,2-c]pyrido[2,3-e]pyrimidin-5(3H)-one;

3-cyclohexyl-6-(4-methoxybenzyl)-8-(morpholin-4-yl)-2,6-dihydroimidazo[1,2-c]pyrido[2,3-e]pyrimidin-5(3H)-one;

6-(4-chlorobenzyl)-2-cyclohexyl-8-(morpholin-4-yl)-2,6-dihydroimidazo[1,2-c]pyrido[2,3-e]pyrimidin-5(3H)-one;

6-(4-chlorobenzyl)-3-cyclohexyl-8-(morpholin-4-yl)-2,6-dihydroimidazo[1,2-c]pyrido[2,3-e]pyrimidin-5(3H)-one;

2-ethyl-6-(4-methoxybenzyl)-8-[(3r)-3-methoxypyrrolidin-1-yl]-2,6-dihydroimidazo[1,2-c]pyrido[2,3-e]pyrimidin-5(3H)-one;

6-(4-methoxybenzyl)-8-(morpholin-4-yl)-2-phenyl-2,6-dihydroimidazo[1,2-c]pyrido[2,3-e]pyrimidin-5(3H)-one;

6-(4-methoxybenzyl)-8-(morpholin-4-yl)-3-phenyl-2,6-dihydroimidazo[1,2-c]pyrido[2,3-e]pyrimidin-5(3H)-one;

6-(4-chlorobenzyl)-2-(2-methylpropyl)-8-(morpholin-4-yl)-2,6-dihydroimidazo[1,2-c]pyrido[2,3-e]pyrimidin-5(3H)-one;

6-(4-chlorobenzyl)-3-(2-methylpropyl)-8-(morpholin-4-yl)-2,6-dihydroimidazo[1,2-c]pyrido[2,3-e]pyrimidin-5(3H)-one;

2-tert-butyl-6-(4-methoxybenzyl)-8-(morpholin-4-yl)-2,6-dihydroimidazo[1,2-c]pyrido[2,3-e]pyrimidin-5(3H)-one;

2-cyclobutyl-6-(4-methoxybenzyl)-8-(morpholin-4-yl)-2,6-dihydroimidazo[1,2-c]pyrido[2,3-e]pyrimidin-5(3H)-one;

2-(2,2-dimethylpropyl)-6-(4-methoxybenzyl)-8-(morpholin-4-yl)-2,6-dihydroimidazo[1,2-c]pyrido[2,3-e]pyrimidin-5(3H)-one;

6-(3,5-dimethoxybenzyl)-3-(2-methylpropyl)-8-(morpholin-4-yl)-2,6-dihydroimidazo[1,2-c]pyrido[2,3-e]pyrimidin-5(3H)-one;

6-(4-chlorobenzyl)-8-(morpholin-4-yl)-2-phenyl-2,6-dihydroimidazo[1,2-c]pyrido[2,3-e]pyrimidin-5(3H)-one;

6-(4-methoxybenzyl)-2-(2-methylpropyl)-8-(morpholin-4-yl)-2,6-dihydroimidazo[1,2-c]pyrido[2,3-e]pyrimidin-5(3H)-one;

6-(4-methoxybenzyl)-3-(2-methylpropyl)-8-(morpholin-4-yl)-2,6-dihydroimidazo[1,2-c]pyrido[2,3-e]pyrimidin-5(3H)-one;

2-ethyl-6-(4-methoxybenzyl)-8-[3-(methoxymethyl)azetidin-1-yl]-2,6-dihydroimidazo[1,2-c]pyrido[2,3-e]pyrimidin-5(3H)-one;

6-(4-chlorobenzyl)-8-(morpholin-4-yl)-2',3',5',6'-tetrahydrospiro[imidazo[1,2-c]pyrido[2,3-e]pyrimidine-2,4'-pyran]-5(6H)-one;

6-(4-chlorobenzyl)-8-(morpholin-4-yl)-2,2',3',5',6,6'-hexahydro-5h-spiro[imidazo[1,2-c]pyrido[2,3-e]pyrimidine-3,4'-pyran]-5-one;

8-(4-aminopiperidin-1-yl)-6-(3,5-dimethoxybenzyl)-2-(propan-2-yl)-2,6-dihydroimidazo[1,2-c]pyrido[2,3-e]pyrimidin-5(3H)-one;

2-cyclohexyl-6-(3,5-dimethoxybenzyl)-8-(morpholin-4-yl)-2,6-dihydroimidazo[1,2-c]pyrido[2,3-e]pyrimidin-5(3H)-one;

3-cyclohexyl-6-(3,5-dimethoxybenzyl)-8-(morpholin-4-yl)-2,6-dihydroimidazo[1,2-c]pyrido[2,3-e]pyrimidin-5(3H)-one;

6-(4-chlorobenzyl)-8-(morpholin-4-yl)-3-phenyl-2,6-dihydroimidazo[1,2-c]pyrido[2,3-e]pyrimidin-5(3H)-one;

6-(3,5-dimethoxybenzyl)-8-(morpholin-4-yl)-2-phenyl-2,6-dihydroimidazo[1,2-c]pyrido[2,3-e]pyrimidin-5(3H)-one;

6-(3,5-dimethoxybenzyl)-8-(morpholin-4-yl)-3-phenyl-2,6-dihydroimidazo[1,2-c]pyrido[2,3-e]pyrimidin-5(3H)-one;

6-(3,5-dimethoxybenzyl)-2-(propan-2-yl)-8-(tetrahydro-2H-pyran-4-ylamino)-2,6-dihydroimidazo[1,2-c]pyrido[2,3-e]pyrimidin-5(3H)-one;

6-(4-chlorobenzyl)-2-ethyl-8-(morpholin-4-yl)-2,6-dihydroimidazo[1,2-c]pyrido[2,3-e]pyrimidin-5(3H)-one;

6-(4-chlorobenzyl)-8-(4-hydroxypiperidin-1-yl)-2-(propan-2-yl)-2,6-dihydroimidazo[1,2-c]pyrido[2,3-e]pyrimidin-5(3H)-one;

2-ethyl-6-(4-methoxybenzyl)-8-(morpholin-4-yl)-2,6-dihydroimidazo[1,2-c]pyrido[2,3-e]pyrimidin-5(3H)-one;

3-ethyl-6-(4-methoxybenzyl)-8-(morpholin-4-yl)-2,6-dihydroimidazo[1,2-c]pyrido[2,3-e]pyrimidin-5(3H)-one;

6-(4-chlorobenzyl)-8-(morpholin-4-yl)-2-(morpholin-4-ylcarbonyl)-2,6-dihydroimidazo[1,2-c]pyrido[2,3-e]pyrimidin-5(3H)-one;

6-(4-chlorobenzyl)-8-(morpholin-4-yl)-3-(morpholin-4-ylcarbonyl)-2,6-dihydroimidazo[1,2-c]pyrido[2,3-e]pyrimidin-5(3H)-one;

6-(4-methoxybenzyl)-8-(morpholin-4-yl)-2-(2,2,2-trifluoroethyl)-2,6-dihydroimidazo[1,2-c]pyrido[2,3-e]pyrimidin-5(3H)-one;

2-(tert-butoxymethyl)-6-(4-methoxybenzyl)-8-(morpholin-4-yl)-2,6-dihydroimidazo[1,2-c]pyrido[2,3-e]pyrimidin-5(3H)-one;

6-(3,5-dimethoxybenzyl)-5-oxo-2-(propan-2-yl)-n-(tetrahydro-2H-pyran-4-yl)-2,3,5,6-tetrahydroimidazo[1,2-c]pyrido[2,3-e]pyrimidine-8-carboxamide;

6-(3,5-dimethoxybenzyl)-5-oxo-2-(propan-2-yl)-2,3,5,6-tetrahydroimidazo[1,2-c]pyrido[2,3-e]pyrimidine-8-carboxylic acid;

6-(3,5-dimethoxybenzyl)-8-(morpholin-4-ylcarbonyl)-2-(propan-2-yl)-2,6-dihydroimidazo[1,2-c]pyrido[2,3-e]pyrimidin-5(3H)-one;

6-(4-chlorobenzyl)-2-(cyclohexylmethyl)-8-(morpholin-4-yl)-2,6-dihydroimidazo[1,2-c]pyrido[2,3-e]pyrimidin-5(3H)-one;

6-(4-chlorobenzyl)-2-(3-methylbutyl)-8-(morpholin-4-yl)-2,6-dihydroimidazo[1,2-c]pyrido[2,3-e]pyrimidin-5(3H)-one;

6-(4-chlorobenzyl)-3-(3-methylbutyl)-8-(morpholin-4-yl)-2,6-dihydroimidazo[1,2-c]pyrido[2,3-e]pyrimidin-5(3H)-one;

6-(4-chlorobenzyl)-3-(2-methylpropyl)-8-(morpholin-4-yl)imidazo[1,2-c]pyrido[2,3-e]pyrimidine-2,5(3H,6H)-dione;

6-(4-methoxybenzyl)-2-(2-methoxyethyl)-8-(morpholin-4-yl)-2,6-dihydroimidazo[1,2-c]pyrido[2,3-e]pyrimidin-5(3H)-one;

6-(4-methoxybenzyl)-3-(2-methoxyethyl)-8-(morpholin-4-yl)-2,6-dihydroimidazo[1,2-c]pyrido[2,3-e]pyrimidin-5(3H)-one;

3-(tert-butoxymethyl)-6-(4-methoxybenzyl)-8-(morpholin-4-yl)-2,6-dihydroimidazo[1,2-c]pyrido[2,3-e]pyrimidin-5(3H)-one;

3-tert-butyl-6-(4-chlorobenzyl)-8-(morpholin-4-yl)imidazo[1,2-c]pyrido[2,3-e]pyrimidine-2,5(3H,6H)-dione;

3-tert-butyl-6-(4-methoxybenzyl)-8-(morpholin-4-yl)imidazo[1,2-c]pyrido[2,3-e]pyrimidine-2,5(3H,6H)-dione;

6-(3,5-dimethoxybenzyl)-2,3-dimethyl-8-{[(oxetan-3-yl)methyl]amino}imidazo[1,2-c]pyrido[2,3-e]pyrimidin-5(6H)-one;

2-(2-methylpropyl)imidazo[1,2-c]pyrido[2,3-e]pyrimidin-5(6H)-one;

6-(4-methylbenzyl)-2-(2-methylpropyl)imidazo[1,2-c]pyrido[2,3-e]pyrimidin-5(6H)-one;

6-(4-chlorobenzyl)-2-(2-methylpropyl)-8-(2-oxa-6-azaspiro[3.3]heptan-6-yl)imidazo[1,2-c]pyrido[2,3-e]pyrimidin-5(6H)-one;

6-(3,5-dimethoxybenzyl)-2-(2-methylpropyl)-8-(morpholin-4-yl)imidazo[1,2-c]pyrido[2,3-e]pyrimidin-5(6H)-one;

6-(4-chloro-2,6-difluorobenzyl)-2-(2-methylpropyl)-8-(morpholin-4-yl)imidazo[1,2-c]pyrido[2,3-e]pyrimidin-5(6H)-one;

6-(3,5-dimethoxybenzyl)-2-ethyl-3-methyl-8-{[(oxetan-3-yl)methyl]amino}imidazo[1,2-c]pyrido[2,3-e]pyrimidin-5(6H)-one;

6-(3,5-dimethoxybenzyl)-3-ethyl-2-methyl-8-{[(oxetan-3-yl)methyl]amino}imidazo[1,2-c]pyrido[2,3-e]pyrimidin-5(6H)-one;

6-(4-methoxybenzyl)-2-(2-methylpropyl)-8-(morpholin-4-yl)imidazo[1,2-c]pyrido[2,3-e]pyrimidin-5(6H)-one;

6-(3,5-dimethoxybenzyl)-3-methyl-8-(morpholin-4-yl)-2-(propan-2-yl)imidazo[1,2-c]pyrido[2,3-e]pyrimidin-5(6H)-one;

6-(3,5-dimethoxybenzyl)-8-[4-(hydroxyacetyl)piperazin-1-yl]-2-(2-methylpropyl)imidazo[1,2-c]pyrido[2,3-e]pyrimidin-5(6H)-one;

6-(3,5-dimethoxybenzyl)-2,3-dimethyl-8-(2-oxa-6-azaspiro[3.3]heptan-6-yl)imidazo[1,2-c]pyrido[2,3-e]pyrimidin-5(6H)-one;

6-(3,5-dimethoxybenzyl)-2,3-dimethyl-8-(morpholin-4-yl)imidazo[1,2-c]pyrido[2,3-e]pyrimidin-5(6H)-one;

6-(3,5-dimethoxybenzyl)-3-methyl-8-[(oxetan-3-ylmethyl)amino]-2-(propan-2-yl)imidazo[1,2-c]pyrido[2,3-e]pyrimidin-5(6H)-one;

8-(4-acetylpiperazin-1-yl)-6-(3,5-dimethoxybenzyl)-3-methyl-2-(propan-2-yl)imidazo[1,2-c]pyrido[2,3-e]pyrimidin-5(6H)-one;

6-(3,5-dimethoxybenzyl)-8-(4-methoxypiperidin-1-yl)-2,3-dimethylimidazo[1,2-c]pyrido[2,3-e]pyrimidin-5(6H)-one;

5-(3,5-dimethoxybenzyl)-8,9-dimethyl-3-(morpholin-4-yl)imidazo[1,2-c]pteridin-6(5h)-one;

6-(3,5-dimethoxybenzyl)-8-(4-methoxypiperidin-1-yl)-3-methyl-2-(propan-2-yl)imidazo[1,2-c]pyrido[2,3-e]pyrimidin-5(6H)-one;

6-(3,5-dimethoxybenzyl)-8-[3-(methoxymethyl)azetidin-1-yl]-3-methyl-2-(propan-2-yl)imidazo[1,2-c]pyrido[2,3-e]pyrimidin-5(6H)-one;

6-(4-methoxybenzyl)-3-methyl-8-(morpholin-4-yl)-2-(propan-2-yl)imidazo[1,2-c]pyrido[2,3-e]pyrimidin-5(6H)-one;

6-(4-chlorobenzyl)-3-methyl-8-(morpholin-4-yl)-2-(propan-2-yl)imidazo[1,2-c]pyrido[2,3-e]pyrimidin-5(6H)-one;

6-(4-chlorobenzyl)-3-methyl-8-(2-oxa-6-azaspiro[3.3]heptan-6-yl)-2-(propan-2-yl)imidazo[1,2-c]pyrido[2,3-e]pyrimidin-5(6H)-one;

6-(4-methoxybenzyl)-8-[3-(methoxymethyl)azetidin-1-yl]-3-methyl-2-(propan-2-yl)imidazo[1,2-c]pyrido[2,3-e]pyrimidin-5(6H)-one;

6-(4-methoxybenzyl)-3-methyl-8-(2-oxa-6-azaspiro[3.3]heptan-6-yl)-2-(propan-2-yl)imidazo[1,2-c]pyrido[2,3-e]pyrimidin-5(6H)-one;

6-(4-chlorobenzyl)-8-[(4-hydroxypiperidin-1-yl)carbonyl]-3-methyl-2-(propan-2-yl)imidazo[1,2-c]pyrido[2,3-e]pyrimidin-5(6H)-one;

3-tert-butyl-6-(4-methoxybenzyl)-8-(morpholin-4-yl)pyrido[2,3-e][1,2,4]triazolo[4,3-c]pyrimidin-5(6H)-one;

6-(4-methoxybenzyl)-8-(morpholin-4-yl)-3-(propan-2-yl)pyrido[2,3-e][1,2,4]triazolo[4,3-c]pyrimidin-5(6H)-one;

6-(4-methoxybenzyl)-8-(morpholin-4-yl)-3-[(tetrahydro-2H-pyran-4-yloxy)methyl]pyrido[2,3-e][1,2,4]triazolo[4,3-c]pyrimidin-5(6H)-one;
6-(4-chlorobenzyl)-8-(morpholin-4-yl)-3-(propan-2-yl)pyrido[2,3-e][1,2,4]triazolo[4,3-c]pyrimidin-5(6H)-one;
6-(4-chlorobenzyl)-8-(morpholin-4-yl)-3-(pyridin-3-ylmethyl)pyrido[2,3-e][1,2,4]triazolo[4,3-c]pyrimidin-5(6H)-one;
6-(3,5-dimethoxybenzyl)-3-methyl-8-(morpholin-4-yl)pyrido[2,3-e][1,2,4]triazolo[4,3-c]pyrimidin-5(6H)-one;
6-(4-chlorobenzyl)-3-(1-methylcyclopropyl)-8-(morpholin-4-yl)pyrido[2,3-e][1,2,4]triazolo[4,3-c]pyrimidin-5(6H)-one;
2-[6-(4-chlorobenzyl)-8-(morpholin-4-yl)-5-oxo-5,6-dihydropyrido[2,3-e][1,2,4]triazolo[4,3-c]pyrimidin-3-yl]-n-(propan-2-yl)acetamide;
6-(4-methoxybenzyl)-3-(2-methylpropyl)-8-(morpholin-4-yl)pyrido[2,3-e][1,2,4]triazolo[4,3-c]pyrimidin-5(6H)-one;
6-(4-chlorobenzyl)-3-[(2-hydroxypyridin-3-yl)methyl]-8-(morpholin-4-yl)pyrido[2,3-e][1,2,4]triazolo[4,3-c]pyrimidin-5(6H)-one;
6-(4-chlorobenzyl)-3-[(2-methylpyridin-3-yl)methyl]-8-(morpholin-4-yl)pyrido[2,3-e][1,2,4]triazolo[4,3-c]pyrimidin-5(6H)-one;
6-(4-chlorobenzyl)-3-(1-ethyl-1h-pyrazol-5-yl)-8-(morpholin-4-yl)pyrido[2,3-e][1,2,4]triazolo[4,3-c]pyrimidin-5(6H)-one;
6-(4-chlorobenzyl)-3-(2-methylpropyl)-8-(morpholin-4-yl)pyrido[2,3-e][1,2,4]triazolo[4,3-c]pyrimidin-5(6H)-one;
6-(4-chlorobenzyl)-3-(1-ethyl-1h-pyrazol-3-yl)-8-(morpholin-4-yl)pyrido[2,3-e][1,2,4]triazolo[4,3-c]pyrimidin-5(6H)-one;
6-(4-chlorobenzyl)-3-(3,5-dimethyl-1,2-oxazol-4-yl)-8-(morpholin-4-yl)pyrido[2,3-e][1,2,4]triazolo[4,3-c]pyrimidin-5(6H)-one;
9,9-dimethyl-5-(4-methylbenzyl)-3-{[(oxetan-3-yl)methyl]amino}-5,8,9,10-tetrahydro-6H-pyrido[2,3-e]pyrimido[1,2-c]pyrimidin-6-one;
5-(3,5-dimethoxybenzyl)-9-methyl-3-(morpholin-4-yl)-5,8,9,10-tetrahydro-6H-pyrido[2,3-e]pyrimido[1,2-c]pyrimidin-6-one;
5-(3,5-dimethoxybenzyl)-9,9-dimethyl-3-(morpholin-4-yl)-5,8,9,10-tetrahydro-6H-pyrido[2,3-e]pyrimido[1,2-c]pyrimidin-6-one;
5-(4-chlorobenzyl)-3-[3-(methoxymethyl)azetidin-1-yl]-9,9-dimethyl-5,8,9,10-tetrahydro-6H-pyrido[2,3-e]pyrimido[1,2-c]pyrimidin-6-one;
5-(3,5-dimethoxybenzyl)-10-ethyl-3-(morpholin-4-yl)-5,8,9,10-tetrahydro-6H-pyrido[2,3-e]pyrimido[1,2-c]pyrimidin-6-one;
5-(3,5-dimethoxybenzyl)-8-ethyl-3-(morpholin-4-yl)-5,8,9,10-tetrahydro-6H-pyrido[2,3-e]pyrimido[1,2-c]pyrimidin-6-one;
10-ethyl-5-(4-methoxybenzyl)-3-(morpholin-4-yl)-5,8,9,10-tetrahydro-6H-pyrido[2,3-e]pyrimido[1,2-c]pyrimidin-6-one;
8-ethyl-5-(4-methoxybenzyl)-3-(morpholin-4-yl)-5,8,9,10-tetrahydro-6H-pyrido[2,3-e]pyrimido[1,2-c]pyrimidin-6-one;
5-(4-chlorobenzyl)-10-ethyl-3-(morpholin-4-yl)-5,8,9,10-tetrahydro-6H-pyrido[2,3-e]pyrimido[1,2-c]pyrimidin-6-one;
5-(4-chlorobenzyl)-8-ethyl-3-(morpholin-4-yl)-5,8,9,10-tetrahydro-6H-pyrido[2,3-e]pyrimido[1,2-c]pyrimidin-6-one;
6-(4-methoxybenzyl)-2-(2-methylpropyl)-8-(morpholin-4-yl)pyrido[2,3-e][1,2,4]triazolo[1,5-c]pyrimidin-5(6H)-one;
2-tert-butyl-6-(4-methoxybenzyl)-8-(morpholin-4-yl)pyrido[2,3-e][1,2,4]triazolo[1,5-c]pyrimidin-5(6H)-one;
6-(4-chlorobenzyl)-8-morpholino-2-(2,2,2-trifluoroethyl)-2,6-dihydroimidazo[1,2-c]pyrido[2,3-e]pyrimidin-5(3H)-one;
6-(4-chlorobenzyl)-8-morpholino-3-(2,2,2-trifluoroethyl)-2,6-dihydroimidazo[1,2-c]pyrido[2,3-e]pyrimidin-5(3H)-one;
6-(3,5-dimethoxybenzyl)-2,2-dimethyl-8-(morpholin-4-yl)-2,6-dihydroimidazo[1,2-c]pyrido[2,3-e]pyrimidin-5(3H)-one;
6-(4-chlorobenzyl)-8-(morpholin-4-yl)-3-(propan-2-yl)-2,6-dihydroimidazo[1,2-c]pyrido[2,3-e]pyrimidin-5(3H)-one;
6-(4-chlorobenzyl)-8-(morpholin-4-yl)-3-(propan-2-yl)imidazo[1,2-c]pyrido[2,3-e]pyrimidine-2,5(3H,6H)-dione;
6-(4-methoxybenzyl)-8-(morpholin-4-yl)-3-(propan-2-yl)imidazo[1,2-c]pyrido[2,3-e]pyrimidine-2,5(3H,6H)-dione;
6-(4-chlorobenzyl)-8-(4-hydroxypiperidin-1-yl)-3-(propan-2-yl)pyrido[2,3-e][1,2,4]triazolo[4,3-c]pyrimidin-5(6H)-one;
6-(4-chlorobenzyl)-2-(1-methylcyclopropyl)-8-(morpholin-4-yl)pyrido[2,3-e][1,2,4]triazolo[1,5-c]pyrimidin-5(6H)-one;
3-tert-butyl-6-[(5-chloropyridin-2-yl)methyl]-8-(morpholin-4-yl)pyrido[2,3-e][1,2,4]triazolo[4,3-c]pyrimidin-5(6H)-one;
6-(4-methoxybenzyl)-3-(1-methylcyclopropyl)-8-(morpholin-4-yl)pyrido[2,3-e][1,2,4]triazolo[4,3-c]pyrimidin-5(6H)-one;
2-tert-butyl-8-(4-hydroxypiperidin-1-yl)-6-(4-methoxybenzyl)pyrido[2,3-e][1,2,4]triazolo[1,5-c]pyrimidin-5(6H)-one;
3-tert-butyl-8-(4-hydroxypiperidin-1-yl)-6-(4-methoxybenzyl)pyrido[2,3-e][1,2,4]triazolo[4,3-c]pyrimidin-5(6H)-one;
9-tert-butyl-5-(4-chlorobenzyl)-3-(morpholin-4-yl)[1,2,4]triazolo[1',5':1,6]pyrimido[5,4-c]pyridazin-6(5h)-one;
8-(4-aminopiperidin-1-yl)-3-tert-butyl-6-(4-chlorobenzyl)[1,2,4]triazolo[4',3':1,6]pyrimido[5,4-c]pyridazin-5(6H)-one;
3-tert-butyl-6-(4-methoxybenzyl)-8-(morpholin-4-yl)[1,2,4]triazolo[4',3':1,6]pyrimido[5,4-c]pyridazin-5(6H)-one;
3-tert-butyl-6-(4-chlorobenzyl)-8-(piperazin-1-yl)pyrido[2,3-e][1,2,4]triazolo[4,3-c]pyrimidin-5(6H)-one;
2-tert-butyl-6-(4-chlorobenzyl)-8-(piperazin-1-yl)pyrido[2,3-e][1,2,4]triazolo[1,5-c]pyrimidin-5(6H)-one;
3-(tert-butyl)-6-(4-chlorobenzyl)-8-(3-methoxypyrrolidin-1-yl)pyrido[2,3-e][1,2,4]triazolo[4,3-c]pyrimidin-5(6H)-one;
3-tert-butyl-6-(4-chlorobenzyl)-8-(tetrahydro-2H-pyran-4-ylamino)pyrido[2,3-e][1,2,4]triazolo[4,3-c]pyrimidin-5(6H)-one;
3-tert-butyl-6-[(5-methylthiophen-2-yl)methyl]-8-(morpholin-4-yl)pyrido[2,3-e][1,2,4]triazolo[4,3-c]pyrimidin-5(6H)-one;

6-(4-chlorobenzyl)-8-(morpholin-4-yl)-3-(tetrahydro-2H-pyran-4-ylmethyl)pyrido[2,3-e][1,2,4]triazolo[4,3-c]pyrimidin-5(6H)-one;
8-(4-acetylpiperazin-1-yl)-6-(4-chlorobenzyl)-3-(propan-2-yl)pyrido[2,3-e][1,2,4]triazolo[4,3-c]pyrimidin-5(6H)-one;
6-(4-chlorobenzyl)-8-(morpholin-4-yl)-3-[(tetrahydro-2H-pyran-4-yloxy)methyl]pyrido[2,3-e][1,2,4]triazolo[4,3-c]pyrimidin-5(6H)-one;
3-tert-butyl-6-(4-methoxybenzyl)-8-(morpholin-4-yl)pyrido[3,4-e][1,2,4]triazolo[4,3-c]pyrimidin-5(6H)-one;
6-(4-methoxybenzyl)-3-(1-methylcyclopropyl)-8-(morpholin-4-yl)pyrido[3,4-e][1,2,4]triazolo[4,3-c]pyrimidin-5(6H)-one;
3-tert-butyl-6-(4-chlorobenzyl)-8-(morpholin-4-yl)[1,2,4]triazolo[4',3':1,6]pyrimido[5,4-c]pyridazin-5(6H)-one;
3-tert-butyl-6-(4-chlorobenzyl)-8-(morpholin-4-yl)pyrido[3,4-e][1,2,4]triazolo[4,3-c]pyrimidin-5(6H)-one;
6-(3,5-dimethoxybenzyl)-2-(2,2-dimethylpropyl)-8-(morpholin-4-yl)-2,6-dihydroimidazo[1,2-c]pyrido[2,3-e]pyrimidin-5(3H)-one; and
6-(3,5-dimethoxybenzyl)-3-(2,2-dimethylpropyl)-8-(morpholin-4-yl)-2,6-dihydroimidazo[1,2-c]pyrido[2,3-e]pyrimidin-5(3H)-one.

\* \* \* \* \*

UNITED STATES PATENT AND TRADEMARK OFFICE
CERTIFICATE OF CORRECTION

| | | |
|---|---|---|
| PATENT NO. | : 11,999,732 B2 | Page 1 of 2 |
| APPLICATION NO. | : 17/259511 | |
| DATED | : June 4, 2024 | |
| INVENTOR(S) | : Davide Graziani | |

It is certified that error appears in the above-identified patent and that said Letters Patent is hereby corrected as shown below:

On the Title Page

Page 2, Column 1 (Item (56) Other Publications), Line 3, delete "Lettters," and insert --Letters,--.

Page 2, Column 2 (Item (56) Other Publications), Line 4, delete ""Noiceptive" and insert --"Nociceptive--.

In the Specification

Column 9-10, Line 39 (approx.) (TABLE 1), delete "clpyrido" and insert --c]pyrido--.

Column 11-12, Line 6 (approx.) (TABLE 1 – continued), delete "clpyrido" and insert --c]pyrido--.

Column 19-20, Line 13 (approx.) (TABLE 1 – continued), delete "clpyrido" and insert --c]pyrido--.

Column 55-56, Line 20 (approx.) (TABLE 2 – continued), delete "elpyrimidin" and insert --e]pyrimidin--.

Column 108, Line 47, delete "$P2X_23$" and insert --$P2X_{2/3}$--.

Column 112, Line 19, delete "produgs" and insert --prodrugs--.

Column 116, Line 67, delete "gastiointestinal" and insert --gastrointestinal--.

Column 123, Line 13, delete "N-methoxynethyl" and insert --N-methoxymethyl--.

In the Claims

Column 194, Line 21 (approx.), Claim 3, delete "thereof," and insert --thereof;--.

Signed and Sealed this
Eighth Day of October, 2024

Katherine Kelly Vidal
*Director of the United States Patent and Trademark Office*

Column 194, Line 31, Claim 3, after "2" delete "b".

Column 195, Line 51 (approx.), Claim 10, after "membered" delete "b".